US010308687B2

(12) United States Patent
Francois et al.

(10) Patent No.: US 10,308,687 B2
(45) Date of Patent: Jun. 4, 2019

(54) CELL-PENETRATING COMPSTATIN ANALOGS AND USES THEREOF

(71) Applicant: Apellis Pharmaceuticals, Inc., Crestwood, KY (US)

(72) Inventors: Cedric Francois, Prospect, KY (US); Pascal Deschatelets, Prospect, KY (US); Monica Gerber, Somerville, MA (US)

(73) Assignee: Apellis Pharmaceuticals, Inc., Crestwood, KY (US)

( * ) Notice: Subject to any disclaimer, the term of this patent is extended or adjusted under 35 U.S.C. 154(b) by 109 days.

(21) Appl. No.: 14/775,663

(22) PCT Filed: Mar. 14, 2014

(86) PCT No.: PCT/US2014/027289
§ 371 (c)(1),
(2) Date: Sep. 11, 2015

(87) PCT Pub. No.: WO2014/152391
PCT Pub. Date: Sep. 25, 2014

(65) Prior Publication Data
US 2016/0215022 A1 Jul. 28, 2016

Related U.S. Application Data

(60) Provisional application No. 61/791,631, filed on Mar. 15, 2013.

(51) Int. Cl.
| | |
|---|---|
| *A61K 38/00* | (2006.01) |
| *A61K 38/12* | (2006.01) |
| *C07K 7/64* | (2006.01) |
| *C07K 7/08* | (2006.01) |
| *C07K 14/47* | (2006.01) |
| *C07K 14/005* | (2006.01) |
| *C07K 14/475* | (2006.01) |
| *C12N 7/00* | (2006.01) |
| *G01N 33/564* | (2006.01) |
| *A61K 47/64* | (2017.01) |

(52) U.S. Cl.
CPC ............. *C07K 7/64* (2013.01); *A61K 47/645* (2017.08); *C07K 7/08* (2013.01); *C07K 14/005* (2013.01); *C07K 14/472* (2013.01); *C07K 14/475* (2013.01); *C12N 7/00* (2013.01); *G01N 33/564* (2013.01); *A61K 38/00* (2013.01); *C07K 2319/01* (2013.01); *C07K 2319/10* (2013.01); *C12N 2740/16022* (2013.01); *C12N 2740/16033* (2013.01); *G01N 2333/4716* (2013.01)

(58) Field of Classification Search
None
See application file for complete search history.

(56) References Cited

U.S. PATENT DOCUMENTS

| | | |
|---|---|---|
| 4,299,838 A | 11/1981 | Durlach |
| 4,576,750 A | 3/1986 | Pitzenberger |
| 4,816,567 A | 3/1989 | Cabilly et al. |
| 4,870,097 A | 9/1989 | Makovec et al. |
| 5,157,110 A | 10/1992 | Kotwal et al. |
| 5,482,135 A | 1/1996 | Phillips et al. |
| 5,492,135 A | 2/1996 | Hubbell |
| 5,632,984 A | 5/1997 | Wong et al. |
| 5,770,589 A | 6/1998 | Billson et al. |
| 5,776,970 A | 7/1998 | Shechter et al. |
| 5,797,898 A | 8/1998 | Santini, Jr. et al. |
| 5,824,072 A | 10/1998 | Wong |
| 5,844,099 A | 12/1998 | Stahl et al. |
| 5,861,486 A | 1/1999 | Devore et al. |
| 5,869,079 A | 2/1999 | Wong et al. |
| 5,942,405 A | 8/1999 | Ames et al. |
| 6,051,698 A | 4/2000 | Janjic et al. |
| 6,129,761 A | 10/2000 | Hubbell |
| 6,140,472 A | 10/2000 | Rosengard et al. |
| 6,169,057 B1 | 1/2001 | Lovatt |
| 6,197,934 B1 | 3/2001 | DeVore et al. |
| 6,204,365 B1 | 3/2001 | Devore et al. |
| 6,214,790 B1 | 4/2001 | Richelson et al. |
| 6,319,897 B1 | 11/2001 | Lambris et al. |
| 6,331,313 B1 | 12/2001 | Wong et al. |
| 6,378,526 B1 | 4/2002 | Bowman et al. |
| 6,436,427 B1 | 8/2002 | Hammang et al. |
| 6,534,058 B2 | 3/2003 | Fung et al. |
| 6,551,595 B1 | 4/2003 | Rosengard et al. |
| 6,582,959 B2 | 6/2003 | Kim |
| 6,692,759 B1 | 2/2004 | Wong et al. |
| 6,818,447 B1 | 11/2004 | Pavco et al. |
| 6,821,950 B1 | 11/2004 | Fairlie et al. |
| 6,897,290 B1 | 5/2005 | Atkinson et al. |
| 6,976,982 B2 | 12/2005 | Santini, Jr. et al. |
| 7,084,106 B1 | 8/2006 | Kotwal et al. |
| 7,108,982 B1 | 9/2006 | Hageman |
| 7,112,327 B2 | 9/2006 | Fung et al. |

(Continued)

FOREIGN PATENT DOCUMENTS

| | | |
|---|---|---|
| EP | 0422681 A1 | 4/1991 |
| EP | 0737484 A2 | 10/1996 |

(Continued)

OTHER PUBLICATIONS

Deshayes et al. "Cell-penetrating peptides: tools for intracellular delivery of therapeutics," Cell. Mol. Life Sci. 62:1839-1849 (2005).*

(Continued)

*Primary Examiner* — Julie Ha
*Assistant Examiner* — Kristina M Hellman
(74) *Attorney, Agent, or Firm* — Choate, Hall & Stewart LLP; Brenda Herschbach Jarrell; Rolando Medina

(57) ABSTRACT

In some aspects, the present invention cell-penetrating compstatin analog and compositions comprising cell-penetrating compstatin analog. In some aspects, the invention further provides methods of using cell-penetrating compstatin analogs treat a complement-mediated disorder, e.g., to inhibit complement-mediated damage to a cell, tissue, or organ, to inhibit production or release of biologically active C3 cleavage products.

13 Claims, No Drawings
Specification includes a Sequence Listing.

(56) References Cited

U.S. PATENT DOCUMENTS

| | | |
|---|---|---|
| 7,745,389 B2 | 6/2010 | Hageman |
| 7,888,323 B2 | 2/2011 | Lambris et al. |
| 7,947,267 B2 | 5/2011 | Francois et al. |
| 7,989,589 B2 | 8/2011 | Lambris |
| 8,043,609 B2 | 10/2011 | Deschatelets et al. |
| 8,168,584 B2 | 5/2012 | Deschatelets et al. |
| 8,521,273 B2 | 8/2013 | Kliman |
| 8,580,735 B2 | 11/2013 | Francois et al. |
| 8,753,625 B2 | 6/2014 | Fung et al. |
| 8,840,893 B2 | 9/2014 | Schwaeble et al. |
| 8,871,230 B2 | 10/2014 | Rudolph et al. |
| 9,056,076 B2 | 6/2015 | Deschatelets et al. |
| 9,421,240 B2 | 8/2016 | Francois et al. |
| 9,512,180 B2 | 12/2016 | Morikis et al. |
| 10,035,822 B2 | 7/2018 | Francois et al. |
| 10,125,171 B2 | 11/2018 | Francois et al. |
| 2002/0086356 A1 | 7/2002 | Tuschl et al. |
| 2002/0102581 A1 | 8/2002 | Hageman et al. |
| 2003/0017501 A1 | 1/2003 | Hageman et al. |
| 2003/0171320 A1 | 9/2003 | Guyer |
| 2003/0175950 A1 | 9/2003 | McSwiggen |
| 2003/0191084 A1 | 10/2003 | Biesecker et al. |
| 2003/0207309 A1 | 11/2003 | Hageman et al. |
| 2004/0018176 A1 | 1/2004 | Tolentino et al. |
| 2004/0038869 A1 | 2/2004 | Finney et al. |
| 2004/0092470 A1 | 5/2004 | Leonard et al. |
| 2004/0115774 A1 | 6/2004 | Kochendoerfer et al. |
| 2004/0177387 A1 | 9/2004 | Jayakrishna |
| 2004/0210041 A1 | 10/2004 | Arbogast et al. |
| 2004/0229266 A1 | 11/2004 | Tuschl et al. |
| 2005/0020525 A1 | 1/2005 | McSwiggen et al. |
| 2005/0032733 A1 | 2/2005 | McSwiggen et al. |
| 2005/0048099 A1 | 3/2005 | Shiah et al. |
| 2005/0054596 A1 | 3/2005 | McSwiggen et al. |
| 2005/0090448 A1 | 4/2005 | Johnson et al. |
| 2005/0244469 A1 | 11/2005 | Whitcup et al. |
| 2005/0244472 A1 | 11/2005 | Hughes et al. |
| 2005/0255144 A1 | 11/2005 | Schultz |
| 2005/0260198 A1 | 11/2005 | Holers et al. |
| 2005/0281861 A1 | 12/2005 | Hughes et al. |
| 2005/0287601 A1 | 12/2005 | Hageman et al. |
| 2006/0002852 A1 | 1/2006 | Saltzman et al. |
| 2006/0002971 A1 | 1/2006 | Saltzman et al. |
| 2006/0105980 A1 | 5/2006 | Benedict et al. |
| 2006/0115476 A1 | 6/2006 | Tedesco et al. |
| 2006/0140939 A1 | 6/2006 | Fung |
| 2006/0142191 A1 | 6/2006 | Francois et al. |
| 2006/0257359 A1 | 11/2006 | Francois et al. |
| 2006/0263819 A1 | 11/2006 | Hageman et al. |
| 2007/0020647 A1 | 1/2007 | Hageman et al. |
| 2007/0065433 A1 | 3/2007 | Mollnes et al. |
| 2007/0149616 A1 | 6/2007 | Clark et al. |
| 2007/0196367 A1 | 8/2007 | Dinu |
| 2007/0238654 A1 | 10/2007 | Deschatelets et al. |
| 2008/0075755 A1 | 3/2008 | Deschatelets et al. |
| 2008/0227717 A1* | 9/2008 | Lambris .............. C07K 7/08 514/1.1 |
| 2009/0196903 A1 | 8/2009 | Kliman |
| 2009/0214538 A1 | 8/2009 | Fung et al. |
| 2009/0220572 A1 | 9/2009 | Deschatelets et al. |
| 2010/0015136 A1 | 1/2010 | Michel et al. |
| 2010/0166862 A1 | 7/2010 | Francois et al. |
| 2010/0222550 A1 | 9/2010 | Lambris |
| 2010/0239659 A1 | 9/2010 | Diwan et al. |
| 2011/0092446 A1 | 4/2011 | Francois et al. |
| 2011/0182877 A1 | 7/2011 | Francois et al. |
| 2011/0311549 A1 | 12/2011 | Schwaeble et al. |
| 2013/0072442 A1 | 3/2013 | Deschatelets et al. |
| 2013/0296254 A1 | 11/2013 | Deschatelets et al. |
| 2013/0324482 A1 | 12/2013 | Francois et al. |
| 2014/0113874 A1 | 4/2014 | Lambris et al. |
| 2014/0323407 A1 | 10/2014 | Francois et al. |
| 2014/0371133 A1 | 12/2014 | Francois et al. |
| 2015/0064176 A1 | 3/2015 | Schwaeble et al. |
| 2015/0158915 A1 | 6/2015 | Lambris et al. |
| 2016/0015810 A1 | 1/2016 | Deschatelets et al. |
| 2016/0060297 A1 | 3/2016 | Deschatelets et al. |
| 2016/0067357 A1 | 3/2016 | Francois et al. |
| 2016/0166862 A1 | 6/2016 | Qui et al. |
| 2016/0194359 A1 | 7/2016 | Francois et al. |
| 2016/0215020 A1 | 7/2016 | Francois et al. |
| 2017/0283461 A1 | 10/2017 | Francois et al. |
| 2017/0349631 A1 | 12/2017 | Deschatelets et al. |

FOREIGN PATENT DOCUMENTS

| | | |
|---|---|---|
| EP | 2278987 A2 | 2/2011 |
| EP | 2311479 A1 | 4/2011 |
| JP | 11-197234 A | 7/1999 |
| JP | 2003-535581 A | 12/2003 |
| JP | 2004-065461 A | 3/2004 |
| JP | 2006-505254 A | 2/2006 |
| JP | 2009-511496 A | 3/2009 |
| JP | 2009-517476 A | 4/2009 |
| JP | 2010-280688 A | 12/2010 |
| JP | 2012-525443 A | 10/2012 |
| JP | 2014-514364 A | 6/2014 |
| RU | 2417099 C2 | 4/2011 |
| RU | 2474586 C2 | 2/2013 |
| WO | WO-96/030046 A1 | 10/1996 |
| WO | WO-97/33603 A1 | 9/1997 |
| WO | WO-99/013899 A1 | 3/1999 |
| WO | WO-00/47130 A1 | 8/2000 |
| WO | WO-00/71147 A1 | 11/2000 |
| WO | WO-01/84149 A2 | 11/2001 |
| WO | WO-2002/011793 A1 | 2/2002 |
| WO | WO-2003/047633 A2 | 6/2003 |
| WO | WO-2003/086448 A1 | 10/2003 |
| WO | WO-2004/026326 A1 | 4/2004 |
| WO | WO-2004/026328 A1 | 4/2004 |
| WO | WO-2004/028635 A1 | 4/2004 |
| WO | WO-2004/037310 A2 | 5/2004 |
| WO | WO-2004/041160 A2 | 5/2004 |
| WO | WO-2005/023296 A1 | 3/2005 |
| WO | WO-2005/110435 A1 | 11/2005 |
| WO | WO-2005/110436 A2 | 11/2005 |
| WO | WO-2006/042329 A2 | 4/2006 |
| WO | WO-2006/062716 A2 | 6/2006 |
| WO | WO-2006/080951 A2 | 8/2006 |
| WO | WO-2006/099330 A2 | 9/2006 |
| WO | WO-2007/044668 A2 | 4/2007 |
| WO | WO-2007/056227 A2 | 5/2007 |
| WO | WO-2007/076437 A2 | 7/2007 |
| WO | WO-2007/084765 A2 | 7/2007 |
| WO | WO-2007/062249 A2 | 9/2007 |
| WO | WO-2009/015087 A2 | 1/2009 |
| WO | WO-2009/046198 A2 | 4/2009 |
| WO | WO-2010/127336 A1 | 11/2010 |
| WO | WO-2010/135717 A2 | 11/2010 |
| WO | WO-2011/076391 A1 | 6/2011 |
| WO | WO-2011/163394 A2 | 12/2011 |
| WO | WO-2012/006599 A2 | 1/2012 |
| WO | WO-2012/040259 A2 | 3/2012 |
| WO | WO-2012/155107 A1 | 11/2012 |
| WO | WO-2014/078734 A2 | 5/2014 |

OTHER PUBLICATIONS

Futaki, "Membrane-permeable arginine-rich peptides and the translocation mechanisms," Adv. Drug. Del. Rev. 57:547-558 (2005).*

International Search Report for PCT/US2014/27289, 4 pages (dated Aug. 19, 2014).

Written Opinion for PCT/US2014/27289, 4 pages (dated Aug. 19, 2014).

Acosta, J. et al., Complement and complement regulatory proteins as potential molecular targets for vascular diseases, Curr. Pharm. Des., 10(2):203-11 (2004).

Acosta, J. et al., Molecular basis for a link between complement and the vascular complications of diabetes, Proc. Nat. Acad. Sci., 97(10):5450 (2000).

(56) References Cited

OTHER PUBLICATIONS

Albrecht, J.C. and Fleckenstein, B., New Member of the Multigene Family of Complement Control Proteins in Herpes Saimiri, Journal of Virology, 66(6):3937-3940 (1992).
Albrecht, J.C. et al., Herpesvirus Saimiri Has a Gene Specifying a Homologue of the Cellular Membrane Glycoprotein CD59, Virology, 190(1):527-530 (1992).
Aldrich, ChemFiles, Peptide Synthesis, 7(2): 20 pages (2007).
Allen, T.M., Ligand-Targeted Therapeutics in Anticancer Therapy, Nature Reviews Cancer, 2(10):750-765 (2002).
Altschul, S.F. et al., Basic local alignment search tool, Journal of Molecular Biology, 215(3):403-410 (1990).
Altschul, S.F., Gapped BLAST and PSI-BLAST: a New Generation of Protein Database Search Programs, Nucleic Acids Research, 25(17):3389-3402 (1997).
Ambati, J. et al., Age-related macular degeneration: etiology, pathogenesis, and therapeutic strategies, Survey of Ophthalmology, 48(3):257-293 (2003).
Ambati, J. et al., An Animal Model of Age-Related Macular Degeneration in Senescent Ccl-2- or Ccr-2-Deficient Mice, Nature Medicine, 9(11):1390-1397 (2003).
American Academy of Ophthalmology, Age-Related Macular Degeneration, Preferred Practice Pattern, American Academy of Ophthalmology, San Francisco, CA (2006).
Anderson, Amy C., The Process of Structure-Based Drug Design, Chemistry & Biology, 10:787-797 (2003).
Anderson, DH, et al., A role for local inflammation in the formation of drusen in the aging eye, Am. J. Ophthalmol, 134: 411-431 (2002).
Author Not Known, Peptide User Guide: A brief introduction into synthesis methods, handling and design of peptides, Bachem Brochure, 24 pages (2009).
Babitzke, P. and Yanofsky, C., Structural Features of L-Tryptophan Required for Activation of TRAP, the trp RNA-Binding Attenuation Protein of Bacillus subtilis, Journal of Biological Chemistry, 270(21):12452-12456 (1995).
Barlett, J.B. et al., The Evolution of Thalidomide and its IMiD Derivatives as Anticancer Agents, Nature Reviews Cancer, 4 (4):314-322 (2004).
Bartz, R. et al., Effective siRNA delivery and target mRNA degradation using an amphipathic peptide to facilitate pH-dependent endosomal escape, Biochem J., 435:475-487 (2011).
Beene, D.L. et al., Cation-π Interactions in Ligand Recognition by Serotonergic (5-HT3A) and Nicotinic Acetylcholine Receptors: The Anomalous Binding Properties of Nicotine, Biochemistry, 41(32):10262-10269 (2002).
Bora, P.S. et al., Immunotherapy for Choroidal Neovascularization in a Laser-Induced Mouse Model Simulating Exudative (Wet) Macular Degeneration, Proceedings of the National Academy of Science, 100(5):2679-2684 (2003).
Bora, PS et al., Complement activation by alternative pathway is critical in the development of laser-induced choroidal neovascularization, Invest Ophthalmol Vis Sci, 47: E-Abstract 4167 (2006).
Bora, PS et al., Neovascularization in a mouse model that simulates exudative macular degeneration is complement dependent, Invest. Ophthalmol. Vis. Sci. 45: E-Abstract 1871 (2004).
Bora, PS et al., Role of complement and complement membrane attack complex in neovascularization, Journal of Immunology, 174 (1): 491-497 (2005).
Bora, PS, et al., Complement Activation is Required in the Murine Model of Laser-induced Choroidal Neovascularization, Invest. Ophthalmol. Vis. Sci., 44: E-Abstract 3940 (2003).
Bourges, J-L. et al., Ocular drug delivery targeting the retina and retinal pigment epithelium using polylactide nanoparticles, Investigative Ophthalmology and Visual Sciences, 44(8):3562-3569 (2003).
Braun, J., UCSB Studies Link Alzheimer's Disease, Macular Degeneration, The Daily Nexus, University of California, Santa Barbara, 83(135): 1-5 (Published May 28, 2003).
Chapple, J.P. et al., Unfolding retinal dystrophies: a role for molecular chaperones?, Trends in Mol. Med., 7: 414-421 (2001).
Chauhan, A. et al., The Taming of the Cell Penetrating Domain of the HIV Tat: Myths and Realities, J. Control Release, 117(2):148-162 (2007).
Conley YP, et al., Candidate gene analysis suggests a role for fatty acid biosynthesis and regulation of the complement system in the etiology of age-related maculopathy, Hum. Mol. Genet., 14:1991-2002 (2005).
Corrales, L. et al., Anaphylatoxin C5a Creates a Favorable Microenvironment for Lung Cancer Progression, The Journal of Immunology, 4674-4683 (2012).
Database BIOSIS on STN, BIOSIS, (Philadelphila, PA, USA), DN: PREV200600053073, & Raisler, B.J. et al., Drusen Complement Components C3a and C5a Promote Choroidal Neovascularization, IOVS, 2005, vol. 46, No. Suppl, p. 1214.
Davenport, R.J., Tarnished Vision, Sci. Aging Knowl. Environ., 2004(37): nf85 (2004).
Debets, M. et al., Aza-dibenzocyclooctynes for fast and efficient enzyme PEGylation via copper-free (3+2) cycloaddition, Chem. Commun., 46:97-99 (2010).
Donoso, L. et al., The role of inflammation in the pathogenesis of age-related macular degeneration, Survey of Ophthalmology, 51(2):137-152 (2006).
Edwards, AO et al., Complement Factor H Polymorphism and Age-Related Macular Degeneration, Science, 308(5720):421-424 (2005).
Eguchi, M. and Kahn, M., Design, Synthesis, and Application of Peptide Secondary Structure Mimetics, Mini Reviews in Medicinal Chemistry, 2(5):447-462 (2002).
Einmahl, S. et al., Evaluation of a Novel Biomaterial in the Suprachoroidal Space of the Rabbit Eye, Investigative Ophthalmology and Visual Science, 43(5):1533-1539 (2002).
Ferrara, N., Vascular Endothelial Growth Factor: Basic Science and Clinical Progress, Endocrine Reviews, 25(4):581-611 (2004).
Fish et al., Anti-vascular Endothelial Growth Factor Therapy for Subfoveal Choroidal Neovascularization Secondary to Age-related Macular Degeneration, Phase II Study Results, The Eyetech Study Group, Ophthalmology, 110: 978-986 (2003).
Frankel, A. et al., Characterization of diphtheria fusion proteins targeted to the human interleukin-3 receptor, Protein Eng, 13(8):575-81 (2000).
Fung, A.E. et al., An Optical Coherence Tomography-Guided, Variable Dosing Regimen with Intravitreal Ranibizumab (Lucentis) for Neovascular Age-related Macular Degeneration, Am. J. Ophthalmol., 143:566-583 (2007).
Gaudreault, J. et al., Preclinical pharmacokinetics of Ranibizumab (rhuFabV2) after a single intravitreal administration, Investigative Ophthalmology and Visual Science, 46(2):726-733 (2005).
Gautam, A. et al., CPPsite: a curated database of cell penetrating peptides, Database, 7 pages (2012).
Gerl, V et al., Extensive Deposits of Complement C3d and C5b-9 in the Choriocapillaris of Eyes of Patients with Diabetic Retinopathy, Investigative Ophthalmology and Visual Sciences, 43(4):1104-1108 (2002).
Gold, B. et al., Variation in factor B (BF) and complement component 2 (C2) genes is associated with age-related macular degeneration, Nature Genetics, 38: 458-462 (2006).
Gonzales, N.R. et al., Minimizing the Immunogenicity of Antibodies for Clinical Application, Tumour Biology, 26(1):31-43 (2005).
Gragoudas et al., Pegaptanib for Neovascular Age-Related Macular Degeneration, NE J Med., 351(27): 2805-2816 (2004).
Haas, A. K. et al., Human protein derived peptides for intracellular delivery of biomolecules, Biochemical Journal Immediate Publication, 25 pages (2011).
Hageman, GS et al., A common haplotype in the complement regulatory gene factor H (HF1/CFH) predisposes individuals to age-related macular degeneration, Proceedings of the National Academy of Sciences, 102(20):7053-7054 (2005).
Hageman, GS et al., An integrated hypothesis that considers drusen as biomarkers of immune-mediated processes at the RPE-Bruch's membrane interface in aging and age-related macular degeneration, Progress in Retinal and Eye Research, 20(6):705-732 (2001).
Haines, JL et al., Complement factor H variant increases the risk of age-related macular degeneration, Science, 308(5720):419-421 (2005).

(56) References Cited

OTHER PUBLICATIONS

Hanes, J. and Plückthun, A., In Vitro Selection and Evolution of Functional Proteins by Using Ribosome Display, Proceedings of the National Academy of Science, 94(10):4937-4947 (1997).
Ho, A. et al., Synthetic Protein Transduction Domains: Enhanced Transduction Potential in Vitro and in Vivo, Cancer Research, 61:474-477 (2001).
Holland, MCH, et al.,, Synthetic small-molecule complement inhibitors, Curr. Op. Invest. Drugs, 5(11) 1164-1173 (2004).
Hrynchak, PK, et al., Optical coherence tomography: an introduction to the technique and its use, Optometry and Vision Science, 77(7): 347-356 (2000).
Hughes et al., A common CFH haplotype, with deletion of CFHR1 and CFHR3, is associated with lower risk of age-related macular degeneration, Nature Genetics, 38(10):1173-1177 (2006).
International Search Report for PCT/US05/036547, 5 pages (dated Jun. 10, 2006).
International Search Report for PCT/US06/039397, 6 pages (dated Oct. 24, 2007).
International Search Report for PCT/US2012/037648, (Cell-Reactive, Long-Acting, or Targeted Compstatin Analogs and Uses Thereof, filed May 11, 2012) issued by ISA, 3 pages (dated Sep. 20, 2012).
International Search Report for PCT/US2013/070417, 3 pages (dated Jun. 5, 2014).
International Search Report for PCT/US2013/070424, 3 pages (dated Jun. 5, 2014).
International Search Report from PCT/US2007/001649 (dated Mar. 31, 2008).
Internet Citation: URL: www.rsinewsrxreportingfrom.com/ content.asp?myid+40&tid=365> Anti-VEGF Agents Useful in Age-Related Macular Degeneration, Am Acad of Ophthalm, (Oct. 15, 2005).
Ishida, T. et al., A Combinational Approach to Producing Sterically Stabilized (Stealth) Immunoliposomal Drugs, FEBS Letters, 460(1):129-133 (1999).
Jaffe, G. Safety and pharmacokinetics of an intraocular fluocinolone acetonide sustained delivery device, Investigative Ophthalmology and Visual Sciences, 41(11):3569-3575 (2000).
Jager et al., Age-related Macular Degeneration, N. Engl. J. Med., 358(24): 2606-2617 (2008).
JHA, P. et al., The complement system plays a critical role in the development of experimental autoimmune anterior uveitis, Investigative Ophthalmology and Visual Sciences, 47(3):1030-1038 (2006).
Johnson, L.V. et al., Complement activation and inflammatory processes in drusen formation and age related macular degeneration, Experimental Eye Research, 73(6):887-896, Academic Press Ltd., London, GB (2001).
Kabouridis, Panagiotis S., Biological applications of protein transduction technology, Trends Biotechnol., 21(11):498-503 (2003).
Kalayoglu, M.V., Emerging Treatment Strategies for Age-related Macular Degeneration, Internet Citation, URL: <www.medcompare.com/spotlight.asp?spotlightid=62> (Retrieved Jun. 30, 2004).
Karlin, S. and Altschul, S.F., Applications and Statistics for Multiple High-Scoring Segments in Molecular Sequences, Proceedings of the National Academy of Science, 90(12):5873-5877 (1993).
Karlin, S. and Altschul, S.F., Methods for Assessing the Statistical Significance of Molecular Sequence Features by Using General Scoring Schemes, Proceedings of the National Academy of Science, 87(6):2264-2268 (1990).
Katragadda et al., Thermodynamic studies on the interaction of the third complement component and its inhibitor, compstatin, Journal of Biological Chemistry, 279(53): 54987-54995 (2004).
Katragadda et al., Expression of compstatin in *Escherichia coli*: Incorporation of unnatural amino acids enhances its activity, Protein Expression and Purification, 47(1):289-295 (2006).
Katragadda et al., Structure-activity-based design of potent compstatin analogs, Molecular Immunology, 44(103): 192 (2007).
Katragadda, M. et al., Hydrophobic effect and hydrogen bonds account for the improved activity of a complement inhibitor, compstatin, Journal of Medicinal Chemistry, 49(15):4616-4622 (2006).

Keam, S. J. et al., Verteporfin, A Review of its Use in the Management of Subfoveal Choroidal Neovascularisation, Drugs, 63: 2521-2554 (2003).
Kent, S., Total Chemical Synthesis of Enzymes, Journal of Peptide Science, 9(9):574-593 (2003).
Klein, RJ et al., Complement Factor H Polymorphism in Age-Related Macular Degeneration, Science, 308(5720):385-389 (2005).
Kohler, G. and Milstein, C., Continuous Cultures of Fused Cells Secreting Antibody of Predetermined Specificity, Nature, 256(5517): 495-497 (1975).
Kozlowski, A. et al., Development of Pegylated Interferons for the Treatment of Chronic Hepatitis C, BioDrugs, 15(7):419-429 (2001).
Lattig-Tunnemann, G. et al., Backbone rigidity and static presentation of guanidinum groups increases cellular uptake or arginine-rich cell-penetrating peptides, Nature Communications, 2:453, 6 pages (2011).
Li, M. et al., CFH haplotypes without the Y402H coding variant show strong association with susceptibility to age-related macular degeneration, Nature Genetics, 38(9):1049-1054 (2006).
Lippinvott Co., Anti-Vascular Endothelial Growth Factor Therapy for Subfoveal choroidal Neovascularization Secondary to Age-Related Macular Degeneration: Phase II Study Results, Opthal., 110(5): 979-986 (2003).
Liszewski, K. et al., Cleavage of intracellular C3 into C3a and C3b by cathepsin L is required for human TH1 induction, Abstract #61, Immunobiology, 217, p. 1150 (2012).
Liu, D. et al., Suppression of Acute Lung Inflammation by Intracellular Peptide Delivery of a Nuclear Import Inhibitor, The American Society of Gene Therapy, 17(5):796-802 (2009).
Liu, X. Y. et al., Peptide-directed Suppression of a Pro-inflammatory Cytokine Response, The Journal of Biological Chemistry, 275(22):16774-16778 (2000).
Lopes, L. et al., Cell Permeant Peptide Analogues of the Small Heat Shock Protein, HSP20, Reduce TGF-β1-Induced CTGF Expression in Keloid Fibroblasts, Journal of Investigative Dermatology, 129:590-598 (2009).
Magnusson, KP, et al., CFH Y402H Confers Similar Risk of Soft Drusen and Both Forms of Advanced AMD, PLoS Med, 3:e5 (2006).
Makrides, S.C. et al., Therapeutic inhibition of the complement system, Pharmacological Reviews, 50(1):59-87, American Society for Pharmacology and Experimental Therapeutics, Bethesda, MD (1998).
Maller, J. et al., Common variation in three genes, including a noncoding variant in CFH, strongly influences risk of age-related macular degeneration, Nature Genetics, 38(9):1055-1059 (2006).
Mallik, B et al.,: Design and NMR characterization of active analogues of compstatin containing non-natural amino acids, Journal of Medicinal Chemistry, 48 (1):274-286 (2005).
McCusker, C. et al., Inhibition of Experimental Allergic Airways Disease by Local Application of a Cell-Penetrating Dominant-Negative STAT-6 Peptide, The Journal of Immunology, 179:2556-2564 (2007).
Michels, S. and Rosenfeld, P.J., Treatment of Neovascular Age-Related Macular Degeneration With Ranibizumab/Lucentis, Klin Monbl Augenheikd, 222(6): 480-484 (2005).
Midena, E., et al., Macular function impairment in eyes with early age-related macular degeneration, Invest. Ophthalmol. Vis. Sci., 38: 467-477 (1997).
Miller, C.G., The Cowpox Virus-Encoded Homolog of the Vaccinia Virus Complement Control Protein is an Inflammation Modulatory Protein, Virology,229(1):129-133 (1997).
Mishra, Ritu, Biological evaluation of novel peptidic vectors for transmembrane delivery of intracellularly targeted probes for molecular imaging, Dissertation, 103 pages (2009).
Morikis, D. et al., Improvement of the anti-C3 activity of compstatin using rational and combinatorial approaches, Biochemical Society Transactions, 32(1):28-32, Biochemical Society, London, UK (2004).
Morikis, D. et al., Solution structure of Compstatin, a potent complement inhibitor, Protein Science, 7(3):619-627 (1998).
Morikis, D. et al., The Structural Basis of Compstatin Activity Examined by Structure-Function-based Design of Peptide Analogs and NMR, J. Biol. Chem., 277(17):14942-14953 (2002).

(56) References Cited

OTHER PUBLICATIONS

Nektar Advanced Pegylation, 34 pages (2005-2006 Product Catalog, Nektar Therapeutics, San Carlos, CA).
Ng et al., Targeting Angiogenesis, the Underlying Disorder in Neovascular Age-Related Macular Degeneration, Canadian Journal of Ophthalmology, 40(3): 352-368 (2005).
Nielsen, M. et al., MHC Class II epitope predictive algorithms, Immunology, 130:319-328 (2010).
No Author Listed, Copper-free Click Chemistry from https://web.archive.org/III0110228014635/http://www.jenabioscience.com/1b94dca880/Newsletter_Copper-Free-ClickChem_Feb11.html, pp. 1-2, published online Feb. 28, 2011.
Novina, C.D. and Sharp, P.A., The RNAi Revolution, Nature, 430(6996):161-164 (2004).
Nozaki, M. et al., Drusen complement components C3a and C5a promote choroidal neovascularization, Proc. Natl. Acad. Sci. USA, 103:2328-2333 (2006).
Nwe, K. and Brechbiel, M. et al., Growing Applications of "Click Chemistry" for Bioconjugation in Contemporary Biomedical Research, Cancer Biotherapy and Radiopharmaceuticals, 24:289-302 (2009).
Pakula, A. and Sauer, R., Genetic analysis of protein stability and function, Annu Rev Genet, 23:289-310 (1989).
Peptide Modifications, Designer Bioscience, created on Jun. 25, 2009, accessed on Jun. 9, 2016, 2 pages.
Pio, R. et al., The Role of Complement in Tumor Growth, C. Koumenis et al. (eds.), Tumor Microenvironment and Cellular Stress, Advances, Experimental Medicine and Biology, 772, Chapter 11, 229-262 (2014).
Rakoczy, P.E. et al., Progressive Age-Related Changes Similar to Age-Related Macular Degeneration in a Transgenic Mouse Model, American Journal of Pathology,161(4):1515-1524 (2002).
Reid, K.B. and Day, A.J., Structure-Function Relationships of the Complement Components, Immunology Today, 10(6):177-180 (1989).
Ricklin, D. et al., Complement—a key system for immune surveillance and homeostasis, Nat. Immunol., 11(9):785-797 (2010).
Rosenfeld et al., URL: www.revophth.com/index.asp?page+1_857.htm> An Update on Bevacizumab (Dec. 1, 2005).
Rosengard, A.M. et al., Variola Virus Immune Evasion Design: Expression of a Highly Efficient Inhibitor of Human Complement, Proceedings of the National Academy of Science, 99(13):8803-8813 (2002).
Sahu, A, et al., Compstatin, a peptide inhibitor of complement, exhibits species-specific binding to complement component C3, Mol. Immunol., 39(10):557-66 (2003).
Sahu, A. et al., Interaction of Vaccinia Virus Complement Control Protein with Human Complement Proteins: Factor I-Mediated Degradation of C3b to iC3b1 Inactivates the Alternative Complement Pathway, Journal of Immunology, 160(11): 5596-5604 (1998).
Sahu, A., et al., Binding kinetics, structure-activity relationship, and biotransformation of the complement inhibitor compstatin, J. Immunol., 165(5):2491-9 (2000).
Sanders, W. et al., Prediction of Cell Penetrating Peptides by Support Vector Machines, PLoS Computational Biology, 7(7):e1002101, 12 pages (2011).
Scullica, L. and Benedetto, F., Diagnosis and classification of macular degenerations: an approach based on retinal function testings, Documenta Ophthalmologica, 102: 237-250 (2001).
Sepp, T. et al., Complement Factor H Variant Y402H is a Major Risk Determinant for Geographic Atrophy and Choroidal Neovascularization in Smokers and Nonsmokers, Invest. Ophthalmol. Vis. Sci., 47:536-540 (2006).
Sivaprasad, S. and Chong, NV. The complement system and age-related macular degeneration, Eye, 20: 867-872 (2006).
Smith, S.S. et al., Conserved Surface-Exposed K/R-X-K/R Motifs and Net Positive Charge on Provirus Complement Control Proteins Serve as Putative Heparin Binding Sites and Contribute to Inhibition of Molecular Interactions with Human Endothelial Cells: a Novel Mechanism for Evasion of Host Defense, Journal of Virology, 74(12):5659-5666 (2000).
Soulika, AM, et al., Studies of structure-activity relations of complement inhibitor compstatin, J. Immunol., 171(4):1881-90 (2003).
Soulika, et al., Compstatin Inhibits Complement Activation by Binding to the Beta-Chain of Complement Factor 3, Mol. Immunol., 43:2023-2029 (2006).
Subasinghe, N. et al., Design and synthesis of polyethylene glycol-modified biphenylsulfonyl-thiop-hene-carboxamidine inhibitors of the complement component C1s, Bioorganic & Medicinal Chemistry Letters, 22:5303-5307 (2012).
Sugita, T. et al., Comparative study on transduction and toxicity of protein transduction domains, British Journal of Pharmacology, 153:1143-1152 (2008).
Suhorutsenko, J. et al., Cell-Penetrating Peptides, PepFects, Show No Evidence of Toxicity and Immunogenicity in Vitro and in Vivo, Bioconjugate Chemistry, 22:2255-2262 (2011).
Supplemental Partial European Search Report for EP13854990, 6 pages (dated Jun. 6, 2016).
Tamai, K. et al., Lipid Hydroperoxide Stimulates Subretinal Choroidal Neovascularization in the Rabbit, Experimental Eye Research, 74(2):301-308 (2002).
Tezel, T.H. et al., Pathogenesis of Age-Related Macular Degeneration, Trends in Molecular Medicine, 10(9):417-420 (2004).
Torchilin, V.P. et al., p-Nitrophenylcarbonyl-PEG-PE-Liposomes: Fast and Simple Attachment of Specific Ligands, Including Monoclonal Antibodies, to Distal Ends of PEG Chains Via p-Nitrophenylcarbonyl Groups, Biochimica Biophysica Acta, 1511(2):497-522 (2001).
Tunnemann, G. et al,. Cargo-dependent mode of uptake and bioavailability of TAT-containing proteins and peptides in living cells, The FASEB Journal, 20:1775-1784 (2006).
Uvarova, E.A. and Shchelkunov, S.N., Species-specific Differences in the Structure of Orthopoxvirus Complement-Binding Protein, Virus Research, 81(1-2):39-45 (2001).
Wang, F. et al., AAV-Mediated Expression of Vascular Endothelial Growth Factor Induces Choroidal Neovascularization in Rat, Investigative Ophthalmology and Visual Science, 44(2):781-790 (2003).
Ward, B. et al., Design of a bioactive cell-penetrating, peptide: when a transduction domain does more than transduce, J. Pept. Sci., 15(10):668-674 (2009).
Wender, P. et al., The design, synthesis, and evaluation of molecules that enable or enhance cellular update: Peptoid molecular transporters, PNAS, 97(24):13003-13008 (2000).
Winter, G. et al., Making Antibody by Phage Display Technology, Annual Reviews in Immunology,12:433-455 (1994).
Written Opinion for PCT/US05/036547, 7 pages (dated Jun. 10, 2006).
Written Opinion for PCT/US2007/001649, 9 pages (dated Mar. 31, 2008).
Written Opinion for PCT/US2012/037648, (Cell-Reactive, Long-Acting, or Targeted Compstatin Analogs and Uses Thereof, filed May 11, 2012) issued by ISA, 7 pages (dated Sep. 20, 2012).
Written Opinion for PCT/US2013/070417, 6 pages (dated Jun. 5, 2014).
Written Opinion for PCT/US2013/070424, 6 pages (dated Jun. 5, 2014).
Written Opinion of PCT/US06/039397, 8 pages (dated Aug. 11, 2007).
Yannuzzi, L. et al., Retinal angiomatous proliferation in age-related macular degeneration, Retina, 21(5): 416-34 (2001).
Yates J.R.W. et al. Complement C3 variant and the risk of age-related macular degeneration, N. Engl. J. Med., 357(6):553-61 (2007).
Zacks, D.N. et al., Verteporfin Photodynamic Therapy in the Rat Model of Choroidal Neovascularization: Angiographic and Histologic Characterization, Investigative Ophthalmology and Visual Science, 43(7):2384-2391 (2002).
Zareparsi, S, et al., Strong association of the Y402H variant in complement factor H at 1q32 with susceptibility to age-related macular degeneration, Am. J. Hum. Genet., 77:149-153 (2005).
Zhang et al, Early complement activation and decreased levels of glycosylphosphatidylinositol-anchored complement inhibitors in human and experimental diabetic retinopathy, Diabetes, 51(12):3499-3504 (2002).

(56) References Cited

OTHER PUBLICATIONS

Zhang, L. et al., TEPITOPEpan: Extending TEPITOPE for Peptide Binding Prediction Covering over 700 HLA-DR Molecules, PLoS ONE, 7(2):e30483, 10 pages (2012).

Zhou et al., Complement Activation by Bisretinoid Constituents of RPE Lipofuscin, Invest. Ophthalmol. Vis. Sci., 50: 1392-1399 (2009).

Zhou, J, et al., Complement activation by photooxidation products of A2E, a lipofuscin constituent of the retinal pigment epithelium, Proc. Natl. Acad. Sci. USA, 103:16182-16187 (2006).

* cited by examiner

SEQUENCE LISTING

```
<160> NUMBER OF SEQ ID NOS: 139

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(12)
<223> OTHER INFORMATION: Disulfide bond

<400> SEQUENCE: 1

Ile Cys Val Val Gln Asp Trp Gly His His Arg Cys Thr
1               5                   10

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(19)
<223> OTHER INFORMATION: Any independently selected amino acid or amino
      acid analog
<220> FEATURE:
<221> NAME/KEY: misc_feature
<222> LOCATION: (1)..(19)
<223> OTHER INFORMATION: This region may encompass 2 to 19 residues,
      wherein some residues may be absent
<220> FEATURE:
<221> NAME/KEY: MOD_RES
<222> LOCATION: (22)..(22)
<223> OTHER INFORMATION: Trp or an analog of Trp
<220> FEATURE:
<221> NAME/KEY: MOD_RES
<222> LOCATION: (24)..(42)
<223> OTHER INFORMATION: Any independently selected amino acid or amino
      acid analog
<220> FEATURE:
<221> NAME/KEY: misc_feature
<222> LOCATION: (24)..(42)
<223> OTHER INFORMATION: This region may encompass 2 to 19 residues,
      wherein some residues may be absent
```

-continued

```
<400> SEQUENCE: 2

Xaa Xaa Xaa Xaa Xaa Xaa Xaa Xaa Xaa Xaa Xaa Xaa Xaa Xaa Xaa
1               5                   10                  15

Xaa Xaa Xaa Gln Asp Xaa Gly Xaa Xaa Xaa Xaa Xaa Xaa Xaa Xaa
            20                  25                  30

Xaa Xaa Xaa Xaa Xaa Xaa Xaa Xaa Xaa Xaa
            35                  40

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp, an analog of Trp, or other amino acid or
      amino acid analog comprising at least one aromatic ring
<220> FEATURE:
<221> NAME/KEY: MOD_RES
<222> LOCATION: (4)..(4)
<223> OTHER INFORMATION: Trp, an analog of Trp, or other amino acid or
      amino acid analog comprising at least one aromatic ring

<400> SEQUENCE: 3

Xaa Gln Asp Xaa Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp, an analog of Trp, or other amino acid or
      amino acid analog comprising at least one aromatic side chain
<220> FEATURE:
<221> NAME/KEY: MOD_RES
<222> LOCATION: (4)..(4)
<223> OTHER INFORMATION: Trp, an analog of Trp, or other amino acid or
      amino acid analog comprising at least one aromatic side chain
<220> FEATURE:
<221> NAME/KEY: MOD_RES
<222> LOCATION: (6)..(6)
<223> OTHER INFORMATION: His, Ala, analog of Ala, Phe, Trp or analog of
      Trp

<400> SEQUENCE: 4

Xaa Gln Asp Xaa Gly Xaa
1               5

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any independently selected amino acid or amino
      acid analog
```

```
<220> FEATURE:
<221> NAME/KEY: MOD_RES
<222> LOCATION: (4)..(4)
<223> OTHER INFORMATION: Trp or analog of Trp
<220> FEATURE:
<221> NAME/KEY: MOD_RES
<222> LOCATION: (7)..(7)
<223> OTHER INFORMATION: Trp or analog of Trp
<220> FEATURE:
<221> NAME/KEY: MOD_RES
<222> LOCATION: (9)..(13)
<223> OTHER INFORMATION: Any independently selected amino acid or amino
      acid analog

<400> SEQUENCE: 5

Xaa Xaa Xaa Xaa Gln Asp Xaa Gly Xaa Xaa Xaa Xaa Xaa
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
<221> NAME/KEY: misc_feature
<222> LOCATION: (1)..(2)
<223> OTHER INFORMATION: This region may encompass 1 to 2 residues,
      wherein some positions may be absent
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Independently selected from Trp or analogs of
      Trp
<220> FEATURE:
<221> NAME/KEY: MOD_RES
<222> LOCATION: (8)..(8)
<223> OTHER INFORMATION: Independently selected from Trp or analogs of
      Trp
<220> FEATURE:
<221> NAME/KEY: MOD_RES
<222> LOCATION: (10)..(10)
<223> OTHER INFORMATION: His, Ala or an analog of Ala, Phe, Trp or an
      analog of Trp
<220> FEATURE:
<221> NAME/KEY: MOD_RES
<222> LOCATION: (14)..(16)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a C-term -OH of any of the L-Thr, D-Thr, Ile,
      Val, Gly, Ala or Asn is optionally replaced by a second blocking
      moiety
<220> FEATURE:
<221> NAME/KEY: misc_feature
<222> LOCATION: (14)..(16)
<223> OTHER INFORMATION: This region may encompass 1 to 3 residues,
      wherein some positions may be absent

<400> SEQUENCE: 6

Xaa Xaa Cys Val Xaa Gln Asp Xaa Gly Xaa His Arg Cys Xaa Xaa Xaa
1               5                   10                  15

<210> SEQ ID NO 7
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ile, Val, Leu, Ac-Ile, Ac-Val, Ac-Leu or a
      dipeptide comprising Gly-Ile or Ac-Gly-Ile
<220> FEATURE:
<221> NAME/KEY: misc_feature
<222> LOCATION: (1)..(2)
<223> OTHER INFORMATION: This region may encompass 1 to 2 residues,
      wherein some positions may be absent
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Independently selected from Trp or analogs of
      Trp
<220> FEATURE:
<221> NAME/KEY: MOD_RES
<222> LOCATION: (8)..(8)
<223> OTHER INFORMATION: Independently selected from Trp or analogs of
      Trp
<220> FEATURE:
<221> NAME/KEY: MOD_RES
<222> LOCATION: (10)..(10)
<223> OTHER INFORMATION: His, Ala or an analog of Ala, Phe, Trp or an
      analog of Trp
<220> FEATURE:
<221> NAME/KEY: MOD_RES
<222> LOCATION: (14)..(16)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a C-term -OH of any of L-Thr, D-Thr, Ile,
      Val, Gly, Ala, or Asn is optionally replaced by -NH2
<220> FEATURE:
<221> NAME/KEY: misc_feature
<222> LOCATION: (14)..(16)
<223> OTHER INFORMATION: This region may encompass 1 to 3 residues,
      wherein some positions may be absent

<400> SEQUENCE: 7

Xaa Xaa Cys Val Xaa Gln Asp Xaa Gly Xaa His Arg Cys Xaa Xaa Xaa
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term CONH2

<400> SEQUENCE: 8

Ile Cys Val Val Gln Asp Trp Gly His His Arg Cys Thr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term Ac
<220> FEATURE:
<223> OTHER INFORMATION: C-term CONH2

<400> SEQUENCE: 9

Ile Cys Val Val Gln Asp Trp Gly His His Arg Cys Thr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 10

Ile Cys Val Tyr Gln Asp Trp Gly Ala His Arg Cys Thr
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term COOH

<400> SEQUENCE: 11

Ile Cys Val Trp Gln Asp Trp Gly Ala His Arg Cys Thr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 12

Ile Cys Val Trp Gln Asp Trp Gly Ala His Arg Cys Thr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (13)..(13)
<223> OTHER INFORMATION: D-Thr
<220> FEATURE:
<223> OTHER INFORMATION: C-term COOH
```

```
<400> SEQUENCE: 13

Ile Cys Val Trp Gln Asp Trp Gly Ala His Arg Cys Thr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Nal
<220> FEATURE:
<223> OTHER INFORMATION: C-term CONH2

<400> SEQUENCE: 14

Ile Cys Val Ala Gln Asp Trp Gly Ala His Arg Cys Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Nal
<220> FEATURE:
<223> OTHER INFORMATION: C-term COOH

<400> SEQUENCE: 15

Ile Cys Val Ala Gln Asp Trp Gly Ala His Arg Cys Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-Nal
<220> FEATURE:
<223> OTHER INFORMATION: C-term COOH

<400> SEQUENCE: 16

Ile Cys Val Ala Gln Asp Trp Gly Ala His Arg Cys Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Igl
<220> FEATURE:
<223> OTHER INFORMATION: C-term CONH2

<400> SEQUENCE: 17

Ile Cys Val Gly Gln Asp Trp Gly Ala His Arg Cys Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Igl
<220> FEATURE:
<223> OTHER INFORMATION: C-term COOH

<400> SEQUENCE: 18

Ile Cys Val Gly Gln Asp Trp Gly Ala His Arg Cys Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Dht
<220> FEATURE:
<223> OTHER INFORMATION: C-term COOH

<400> SEQUENCE: 19

Ile Cys Val Trp Gln Asp Trp Gly Ala His Arg Cys Thr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bpa
<220> FEATURE:
<223> OTHER INFORMATION: C-term COOH

<400> SEQUENCE: 20

Ile Cys Val Phe Gln Asp Trp Gly Ala His Arg Cys Thr
```

```
<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bpa
<220> FEATURE:
<223> OTHER INFORMATION: C-term CONH2

<400> SEQUENCE: 21

Ile Cys Val Phe Gln Asp Trp Gly Ala His Arg Cys Thr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bta
<220> FEATURE:
<223> OTHER INFORMATION: C-term COOH

<400> SEQUENCE: 22

Ile Cys Val Xaa Gln Asp Trp Gly Ala His Arg Cys Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bta
<220> FEATURE:
<223> OTHER INFORMATION: C-term CONH2

<400> SEQUENCE: 23

Ile Cys Val Xaa Gln Asp Trp Gly Ala His Arg Cys Thr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (9)..(9)
<223> OTHER INFORMATION: 2-Abu
<220> FEATURE:
<223> OTHER INFORMATION: C-term CONH2

<400> SEQUENCE: 24

Ile Cys Val Trp Gln Asp Trp Gly Xaa His Arg Cys Thr
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term COOH

<400> SEQUENCE: 25

Gly Ile Cys Val Trp Gln Asp Trp Gly Ala His Arg Cys Thr Ala Asn
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5f-Trp
<220> FEATURE:
<223> OTHER INFORMATION: C-term CONH2

<400> SEQUENCE: 26

Ile Cys Val Trp Gln Asp Trp Gly Ala His Arg Cys Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5-methyl-Trp
<220> FEATURE:
<223> OTHER INFORMATION: C-term CONH2

<400> SEQUENCE: 27

Ile Cys Val Trp Gln Asp Trp Gly Ala His Arg Cys Thr
1               5                   10

<210> SEQ ID NO 28
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methyl-Trp
<220> FEATURE:
<223> OTHER INFORMATION: C-term CONH2

<400> SEQUENCE: 28

Ile Cys Val Trp Gln Asp Trp Gly Ala His Arg Cys Thr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 29

Ile Cys Val Trp Gln Asp Trp Gly Ala His Arg Cys Thr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5f-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 30

Ile Cys Val Trp Gln Asp Trp Gly Ala His Arg Cys Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5-methyl-Trp
<220> FEATURE:
```

```
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 31

Ile Cys Val Trp Gln Asp Trp Gly Ala His Arg Cys Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methyl-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 32

Ile Cys Val Trp Gln Asp Trp Gly Ala His Arg Cys Thr
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: 6f-Trp
<220> FEATURE:
<221> NAME/KEY: MOD_RES
<222> LOCATION: (8)..(8)
<223> OTHER INFORMATION: 6f-Trp
<220> FEATURE:
<223> OTHER INFORMATION: C-term COOH

<400> SEQUENCE: 33

Gly Ile Cys Val Trp Gln Asp Trp Gly Ala His Arg Cys Thr Asn
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-formyl-Trp
<220> FEATURE:
<223> OTHER INFORMATION: C-term CONH2
```

```
<400> SEQUENCE: 34

Ile Cys Val Trp Gln Asp Trp Gly Ala His Arg Cys Thr
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methoxy-Trp
<220> FEATURE:
<223> OTHER INFORMATION: C-term CONH2

<400> SEQUENCE: 35

Ile Cys Val Trp Gln Asp Trp Gly Ala His Arg Cys Thr
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: 5f-Trp
<220> FEATURE:
<221> NAME/KEY: MOD_RES
<222> LOCATION: (8)..(8)
<223> OTHER INFORMATION: 5f-Trp
<220> FEATURE:
<223> OTHER INFORMATION: C-term COOH

<400> SEQUENCE: 36

Gly Ile Cys Val Trp Gln Asp Trp Gly Ala His Arg Cys Thr Asn
1               5                   10                  15

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp

<400> SEQUENCE: 37

Ile Cys Val Trp Gln Asp Trp Gly Ala His Arg Cys Thr
1               5                   10

<210> SEQ ID NO 38
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)5-C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 38

Ile Cys Val Trp Gln Asp Trp Gly Ala His Arg Cys Thr
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term (C=O)-(CH2)5-maleimide

<400> SEQUENCE: 39

Ile Cys Val Trp Gln Asp Trp Gly Ala His Arg Cys Thr
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)2-C(=O)-NH-
      CH2CH2OCH2CH2OCH2CH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 40

Ile Cys Val Trp Gln Asp Trp Gly Ala His Arg Cys Thr
1               5                   10

<210> SEQ ID NO 41
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)2-C(=O)-NH-
      CH2CH2OCH2CH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 41

Ile Cys Val Trp Gln Asp Trp Gly Ala His Arg Cys Thr
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)3-C(=O)-NH-
      CH2CH2OCH2CH2OCH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 42

Ile Cys Val Trp Gln Asp Trp Gly Ala His Arg Cys Thr
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)5-C(=O)-NH-
      CH2CH2OCH2CH2OCH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 43

Ile Cys Val Trp Gln Asp Trp Gly Ala His Arg Cys Thr
1               5                   10
```

```
<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)4-C(=O)-NH-
      CH2CH2OCH2CH2OCH2CH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 44

Ile Cys Val Trp Gln Asp Trp Gly Ala His Arg Cys Thr
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)2-C(=O)-NH-
      CH2CH2OCH2CH2OCH2CH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 45

Ile Cys Val Trp Gln Asp Trp Gly Ala His Arg Cys Thr
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)5-C(=O)-NH-
      CH2CH2OCH2CH2OCH2C(=O)
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 46

Ile Cys Val Trp Gln Asp Trp Gly Ala His Arg Cys Thr
1               5                   10
```

```
<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 47

Ile Cys Val Trp Gln Asp Trp Gly Ala His Arg Cys Thr Lys
1               5                   10

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 48

Ile Cys Val Trp Gln Asp Trp Gly Ala His Arg Cys Thr Gly Gly Gly
1               5                   10                  15

Gly Gly Lys

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2(CH2)5C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 49

Ile Cys Val Trp Gln Asp Trp Gly Ala His Arg Cys Thr
1               5                   10

<210> SEQ ID NO 50
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2(CH2CH2O)2CH2C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 50

Ile Cys Val Trp Gln Asp Trp Gly Ala His Arg Cys Thr
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys
<220> FEATURE:
<223> OTHER INFORMATION: C-term NH2

<400> SEQUENCE: 51

Ile Cys Val Trp Gln Asp Trp Gly Ala His Arg Cys Thr Lys
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-(C(=O)-(CH2)5-Mal)
<220> FEATURE:
<223> OTHER INFORMATION: C-term NH2

<400> SEQUENCE: 52

Ile Cys Val Trp Gln Asp Trp Gly Ala His Arg Cys Thr Lys
1               5                   10
```

```
<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (19)..(19)
<223> OTHER INFORMATION: Lys-(C(=O)-(CH2)5-Mal)
<220> FEATURE:
<223> OTHER INFORMATION: C-term NH2

<400> SEQUENCE: 53

Ile Cys Val Trp Gln Asp Trp Gly Ala His Arg Cys Thr Gly Gly
1               5                   10                  15

Gly Gly Lys

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Mal-(CH2)5-(C(=O)-NH(CH2)5C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 54

Ile Cys Val Trp Gln Asp Trp Gly Ala His Arg Cys Thr
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Mal-(CH2)5-(C(=O)NH(CH2CH2O)2CH2C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 55

Ile Cys Val Trp Gln Asp Trp Gly Ala His Arg Cys Thr
1               5                   10

<210> SEQ ID NO 56
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-
      (CH2)5-Mal)
<220> FEATURE:
<223> OTHER INFORMATION: C-term NH2

<400> SEQUENCE: 56

Ile Cys Val Trp Gln Asp Trp Gly Ala His Arg Cys Thr Lys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-C(=O)-CH2(OCH2CH2)2NH(C(=O)-(CH2)5-Mal)
<220> FEATURE:
<223> OTHER INFORMATION: C-term NH2

<400> SEQUENCE: 57

Ile Cys Val Trp Gln Asp Trp Gly Ala His Arg Cys Thr Lys
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term (CH2CH2O)nC(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 58

Ile Cys Val Trp Gln Asp Trp Gly Ala His Arg Cys Thr
```

-continued

```
<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-C(=O)-(CH2CH2O)n
<220> FEATURE:
<223> OTHER INFORMATION: C-term NH2

<400> SEQUENCE: 59

Ile Cys Val Trp Gln Asp Trp Gly Ala His Arg Cys Thr Lys
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-C(=O)-(CH2CH2O)n
<220> FEATURE:
<223> OTHER INFORMATION: C-term NH2

<400> SEQUENCE: 60

Ile Cys Val Trp Gln Asp Trp Gly Ala His Arg Cys Thr Lys
1               5                   10

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
```

```
<223> OTHER INFORMATION: (1Me)Trp
<220> FEATURE:
<221> NAME/KEY: MOD_RES
<222> LOCATION: (19)..(19)
<223> OTHER INFORMATION: Lys-C(=O)-(CH2CH2O)n
<220> FEATURE:
<223> OTHER INFORMATION: C-term NH2

<400> SEQUENCE: 61

Ile Cys Val Trp Gln Asp Trp Gly Ala His Arg Cys Thr Gly Gly
1               5                   10                  15

Gly Gly Lys

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: (CH2CH2O)nC(=O)Lys
<220> FEATURE:
<221> NAME/KEY: misc_feature
<222> LOCATION: (8)..(18)
<223> OTHER INFORMATION: Disulfide bond
<220> FEATURE:
<221> NAME/KEY: MOD_RES
<222> LOCATION: (10)..(10)
<223> OTHER INFORMATION: (1Me)Trp
<220> FEATURE:
<223> OTHER INFORMATION: C-term NH2

<400> SEQUENCE: 62

Lys Gly Gly Gly Gly Gly Ile Cys Val Trp Gln Asp Trp Gly Ala His
1               5                   10                  15

Arg Cys Thr

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: (CH2CH2O)nC(=O)Lys
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: (1Me)Trp
<220> FEATURE:
<223> OTHER INFORMATION: C-term NH2

<400> SEQUENCE: 63

Lys Ile Cys Val Trp Gln Asp Trp Gly Ala His Arg Cys Thr
1               5                   10

<210> SEQ ID NO 64
```

-continued

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-
      (CH2CH2O)n-R)
<220> FEATURE:
<223> OTHER INFORMATION: C-term NH2

<400> SEQUENCE: 64

Ile Cys Val Trp Gln Asp Trp Gly Ala His Arg Cys Thr Lys
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-
      (CH2CH2O)n-R)
<220> FEATURE:
<223> OTHER INFORMATION: C-term NH2

<400> SEQUENCE: 65

Ile Cys Val Trp Gln Asp Trp Gly Ala His Arg Cys Thr Lys
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
```

```
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-
      C(=O)-(CH2CH2O)n-R)
<220> FEATURE:
<223> OTHER INFORMATION: C-term NH2

<400> SEQUENCE: 66

Ile Cys Val Trp Gln Asp Trp Gly Ala His Arg Cys Thr Lys
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-
      C(=O)-(CH2)j(CH2CH2O)n-R)
<220> FEATURE:
<223> OTHER INFORMATION: C-term NH2

<400> SEQUENCE: 67

Ile Cys Val Trp Gln Asp Trp Gly Ala His Arg Cys Thr Lys
1               5                   10

<210> SEQ ID NO 68
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(3)
<223> OTHER INFORMATION: D-Arg
<220> FEATURE:
<221> NAME/KEY: MOD_RES
<222> LOCATION: (4)..(4)
<223> OTHER INFORMATION: D-Gln
<220> FEATURE:
<221> NAME/KEY: MOD_RES
<222> LOCATION: (5)..(6)
<223> OTHER INFORMATION: D-Arg
<220> FEATURE:
<221> NAME/KEY: MOD_RES
<222> LOCATION: (7)..(8)
<223> OTHER INFORMATION: D-Lys
<220> FEATURE:
<221> NAME/KEY: MOD_RES
<222> LOCATION: (9)..(9)
<223> OTHER INFORMATION: D-Arg
<220> FEATURE:
<221> NAME/KEY: misc_feature
<222> LOCATION: (9)..(10)
<223> OTHER INFORMATION: Residues at these positions are linked by an
      AEEAc moiety
<220> FEATURE:
```

```
<221> NAME/KEY: MOD_RES
<222> LOCATION: (13)..(13)
<223> OTHER INFORMATION: (1Me)Trp
<220> FEATURE:
<223> OTHER INFORMATION: C-term NH2

<400> SEQUENCE: 68

Arg Arg Arg Gln Arg Arg Lys Lys Arg Ile Cys Val Trp Gln Asp Trp
1               5                   10                  15

Gly Ala His Arg Cys Thr
            20

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (12)..(13)
<223> OTHER INFORMATION: Residues at these positions are linked by an
      AEEAc moiety
<220> FEATURE:
<221> NAME/KEY: misc_feature
<222> LOCATION: (14)..(24)
<223> OTHER INFORMATION: Disulfide bond
<220> FEATURE:
<221> NAME/KEY: MOD_RES
<222> LOCATION: (16)..(16)
<223> OTHER INFORMATION: (1Me)Trp
<220> FEATURE:
<223> OTHER INFORMATION: C-term NH2

<400> SEQUENCE: 69

Tyr Ala Arg Ala Ala Ala Arg Gln Ala Arg Ala Gly Ile Cys Val Trp
1               5                   10                  15

Gln Asp Trp Gly Ala His Arg Cys Thr
            20                  25

<210> SEQ ID NO 70
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (16)..(17)
<223> OTHER INFORMATION: Residues at these positions are linked by an
      AEEAc moiety
<220> FEATURE:
<221> NAME/KEY: misc_feature
<222> LOCATION: (18)..(28)
<223> OTHER INFORMATION: Disulfide bond
<220> FEATURE:
<221> NAME/KEY: MOD_RES
<222> LOCATION: (20)..(20)
<223> OTHER INFORMATION: (1Me)Trp
<220> FEATURE:
<223> OTHER INFORMATION: C-term NH2

<400> SEQUENCE: 70

Ala Ala Val Ala Leu Leu Pro Ala Val Leu Leu Ala Leu Leu Ala Pro
1               5                   10                  15
```

Ile Cys Val Trp Gln Asp Trp Gly Ala His Arg Cys Thr
            20                  25

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 71

His His His His His His
1               5

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(4)
<223> OTHER INFORMATION: Any independently selected amino acid or amino
      acid analog
<220> FEATURE:
<221> NAME/KEY: MOD_RES
<222> LOCATION: (5)..(5)
<223> OTHER INFORMATION: Trp or analog of Trp
<220> FEATURE:
<221> NAME/KEY: MOD_RES
<222> LOCATION: (8)..(8)
<223> OTHER INFORMATION: Trp or analog of Trp
<220> FEATURE:
<221> NAME/KEY: MOD_RES
<222> LOCATION: (10)..(14)
<223> OTHER INFORMATION: Any independently selected amino acid or amino
      acid analog
<220> FEATURE:
<221> NAME/KEY: MOD_RES
<222> LOCATION: (15)..(15)
<223> OTHER INFORMATION: Any amino acid

<400> SEQUENCE: 72

Xaa Xaa Xaa Xaa Xaa Gln Asp Xaa Gly Xaa Xaa Xaa Xaa Xaa Xaa
1               5                   10                  15

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(3)
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
<221> NAME/KEY: misc_feature
<222> LOCATION: (2)..(3)
<223> OTHER INFORMATION: This region may encompass 1 to 2 residues,

```
      wherein some positions may be absent
<220> FEATURE:
<221> NAME/KEY: misc_feature
<222> LOCATION: (4)..(14)
<223> OTHER INFORMATION: Disulfide bond
<220> FEATURE:
<221> NAME/KEY: MOD_RES
<222> LOCATION: (6)..(6)
<223> OTHER INFORMATION: Independently selected from Trp or analogs of
      Trp
<220> FEATURE:
<221> NAME/KEY: MOD_RES
<222> LOCATION: (9)..(9)
<223> OTHER INFORMATION: Independently selected from Trp or analogs of
      Trp
<220> FEATURE:
<221> NAME/KEY: MOD_RES
<222> LOCATION: (11)..(11)
<223> OTHER INFORMATION: His, Ala or an analog of Ala, Phe, Trp or an
      analog of Trp
<220> FEATURE:
<221> NAME/KEY: MOD_RES
<222> LOCATION: (15)..(17)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a C-term -OH of any of the L-Thr, D-Thr, Ile,
      Val, Gly, Ala or Asn is optionally replaced by a second blocking
      moiety
<220> FEATURE:
<221> NAME/KEY: misc_feature
<222> LOCATION: (15)..(17)
<223> OTHER INFORMATION: This region may encompass 1 to 3 residues,
      wherein some positions may be absent
<220> FEATURE:
<221> NAME/KEY: MOD_RES
<222> LOCATION: (18)..(18)
<223> OTHER INFORMATION: Any amino acid

<400> SEQUENCE: 73

Xaa Xaa Xaa Cys Val Xaa Gln Asp Xaa Gly Xaa His Arg Cys Xaa Xaa
1               5                   10                  15

Xaa Xaa

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Ile or Gly
<220> FEATURE:
<221> NAME/KEY: MOD_RES
<222> LOCATION: (3)..(3)
<223> OTHER INFORMATION: Ile or Cys
<220> FEATURE:
<221> NAME/KEY: MOD_RES
<222> LOCATION: (4)..(4)
<223> OTHER INFORMATION: Val or Cys
<220> FEATURE:
<221> NAME/KEY: MOD_RES
<222> LOCATION: (5)..(5)
<223> OTHER INFORMATION: Val, Tyr, Trp, 2-Nal, 1-Nal, 2-Igl, Dht, Bpa,
      Bta, 5f-Trp, 5-methyl-Trp, 1-methyl-Trp, 1-formyl-Trp or
      1-methyoxy-Trp
<220> FEATURE:
<221> NAME/KEY: MOD_RES
<222> LOCATION: (6)..(6)
<223> OTHER INFORMATION: Gln, Trp, 6f-Trp or 5f-Trp
```

```
<220> FEATURE:
<221> NAME/KEY: MOD_RES
<222> LOCATION: (7)..(7)
<223> OTHER INFORMATION: Asp or Gln
<220> FEATURE:
<221> NAME/KEY: MOD_RES
<222> LOCATION: (8)..(8)
<223> OTHER INFORMATION: Trp, Asp or 5f-Trp
<220> FEATURE:
<221> NAME/KEY: MOD_RES
<222> LOCATION: (9)..(9)
<223> OTHER INFORMATION: Gly, Trp, 6f-Trp or 5f-Trp
<220> FEATURE:
<221> NAME/KEY: MOD_RES
<222> LOCATION: (10)..(10)
<223> OTHER INFORMATION: His, Ala, 2-Abu or Gly
<220> FEATURE:
<221> NAME/KEY: MOD_RES
<222> LOCATION: (11)..(11)
<223> OTHER INFORMATION: His or Ala
<220> FEATURE:
<221> NAME/KEY: MOD_RES
<222> LOCATION: (12)..(12)
<223> OTHER INFORMATION: Arg or His
<220> FEATURE:
<221> NAME/KEY: MOD_RES
<222> LOCATION: (13)..(13)
<223> OTHER INFORMATION: Cys or Arg
<220> FEATURE:
<221> NAME/KEY: MOD_RES
<222> LOCATION: (14)..(14)
<223> OTHER INFORMATION: Thr, D-Thr or Cys
<220> FEATURE:
<221> NAME/KEY: MOD_RES
<222> LOCATION: (15)..(15)
<223> OTHER INFORMATION: Any amino acid

<400> SEQUENCE: 74

Xaa Xaa Xaa Xaa Xaa Xaa Xaa Xaa Xaa Xaa Xaa Xaa Xaa Xaa Xaa
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Trp(Me)
<220> FEATURE:
<221> NAME/KEY: MOD_RES
<222> LOCATION: (9)..(9)
<223> OTHER INFORMATION: mGly
<220> FEATURE:
<221> NAME/KEY: MOD_RES
<222> LOCATION: (14)..(14)
<223> OTHER INFORMATION: mIle
<220> FEATURE:
<221> NAME/KEY: MOD_RES
<222> LOCATION: (15)..(15)
<223> OTHER INFORMATION: Any amino acid

<400> SEQUENCE: 75

Xaa Ile Cys Val Trp Gln Asp Trp Gly Ala His Arg Cys Ile Xaa
1               5                   10                  15
```

```
<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Trp(Me)
<220> FEATURE:
<221> NAME/KEY: MOD_RES
<222> LOCATION: (9)..(9)
<223> OTHER INFORMATION: mGly
<220> FEATURE:
<221> NAME/KEY: MOD_RES
<222> LOCATION: (14)..(14)
<223> OTHER INFORMATION: mIle
<220> FEATURE:
<221> NAME/KEY: MOD_RES
<222> LOCATION: (15)..(15)
<223> OTHER INFORMATION: Any amino acid

<400> SEQUENCE: 76

Xaa Ile Cys Val Trp Gln Asp Trp Gly Ala His Arg Cys Ile Xaa
1               5                   10                  15

<210> SEQ ID NO 77
<211> LENGTH: 13
<212> TYPE: PRT
<213> ORGANISM: Human immunodeficiency virus

<400> SEQUENCE: 77

Gly Arg Lys Lys Arg Arg Gln Arg Arg Arg Pro Pro Gln
1               5                   10

<210> SEQ ID NO 78
<211> LENGTH: 17
<212> TYPE: PRT
<213> ORGANISM: Human immunodeficiency virus

<400> SEQUENCE: 78

Gly Ile Ser Tyr Gly Arg Lys Lys Arg Arg Gln Arg Arg Pro Pro
1               5                   10                  15

Gln

<210> SEQ ID NO 79
<211> LENGTH: 23
<212> TYPE: PRT
<213> ORGANISM: Human immunodeficiency virus

<400> SEQUENCE: 79

Phe Ile Thr Lys Ala Leu Gly Ile Ser Tyr Gly Arg Lys Lys Arg Arg
1               5                   10                  15

Gln Arg Arg Arg Pro Pro Gln
            20

<210> SEQ ID NO 80
```

-continued

```
<211> LENGTH: 10
<212> TYPE: PRT
<213> ORGANISM: Human immunodeficiency virus

<400> SEQUENCE: 80

Gly Arg Lys Lys Arg Arg Gln Arg Arg Arg
1               5                   10

<210> SEQ ID NO 81
<211> LENGTH: 9
<212> TYPE: PRT
<213> ORGANISM: Human immunodeficiency virus

<400> SEQUENCE: 81

Arg Lys Lys Arg Arg Gln Arg Arg Arg
1               5

<210> SEQ ID NO 82
<211> LENGTH: 8
<212> TYPE: PRT
<213> ORGANISM: Human immunodeficiency virus

<400> SEQUENCE: 82

Arg Lys Lys Arg Arg Gln Arg Arg
1               5

<210> SEQ ID NO 83
<211> LENGTH: 9
<212> TYPE: PRT
<213> ORGANISM: Human immunodeficiency virus
<220> FEATURE:
<221> NAME/KEY: MOD_RES
<222> LOCATION: (1)..(9)
<223> OTHER INFORMATION: D-amino acid

<400> SEQUENCE: 83

Arg Lys Lys Arg Arg Gln Arg Arg Arg
1               5

<210> SEQ ID NO 84
<211> LENGTH: 9
<212> TYPE: PRT
<213> ORGANISM: Human immunodeficiency virus

<400> SEQUENCE: 84

Arg Arg Arg Gln Arg Arg Lys Lys Arg
1               5

<210> SEQ ID NO 85
<211> LENGTH: 9
<212> TYPE: PRT
<213> ORGANISM: Human immunodeficiency virus
<220> FEATURE:
<221> NAME/KEY: MOD_RES
<222> LOCATION: (1)..(9)
<223> OTHER INFORMATION: D-amino acid

<400> SEQUENCE: 85

Arg Arg Arg Gln Arg Arg Lys Lys Arg
1               5

<210> SEQ ID NO 86
<211> LENGTH: 9
<212> TYPE: PRT
<213> ORGANISM: Human immunodeficiency virus

<400> SEQUENCE: 86
```

```
Arg Lys Lys Arg Arg Ala Arg Arg Arg
1               5

<210> SEQ ID NO 87
<211> LENGTH: 11
<212> TYPE: PRT
<213> ORGANISM: Human immunodeficiency virus

<400> SEQUENCE: 87

Gly Arg Lys Lys Arg Arg Gln Arg Arg Cys
1               5                   10

<210> SEQ ID NO 88
<211> LENGTH: 17
<212> TYPE: PRT
<213> ORGANISM: Human immunodeficiency virus

<400> SEQUENCE: 88

Thr Arg Gln Ala Arg Arg Asn Arg Arg Arg Arg Trp Arg Glu Arg Gln
1               5                   10                  15

Arg

<210> SEQ ID NO 89
<211> LENGTH: 30
<212> TYPE: PRT
<213> ORGANISM: Unknown
<220> FEATURE:
<223> OTHER INFORMATION: Description of Unknown:
      galanin polypeptide

<400> SEQUENCE: 89

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
            20                  25                  30

<210> SEQ ID NO 90
<211> LENGTH: 14
<212> TYPE: PRT
<213> ORGANISM: Unknown
<220> FEATURE:
<223> OTHER INFORMATION: Description of Unknown:
      MP Wasp venom peptide Mastoparan

<400> SEQUENCE: 90

Ile Asn Leu Lys Ala Leu Ala Ala Leu Ala Lys Lys Ile Leu
1               5                   10

<210> SEQ ID NO 91
<211> LENGTH: 16
<212> TYPE: PRT
<213> ORGANISM: Drosophila sp.

<400> SEQUENCE: 91

Arg Gln Ile Lys Ile Trp Phe Gln Asn Arg Arg Met Lys Trp Lys Lys
1               5                   10                  15

<210> SEQ ID NO 92
<211> LENGTH: 16
<212> TYPE: PRT
<213> ORGANISM: Drosophila sp.

<400> SEQUENCE: 92

Arg Gln Ile Lys Ile Trp Phe Gln Asn Arg Arg Met Lys Trp Lys Lys
```

<210> SEQ ID NO 93
<211> LENGTH: 16
<212> TYPE: PRT
<213> ORGANISM: Drosophila sp.

<400> SEQUENCE: 93

Lys Lys Trp Lys Met Arg Arg Asn Gln Phe Trp Ile Lys Ile Gln Arg
1               5                   10                  15

<210> SEQ ID NO 94
<211> LENGTH: 16
<212> TYPE: PRT
<213> ORGANISM: Drosophila sp.
<220> FEATURE:
<221> NAME/KEY: MOD_RES
<222> LOCATION: (1)..(16)
<223> OTHER INFORMATION: D-amino acid

<400> SEQUENCE: 94

Arg Gln Ile Lys Ile Trp Phe Gln Asn Arg Arg Met Lys Trp Lys Lys
1               5                   10                  15

<210> SEQ ID NO 95
<211> LENGTH: 16
<212> TYPE: PRT
<213> ORGANISM: Drosophila sp.

<400> SEQUENCE: 95

Arg Gln Ile Lys Ile Trp Phe Pro Asn Arg Arg Met Lys Trp Lys Lys
1               5                   10                  15

<210> SEQ ID NO 96
<211> LENGTH: 16
<212> TYPE: PRT
<213> ORGANISM: Drosophila sp.

<400> SEQUENCE: 96

Arg Gln Pro Lys Ile Trp Phe Pro Asn Arg Arg Lys Pro Trp Lys Lys
1               5                   10                  15

<210> SEQ ID NO 97
<211> LENGTH: 16
<212> TYPE: PRT
<213> ORGANISM: Drosophila sp.

<400> SEQUENCE: 97

Arg Gln Ile Lys Ile Trp Phe Gln Asn Arg Arg Met Lys Trp Lys Lys
1               5                   10                  15

<210> SEQ ID NO 98
<211> LENGTH: 15
<212> TYPE: PRT
<213> ORGANISM: Drosophila sp.

<400> SEQUENCE: 98

Arg Gln Ile Lys Ile Trp Phe Gln Asn Arg Arg Met Lys Trp Lys
1               5                   10                  15

<210> SEQ ID NO 99
<211> LENGTH: 14
<212> TYPE: PRT
<213> ORGANISM: Drosophila sp.

<400> SEQUENCE: 99

```
Arg Gln Ile Lys Ile Trp Phe Gln Asn Arg Arg Met Lys Trp
1               5                   10
```

<210> SEQ ID NO 100
<211> LENGTH: 14
<212> TYPE: PRT
<213> ORGANISM: Drosophila sp.

<400> SEQUENCE: 100

```
Ile Lys Ile Trp Phe Gln Asn Arg Arg Met Lys Trp Lys Lys
1               5                   10
```

<210> SEQ ID NO 101
<211> LENGTH: 16
<212> TYPE: PRT
<213> ORGANISM: Drosophila sp.

<400> SEQUENCE: 101

```
Arg Gln Ile Lys Ile Trp Phe Pro Asn Arg Arg Met Lys Trp Lys Lys
1               5                   10                  15
```

<210> SEQ ID NO 102
<211> LENGTH: 10
<212> TYPE: PRT
<213> ORGANISM: Unknown
<220> FEATURE:
<223> OTHER INFORMATION: Description of Unknown:
      PTD4 peptide

<400> SEQUENCE: 102

```
Arg Ala Ala Ala Arg Gln Ala Arg Ala Gly
1               5                   10
```

<210> SEQ ID NO 103
<211> LENGTH: 12
<212> TYPE: PRT
<213> ORGANISM: Unknown
<220> FEATURE:
<223> OTHER INFORMATION: Description of Unknown:
      PTD4 peptide

<400> SEQUENCE: 103

```
Tyr Ala Arg Ala Ala Ala Arg Gln Ala Arg Ala Gly
1               5                   10
```

<210> SEQ ID NO 104
<211> LENGTH: 13
<212> TYPE: PRT
<213> ORGANISM: Crotalus sp.

<400> SEQUENCE: 104

```
Lys Met Asp Cys Arg Trp Arg Trp Lys Cys Cys Lys Lys
1               5                   10
```

<210> SEQ ID NO 105
<211> LENGTH: 16
<212> TYPE: PRT
<213> ORGANISM: Homo sapiens

<400> SEQUENCE: 105

```
Arg Lys Lys Arg Arg Arg Glu Ser Arg Lys Lys Arg Arg Arg Glu Ser
1               5                   10                  15
```

<210> SEQ ID NO 106
<211> LENGTH: 17

```
<212> TYPE: PRT
<213> ORGANISM: Homo sapiens

<400> SEQUENCE: 106

Gly Arg Pro Arg Glu Ser Gly Lys Lys Arg Lys Arg Lys Arg Leu Lys
1               5                   10                  15

Pro

<210> SEQ ID NO 107
<211> LENGTH: 15
<212> TYPE: PRT
<213> ORGANISM: Homo sapiens

<400> SEQUENCE: 107

Gly Lys Arg Lys Lys Lys Gly Lys Leu Gly Lys Lys Arg Asp Pro
1               5                   10                  15

<210> SEQ ID NO 108
<211> LENGTH: 19
<212> TYPE: PRT
<213> ORGANISM: Unknown
<220> FEATURE:
<223> OTHER INFORMATION: Description of Unknown:
      DPV10/6 peptide

<400> SEQUENCE: 108

Ser Arg Arg Ala Arg Arg Ser Pro Arg Glu Ser Gly Lys Lys Arg Lys
1               5                   10                  15

Arg Lys Arg

<210> SEQ ID NO 109
<211> LENGTH: 5
<212> TYPE: PRT
<213> ORGANISM: Homo sapiens

<400> SEQUENCE: 109

Val Pro Met Leu Lys
1               5

<210> SEQ ID NO 110
<211> LENGTH: 5
<212> TYPE: PRT
<213> ORGANISM: Homo sapiens

<400> SEQUENCE: 110

Lys Leu Pro Val Met
1               5

<210> SEQ ID NO 111
<211> LENGTH: 22
<212> TYPE: PRT
<213> ORGANISM: Mycobacterium sp.

<400> SEQUENCE: 111

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 112
<211> LENGTH: 26
<212> TYPE: PRT
<213> ORGANISM: Mycobacterium sp.
```

-continued

<400> SEQUENCE: 112

Ala Glu Lys Val Asp Pro Val Lys Leu Asn Leu Thr Leu Ser Ala Ala
1               5                   10                  15

Ala Glu Ala Leu Thr Gly Leu Gly Asp Lys
            20                  25

<210> SEQ ID NO 113
<211> LENGTH: 22
<212> TYPE: PRT
<213> ORGANISM: Mycobacterium sp.

<400> SEQUENCE: 113

Thr Lys Arg Arg Ile Thr Pro Lys Asp Val Ile Asp Val Arg Ser Val
1               5                   10                  15

Thr Thr Lys Ile Asn Thr
            20

<210> SEQ ID NO 114
<211> LENGTH: 29
<212> TYPE: PRT
<213> ORGANISM: Unknown
<220> FEATURE:
<223> OTHER INFORMATION: Description of Unknown:
      Res1 L3 loop of restrictocin peptide

<400> SEQUENCE: 114

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met Gly Lys
            20                  25

<210> SEQ ID NO 115
<211> LENGTH: 37
<212> TYPE: PRT
<213> ORGANISM: Human respiratory syncytial virus

<400> SEQUENCE: 115

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys Asp Leu Lys Pro Gln
            20                  25                  30

Thr Thr Lys Pro Lys
        35

<210> SEQ ID NO 116
<211> LENGTH: 22
<212> TYPE: PRT
<213> ORGANISM: Human immunodeficiency virus

<400> SEQUENCE: 116

Asp Arg Arg Arg Arg Gly Ser Arg Pro Ser Gly Ala Glu Arg Arg Arg
1               5                   10                  15

Arg Arg Ala Ala Ala Ala
            20

<210> SEQ ID NO 117
<211> LENGTH: 25
<212> TYPE: PRT
<213> ORGANISM: Homo sapiens

```
<400> SEQUENCE: 117

Gly Thr Lys Met Ile Phe Val Gly Ile Lys Lys Glu Glu Arg Ala
1               5                   10                  15

Asp Leu Ile Ala Tyr Leu Lys Lys Ala
            20                  25

<210> SEQ ID NO 118
<211> LENGTH: 17
<212> TYPE: PRT
<213> ORGANISM: Flock house virus

<400> SEQUENCE: 118

Arg Arg Arg Arg Asn Arg Thr Arg Arg Asn Arg Arg Arg Val Arg Gly
1               5                   10                  15

Cys

<210> SEQ ID NO 119
<211> LENGTH: 11
<212> TYPE: PRT
<213> ORGANISM: Homo sapiens

<400> SEQUENCE: 119

Met Ile Ile Tyr Arg Asp Leu Ile Ser Lys Lys
1               5                   10

<210> SEQ ID NO 120
<211> LENGTH: 10
<212> TYPE: PRT
<213> ORGANISM: Homo sapiens

<400> SEQUENCE: 120

Met Ile Ile Tyr Arg Asp Lys Lys Ser His
1               5                   10

<210> SEQ ID NO 121
<211> LENGTH: 10
<212> TYPE: PRT
<213> ORGANISM: Homo sapiens

<400> SEQUENCE: 121

Met Ile Ile Phe Arg Asp Leu Ile Ser His
1               5                   10

<210> SEQ ID NO 122
<211> LENGTH: 10
<212> TYPE: PRT
<213> ORGANISM: Homo sapiens

<400> SEQUENCE: 122

Met Ile Ile Tyr Arg Asp Leu Ile Ser His
1               5                   10

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Arg Arg Arg Arg Arg Arg Arg
1               5
```

```
<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Arg Arg Arg Arg Arg Arg Arg Arg
1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: D-amino acid

<400> SEQUENCE: 125

Arg Arg Arg Arg Arg Arg
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: D-amino acid

<400> SEQUENCE: 126

Arg Arg Arg Arg Arg Arg Arg
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(8)
<223> OTHER INFORMATION: D-amino acid

<400> SEQUENCE: 127

Arg Arg Arg Arg Arg Arg Arg Arg
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: D-amino acid
```

```
<400> SEQUENCE: 128

Arg Arg Arg Arg Arg Arg Arg Arg Arg
1               5

<210> SEQ ID NO 129
<211> LENGTH: 27
<212> TYPE: PRT
<213> ORGANISM: Unknown
<220> FEATURE:
<223> OTHER INFORMATION: Description of Unknown:
      transportan (TP) peptide

<400> SEQUENCE: 129

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 130
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Leu Trp Lys Thr Leu Leu Lys Lys Val Leu Lys Ala Pro Lys Lys
1               5                   10                  15

Lys Arg Lys Val
            20

<210> SEQ ID NO 131
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Glu Glu Ala Ala Gly Arg Lys Arg Lys Lys Arg Thr
1               5                   10

<210> SEQ ID NO 132
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 133
<211> LENGTH: 18
<212> TYPE: PRT
<213> ORGANISM: Homo sapiens
```

```
<400> SEQUENCE: 133

Gly Leu Arg Arg Leu Arg Gln Arg Arg Leu Arg Arg Glu Arg Val
1               5                   10                  15

Arg Ala

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Ala Val Ala Leu Leu Pro Ala Val Leu Leu Ala Leu Leu Ala Pro
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Lys Trp Lys Leu Phe Lys Lys Ile Gly Ala Val Leu Lys Val Leu
1               5                   10                  15

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys Lys Leu Phe Lys Lys Ile Leu Lys Tyr Leu
1               5                   10

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 137

Lys Trp Lys Leu Phe Lys Lys Ile Gly Ala Val Leu Lys Val Leu
1               5                   10                  15

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2
```

```
<400> SEQUENCE: 138

Lys Lys Leu Phe Lys Lys Ile Leu Lys Tyr Leu
1               5                   10

<210> SEQ ID NO 139
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: misc_feature
<222> LOCATION: (13)..(14)
<223> OTHER INFORMATION: Residues at these positions are linked by an
      AEEAc moiety
<220> FEATURE:
<221> NAME/KEY: MOD_RES
<222> LOCATION: (14)..(14)
<223> OTHER INFORMATION: Lys-(C(=O)-(CH2)5-Mal)
<220> FEATURE:
<223> OTHER INFORMATION: C-term NH2

<400> SEQUENCE: 139

Ile Cys Val Trp Gln Asp Trp Gly Ala His Arg Cys Thr Lys
1               5                   10
```

CELL-PENETRATING COMPSTATIN ANALOGS AND USES THEREOF

CROSS REFERENCE TO RELATED APPLICATIONS

This application claims priority to U.S. Provisional Patent Application Ser. No. 61/791,631 filed Mar. 15, 2013, the entire contents of which are hereby incorporated by reference.

SEQUENCE LISTING

The present specification makes reference to a Sequence Listing submitted electronically as a .txt file named "2008575-0099_Sequence_Listing" on Dec. 18, 2018. The .txt file was generated on Dec. 18, 2018 and is 53.7 kilobytes in size. The entire contents of the Sequence Listing are herein incorporated by reference.

BACKGROUND

Complement is a system consisting of more than 30 plasma and cell-bound proteins that plays a significant role in both innate and adaptive immunity. The proteins of the complement system act in a series of enzymatic cascades through a variety of protein interactions and cleavage events. Complement activation occurs via three main pathways: the antibody-dependent classical pathway, the alternative pathway, and the mannose-binding lectin (MBL) pathway. Inappropriate or excessive complement activation is an underlying cause or contributing factor to a number of serious diseases and conditions, and considerable effort has been devoted over the past several decades to exploring various complement inhibitors as therapeutic agents. However, there remains a need for innovative approaches to inhibiting complement activation for a variety of therapeutic purposes.

SUMMARY

In some aspects, the invention provides cell-penetrating compstatin analogs. In some aspects, the invention provides methods of making, identifying, characterizing, and/or using cell-penetrating compstatin analogs. In some aspects the invention provides compositions comprising cell-penetrating compstatin analogs. In some aspects, the invention provides a physiologically acceptable composition comprising a cell-penetrating compstatin analog. In some aspects, the invention provides a pharmaceutical grade composition comprising a cell-penetrating compstatin analog.

In some aspects, the invention provides a composition comprising an isolated cell, tissue, or organ, and a cell-penetrating compstatin analog. In some embodiments the invention provides an isolated cell comprising a cell-penetrating compstatin analog inside the cell. In some embodiments the invention provides an isolated tissue or organ, wherein at least some of the cells of the tissue or organ comprise a cell-penetrating compstatin analog inside them.

In some aspects, the invention provides methods of protecting a cell, tissue, organ, or subject from one or more effects of complement. In some embodiments, the methods comprise contacting the cell, tissue, or organ with a cell-penetrating compstatin analog. In some embodiments a cell is contacted with a cell-penetrating compstatin analog for a time and under conditions sufficient for internalization of the cell-penetrating compstatin analog by the cell. In some embodiments a tissue or organ is contacted with a cell-penetrating compstatin analog for a time and under conditions sufficient for internalization of the cell-penetrating compstatin analog by at least some cells of the tissue or organ. In some embodiments the cell, tissue, organ, or subject is the protected from one or more effects of primate complement, e.g., human complement. In some embodiments the cell, tissue, organ, or subject is the protected from one or more effects resulting from activation of complement component C3, e.g., primate complement component C3, e.g., human complement component C3.

A cell can be any type of cell in certain embodiments of any aspect of the invention. In some embodiments the cell is of a cell type that normally produces C3 in healthy subjects. In some embodiments the cell is of a cell type that exhibits increased C3 production and/or increased C3 secretion in subjects suffering from or at risk of a complement-mediated disease as compared with subjects not suffering from or at risk of such disease. In some embodiments the cell is of a cell type that exhibits increased C3 production and/or increased C3 secretion, e.g., in response to a stimulus. In some embodiments the cell is of a cell type that exhibits increased C3a production and/or increased C3a secretion, e.g., in response to a stimulus. In some embodiments the cell is of a cell type that exhibits increased C3b production and/or increased C3b secretion, e.g., in response to a stimulus. In some embodiments the stimulus is a stimulus that may cause or contribute to development or progression of a disease or manifestation of a disease, e.g., a complement-mediated disease. In some embodiments, the cell is an immune system cell. In some embodiments, the cell is a lymphoid cell. In some embodiments, the cell is a myeloid cell. In some embodiments, the cell is an epithelial cell. In some embodiments, the cell is a respiratory epithelial cell. In some embodiments, the cell is a retinal pigment epithelial cell. In some embodiments the cell is an endothelial cell. In some embodiments the cell is a nervous system cell, e.g., a neuron or glial cell.

In some embodiments, a cell, tissue, or organ is contacted ex vivo (outside the body of a subject). In some embodiments a cell, tissue, or organ is contacted in vivo (in a subject, e.g., a human). In some embodiments a cell, tissue, or organ is to be transplanted into a subject or has been transplanted into a subject. In some embodiments a cell-penetrating compstatin analog is administered to a subject.

In some aspects the invention provides methods of treating a subject in need of treatment for a complement-mediated disorder. In some embodiments the methods comprise administering a cell-penetrating compstatin analog to the subject.

All articles, books, patent applications, patents, other publications, websites, and databases mentioned in this application are incorporated herein by reference. In the event of a conflict between the specification and any of the incorporated references the specification (including any amendments thereto) shall control. Unless otherwise indicated, art-accepted meanings of terms and abbreviations are used herein. The practice of certain aspects described herein may employ conventional techniques of molecular biology, cell culture, recombinant nucleic acid (e.g., DNA) technology, immunology, and/or nucleic acid and polypeptide synthesis, detection, manipulation, and quantification, etc., that are within the ordinary skill of the art. See, e.g., Ausubel, F., et al., (eds.), Current Protocols in Molecular Biology, Current Protocols in Immunology, Current Protocols in Protein Science, and Current Protocols in Cell Biology, all John Wiley & Sons, N.Y., e.g., edition current as of January 2010 or later; Sambrook, Russell, and Sambrook, Molecular Cloning: A Laboratory Manual, 3$^{rd}$ ed., Cold Spring Harbor Laboratory Press, Cold Spring Harbor, 2001 or 4$^{th}$ ed, 2012, Harlow, E. and Lane, D., Antibodies: A Laboratory Manual, Cold Spring Harbor Laboratory Press, Cold Spring Harbor, 1988.

DETAILED DESCRIPTION OF CERTAIN EMBODIMENTS

I. Definitions

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value).

A "complement component" or "complement protein" is a protein that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, and properdin. Components of the lectin pathway include, e.g., MBL2, MASP-1, and MASP-2. Complement components also include cell-bound receptors for soluble complement components, wherein such receptor mediates one or more biological activities of such soluble complement component following binding of the soluble complement component. Such receptors include, e.g., C5a receptor (C5aR), C3a receptor (C3aR), Complement Receptor 1 (CR1), Complement Receptor 2 (CR2), Complement Receptor 3 (CR3, also known as CD45), etc. It will be appreciated that the term "complement component" is not intended to include those molecules and molecular structures that serve as "triggers" for complement activation, e.g., antigen-antibody complexes, foreign structures found on microbial or artificial surfaces, etc.

A "complement-mediated disorder" is any disorder in which complement activation is known or suspected of being a contributing and/or at least partially causative factor in at least some subjects suffering from the disorder, e.g., disorders in which complement activation results in tissue damage. Non-limiting examples of complement-mediated disorders include, but are not limited to, (i) various disorders characterized by hemolysis or hemolytic anemia such as atypical hemolytic uremic syndrome, cold agglutinin disease, paroxysmal nocturnal hemoglobinuria, transfusion reactions; (ii) transplant rejection (e.g., hyperacute or acute transplant rejection) or transplant dysfunction; (iii) disorders involving ischemia/reperfusion injury such as trauma, surgery (e.g., aneurysm repair), myocardial infarction, ischemic stroke; (iv) disorders of the respiratory system such as asthma and chronic obstructive pulmonary disease (COPD); (v) arthritis, e.g., rheumatoid arthritis; (vi) ocular disorders such as age-related macular degeneration (AMD), diabetic retinopathy, glaucoma, and uveitis. "Disorder" is used interchangeably herein with "disease", "condition", and similar words to refer to any impairment of health or state of abnormal functioning of an organism, e.g., any state in which medical and/or surgical management is indicated or for which a subject appropriately seeks medical and/or surgical attention. It should also be understood that the listing of a particular disorder within a particular category is for convenience and is not intended to limit the invention. It will be understood that certain disorders could appropriately be listed in multiple categories.

A "complement regulatory protein" is a protein involved in regulating complement activity. A complement regulatory protein may down-regulate complement activity by, e.g., inhibiting complement activation or by inactivating or accelerating decay of one or more activated complement proteins. Examples of complement regulatory proteins include C1 inhibitor, C4 binding protein, clusterin, vitronectin, CFH, factor I, and the cell-bound proteins CD46, CD55, CD59, CR1, CR2, and CR3.

"Isolated", as used herein, means 1) separated from at least some of the components with which it is usually associated in nature; 2) prepared or purified by a process that involves the hand of man; and/or 3) not occurring in nature, e.g., present in an artificial environment. In general, unless otherwise indicated or clearly evident, any entity, product, agent, composition, etc., may be deemed "isolated", if desired.

"Linked", as used herein with respect to two or more moieties, means that the moieties are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linking moiety" or "linking portion", the linkage between the two linked moieties is indirect, and typically each of the linked moieties is covalently bonded to the linking moiety. Two moieties may be linked using a "linker". A linker can be any suitable moiety that reacts with the entities to be linked within a reasonable period of time, under conditions consistent with stability of the entities (portions of which may be protected as appropriate, depending upon the conditions), and in sufficient amount, to produce a reasonable yield. Typically the linker will contain at least two functional groups, one of which reacts with a first entity and the other of which reacts with a second entity. It will be appreciated that after the linker has reacted with the entities to be linked, the term "linker" may refer to the part of the resulting structure that originated from the linker, or at least the portion that does not include the reacted functional groups. A linking moiety may comprise a portion that does not participate in a bond with the entities being linked, and whose main purpose may be to spatially separate the entities from each other. Such portion may be referred to as a "spacer".

As used herein, "physiological conditions" refers to a set of conditions such as temperature, salt concentration, pH that at least in part mimic those conditions as typically found in a living subject, e.g., a mammalian subject. In some aspects, physiological conditions refer to conditions in an aqueous medium, e.g., a medium comprising at least 90%, 95%, 96%, 97%, 97%, 99%, or about 100% water on a volume/volume basis. In some embodiments other liquids, if present, do not substantially affect protein secondary or tertiary structure. In some embodiments physiological conditions at least in part mimic those found in a body fluid such as blood or extracellular fluid, e.g., interstitial fluid, e.g., of a mammalian subject. A variety of physiological conditions useful for, e.g., in vitro assays, are known in the art. Generally, a medium under physiological conditions contains a physiological concentration of salt, e.g., sodium chloride. In some embodiments a physiological concentration of salt refers to a concentration ranging from about 250 mOsm/L to about 350 mOsm/L, e.g., about 275 mOsm/L to about 325 mOsm/L, e.g., about 300 mOsm/L. In some embodiments physiological conditions are approximately isotonic to a body fluid, e.g., blood or extracellular fluid, e.g., interstitial fluid. In some embodiments physiological conditions include a pH ranging from about 6.5 to about 7.8, e.g., about 7.0 to about 7.5. In some embodiments a physiological medium comprises a buffer substance that helps maintain the pH of the medium within a physiological range. In some embodiments physiological conditions comprise conditions such that a typical mammalian protein, e.g., a protein typically found in a body fluid, such as blood or extracellular fluid, substantially retains the secondary and, if applicable, tertiary structure that such protein has in the body fluid in which it is normally found. In some embodiments components of a physiological medium are typically substantially non-toxic to mammalian cells at the concentration at which they are present in the physiological medium. A variety of physiological media (sometimes termed "buffers") are listed in various standard references, such as those cited above (e.g., Sambrook, et al., Protocols series). In some embodiments a physiological temperature ranges from about 25 degrees C. to about 38 degrees C., e.g., from about 30 degrees C. to about 37 degrees C., e.g., 35 degrees C. to 37 degrees C.

"Polypeptide", as used herein, refers to a polymer of amino acids, optionally including one or more amino acid analogs. A protein is a molecule composed of one or more polypeptides. A peptide is a relatively short polypeptide, typically between about 2 and 60 amino acids in length, e.g., between 8 and 40 amino acids in length. The terms "protein", "polypeptide", and "peptide" may be used interchangeably. Polypeptides used herein may contain amino acids such as those that are naturally found in proteins, amino acids that are not naturally found in proteins, and/or amino acid analogs that are not amino acids. As used herein, an "analog" of an amino acid may be a different amino acid that structurally resembles the amino acid or a compound other than an amino acid that structurally resembles the amino acid. A large number of art-recognized analogs of the 20 amino acids commonly found in proteins (the "standard" amino acids) are known. One or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. Certain non-limiting suitable analogs and modifications are described in WO2004026328 and/or below. The polypeptide may be acetylated, e.g., at the N-terminus and/or amidated, e.g., at the C-terminus.

The term "purified", as used herein, refers to substances that have been separated from at least some or most of the components with which they are associated in nature or when originally generated or with which they were associated prior to purification. In general, such purification involves action of the hand of man. Purified agents may be partially purified, substantially purified, or pure. Such agents may be, for example, at least 50%, 60%, 70%, 75%, 80%, 85%, 90%, 95%, 96%, 97%, 98%, 99%, or more than 99% pure. In some embodiments, a nucleic acid, polypeptide, or small molecule is purified such that it constitutes at least 75%, 80%, 85%, 90%, 95%, 96%, 97%, 98%, 99%, or more, of the total nucleic acid, polypeptide, or small molecule material, respectively, present in a preparation. In some embodiments, an organic substance, e.g., a nucleic acid, polypeptide, or small molecule, is purified such that it constitutes at least 75%, 80%, 85%, 90%, 95%, 96%, 97%, 98%, 99%, or more, of the total organic material present in a preparation. Purity may be based on, e.g., dry weight, size of peaks on a chromatography tracing (GC, HPLC, etc.), molecular abundance, electrophoretic methods, intensity of bands on a gel, spectroscopic data (e.g., NMR), elemental analysis, high throughput sequencing, mass spectrometry, or any art-accepted quantification method. In some embodiments, water, buffer substances, ions, and/or small molecules (e.g., synthetic precursors such as nucleotides or amino acids), can optionally be present in a purified preparation. A purified agent may be prepared by separating it from other substances (e.g., other cellular materials), or by producing it in such a manner to achieve a desired degree of purity. In some embodiments "partially purified" with respect to a molecule produced by a cell means that a molecule produced by a cell is no longer present within the cell, e.g., the cell has been lysed and, optionally, at least some of the cellular material (e.g., cell wall, cell membrane(s), cell organelle(s)) has been removed and/or the molecule has been separated or segregated from at least some molecules of the same type (protein, RNA, DNA, etc.) that were present in the lysate.

"Recombinant host cells", "host cells", and other such terms, denote prokaryotic or eukaryotic cells or cell lines that contain an exogenous nucleic acid (typically DNA) such as an expression vector comprising a nucleic acid that encodes a polypeptide of interest. It will be understood that such terms include the descendants of the original cell(s) into which the vector or other nucleic acid has been introduced. Appropriate host cells include any of those routinely used in the art for expressing polynucleotides (e.g., for purposes of producing polypeptide(s) encoded by such polynucleotides) including, for example, prokaryotes, such as *E. coli* or other bacteria such as species of *Escherichia; Lactobacillus, Bacillus* (e.g., *B. subtilis*), *Salmonella Pseudomonas, Streptomyces, Staphylococcus*, etc; and eukaryotes, including for example, fungi, such as yeast (e.g., *Pichia* (e.g., *Pichia pastoris*), *Kluyveromyces*, such as *K. lactis, Hansenula*, e.g. *H. polymorpha*). Examples of other fungal cells are cells of filamentous fungi, e.g. *Aspergillus* spp., *Neurospora* spp., *Fusarium* spp. or *Trichoderma* spp., e.g., strains of *A. oryzae, A. nidulans* or *A. niger*; insect cells (e.g., Sf9), plant cells, and animal cells, e.g., mammalian cells such as CHO, R1.1, B-W, L-M, African Green Monkey Kidney cells (e.g. COS-1, COS-7, BSC-1, BSC-40 and BMT-10), and cultured human cells. Also encompassed are genetically modified cells in genetically modified (e.g., transgenic) plants or animals, wherein a recombinant polypeptide is produced by at least some such cells. A polypeptide may be secreted in milk, harvested from plant material, etc. The exogenous nucleic acid may be stably maintained as an episome such as a plasmid or may at least in part be integrated into the host cell's genome, optionally after being copied or reverse transcribed. Terms such as "host cells", etc., are also used to refer to cells or cell lines that can be used as recipients for an exogenous nucleic acid, prior to introduction of the nucleic acid. A "recombinant polynucleotide" generally is a polynucleotide that contains nucleic acid sequences that are not found joined directly to one another in nature. For example, the nucleic acid sequences may occur in different genes or different species or one or more of the sequence(s) may be a variant of a naturally occurring sequence or may at least in part be an artificial sequence that is not homologous to a naturally occurring sequence. A "recombinant polypeptide" generally is a polypeptide that is at least in part produced by transcription and translation of an exogenous nucleic acid by a recombinant host cell or by a cell-free in vitro expression system and/or that contains amino acid sequences that are not found joined directly to one another in nature. In the latter case, the recombinant polypeptide may be referred to as a "chimeric polypeptide". The amino acid sequences in a chimeric polypeptide may, for example, occur in different genes or in different species or one or more of the sequence(s) may be a variant of a naturally occurring sequence or may at least in part be an artificial sequence that is not identical or in some embodiments is not homologous to a naturally occurring sequence over a substantial portion of the length. It will be understood that a chimeric polypeptide may comprise two or more polypeptides. For example, first and second polypeptides A and B of a chimeric polypeptide may be directly linked (A-B or B-A) or may be separated by a third polypeptide portion C (A-C-B or B-C-A). In some embodiments, portion C represents a polypeptide linker which may, for example, comprise multiple glycine and/or serine residues or any of a variety of other amino acids. In some embodiments, two or more polypeptides may be linked by non-polypeptide linker(s). "Recombinant" as used herein encompasses in certain embodiments polypeptides produced by joining (e.g., chemically conjugating, enzymatically conjugating), shorter recombinant polypeptides that may be produced in recombinant host cells. In some embodiments a recombinant polypeptide may comprise a signal sequence that directs secretion of the polypeptide or a sequence that directs the expressed polypeptide to a specific compartment or organelle. Suitable sequences are known in the art. Appropriate sequences for a host cell type of interest (e.g., bacterial, fungal, mammalian, plant, etc.) may be selected. A signal sequence may be located at or near (e.g., within up to 10-50 amino acids of) the N-terminus or C-terminus in some embodiments. In some embodiments a polypeptide comprises a tag. A tag may be useful to facilitate detection and/or purification of a protein that contains it. Examples of tags include polyhistidine-tag (e.g., 6×-His tag (SEQ ID NO: 71)), glutathione-S-transferase, maltose binding protein, NUS tag, SNUT tag, Strep tag, epitope tags such as V5, HA, Myc, or FLAG. In some embodiments a protease cleavage site is located in the region between the tag and the polypeptide, allowing the polypeptide to be separated from the tag by exposure to the protease. In some embodiments a polynucleotide that encodes a recombinant polypeptide is at least in part codon optimized for expression in a host cell of interest (e.g., bacterial, fungal, mammalian, plant, etc.). A tag may be located at or near (e.g., within up to 10-50 amino acids of) the N- or C-terminus of a polypeptide in various embodiments. A recombinant polypeptide may be isolated, purified, etc., using any of a variety of methods. See, e.g., Sambrook, Protocols series, or other standard references. Methods of use may include, e.g., dialysis (e.g., using membranes having defined pore size), chromatography, precipitation, gel purification, or affinity-based methods that may, in some embodiments, utilize a tag or a specific binding reagent such as an antibody.

"Reactive functional groups" as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds, N-hydroxysuccinimide esters, maleimides, sulfhydryls, and the like. Methods to prepare each of these functional groups are well known in the art and their application to or modification for a particular purpose is within the ability of one of skill in the art (see, for example, Sandier and Karo, eds. ORGANIC FUNCTIONAL GROUP PREPARATIONS, Academic Press, San Diego, 1989, and Hermanson, G., *Bioconjugate Techniques*, $2^{nd}$ ed., Academic Press, San Diego, 2008).

"Specific binding" generally refers to a physical association between a target polypeptide (or, more generally, a target molecule) and a binding molecule such as an antibody or ligand. The association is typically dependent upon the presence of a particular structural feature of the target such as an antigenic determinant, epitope, binding pocket or cleft, recognized by the binding molecule. For example, if an antibody is specific for epitope A, the presence of a polypeptide containing epitope A or the presence of free unlabeled A in a reaction containing both free labeled A and the binding molecule that binds thereto, will reduce the amount of labeled A that binds to the binding molecule. It is to be understood that specificity need not be absolute but generally refers to the context in which the binding occurs. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies or ligands having a sufficient degree of specificity to perform appropriately in any given application (e.g., for detection of a target molecule, for therapeutic purposes, etc). It is also to be understood that specificity may be evaluated in the context of additional factors such as the affinity of the binding molecule for the target versus the affinity of the binding molecule for other targets, e.g., competitors. If a binding molecule exhibits a high affinity for a target molecule that it is desired to detect and low affinity for nontarget molecules, the antibody will likely be an acceptable reagent. Once the specificity of a binding molecule is established in one or more contexts, it may be employed in other, preferably similar, contexts without necessarily re-evaluating its specificity. In some embodiments, the affinity (as measured by the equilibrium dissociation constant, Kd) of two molecules that exhibit specific binding is $10^{-3}$ M or less, e.g., $10^{-4}$ M or less, e.g., $10^{-5}$ M or less, e.g., $10^{-6}$ M or less, $10^{-7}$ M or less, $10^{-8}$ M or less, or $10^{-9}$ M or less under the conditions tested, e.g., under physiological conditions.

A "subject" treated according to the instant invention is typically a human, a non-human primate, or a lower animal (e.g., a mouse or rat), which expresses or contains at least some primate (e.g., human) complement component C3 and, optionally, one or more additional primate complement component(s). In some embodiments the subject is male. In some embodiments the subject is female. In some embodiments the subject is an adult, e.g., a human at least 18 years of age, e.g., between 18 and 100 years of age. In some embodiments, a human subject is at least 12 years of age. In some embodiments a subject is an adult, e.g., a human at least 18 years of age, e.g., between 18 and 100 years of age. In some embodiments a subject is at least 40, 45, 50, 55, 60, 65, 70, 75, or 80 years of age. In some embodiments the subject is a child, e.g., a human between 0 and 4 years of age, or between 5 and 11 years of age.

"Treating", as used herein in regard to treating a subject, refers to providing treatment, i.e., providing any type of medical or surgical management of a subject. The treatment can be provided in order to reverse, alleviate, inhibit the progression of, prevent or reduce the likelihood of a disease, or in order to reverse, alleviate, inhibit or prevent the progression of, prevent or reduce the likelihood of one or more symptoms or manifestations of a disease. "Prevent" refers to causing a disease or symptom or manifestation of a disease not to occur for at least a period of time in at least some individuals. Treating can include administering a compound or composition to the subject following the development of one or more symptoms or manifestations indicative of a disease, e.g., in order to reverse, alleviate, reduce the severity of, and/or inhibit or prevent the progression of the disease and/or to reverse, alleviate, reduce the severity of, and/or inhibit or one or more symptoms or manifestations of the disease. A compound or composition can be administered to a subject who has developed a disease, or is at increased risk of developing the disease relative to a member of the general population. A compound or composition can be administered to a subject who has developed a disease and is at increased risk of developing one or more particular symptoms or manifestations of the disease or an exacerbation of the disease relative to other individuals diagnosed with the disease, or relative to the subject's typical or average risk for such symptom or manifestation or exacerbation. For example, the subject may have been exposed to a "trigger" that places the subject at increased risk (e.g., temporarily increased risk) of experiencing an exacerbation. A compound or composition can be administered prophylactically, i.e., before development of any symptom or manifestation of the disease. Typically in this case the subject will be at risk of developing the disease, e.g., relative to a member of the general population, optionally matched in terms of age, sex, and/or other demographic variable(s).

A "vector" may be any of a variety of nucleic acid molecules, viruses, or portions thereof that are capable of mediating entry of, e.g., transferring, transporting, etc., a nucleic acid of interest between different genetic environments or into a cell. The nucleic acid of interest may be linked to, e.g., inserted into, the vector using, e.g., restriction and ligation. Vectors include, for example, DNA or RNA plasmids, cosmids, naturally occurring or modified viral genomes or portions thereof, nucleic acids that can be packaged into viral capsids, mini-chromosomes, artificial chromosomes, etc. Plasmid vectors typically include an origin of replication (e.g., for replication in prokaryotic cells). A plasmid may include part or all of a viral genome (e.g., a viral promoter, enhancer, processing or packaging signals, and/or sequences sufficient to give rise to a nucleic acid that can be integrated into the host cell genome and/or to give rise to infectious virus). Viruses or portions thereof that can be used to introduce nucleic acids into cells may be referred to as viral vectors. Viral vectors include, e.g., adenoviruses, adeno-associated viruses, retroviruses (e.g., lentiviruses, vaccinia virus and other poxviruses, herpes viruses (e.g., herpes simplex virus), and others. Baculovirus are of use, e.g., in insect cells. A wide range of plant viral vectors are known and include, e.g., those based on or comprising Cauliflower Mosaic Virus, Tobacco Mosaic Virus, or one or more genetic elements thereof (e.g., Cauliflower Mosaic Virus 35S promoter). Viral vectors may or may not contain sufficient viral genetic information for production of infectious virus when introduced into host cells, i.e., viral vectors may be replication-competent or replication-defective. In some embodiments, e.g., where sufficient information for production of infectious virus is lacking, it may be supplied by a host cell or by another vector introduced into the cell, e.g., if production of virus is desired. In some embodiments such information is not supplied, e.g., if production of virus is not desired. A nucleic acid to be transferred may be incorporated into a naturally occurring or modified viral genome or a portion thereof or may be present within a viral capsid as a separate nucleic acid molecule. A vector may contain one or more nucleic acids encoding a marker suitable for identifying and/or selecting cells that have taken up the vector. Markers include, for example, various proteins that increase or decrease either resistance or sensitivity to antibiotics or other agents (e.g., a protein that confers resistance to an antibiotic such as puromycin, hygromycin or blasticidin), enzymes whose activities are detectable by assays known in the art (e.g., β-galactosidase or alkaline phosphatase), and proteins or RNAs that detectably affect the phenotype of cells that express them (e.g., fluorescent proteins). Vectors often include one or more appropriately positioned sites for restriction enzymes, which may be used to facilitate insertion into the vector of a nucleic acid, e.g., a nucleic acid to be expressed. An expression vector is a vector into which a desired nucleic acid has been inserted or may be inserted such that it is operably linked to regulatory elements (also termed "regulatory sequences", "expression control elements", or "expression control sequences") and may be expressed as an RNA transcript (e.g., an mRNA that can be translated into protein or a noncoding RNA). Expression vectors include regulatory sequence(s), e.g., expression control sequences, sufficient to direct transcription of an operably linked nucleic acid under at least some conditions; other elements required or helpful for expression may be supplied by, e.g., the host cell or by an in vitro expression system. Such regulatory sequences typically include a promoter and may include enhancer sequences or upstream activator sequences. In some embodiments a vector may include sequences that encode a 5' untranslated region and/or a 3' untranslated region, which may comprise a cleavage and/or polyadenylation signal. In general, regulatory elements may be contained in a vector prior to insertion of a nucleic acid whose expression is desired or may be contained in an inserted nucleic acid or may be inserted into a vector following insertion of a nucleic acid whose expression is desired. As used herein, a nucleic acid and regulatory element(s) are said to be "operably linked" when they are covalently linked so as to place the expression or transcription of the nucleic acid under the influence or control of the regulatory element(s). For example, a promoter region would be operably linked to a nucleic acid if the promoter region were capable of effecting transcription of that nucleic acid. One of ordinary skill in the art will be aware that the precise nature of the regulatory sequences useful for gene expression may vary between species or cell types, but may in general include, as appropriate, sequences involved with the initiation of transcription, RNA processing, or initiation of translation. The choice and design of an appropriate vector and regulatory element(s) is within the ability and discretion of one of ordinary skill in the art. For example, one of skill in the art will select an appropriate promoter (or other expression control sequences) for expression in a desired species (e.g., a prokaryotic (bacterial) or eukaryotic (e.g., fungal, plant, mammalian species) or cell type. A vector may contain a promoter capable of directing expression in mammalian cells, such as a suitable viral promoter, e.g., from a cytomegalovirus (CMV), retrovirus, simian virus (e.g., SV40), papilloma virus, herpes virus or other virus that infects mammalian cells, or a mammalian promoter from, e.g., a gene such as EF1alpha, ubiquitin (e.g., ubiquitin B or C), globin, actin, phosphoglycerate kinase (PGK), etc., or a composite promoter such as a CAG promoter (combination of the CMV early enhancer element and chicken beta-actin promoter). In some embodiments a human promoter may be used. In some embodiments, a promoter that ordinarily directs transcription by a eukaryotic RNA polymerase I (a "pol I promoter"), e.g., (a U6, H1, 7SK or tRNA promoter or a functional variant thereof) may be used. In some embodiments, a promoter that ordinarily directs transcription by a eukaryotic RNA polymerase II (a "pol II promoter") or a functional variant thereof is used. In some embodiments, a promoter that ordinarily directs transcription by a eukaryotic RNA polymerase III (a "pol III promoter"), e.g., a promoter for transcription of ribosomal RNA (other than 5S rRNA) or a functional variant thereof is used. One of ordinary skill in the art will select an appropriate promoter for directing transcription of a sequence of interest. Examples of expression vectors that may be used in mammalian cells include, e.g., the pcDNA vector series, pSV2 vector series, pCMV vector series, pRSV vector series, pEF1 vector series, Gateway® vectors, etc. In some embodiments, regulatable (e.g., inducible or repressible) expression control element(s), e.g., a regulatable promoter, is/are used so that expression can be regulated, e.g., turned on or increased or turned off or decreased. In some embodiments a vector may comprise a polynucleotide sequence that encodes a polypeptide, wherein the polynucleotide sequence is positioned in frame with a nucleic acid inserted into the vector so that an N- or C-terminal fusion is created. In some embodiments a polypeptide encoded by the polynucleotide sequence may comprise a signal sequence (which directs secretion of a protein) or a sequence that directs the expressed protein to a specific organelle or location in the cell such as the nucleus or mitochondria. In some embodiments a polypeptide comprises a tag. A tag may be useful to facilitate detection and/or purification of a protein that contains it. Examples of tags include polyhistidine-tag (e.g., 6×-His tag), glutathione-S-transferase, maltose binding protein, NUS tag, SNUT tag, Strep tag, epitope tags such as V5, HA, Myc, or FLAG. In some embodiments a protease cleavage site is located in the region between the protein encoded by the inserted nucleic acid and the polypeptide, allowing the polypeptide to be removed by exposure to the protease. Vectors may be introduced into host cells using methods known in the art. One of ordinary skill will select an appropriate method based, e.g., on the vector, cell type, etc. Examples of suitable methods include, e.g., calcium phosphate-mediated transfection, transfection with any of a variety of commercially available reagents, e.g., lipid-based or non-lipid based, such as FuGENE, Lipofectamine, TurboFect; electroporation; microparticle bombardment, etc.

Such methods are explained in detail in standard references such as Sambrook, Protocols series, and others.

As used herein the term "aliphatic" denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-30 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

As used herein, "alkyl" refers to a saturated straight, branched, or cyclic hydrocarbon having from about 1 to about 22 carbon atoms (and all combinations and subcombinations of ranges and specific numbers of carbon atoms therein), with from about 1 to about 12, or about 1 to about 7 carbon atoms being preferred in certain embodiments of the invention. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "halo" refers to F, Cl, Br or I.

As used herein, "alkanoyl" refers to an optionally substituted straight or branched aliphatic acyclic residue having about 1 to 10 carbon atoms (and all combinations and subcombinations of ranges and specific number of carbon atoms) therein, e.g., from about 1 to 7 carbon atoms which, as will be appreciated, is attached to a terminal C=O group with a single bond (and may also be referred to as an "acyl group"). Alkanoyl groups include, but are not limited to, formyl, acetyl, propionyl, butyryl, isobutyryl, pentanoyl, isopentanoyl, 2-methyl-butyryl, 2,2-dimethoxypropionyl, hexanoyl, heptanoyl, octanoyl, and the like, and for purposes of the present invention a formyl group is considered an alkanoyl group. "Lower alkanoyl" refers to an optionally substituted straight or branched aliphatic acyclic residue having about 1 to about 5 carbon atoms (and all combinations and subcombinations of ranges and specific number of carbon atoms). Such groups include, but are not limited to, formyl, acetyl, propionyl, butyryl, isobutyryl, pentanoyl, isopentanoyl, etc.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and having from about 6 to about 22 carbon atoms (and all combinations and subcombinations of ranges and specific numbers of carbon atoms therein), with from about 6 to about 12 carbon atoms being preferred in certain embodiments. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

The term "cyclic ring system" refers to an aromatic or non-aromatic, partially unsaturated or fully saturated, 3- to 10-membered ring system, which includes single rings of 3 to 8 atoms in size and bi- and tri-cyclic ring systems which may include aromatic 5- or 6-membered aryl or aromatic heterocyclic groups fused to a non-aromatic ring. These heterocyclic rings include those having from 1 to 3 heteroatoms independently selected from the group consisting of oxygen, sulfur, and nitrogen. In certain embodiments, the term heterocyclic refers to a non-aromatic 5-, 6-, or 7-membered ring or a polycyclic group wherein at least one ring atom is a heteroatom selected from the group consisting of O, S, and N, including, but not limited to, a bi- or tri-cyclic group, comprising fused six-membered rings having between one and three heteroatoms independently selected from the group consisting of the oxygen, sulfur, and nitrogen. In some embodiments, "cyclic ring system" refers to a cycloalkyl group which, as used herein, refers to groups having 3 to 10, e.g., 4 to 7 carbon atoms. Cycloalkyls include, but are not limited to cyclopropyl, cyclobutyl, cyclopentyl, cyclohexyl, cycloheptyl and the like, which, is optionally substituted. In some embodiments, "cyclic ring system" refers to a cycloalkenyl or cycloalkynyl moiety, which is optionally substituted.

Typically, substituted chemical moieties include one or more substituents that replace hydrogen. Exemplary substituents include, for example, halo, alkyl, cycloalkyl, aralkyl, aryl, sulfhydryl, hydroxyl (—OH), alkoxyl, cyano (—CN), carboxyl (—COOH), —C(=O)O-alkyl, aminocarbonyl (—C(=O)NH$_2$), —N-substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term "D-amino acid" refers to dextrorotatory alpha-amino acids. Unless specified otherwise, all amino acids referred to herein are L-amino acids.

As used herein, an "aromatic amino acid" is an amino acid that comprises at least one aromatic ring, e.g., it comprises an aryl group.

As used herein, an "aromatic amino acid analog" is an amino acid analog that comprises at least one aromatic ring, e.g., it comprises an aryl group.

II. Overview

In some aspects, the invention provides cell-penetrating compstatin analogs. Cell-penetrating compstatin analogs (CPCA) are compounds that comprise a compstatin analog moiety and a cell penetrating moiety (CPM), wherein the cell penetrating moiety is capable of enhancing entry of the compound into cells as compared to entry of a compstatin analog of the same sequence but lacking the cell penetrating moiety. A CPCA is thus able to enter the cell in increased amounts relative to the compstatin analog of the same sequence but lacking the cell penetrating moiety. Without wishing to be bound by any theory, a cell-penetrating compstatin analog may (i) bind to C3 within the cell and inhibit its activation within the cell; bind to C3 or C3b within the cell and inhibit its secretion; and/or (iii) bind to C3 or C3b within the cell and thus inhibit activity or activation of C3 or C3b that is subsequently secreted by the cell. C3 or C3b bound to a CPCA may thus be inhibited from participation in the complement activation cascade.

In some aspects, the invention provides methods of making cell-penetrating compstatin analogs. In some aspects, the invention provides methods of characterizing cell-penetrating compstatin analogs. In some aspects, the invention provides methods of using cell-penetrating compstatin analogs. In some aspects, the invention provides compositions comprising cell-penetrating compstatin analogs.

III. Complement System

In order to facilitate understanding of the invention, and without intending to limit the invention in any way, this section provides an overview of complement and its pathways of activation. Further details are found, e.g., in *Kuby Immunology*, 6$^{th}$ ed., 2006; Paul, W. E., *Fundamental Immunology*, Lippincott Williams & Wilkins; 6$^{th}$ ed., 2008; and Walport M J., Complement. First of two parts. *N Engl J Med.*, 344(14):1058-66, 2001.

Complement is an arm of the innate immune system that plays an important role in defending the body against infectious agents. The complement system comprises more than 30 serum and cellular proteins that are involved in three major pathways, known as the classical, alternative, and lectin pathways. The classical pathway is usually triggered by binding of a complex of antigen and IgM or IgG antibody to C1 (though certain other activators can also initiate the pathway). Activated C1 cleaves C4 and C2 to produce C4a and C4b, in addition to C2a and C2b. C4b and C2a combine to form C3 convertase, which cleaves C3 to form C3a and C3b. Binding of C3b to C3 convertase produces C5 convertase, which cleaves C5 into C5a and C5b. C3a, C4a, and C5a are anaphylotoxins and mediate multiple reactions in the acute inflammatory response. C3a and C5a are also chemotactic factors that attract immune system cells such as neutrophils.

The alternative pathway is initiated by and amplified at, e.g., microbial surfaces and various complex polysaccharides. In this pathway, hydrolysis of C3 to C3(H2O), which occurs spontaneously at a low level, leads to binding of factor B, which is cleaved by factor D, generating a fluid phase C3 convertase that activates complement by cleaving C3 into C3a and C3b. C3b binds to targets such as cell surfaces and forms a complex with factor B, which is later cleaved by factor D, resulting in a C3 convertase. Surface-bound C3 convertases cleave and activate additional C3 molecules, resulting in rapid C3b deposition in close proximity to the site of activation and leading to formation of additional C3 convertase, which in turn generates additional C3b. This process results in a cycle of C3 cleavage and C3 convertase formation that significantly amplifies the response. Cleavage of C3 and binding of another molecule of C3b to the C3 convertase gives rise to a C5 convertase. C3 and C5 convertases of this pathway are regulated by host cell molecules CR1, DAF, MCP, CD59, and fH. The mode of action of these proteins involves either decay accelerating activity (i.e., ability to dissociate convertases), ability to serve as cofactors in the degradation of C3b or C4b by factor I, or both. Normally the presence of complement regulatory proteins on host cell surfaces prevents significant complement activation from occurring thereon.

The C5 convertases produced in both pathways cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Small amounts of MAC on the membrane of cells may have a variety of consequences other than cell death.

The lectin complement pathway is initiated by binding of mannose-binding lectin (MBL) and MBL-associated serine protease (MASP) to carbohydrates. The MB1-1 gene (known as LMAN-1 in humans) encodes a type I integral membrane protein localized in the intermediate region between the endoplasmic reticulum and the Golgi. The MBL-2 gene encodes the soluble mannose-binding protein found in serum. In the human lectin pathway, MASP-1 and MASP-2 are involved in the proteolysis of C4 and C2, leading to a C3 convertase described above.

Complement activity is regulated by various mammalian proteins referred to as complement control proteins (CCPs) or regulators of complement activation (RCA) proteins (U.S. Pat. No. 6,897,290). These proteins differ with respect to ligand specificity and mechanism(s) of complement inhibition. They may accelerate the normal decay of convertases and/or function as cofactors for factor I, to enzymatically cleave C3b and/or C4b into smaller fragments. CCPs are characterized by the presence of multiple (typically 4-56) homologous motifs known as short consensus repeats (SCR), complement control protein (CCP) modules, or SUSHI domains, about 50-70 amino acids in length that contain a conserved motif including four disulfide-bonded cysteines (two disulfide bonds), proline, tryptophan, and many hydrophobic residues. The CCP family includes complement receptor type 1 (CR1; C3b:C4b receptor), complement receptor type 2 (CR2), membrane cofactor protein (MCP; CD46), decay-accelerating factor (DAF), complement factor H (fH), and C4b-binding protein (C4 bp). CD59 is a membrane-bound complement regulatory protein unrelated structurally to the CCPs. Complement regulatory proteins normally serve to limit complement activation that might otherwise occur on cells and tissues of the mammalian, e.g., human host. Thus, "self" cells are normally protected from the deleterious effects that would otherwise ensue were complement activation to proceed on these cells. Deficiencies or defects in complement regulatory protein(s) are involved in the pathogenesis of a variety of complement-mediated disorders.

IV. Compstatin Analogs

Compstatin is a cyclic peptide that binds to C3 and inhibits complement activation. U.S. Pat. No. 6,319,897 describes a peptide having the sequence (SEQ ID NO: 1)
Ile-[Cys-Val-Val-Gln-Asp-Trp-Gly-His-His-Arg-Cys]-

Thr, with the disulfide bond between the two cysteines denoted by brackets. It will be understood that the name "compstatin" was not used in U.S. Pat. No. 6,319,897 but was subsequently adopted in the scientific and patent literature (see, e.g., Morikis, et al., *Protein Sci.*, 7(3):619-27, 1998) to refer to a peptide having the same sequence as SEQ ID NO: 2 disclosed in U.S. Pat. No. 6,319,897, but amidated at the C terminus as shown in Table 1 (SEQ ID NO: 8). The term "compstatin" is used herein consistently with such usage (i.e., to refer to SEQ ID NO: 8). Compstatin analogs that have higher complement inhibiting activity than compstatin have been developed. See, e.g., WO2004/026328 (PCT/US2003/029653), Morikis, D., et al., *Biochem Soc Trans.* 32(Pt 1):28-32, 2004, Mallik, B., et al., *J. Med. Chem.*, 274-286, 2005; Katragadda, M., et al. *J. Med. Chem.*, 49: 4616-4622, 2006; WO2007062249 (PCT/US2006/045539); WO2007044668 (PCT/US2006/039397), WO/2009/046198 (PCT/US2008/078593); WO/2010/127336 (PCT/US2010/033345) and discussion below.

Compstatin analogs may be acetylated or amidated, e.g., at the N-terminus and/or C-terminus. For example, compstatin analogs may be acetylated at the N-terminus and amidated at the C-terminus. Consistent with usage in the art, "compstatin" as used herein, and the activities of compstatin analogs described herein relative to that of compstatin, refer to compstatin amidated at the C-terminus (Mallik, 2005, supra).

Concatamers or multimers of compstatin or a complement inhibiting analog thereof are also of use in the present invention.

As used herein, the term "compstatin analog" includes compstatin and any complement inhibiting analog thereof. The term "compstatin analog" encompasses compstatin and other compounds designed or identified based on compstatin and whose complement inhibiting activity is at least 50% as great as that of compstatin as measured, e.g., using any complement activation assay accepted in the art or substantially similar or equivalent assays. Certain suitable assays are described in U.S. Pat. No. 6,319,897, WO2004/026328, Morikis, supra, Mallik, supra, Katragadda 2006, supra, WO2007062249 (PCT/US2006/045539); WO2007044668 (PCT/US2006/039397), WO/2009/046198 (PCT/US2008/078593); and/or WO/2010/127336 (PCT/US2010/033345). The assay may, for example, measure alternative or classical pathway-mediated erythrocyte lysis or be an ELISA assay. In some embodiments, an assay described in WO/2010/135717 (PCT/US2010/035871) is used.

The activity of a compstatin analog may be expressed in terms of its $IC_{50}$ (the concentration of the compound that inhibits complement activation by 50%), with a lower $IC_{50}$ indicating a higher activity as recognized in the art. The activity of a preferred compstatin analog for use in the present invention is at least as great as that of compstatin. It is noted that certain modifications known to reduce or eliminate complement inhibiting activity and may be explicitly excluded from any embodiment of the invention. The $IC_{50}$ of compstatin has been measured as 12 μM using an alternative pathway-mediated erythrocyte lysis assay (WO2004/026328). It will be appreciated that the precise $IC_{50}$ value measured for a given compstatin analog will vary with experimental conditions (e.g., the serum concentration used in the assay). Comparative values, e.g., obtained from experiments in which $IC_{50}$ is determined for multiple different compounds under substantially identical conditions, are of use. In one embodiment, the $IC_{50}$ of the compstatin analog is no more than the $IC_{50}$ of compstatin. In certain embodiments of the invention the activity of the compstatin analog is between 2 and 99 times that of compstatin (i.e., the analog has an $IC_{50}$ that is less than the $IC_{50}$ of compstatin by a factor of between 2 and 99). For example, the activity may be between 10 and 50 times as great as that of compstatin, or between 50 and 99 times as great as that of compstatin. In certain embodiments of the invention the activity of the compstatin analog is between 99 and 264 times that of compstatin. For example, the activity may be 100, 110, 120, 130, 140, 150, 160, 170, 180, 190, 200, 210, 220, 230, 240, 250, 260, or 264 times as great as that of compstatin. In certain embodiments the activity is between 250 and 300, 300 and 350, 350 and 400, or 400 and 500 times as great as that of compstatin. The invention further contemplates compstatin analogs having activities between 500 and 1000 times that of compstatin, or more. In certain embodiments the $IC_{50}$ of the compstatin analog is between about 0.2 µM and about 0.5 µM. In certain embodiments the $IC_{50}$ of the compstatin analog is between about 0.1 µM and about 0.2 µM. In certain embodiments the $IC_{50}$ of the compstatin analog is between about 0.05 µM and about 0.1 µM. In certain embodiments the $IC_{50}$ of the compstatin analog is between about 0.001 µM and about 0.05 µM.

The $K_d$ of compstatin binding to C3 can be measured using isothermal titration calorimetry (Katragadda, et al., *J. Biol. Chem.*, 279(53), 54987-54995, 2004). Binding affinity of a variety of compstatin analogs for C3 has been correlated with their activity, with a lower $K_d$ indicating a higher binding affinity, as recognized in the art. A linear correlation between binding affinity and activity was shown for certain analogs tested (Katragadda, 2004, supra; Katragadda 2006, supra). In certain embodiments of the invention the compstatin analog binds to C3 with a $K_d$ of between 0.1 µM and 1.0 µM, between 0.05 µM and 0.1 µM, between 0.025 µM and 0.05 µM, between 0.015 µM and 0.025 µM, between 0.01 µM and 0.015 µM, or between 0.001 µM and 0.01 µM.

Compounds "designed or identified based on compstatin" include, but are not limited to, compounds that comprise an amino acid chain whose sequence is obtained by (i) modifying the sequence of compstatin (e.g., replacing one or more amino acids of the sequence of compstatin with a different amino acid or amino acid analog, inserting one or more amino acids or amino acid analogs into the sequence of compstatin, or deleting one or more amino acids from the sequence of compstatin); (ii) selection from a phage display peptide library in which one or more amino acids of compstatin is randomized, and optionally further modified according to method (i); or (iii) identified by screening for compounds that compete with compstatin or any analog thereof obtained by methods (i) or (ii) for binding to C3 or a fragment thereof. Many useful compstatin analogs comprise a hydrophobic cluster, a β-turn, and a disulfide bridge.

In certain embodiments of the invention the sequence of the compstatin analog comprises or consists essentially of a sequence that is obtained by making 1, 2, 3, or 4 substitutions in the sequence of compstatin, i.e., 1, 2, 3, or 4 amino acids in the sequence of compstatin is replaced by a different standard amino acid or by a non-standard amino acid. In certain embodiments of the invention the amino acid at position 4 is altered. In certain embodiments of the invention the amino acid at position 9 is altered. In certain embodiments of the invention the amino acids at positions 4 and 9 are altered. In certain embodiments of the invention only the amino acids at positions 4 and 9 are altered. In certain embodiments of the invention the amino acid at position 4 or 9 is altered, or in certain embodiments both amino acids 4 and 9 are altered, and in addition up to 2 amino acids located at positions selected from 1, 7, 10, 11, and 13 are altered. In certain embodiments of the invention the amino acids at positions 4, 7, and 9 are altered. In certain embodiments of the invention amino acids at position 2, 12, or both are altered, provided that the alteration preserves the ability of the compound to be cyclized. Such alteration(s) at positions 2 and/or 12 may be in addition to the alteration(s) at position 1, 4, 7, 9, 10, 11, and/or 13. Optionally the sequence of any of the compstatin analogs whose sequence is obtained by replacing one or more amino acids of compstatin sequence further includes up to 1, 2, or 3 additional amino acids at the C-terminus. In one embodiment, the additional amino acid is Gly. Optionally the sequence of any of the compstatin analogs whose sequence is obtained by replacing one or more amino acids of compstatin sequence further includes up to 5, or up to 10 additional amino acids at the C-terminus. It should be understood that compstatin analogs may have any one or more of the characteristics or features of the various embodiments described herein, and characteristics or features of any embodiment may additionally characterize any other embodiment described herein, unless otherwise stated or evident from the context. In certain embodiments of the invention the sequence of the compstatin analog comprises or consists essentially of a sequence identical to that of compstatin except at positions corresponding to positions 4 and 9 in the sequence of compstatin.

Compstatin and certain compstatin analogs having somewhat greater activity than compstatin contain only standard amino acids ("standard amino acids" are glycine, leucine, isoleucine, valine, alanine, phenylalanine, tyrosine, tryptophan, aspartic acid, asparagine, glutamic acid, glutamine, cysteine, methionine, arginine, lysine, proline, serine, threonine and histidine). Certain compstatin analogs having improved activity incorporate one or more non-standard amino acids. Useful non-standard amino acids include singly and multiply halogenated (e.g., fluorinated) amino acids, D-amino acids, homo-amino acids, N-alkyl amino acids, dehydroamino acids, aromatic amino acids (other than phenylalanine, tyrosine and tryptophan), ortho-, meta- or para-aminobenzoic acid, phospho-amino acids, methoxylated amino acids, and α,α-disubstituted amino acids. In certain embodiments of the invention, a compstatin analog is designed by replacing one or more L-amino acids in a compstatin analog described elsewhere herein with the corresponding D-amino acid. Such compounds and methods of use thereof are an aspect of the invention. Exemplary non-standard amino acids of use include 2-naphthylalanine (2-Nal), 1-naphthylalanine (1-Nal), 2-indanylglycine carboxylic acid (2Ig1), dihydrotrpytophan (Dht), 4-benzoyl-L-phenylalanine (Bpa), 2-α-aminobutyric acid (2-Abu), 3-α-aminobutyric acid (3-Abu), 4-α-aminobutyric acid (4-Abu), cyclohexylalanine (Cha), homocyclohexylalanine (hCha), 4-fluoro-L-tryptophan (4fW), 5-fluoro-L-tryptophan (5fW), 6-fluoro-L-tryptophan (6fW), 4-hydroxy-L-tryptophan (4OH—W), 5-hydroxy-L-tryptophan (5OH—W), 6-hydroxy-L-tryptophan (6OH—W), 1-methyl-L-tryptophan (1MeW), 4-methyl-L-tryptophan (4MeW), 5-methyl-L-tryptophan (5MeW), 7-aza-L-tryptophan (7aW), α-methyl-L-tryptophan (αMeW), β-methyl-L-tryptophan (βMeW), N-methyl-L-tryptophan (NMeW), omithine (orn), citrulline, norleucine, γ-glutamic acid, etc.

In certain embodiments of the invention the compstatin analog comprises one or more Trp analogs (e.g., at position 4 and/or 7 relative to the sequence of compstatin). Exemplary Trp analogs are mentioned above. See also Beene, et. al. *Biochemistry* 41: 10262-10269, 2002 (describing, inter alia, singly- and multiply-halogenated Trp analogs); Babitzke & Yanofsky, *J. Biol. Chem.* 270: 12452-12456, 1995 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Other Trp analogs include variants that are substituted (e.g., by a methyl group) at the α or β carbon and, optionally, also at one or more positions of the indole ring. Amino acids comprising two or more aromatic rings, including substituted, unsubstituted, or alternatively substituted variants thereof, are of interest as Trp analogs. In certain embodiments of the invention the Trp analog, e.g., at position 4, is 5-methoxy, 5-methyl-, 1-methyl-, or 1-formyl-tryptophan. In certain embodiments of the invention a Trp analog (e.g., at position 4) comprising a 1-alkyl substituent, e.g., a lower alkyl (e.g., $C_1$-$C_5$) substituent is used. In certain embodiments, N($\alpha$) methyl tryptophan or 5-methyltryptophan is used. In some embodiments, an analog comprising a 1-alkanyol substituent, e.g., a lower alkanoyl (e.g., $C_1$-$C_5$) is used. Examples include 1-acetyl-L-tryptophan and L-$\beta$-tryptophan.

In certain embodiments the Trp analog has increased hydrophobic character relative to Trp. For example, the indole ring may be substituted by one or more alkyl (e.g., methyl) groups. In certain embodiments the Trp analog participates in a hydrophobic interaction with C3. Such a Trp analog may be located, e.g., at position 4 relative to the sequence of compstatin. In certain embodiments the Trp analog comprises a substituted or unsubstituted bicyclic aromatic ring component or two or more substituted or unsubstituted monocyclic aromatic ring components.

In certain embodiments the Trp analog has increased propensity to form hydrogen bonds with C3 relative to Trp but does not have increased hydrophobic character relative to Trp. The Trp analog may have increased polarity relative to Trp and/or an increased ability to participate in an electrostatic interaction with a hydrogen bond donor on C3. Certain exemplary Trp analogs with an increased hydrogen bond forming character comprise an electronegative substituent on the indole ring. Such a Trp analog may be located, e.g., at position 7 relative to the sequence of compstatin.

In certain embodiments of the invention the compstatin analog comprises one or more Ala analogs (e.g., at position 9 relative to the sequence of compstatin), e.g., Ala analogs that are identical to Ala except that they include one or more $CH_2$ groups in the side chain. In certain embodiments the Ala analog is an unbranched single methyl amino acid such as 2-Abu. In certain embodiments of the invention the compstatin analog comprises one or more Trp analogs (e.g., at position 4 and/or 7 relative to the sequence of compstatin) and an Ala analog (e.g., at position 9 relative to the sequence of compstatin).

In certain embodiments of the invention the compstatin analog is a compound that comprises a peptide that has a sequence of (SEQ ID NO: 2)
(X'aa)$_n$-Gln-Asp-Xaa-Gly-(X"aa)$_m$, wherein each X'aa and each X"aa is an independently selected amino acid or amino acid analog, wherein Xaa is Trp or an analog of Trp, and wherein n>1 and m>1 and n+m is between 5 and 21. The peptide has a core sequence of Gln-Asp-Xaa-Gly, where Xaa is Trp or an analog of Trp, e.g., an analog of Trp having increased propensity to form hydrogen bonds with an H-bond donor relative to Trp but, in certain embodiments, not having increased hydrophobic character relative to Trp. For example, the analog may be one in which the indole ring of Trp is substituted with an electronegative moiety, e.g., a halogen such as fluorine. In one embodiment Xaa is 5-fluorotryptophan. Absent evidence to the contrary, one of skill in the art would recognize that any non-naturally occurring peptide whose sequence comprises this core sequence and that inhibits complement activation and/or binds to C3 will have been designed based on the sequence of compstatin. In an alternative embodiment Xaa is an amino acid or amino acid analog other than a Trp analog that allows the Gin-Asp-Xaa-Gly peptide to form a $\beta$-turn.

In certain embodiments of the invention the peptide has a core sequence of (SEQ ID NO: 3)
X'aa-Gln-Asp-Xaa-Gly, where X'aa and Xaa are selected from Trp and analogs of Trp. In certain embodiments of the invention the peptide has a core sequence of (SEQ ID NO: 3)
X'aa-Gln-Asp-Xaa-Gly, where X'aa and Xaa are selected from Trp, analogs of Trp, and other amino acids or amino acid analogs comprising at least one aromatic ring. In certain embodiments of the invention the core sequence forms a $\beta$-turn in the context of the peptide. The $\beta$-turn may be flexible, allowing the peptide to assume two or more conformations as assessed for example, using nuclear magnetic resonance (NMR). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention X'aa is an analog of Trp that has increased hydrophobic character relative to Trp. For example, X'aa may be 1-methyltryptophan. In certain embodiments of the invention Xaa is an analog of Trp that has increased propensity to form hydrogen bonds relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan.

In certain embodiments of the invention the peptide has a core sequence of (SEQ ID NO: 4)
X'aa-Gln-Asp-Xaa-Gly-X"aa, where X'aa and Xaa are each independently selected from Trp and analogs of Trp and X'aa is selected from His, Ala, analogs of Ala, Phe, and Trp. In certain embodiments of the invention X'aa is an analog of Trp that has increased hydrophobic character relative to Trp, such as 1-methyltryptophan or another Trp analog having an alkyl substituent on the indole ring (e.g., at position 1, 4, 5, or 6). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention Xaa is an analog of Trp that has increased propensity to form hydrogen bonds with C3 relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluoro-tryptophan. In certain embodiments X'aa is Ala or an analog of Ala such as Abu or another unbranched single methyl amino acid. In certain embodiments of the invention peptide has a core sequence of

```
                                              (SEQ ID NO: 4)
           X'aa-Gln-Asp-Xaa-Gly-X"aa,
``` where X'aa and Xaa are each independently selected from Trp, analogs of Trp, and amino acids or amino acid analogs comprising at least one aromatic side chain, and X"aa is selected from His, Ala, analogs of Ala, Phe, and Trp. In certain embodiments X"aa is selected from analogs of Trp, aromatic amino acids, and aromatic amino acid analogs.

In certain preferred embodiments of the invention the peptide is cyclic. The peptide may be cyclized via a bond between any two amino acids, one of which is $(X'aa)_n$ and the other of which is located within $(X'aa)_m$. In certain embodiments the cyclic portion of the peptide is between 9 and 15 amino acids in length, e.g., 10-12 amino acids in length. In certain embodiments the cyclic portion of the peptide is 11 amino acids in length, with a bond (e.g., a disulfide bond) between amino acids at positions 2 and 12. For example, the peptide may be 13 amino acids long, with a bond between amino acids at positions 2 and 12 resulting in a cyclic portion 11 amino acids in length.

In certain embodiments the peptides comprises or consists of the sequence

```
                                              (SEQ ID NO: 5)
X'aa1-X'aa2-X'aa3-X'aa4-Gln-Asp-Xaa-Gly-X"aa1-

X"aa2-X"aa3-X"aa4-X"aa5,
```

In certain embodiments X'aa4 and Xaa are selected from Trp and analogs of Trp, and X'aa1, X'aa2, X'aa3, X"aa1, X"aa2, X"aa3, X"aa4, and X"aa5 are independently selected from among amino acids and amino acid analogs. In certain embodiments X'aa4 and Xaa are selected from aromatic amino acids and aromatic amino acid analogs. Any one or more of X'aa1, X'aa2, X'aa3, X"aa1, X"aa2, X"aa3, X"aa4, and X"aa5 may be identical to the amino acid at the corresponding position in compstatin. In one embodiment, X"aa1 is Ala or a single methyl unbranched amino acid. The peptide may be cyclized via a covalent bond between (i) X'aa1, X'aa2, or X'aa3; and (ii) X"aa2, X"aa3, X"aa4 or X"aa5. In one embodiment the peptide is cyclized via a covalent bond between X'aa2 and X"aa4. In one embodiment the covalently bound amino acid are each Cys and the covalent bond is a disulfide (S—S) bond. In other embodiments the covalent bond is a C—C, C—O, C—S, or C—N bond. In certain embodiments one of the covalently bound residues is an amino acid or amino acid analog having a side chain that comprises a primary or secondary amine, the other covalently bound residue is an amino acid or amino acid analog having a side chain that comprises a carboxylic acid group, and the covalent bond is an amide bond. Amino acids or amino acid analogs having a side chain that comprises a primary or secondary amine include lysine and diaminocarboxylic acids of general structure $NH_2(CH_2)_nCH(NH_2)$ COOH such as 2,3-diaminopropionic acid (dapa), 2,4-diaminobutyric acid (daba), and ornithine (orn), wherein n=1 (dapa), 2 (daba), and 3 (orn), respectively. Examples of amino acids having a side chain that comprises a carboxylic acid group include dicarboxylic amino acids such as glutamic acid and aspartic acid. Analogs such as beta-hydroxy-L-glutamic acid may also be used. In some embodiments a peptide is cyclized with a thioether bond, e.g., as described in PCT/US2011/052442 (WO/2012/040259). For example, in some embodiments a disulfide bond in any of the peptides is replaced with a thioether bond. In some embodiments, a cystathionine is formed. In some embodiments the cystathionine is a delta-cystathionine or a gamma-cystathionine. In some embodiments a modification comprises replacement of a Cys-Cys disulfide bond between cysteines at X'aa2 and X"aa4 in SEQ ID NO: 5 (or corresponding positions in other sequences) with addition of a $CH_2$, to form a homocysteine at X'aa2 or X"aa4, and introduction of a thioether bond, to form a cystathionine. In one embodiment, the cystathionine is a gamma-cystathionine. In another embodiment, the cystathionine is a delta-cystathionine. Another modification in accordance with the present invention comprises replacement of the disulfide bond with a thioether bond without the addition of a $CH_2$, thereby forming a lantithionine. In some embodiments a compstatin analog having a thioether in place of a disulfide bond has increased stability, at least under some conditions, as compared with the compstatin analog having the disulfide bond.

In certain embodiments, the compstatin analog is a compound that comprises a peptide having a sequence:

```
                                              (SEQ ID NO: 6)
Xaa1-Cys-Val-Xaa2-Gln-Asp-Xaa2*-Gly-Xaa3-His-Arg-

Cys-Xaa4;
``` wherein:
Xaa1 is Ile, Val, Leu, $B^1$-Ile, $B^1$-Val, $B^1$-Leu or a dipeptide comprising Gly-Ile or $B^1$-Gly-Ile, and $B^1$ represents a first blocking moiety;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B^2$; and the two Cys residues are joined by a disulfide bond. In some embodiments, Xaa4 is Leu, Nle, His, or Phe or a dipeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety $B^2$; and the two Cys residues are joined by a disulfide bond.

In other embodiments Xaa1 is absent or is any amino acid or amino acid analog, and Xaa2, Xaa2*, Xaa3, and Xaa4 are as defined above. If Xaa1 is absent, the N-terminal Cys residue may have a blocking moiety $B^1$ attached thereto.

In another embodiment, Xaa4 is any amino acid or amino acid analog and Xaa1, Xaa2, Xaa2*, and Xaa3 are as defined above. In another embodiment Xaa4 is a dipeptide selected from the group consisting of: Thr-Ala and Thr-Asn, wherein the carboxy terminal —OH or the Ala or Asn is optionally replaced by a second blocking moiety $B^2$.

In any of the embodiments of the compstatin analog of SEQ ID NO: 6, Xaa2 may be Trp.

In any of the embodiments of the compstatin analog of SEQ ID NO: 6, Xaa2 may be an analog of Trp comprising a substituted or unsubstituted bicyclic aromatic ring component or two or more substituted or unsubstituted monocyclic aromatic ring components. For example, the analog of Trp may be selected from 2-naphthylalanine (2-Nal), 1-naphthylalanine (1-Nal), 2-indanylglycine carboxylic acid (Ig1), dihydrotrpytophan (Dht), and 4-benzoyl-L-phenylalanine.

In any of the embodiments of the compstatin analog of SEQ ID NO: 6, Xaa2 may be an analog of Trp having increased hydrophobic character relative to Trp. For example, the analog of Trp may be selected from 1-methyltryptophan, 4-methyltryptophan, 5-methyltryptophan, and 6-methyltryptophan. In one embodiment, the analog of Trp is 1-methyltryptophan. In one embodiment, Xaa2 is 1-methyltryptophan, Xaa2* is Trp, Xaa3 is Ala, and the other amino acids are identical to those of compstatin.

In any of the embodiments of the compstatin analog of SEQ ID NO: 6, Xaa2* may be an analog of Trp such as an analog of Trp having increased hydrogen bond forming propensity with C3 relative to Trp, which, in certain embodiments, does not have increased hydrophobic character relative to Trp. In certain embodiments the analog of Trp comprises an electronegative substituent on the indole ring. For example, the analog of Trp may be selected from 5-fluorotryptophan and 6-fluorotryptophan.

In certain embodiments of the invention Xaa2 is Trp and Xaa2* is an analog of Trp having increased hydrogen bond forming propensity with C3 relative to Trp which, in certain embodiments, does not have increased hydrophobic character relative to Trp. In certain embodiments of the compstatin analog of SEQ ID NO: 6, Xaa2 is analog of Trp having increased hydrophobic character relative to Trp such as an analog of Trp selected from 1-methyltryptophan, 4-methyltryptophan, 5-methyltryptophan, and 6-methyltryptophan, and Xaa2* is an analog of Trp having increased hydrogen bond forming propensity with C3 relative to Trp which, in certain embodiments, does not have increased hydrophobic character relative to Trp. For example, in one embodiment Xaa2 is methyltryptophan and Xaa2* is 5-fluorotryptophan.

In certain of the afore-mentioned embodiments, Xaa3 is Ala. In certain of the afore-mentioned embodiments Xaa3 is a single methyl unbranched amino acid, e.g., Abu.

The invention further provides compstatin analogs of SEQ ID NO: 6, as described above, wherein Xaa2 and Xaa2* are independently selected from Trp, analogs of Trp, and other amino acids or amino acid analogs that comprise at least one aromatic ring, and Xaa3 is His, Ala or an analog of Ala, Phe, Trp, an analog of Trp, or another aromatic amino acid or aromatic amino acid analog.

In certain embodiments of the invention the blocking moiety present at the N- or C-terminus of any of the compstatin analogs described herein is any moiety that stabilizes a peptide against degradation that would otherwise occur in mammalian (e.g., human or non-human primate) blood or interstitial fluid. For example, blocking moiety $B^1$ could be any moiety that alters the structure of the N-terminus of a peptide so as to inhibit cleavage of a peptide bond between the N-terminal amino acid of the peptide and the adjacent amino acid. Blocking moiety $B^2$ could be any moiety that alters the structure of the C-terminus of a peptide so as to inhibit cleavage of a peptide bond between the C-terminal amino acid of the peptide and the adjacent amino acid. Any suitable blocking moieties known in the art could be used. In certain embodiments of the invention blocking moiety $B^1$ comprises an acyl group (i.e., the portion of a carboxylic acid that remains following removal of the —OH group). The acyl group typically comprises between 1 and 12 carbons, e.g., between 1 and 6 carbons. For example, in certain embodiments of the invention blocking moiety $B^1$ is selected from the group consisting of: formyl, acetyl, proprionyl, butyryl, isobutyryl, valeryl, isovaleryl, etc. In one embodiment, the blocking moiety $B^1$ is an acetyl group, i.e., Xaa1 is Ac-Ile, Ac-Val, Ac-Leu, or Ac-Gly-Ile.

In certain embodiments of the invention blocking moiety $B^2$ is a primary or secondary amine (—NH$_2$ or —NHR$^1$, wherein R is an organic moiety such as an alkyl group).

In certain embodiments of the invention blocking moiety $B^1$ is any moiety that neutralizes or reduces the positive charge that may otherwise be present at the N-terminus at physiological pH. In certain embodiments of the invention blocking moiety $B^2$ is any moiety that neutralizes or reduces the negative charge that may otherwise be present at the C-terminus at physiological pH.

In certain embodiments of the invention, the compstatin analog is acetylated or amidated at the N-terminus and/or C-terminus, respectively. A compstatin analog may be acetylated at the N-terminus, amidated at the C-terminus, and or both acetylated at the N-terminus and amidated at the C-terminus. In certain embodiments of the invention a compstatin analog comprises an alkyl or aryl group at the N-terminus rather than an acetyl group.

In certain embodiments, the compstatin analog is a compound that comprises a peptide having a sequence:

(SEQ ID NO: 7)
Xaa1-Cys-Val-Xaa2-Gln-Asp-Xaa2*-Gly-Xaa3-His-Arg-Cys-Xaa4;

wherein:
Xaa1 is Ile, Val, Leu, Ac-Ile, Ac-Val, Ac-Leu or a dipeptide comprising Gly-Ile or Ac-Gly-Ile;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of L-Thr, D-Thr, Ile, Val, Gly, Ala, or Asn optionally is replaced by —NH$_2$; and the two Cys residues are joined by a disulfide bond. In some embodiments, Xaa4 is Leu, Nle, His, or Phe or a dipeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety B2; and the two Cys residues are joined by a disulfide bond.

In some embodiments, Xaa1, Xaa2, Xaa2*, Xaa3, and Xaa4 are as described above for the various embodiments of SEQ ID NO: 6. For example, in certain embodiments Xaa2* is Trp. In certain embodiments Xaa2 is an analog of Trp having increased hydrophobic character relative to Trp, e.g., 1-methyltryptophan. In certain embodiments Xaa3 is Ala. In certain embodiments Xaa3 is a single methyl unbranched amino acid.

In certain embodiments of the invention Xaa1 is Ile and Xaa4 is L-Thr.

In certain embodiments of the invention Xaa1 is Ile, Xaa2* is Trp, and Xaa4 is L-Thr.

The invention further provides compstatin analogs of SEQ ID NO: 7, as described above, wherein Xaa2 and Xaa2* are independently selected from Trp, analogs of Trp, other amino acids or aromatic amino acid analogs, and Xaa3 is His, Ala or an analog of Ala, Phe, Trp, an analog of Trp, or another aromatic amino acid or aromatic amino acid analog.

In certain embodiments of any of the compstatin analogs described herein, an analog of Phe is used rather than Phe.

Table 1 provides a non-limiting list of compstatin analogs useful in the present invention. The analogs are referred to in abbreviated form in the left column by indicating specific modifications at designated positions (1-13) as compared to the parent peptide, compstatin. Consistent with usage in the art, "compstatin" as used herein, and the activities of compstatin analogs described herein relative to that of compstatin, refer to the compstatin peptide amidated at the C-terminus. Unless otherwise indicated, peptides in Table 1 are amidated at the C-terminus. Bold text is used to indicate certain modifications. Activity relative to compstatin is based on published data and assays described therein (WO2004/026328, WO2007044668, Mallik, 2005; Katragadda, 2006). Where multiple publications reporting an activity were consulted, the more recently published value is used, and it will be recognized that values may be adjusted in the case of differences between assays. It will also be appreciated that in certain embodiments of the invention the peptides listed in Table 1 are cyclized via a disulfide bond between the two Cys residues when used in the therapeutic compositions and methods of the invention. Alternate means for cyclizing the peptides are also within the scope of the invention. As noted above, in various embodiments of the invention one or more amino acid(s) of a compstatin analog (e.g., any of the compstatin analogs disclosed herein) can be an N-alkyl amino acid (e.g., an N-methyl amino acid). For example, and without limitation, at least one amino acid within the cyclic portion of the peptide, at least one amino acid N-terminal to the cyclic portion, and/or at least one amino acid C-terminal to the cyclic portion may be an N-alkyl amino acid, e.g., an N-methyl amino acid. In some embodiments of the invention, for example, a compstatin analog comprises an N-methyl glycine, e.g., at the position corresponding to position 8 of compstatin and/or at the position corresponding to position 13 of compstatin. In some embodiments, one or more of the compstatin analogs in Table 1 contains at least one N-methyl glycine, e.g., at the position corresponding to position 8 of compstatin and/or at the position corresponding to position 13 of compstatin. In some embodiments, one or more of the compstatin analogs in Table 1 contains at least one N-methyl isoleucine, e.g., at the position corresponding to position 13 of compstatin. For example, a Thr at or near the C-terminal end of a peptide whose sequence is listed in Table 1 or any other compstatin analog sequence may be replaced by N-methyl Ile. As will be appreciated, in some embodiments the N-methylated amino acids comprise N-methyl Gly at position 8 and N-methyl Ile at position 13. In some embodiments the N-methylated amino acids comprise N-methyl Gly in a core sequence such as SEQ ID NO: 3 or SEQ ID NO: 4. In some embodiments the N-methylated amino acids comprise N-methyl Gly in a core sequence such as SEQ ID NO: 5, SEQ ID NO: 6, or SEQ ID NO: 7.

TABLE 1

| Peptide | Sequence | SEQ ID NO: | Activity over compstatin |
|---|---|---|---|
| Compstatin | H-ICVVQDWGHHRCT-CONH2 | 8 | * |
| Ac-compstatin | Ac-ICVVQDWGHHRCT-CONH2 | 9 | 3xmore |
| Ac-V4Y/H9A | Ac-ICVYQDWGAHRCT-CONH2 | 10 | 14xmore |
| Ac-V4W/H9A -OH | Ac-ICVWQDWGAHRCT-COOH | 11 | 27xmore |
| Ac-V4W/H9A | Ac-ICVWQDWGAHRCT-CONH2 | 12 | 45xmore |
| Ac-V4W/H9A/T13dT -OH | Ac-ICVWQDWGAHRCdT-COOH | 13 | 55xmore |
| Ac-V4(2-Nal)/H9A | Ac-ICV**(2-Nal)QDWGA**HRCT-CONH2 | 14 | 99xmore |
| Ac V4(2-Nal)/H9A -OH | Ac-ICV**(2-Nal)QDWGA**HRCT-COOH | 15 | 38xmore |
| Ac V4(1-Nal)/H9A -OH | Ac-ICV**(1-Nal)QDWGA**HRCT-COOH | 16 | 30xmore |
| Ac-V42IgI/H9A | Ac-ICV**(2-IgI)QDWGA**HRCT-CONH2 | 17 | 39xmore |
| Ac-V42IgI/H9A -OH | Ac-ICV**(2-IgI)QDWGA**HRCT-COOH | 18 | 37xmore |
| Ac-V4Dht/H9A -OH | Ac-ICVDhtQDWGAHRCT-COOH | 19 | 5xmore |
| Ac-V4(Bpa)/H9A -OH | Ac-ICV**(Bpa)QDWGA**HRCT-COOH | 20 | 49xmore |
| Ac-V4(Bpa)/H9A | Ac-ICV**(Bpa)QDWGA**HRCT-CONH2 | 21 | 86xmore |
| Ac-V4(Bta)/H9A -OH | Ac-ICV**(Bta)QDWGA**HRCT-COOH | 22 | 65xmore |
| Ac-V4(Bta)/H9A | Ac-ICV**(Bta)QDWGA**HRCT-CONH2 | 23 | 64xmore |
| Ac-V4W/H9(2-Abu) | Ac-ICVWQDWG(2-Abu)HRCT-CONH2 | 24 | 64xmore |
| +G/V4W/H9A +AN -OH | H-GICVWQDWGAHRCTAN-COOH | 25 | 38xmore |

TABLE 1-continued

| Peptide | Sequence | SEQ ID NO: | Activity over compstatin |
|---|---|---|---|
| Ac-V4(5fW)/H9A | Ac-ICV**(5fW)QDWGA**HRCT-CONH$_2$ | 26 | 31xmore |
| Ac-V4(5-MeW)/H9A | Ac-ICV**(5-methyl-W)QDWGA**HRCT-CONH$_2$ | 27 | 67xmore |
| Ac-V4(1-MeW)/H9A | Ac-ICV**(1-methyl-W)QDWGA**HRCT-CONH$_2$ | 28 | 264xmore |
| Ac-V4W/W7(5fW)/H9A | Ac-ICVWQD**(5fW)GA**HRCT-CONH$_2$ | 29 | 121xmore |
| Ac-V4(5fW)/W7(5fW)/H9A | Ac-ICV**(5fW)QD(5fW)GA**HRCT-CONH$_2$ | 30 | NA |
| Ac-V4(5-MeW)/W7(5fW)H9A | Ac-ICV**(5-methyl-W)QD(5fW)GA**HRCT-CONH$_2$ | 31 | NA |
| Ac-V4(1MeW)/W7(5fW)/H9A | Ac-ICV**(1-methyl-W)QD(5fW)GA**HRCT-CONH$_2$ | 32 | 264xmore |
| +G/V4(6fW)/W7(6fW)H9A+N-OH | H-GICV**(6fW)**QD(6fW)GAHRCTN-COOH | 33 | 126xmore |
| Ac-V4(1-formyl-W)/H9A | Ac-ICV**(1-formyl-W)QDWGA**HRCT-CONH$_2$ | 34 | 264xmore |
| Ac-V4(5-methoxy-W)/H9A | Ac-ICV**(1-methyoxy-W)QDWGA**HRCT-CONH$_2$ | 35 | 76xmore |
| G/V4(5f-W)/W7(5fW)/H9A+N-OH | H-GICV**(5fW)QD(5fW)GAHRCTN**-COOH | 36 | 112xmore |

NA = not available

In certain embodiments of the compositions and methods of the invention the compstatin analog has a sequence selected from sequences 9-36. In certain embodiments of the compositions and methods of the invention the compstatin analog has a sequence selected from SEQ ID NOs: 14, 21, 28, 29, 32, 33, 34, and 36. In certain embodiments of the compositions and/or methods of the invention the compstatin analog has a sequence selected from SEQ ID NOs: 30 and 31. In one embodiment of the compositions and methods of the invention the compstatin analog has a sequence of SEQ ID NO: 28. In one embodiment of the compositions and methods of the invention the compstatin analog has a sequence of SEQ ID NO: 32. In one embodiment of the compositions and methods of the invention the compstatin analog has a sequence of SEQ ID NO: 34. In one embodiment of the compositions and methods of the invention the compstatin analog has a sequence of SEQ ID NO: 36.

In some embodiments a blocking moiety $B^1$ comprises an amino acid, which may be represented as Xaa0. In some embodiments blocking moiety $B^2$ comprises an amino acid, which may be represented as XaaN. In some embodiments blocking moiety $B^1$ and/or $B^2$ comprises a non-standard amino acid, such as a D-amino acid, N-alkyl amino acid (e.g., N-methyl amino acid). In some embodiments a blocking moiety $B^1$ and/or $B^2$ comprises a non-standard amino acid that is an analog of a standard amino acid. In some embodiments an amino acid analog comprises a lower alkyl, lower alkoxy, or halogen substituent, as compared with a standard amino acid of which it is an analog. In some embodiments a substituent is on a side chain. In some embodiments a substituent is on an alpha carbon atom. In some embodiments, a blocking moiety $B^1$ comprising an amino acid, e.g., a non-standard amino acid, further comprises a moiety $B^{1a}$. For example, blocking moiety $B^1$ may be represented as $B^{1a}$-Xaa0. In some embodiments $B^{1a}$ neutralizes or reduces a positive charge that may otherwise be present at the N-terminus at physiological pH. In some embodiments $B^{1a}$ comprises or consists of, e.g., an acyl group that, e.g., comprises between 1 and 12 carbons, e.g., between 1 and 6 carbons. In certain embodiments blocking moiety $B^{1a}$ is selected from the group consisting of: formyl, acetyl, proprionyl, butyryl, isobutyryl, valeryl, isovaleryl, etc. In some embodiments, a blocking moiety $B^2$ comprising an amino acid, e.g., a non-standard amino acid, may further comprise a moiety $B^{2a}$. For example, blocking moiety $B^2$ may be represented as XaaN-$B^{2a}$, where N represents the appropriate number for the amino acid (which will depend on the numbering used in the rest of the peptide). In some embodiments $B^{2a}$ neutralizes or reduces a negative charge that may otherwise be present at the C-terminus at physiological pH. In some embodiments $B^{2a}$ comprises or consists of a primary or secondary amine (e.g., NH$_2$). It will be understood that a blocking activity of moiety $B^{1a}$-Xaa0 and/or XaaN-$B^{2a}$ may be provided by either or both components of the moiety in various embodiments. In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid residue may be at least as important as a contribution to blocking activity. For example, in some embodiments Xaa0 and/or XaaN in $B^{1a}$-Xaa0 and/or XaaN-$B^{2a}$ may function mainly to increase affinity or activity of the compound, while $B^{1a}$ and/or $B^{2a}$ may inhibit digestion of and/or neutralize a charge of the peptide. In some embodiments a compstatin analog comprises the amino acid sequence of any of SEQ ID NOs: 5-36, wherein SEQ ID NOs: 5-36 is further extended at the N- and/or C-terminus. In some embodiments, the sequence may be represented as $B^{1a}$-Xaa0-SEQUENCE-XaaN-$B^{2a}$, where SEQUENCE represents any of SEQ ID NOs: 5-36, wherein $B^{1a}$ and $B^{2a}$ may independently be present or absent. For example, in some embodiments a compstatin analog comprises (SEQ ID NO: 72)
$B^{1a}$-Xaa0-X'aa1-X'aa2-X'aa3-X'aa4-Gln-Asp-Xaa-Gly-X"aa1-X"aa2-X"aa3-X"aa4-X"aa5-XaaN-$B^{2a}$, where X'aa1-X'aa2-X'aa3-X'aa4, Xaa, X"aa1, X"aa2, X"aa3, X"aa4, and X"aa5 are as set forth above for SEQ ID NO: 5.

In some embodiments a compstatin analog comprises (SEQ ID NO: 73)
B$^{1a}$-Xaa0-Xaa1-Cys-Val-Xaa2-Gln-Asp-Xaa2*-Gly-Xaa3-

His-Arg-Cys-Xaa4-XaaN-B$^{2a}$, where Xaa1, Xaa2, Xaa2*, Xaa3, and Xaa4 are as set forth above for SEQ ID NO: 6 or
wherein Xaa1, Xaa2, Xaa2*, Xaa3, and Xaa4 are as set forth for SEQ ID NO: 6 or SEQ ID NO: 7.

In some embodiments a compstatin analog comprises (SEQ ID NO: 74)
B$^{1a}$-Xaa0-Xaa1-Xaa2-Xaa3-Xaa4-Xaa5-Xaa6-Xaa7-Xaa8-

Xaa9-Xaa10-Xaa11-Xaa12-Xaa13-XaaN-B$^{2a}$ wherein Xaa1, Xaa2, Xaa3, Xaa4, Xaa5, Xaa6, Xaa7, Xaa8, Xaa9, Xaa10, Xaa11, Xaa12, and Xaa13 are identical to amino acids at positions 1-13 of any of SEQ ID NOs: 9-36.

In some embodiments Xaa0 and/or XaaN in any compstatin analog sequence comprises an amino acid that comprises an aromatic ring having an alkyl substituent at one or more positions. In some embodiments an alkyl substituent is a lower alkyl substituent. For example, in some embodiments an alkyl substituent is a methyl or ethyl group. In some embodiments a substituent is located at any position that does not destroy the aromatic character of the compound. In some embodiments a substituent is located at any position that does not destroy the aromatic character of a ring to which the substituent is attached. In some embodiments a substituent is located at position 1, 2, 3, 4, or 5. In some embodiments Xaa0 comprises an O-methyl analog of tyrosine, 2-hydroxyphenylalanine or 3-hydroxyphenylalanine. For purposes of the present disclosure, a lower case "m" followed by a three letter amino acid abbreviation may be used to specifically indicate that the amino acid is an N-methyl amino acid. For example, where the abbreviation "mGly" appears herein, it denotes N-methyl glycine (also sometimes referred to as sarcosine or Sar). In some embodiments Xaa0 is or comprises mGly, Tyr, Phe, Arg, Trp, Thr, Tyr(Me), Cha, mPhe, mVal, mIle, mAla, DTyr, DPhe, DArg, DTrp, DThr, DTyr(Me), mPhe, mVal, mIle, DAla, or DCha. For example, in some embodiments a compstatin analog comprises a peptide having a sequence (SEQ ID NO: 75)
B$^1$-Ile-[Cys-Val-Trp(Me)-Gln-Asp-Trp-mGly-Ala-His- Arg-Cys]-mIle-B$^2$
or (SEQ ID NO: 76)
B$^1$-Ile-[Cys-Val-Trp(Me)-Gln-Asp-Trp-mGly-Ala-His- Arg-Cys]-mIle-B$^2$.

The two Cys residues are joined by a disulfide bond in the active compounds. In some embodiments the peptide is acetylated at the N-terminus and/or amidated at the C-terminus. In some embodiments B$^1$ comprises B$^{1a}$-Xaa0 and/or B$^2$ comprises XaaN-B$^{2a}$, as described above. For example, in some embodiments B$^1$ comprises or consists of Gly, mGly, Tyr, Phe, Arg, Trp, Thr, Tyr(Me), mPhe, mVal, mIle, mAla, DTyr, DPhe, DTrp, DCha, DAla and B$^2$ comprises NH$_2$, e.g., a carboxy terminal —OH of mIle is replaced by NH$_2$. In some embodiments B$^1$ comprises or consists of mGly, Tyr, DTyr, or Tyr(Me) and B$^2$ comprises NH$_2$, e.g., a carboxy terminal —OH of mIle is replaced by NH$_2$. In some embodiments an Ile at position Xaa1 is replaced by Gly. Complement inhibition potency and/or C3b binding parameters of selected compstatin analogs are described in WO/2010/127336 (PCT/US2010/033345) and/or in Qu, et al., Immunobiology (2012), doi:10.1016/j.imbio.2012.06.003.

In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid or amino acid analog may be more significant than a blocking activity.

In certain embodiments of the compositions and methods of the invention the compstatin analog has a sequence as set forth in Table 1, but where the Ac-group is replaced by an alternate blocking moiety B$^1$, as described herein. In some embodiments the —NH$_2$ group is replaced by an alternate blocking moiety B$^2$, as described herein.

In one embodiment, the compstatin analog binds to substantially the same region of the β chain of human C3 as does compstatin. In one embodiment the compstatin analog is a compound that binds to a fragment of the C-terminal portion of the β chain of human C3 having a molecular weight of about 40 kDa to which compstatin binds (Soulika, A. M., et al., Mol. Immunol., 35:160, 1998; Soulika, A. M., et al., Mol. Immunol. 43(12):2023-9, 2006). In certain embodiments the compstatin analog is a compound that binds to the binding site of compstatin as determined in a compstatin-C3 structure, e.g., a crystal structure or NMR-derived 3D structure. In certain embodiments the compstatin analog is a compound that could substitute for compstatin in a compstatin-C3 structure and would form substantially the same intermolecular contacts with C3 as compstatin. In certain embodiments the compstatin analog is a compound that binds to the binding site of a peptide having a sequence set forth in Table 1, e.g., SEQ ID NO: 14, 21, 28, 29, 32, 33, 34, or 36, 37, 72, 73, 74, 75, or 76 or another compstatin analog sequence disclosed herein in a peptide-C3 structure, e.g., a crystal structure. In certain embodiments the compstatin analog is a compound that binds to the binding site of a peptide having SEQ ID NO: 30 or 31 in a peptide-C3 structure, e.g., a crystal structure. In certain embodiments the compstatin analog is a compound that could substitute for the peptide of SEQ ID NO: 9-36, e.g., a compound that could substitute for the peptide of SEQ ID NO: 14, 21, 28, 29, 32, 33, 34, or 36, 37, 72, 73, 74, 75, or 76 or another compstatin analog sequence disclosed herein in a peptide-C3 structure and would form substantially the same intermolecular contacts with C3 as the peptide. In certain embodiments the compstatin analog is a compound that could substitute for the peptide of SEQ ID NO: 30 or 31 in a peptide-C3 structure and would form substantially the same intermolecular contacts with C3 as the peptide.

One of ordinary skill in the art will readily be able to determine whether a compstatin analog binds to a fragment of the C-terminal portion of the R3 chain of C3 using routine experimental methods. For example, one of skill in the art could synthesize a photocrosslinkable version of the compstatin analog by including a photo-crosslinking amino acid such as p-benzoyl-L-phenylalanine (Bpa) in the compound, e.g., at the C-terminus of the sequence (Soulika, A. M., et al, supra). Optionally additional amino acids, e.g., an epitope tag such as a FLAG tag or an HA tag could be included to facilitate detection of the compound, e.g., by Western blotting. The compstatin analog is incubated with the fragment and crosslinking is initiated. Colocalization of the compstatin analog and the C3 fragment indicates binding. Surface plasmon resonance may also be used to determine whether a compstatin analog binds to the compstatin binding site on C3 or a fragment thereof. One of skill in the art would be able to use molecular modeling software programs to predict whether a compound would form substantially the same intermolecular contacts with C3 as would compstatin or a peptide having the sequence of any of the peptides in Table 1, e.g., SEQ ID NO: 14, 21, 28, 29, 32, 33, 34, or 36, or in some embodiments SEQ ID NO: 30 or 31, 37, 72, 73, 74, 75, or 76 or another compstatin analog sequence disclosed herein.

Compstatin analogs may be prepared by various synthetic methods of peptide synthesis known in the art via condensation of amino acid residues, e.g., in accordance with conventional peptide synthesis methods, may be prepared by expression in vitro or in living cells from appropriate nucleic acid sequences encoding them using methods known in the art. For example, peptides may be synthesized using standard solid-phase methodologies as described in Malik, supra, Katragadda, supra, WO2004026328, and/or WO2007062249. Potentially reactive moieties such as amino and carboxyl groups, reactive functional groups, etc., may be protected and subsequently deprotected using various protecting groups and methodologies known in the art. See, e.g., "Protective Groups in Organic Synthesis", $3^{rd}$ ed. Greene, T. W. and Wuts, P. G., Eds., John Wiley & Sons, New York: 1999. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass and/or disulfide bond formation. See, e.g., Mallik, 2005, and Katragadda, 2006.

A compstatin analog, optionally linked to a cell penetrating moiety, can be modified by addition of a molecule such as polyethylene glycol (PEG) or similar molecules to stabilize the compound, reduce its immunogenicity, increase its lifetime in the body, increase or decrease its solubility, and/or increase its resistance to degradation. Methods for pegylation are well known in the art (Veronese, F. M. & Harris, Adv. Drug Deliv. Rev. 54, 453-456, 2002; Davis, F. F., Adv. Drug Deliv. Rev. 54, 457-458, 2002); Hinds, K. D. & Kim, S. W. *Adv. Drug Deliv. Rev.* 54, 505-530 (2002; Roberts, M. J., Bentley, M. D. & Harris, J. M. *Adv. Drug Deliv. Rev.* 54, 459-476; 2002); Wang, Y. S. et al. *Adv. Drug Deliv. Rev.* 54, 547-570, 2002). A wide variety of polymers such as PEGs and modified PEGs, including derivatized PEGs to which polypeptides can conveniently be attached are described in Nektar Advanced Pegylation 2005-2006 Product Catalog, Nektar Therapeutics, San Carlos, Calif., which also provides details of appropriate conjugation procedures. In some embodiments a compstatin analog is fused to the Fc domain of an immunoglobulin or a portion thereof. In some other embodiments a compstatin analog is conjugated to an albumin moiety or to an albumin binding peptide. Thus in some embodiments a CPCA is modified with one or more polypeptide or non-polypeptide components, e.g., the compstatin analog is pegylated or conjugated to another moiety. In some embodiments the component is not the Fc domain of an immunoglobulin or a portion thereof. A compstatin analog can be provided as a multimer or as part of a supramolecular complex, which can include either a single molecular species or multiple different species (e.g., multiple different analogs).

In some embodiments, a compstatin analog is a multivalent compound comprising a plurality of cell-penetrating compstatin analog moieties covalently or noncovalently linked to a polymeric backbone or scaffold. The cell-penetrating compstatin analog moieties can be identical or different. In certain embodiments of the invention the multivalent compound comprises multiple instances, or copies, of a single cell-penetrating compstatin analog moiety. In other embodiments of the invention the multivalent compound comprises one or more instances of each of two of more non-identical cell-penetrating compstatin analog moieties, e.g., 3, 4, 5, or more different cell-penetrating compstatin analog moieties. In certain embodiments of the invention the number of cell-penetrating compstatin analog moieties ("n") is between 2 and 6. In other embodiments of the invention n is between 7 and 20. In other embodiments of the invention n is between 20 and 100. In other embodiments n is between 100 and 1,000. In other embodiments of the invention n is between 1,000 and 10,000. In other embodiments n is between 10,000 and 50,000. In other embodiments n is between 50,000 and 100,000. In other embodiments n is between 100,000 and 1,000,000.

The cell-penetrating compstatin analog moieties may be attached directly to the polymeric scaffold or may be attached via a linking moiety that connects the compstatin analog moiety to the polymeric scaffold. The linking moiety may be attached to a single cell-penetrating compstatin analog moiety and to the polymeric scaffold. Alternately, a linking moiety may have multiple cell-penetrating compstatin analog moieties joined thereto so that the linking moiety attaches multiple cell-penetrating compstatin analog moieties to the polymeric scaffold. In some embodiments the polymeric scaffold may further have at least some compstatin analog moieties that do not comprise a CPM attached thereto. In some embodiments at least some compstatin analog moieties, e.g., cell-penetrating compstatin analog moieties, are attached via a cleavable linker. The linker may be hydrolysable or susceptible to enzyme-mediated cleavage in the blood or extravascular space, wherein such cleavage may release active compstatin analogs, e.g., cell-penetrating compstatin analogs. Released cell-penetrating compstatin analogs may be internalized by cells, e.g., at or near their site of release or may be carried in the circulatory system to be internalized by cells at distant locations or in the blood or lymph.

In some embodiments, the compstatin analog comprises an amino acid having a side chain comprising a primary or secondary amine, e.g., a Lys residue. For example, a Lys residue, or a sequence comprising a Lys residue, is added at the N-terminus and/or C-terminus of the compstatin analog. In some embodiments, the Lys residue is separated from the cyclic portion of the compstatin analog by a rigid or flexible spacer. The spacer may, for example, comprise a substituted or unsubstituted, saturated or unsaturated alkyl chain, oligo (ethylene glycol) chain, and/or other moieties, e.g., as described in Section VI with regard to linkers. The length of the chain may be, e.g., between 2 and 20 carbon atoms. In other embodiments the spacer is a peptide. The peptide spacer may be, e.g., between 1 and 20 amino acids in length, e.g., between 4 and 20 amino acids in length. Suitable spacers can comprise or consist of multiple Gly residues, Ser residues, or both, for example. Optionally, the amino acid having a side chain comprising a primary or secondary amine and/or at least one amino acid in a spacer is a D-amino acid. Any of a variety of polymeric backbones or scaffolds could be used. For example, the polymeric backbone or scaffold may be a polyamide, polysaccharide, polyanhydride, polyacrylamide, polymethacrylate, polypeptide, polyethylene oxide, or dendrimer. Suitable methods and polymeric backbones are described, e.g., in WO98/46270 (PCT/US98/07171) or WO98/47002 (PCT/US98/06963). In one embodiment, the polymeric backbone or scaffold comprises multiple reactive functional groups, such as carboxylic acids, anhydride, or succinimide groups. The polymeric backbone or scaffold is reacted with the compstatin analogs. In one embodiment, the compstatin analog comprises any of a number of different reactive functional groups, such as carboxylic acids, anhydride, or succinimide groups, which are reacted with appropriate groups on the polymeric backbone. Alternately, monomeric units that could be joined to one another to form a polymeric backbone or scaffold are first reacted with the compstatin analogs and the resulting monomers are polymerized. In another embodiment, short chains are prepolymerized, functionalized, and then a mixture of short chains of different composition are assembled into longer polymers.

V. Compstatin Mimetis

The structure of compstatin is known in the art, and NMR structures for a number of compstatin analogs having higher activity than compstatin are also known (Malik, supra). Structural information may be used to design compstatin mimetics.

In one embodiment, the compstatin mimetic is any compound that competes with compstatin or any compstatin analog (e.g., a compstatin analog whose sequence is set forth in Table 1) for binding to C3 or a fragment thereof (such as a 40 kD fragment of the β chain to which compstatin binds). In some embodiments, the compstatin mimetic has an activity equal to or greater than that of compstatin. In some embodiments, the compstatin mimetic is more stable, orally available, or has a better bioavailability than compstatin. The compstatin mimetic may be a peptide, nucleic acid, or small molecule. In certain embodiments the compstatin mimetic is a compound that binds to the binding site of compstatin as determined in a compstatin-C3 structure, e.g., a crystal structure or a 3-D structure derived from NMR experiments. In certain embodiments the compstatin mimetic is a compound that could substitute for compstatin in a compstatin-C3 structure and would form substantially the same intermolecular contacts with C3 as compstatin. In certain embodiments the compstatin mimetic is a compound that binds to the binding site of a peptide having a sequence set forth in Table 1, e.g., SEQ ID NO: 14, 21, 28, 29, 32, 33, 34, or 36 or in certain embodiments SEQ ID NO: 30 or 31 or other compstatin analog sequence, in a peptide-C3 structure. In certain embodiments the compstatin mimetic is a compound that could substitute for a peptide having a sequence set forth in Table 1, e.g., SEQ ID NO: 14, 21, 28, 29, 32, 33, 34, or 36 or in certain embodiments SEQ ID NO: 30 or 31 or other compstatin analog sequence, in a peptide-C3 structure and would form substantially the same intermolecular contacts with C3 as the peptide. In certain embodiments the compstatin mimetic has a non-peptide backbone but has side chains arranged in a sequence designed based on the sequence of compstatin.

One of skill in the art will appreciate that once a particular desired conformation of a short peptide has been ascertained, methods for designing a peptide or peptidomimetic to fit that conformation are well known. See, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, PP. 429-455), Eguchi M, Kahn M., Mini Rev Med Chem., 2(5):447-62, 2002. Of particular relevance to the present invention, the design of peptide analogs may be further refined by considering the contribution of various side chains of amino acid residues, e.g., for the effect of functional groups or for steric considerations as described in the art for compstatin and analogs thereof, among others.

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce and utilize C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of a peptide that possesses much the same backbone conformational features and/or other functionalities, so as to be sufficiently similar to the exemplified peptides to inhibit complement activation. More generally, a compstatin mimetic is any compound that would position pharmacophores similarly to their positioning in compstatin, even if the backbone differs.

The use of peptidomimetics for the development of high-affinity peptide analogs is well known in the art. Assuming rotational constraints similar to those of amino acid residues within a peptide, analogs comprising non-amino acid moieties may be analyzed, and their conformational motifs verified, by means of the Ramachandran plot (Hruby & Nikiforovich 1991), among other known techniques.

One of skill in the art will readily be able to establish suitable screening assays to identify additional compstatin mimetics and to select those having desired inhibitory activities. For example, compstatin or an analog thereof could be labeled (e.g., with a radioactive or fluorescent label) and contacted with C3 in the presence of different concentrations of a test compound. The ability of the test compound to diminish binding of the compstatin analog to C3 is evaluated. A test compound that significantly diminishes binding of the compstatin analog to C3 is a candidate compstatin mimetic. For example, a test compound that diminishes steady-state concentration of a compstatin analog-C3 complex, or that diminishes the rate of formation of a compstatin analog-C3 complex by at least 25%, or by at least 50%, is a candidate compstatin mimetic. One of skill in the art will recognize that a number of variations of this screening assay may be employed. Compounds to be screened include natural products, libraries of aptamers, phage display libraries, compound libraries synthesized using combinatorial chemistry, etc. The invention encompasses synthesizing a combinatorial library of compounds based upon the core sequence described above and screening the library to identify compstatin mimetics. Any of these methods could also be used to identify new compstatin analogs having higher inhibitory activity than compstatin analogs tested thus far. It will be appreciated that compstatin mimetics could be used in cell-penetrating compstatin analogs of the invention, and the invention provides such cell-penetrating compstatin analog mimetics.

VI. Cell-Penetrating Compstatin Analogs

The invention provides a variety of cell-penetrating compstatin analogs. In some aspects, a cell-penetrating compstatin analog comprises a compound of formula A-L-M, wherein A is a moiety that comprises a cell penetrating moiety (CPM), L is an optionally present linking portion, and M comprises a compstatin analog moiety. The compstatin analog moiety can comprise any compstatin analog, e.g., any compstatin analog described above, in various embodiments. Formula A-L-M encompasses embodiments in which A-L is present at the N-terminus of the compstatin analog moiety, embodiments in which A-L is present at the C-terminus of the compstatin analog moiety, embodiments in which A-L is attached to a side chain of an amino acid of the compstatin analog moiety, and embodiments where the same or different A-Ls are present at both ends of M. It will be appreciated that when certain compstatin analog(s) are present as a compstatin analog moiety in a compound of formula A-L-M, a functional group of the compstatin analog will have reacted with a functional group of L to form a covalent bond to A or L. For example, a cell-penetrating compstatin analog in which the compstatin analog moiety comprises a compstatin analog that contains an amino acid with a side chain containing a primary amine ($NH_2$) group (which compstatin analog can be represented by formula $R^1$—($NH_2$)), can have a formula $R^1$—NH-L-A in which a new covalent bond to L (e.g., N—C) has been formed and a hydrogen lost. Thus the term "compstatin analog moiety" includes molecular structures in which at least one atom of a compstatin analog participates in a covalent bond with a second moiety, which may, e.g., modification of a side chain. Similar considerations apply to compstatin analog moieties present in multivalent compound described above. In some embodiments, a blocking moiety at the N-terminus or C-terminus of a compstatin analog, e.g., a compstatin analog described in Section IV above, is replaced by A-L in the structure of a cell-penetrating compstatin analog. In some embodiments, A or L comprises a blocking moiety. In some embodiments, a cell-penetrating compstatin analog has a molar activity of at least about 10%, 20%, or 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a cell penetrating moiety. In some embodiments in which a cell-penetrating compstatin analog comprises multiple compstatin analog moieties, the molar activity of the cell-penetrating compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties.

The term "cell penetrating moiety" (CPM) refers to an entity that can be internalized by a living cell and is capable of delivering or enhancing delivery of a cargo to the interior of the cell. A cargo may be, e.g., a peptide, protein, nucleic acid, small molecule, or nanoparticle or other entity of similar dimensions. The term "internalized by a cell" refers to gaining access to the interior (inside) of the cell. The "interior of a cell" refers to locations within the boundary of the plasma membrane. For purposes hereof, membrane-bound intracellular vesicles and their contents are considered to be inside the cell. Internalization may occur via endocytotic processes and/or non-endocytotic processes (e.g., pinocytosis, direct penetration, and transporter-mediated uptake) in various embodiments. Entities that are contained in vesicles inside the cell, e.g., following endocytosis or pinocytosis, may be released from such vesicles and enter the cytoplasm by various routes. For example, such entities may undergo retrograde transport from vesicles to the interior of the endoplasmic reticulum (ER) and translocate from there into the cytoplasm or may directly translocate across vesicular membranes.

In some embodiments a CPM is capable of entering cells of at least 5 different cell types. In some embodiments a CPM is capable of entering epithelial cells. It will be appreciated that "epithelium" refers to layers of cells that line the cavities and surfaces of numerous structures in the body and is the type of tissue from which many glands are at least partly formed. Epithelial tissues include, for example, tissues found in the respiratory tract (e.g., nasal passages, trachea, bronchioles, bronchi, lungs), skin, gastrointestinal tract (e.g., stomach, small intestine, colon), liver, biliary tract, pancreas, kidneys, ovaries, breast, prostate, cervix, uterus, bladder, ureter, testes, exocrine glands, endocrine glands, blood vessels, lymph vessels, etc. In some embodiments a CPM is capable of entering respiratory epithelial cells. In some embodiments a CPM is capable of entering retinal pigment epithelial (RPE) cells. In some embodiments a CPM is capable of entering endothelial cells. In some embodiments a CPM is capable of entering immune system cells, e.g., lymphocytes (B cells, T cells, NK cells), granulocytes (e.g., neutrophils, eosinophils, basophils), mast cells, monocytes, and/or macrophages. In some embodiments a CPM is capable of entering nervous system cells, e.g., neural cells, glial cells.

In some embodiments a cell penetrating moiety comprises a cell penetrating peptide (CPP), sometimes referred to as a "protein transduction domain". Such peptides can be internalized by a cell and delivering or enhancing delivery of a cargo to the interior of the cell. Naturally occurring CPPs occur in a number of different naturally occurring proteins including various viral proteins, animal proteins (e.g., insect, mammalian), and plant proteins. CPPs have been identified in certain secreted proteins, transcription factors, venoms, and toxins, among others. They are typically linear sequences ranging from about 6 to about 30 amino acids in length that are able to mediate transport of the protein in which they occur into cells. In some embodiments a CPP comprises or consists of such a naturally occurring amino acid sequence. In some embodiments a CPP comprises or consists of a non-naturally occurring amino acid sequence, i.e., an amino acid sequence not known to occur in nature either alone or as part of a longer polypeptide. A non-naturally occurring CPP may comprise a variant of a naturally occurring CPP, a chimeric sequence comprising portions of two or more naturally occurring CPPs, or a sequence designed to have one or more properties of a naturally occurring CPP wherein such property correlates with and/or is believed to be at least in part responsible for the ability of the naturally occurring CPP to be internalized by a cell and/or to enter a particular subcellular compartment (e.g., the cytoplasm) or organelle. In some embodiments a CPP is derived from a different CPP or from a polypeptide (e.g., a naturally occurring polypeptide able to enter cells). For purposes of this disclosure, a CPP is considered to be "derived from" a particular polypeptide if the CPP (i) comprises or consists of a fragment of the polypeptide, wherein the fragment is at least 6 amino acids long, e.g., 6, 7, 8, 9, 10, 11, 12, 13, 14, 15, 16, 17, 18, 19, 20, 21, 22, 23, 24, 25, 26, 27, 28, 29, or 30 amino acids long; (ii) comprises or consists of a peptide that is at least 70% identical to a fragment of the polypeptide that is at least 10 amino acids long; (iii) comprises or consists of a peptide whose sequence can be generated by making no more than 3 alterations (which may be substitution(s), deletion(s), or addition(s), in any combination) to the sequence of a fragment of the protein that is at least 10 amino acids long; (iv) comprises or consists of a peptide that is a cyclized, circularly permuted, inverso, retro, or retro-inverso version of a peptide as described in any of (i), (ii), or (iii). In certain embodiments any of the peptides of (i), (ii), (iii), or (iv) may have one or more modifications to one or more side chains, backbone, and/or to an N- or C-terminus. As will be appreciated, an inverso version of a peptide is the D-enantiomer of the peptide and has the same sequence as the peptide but is composed of D-amino acids and has a mirror conformation; a retro version of a peptide consists of the same sequence of L amino acids but in reverse order, a retro-inverso version of a peptide consists of D-amino acids in the reverse order and is the D-retro-enantiomer of the peptide. In some embodiments a cell penetrating moiety may be related to a CPP in that the CPM is designed, generated, derived, etc., from or based on the CPP, e.g., using a design principle or experimental approach intended to preserve, mimic, enhance, or select for ability to be internalized by a cell and/or to enter a particular subcellular compartment (e.g., the cytoplasm or an organelle).

In general, many CPPs may be broadly classified as cationic, hydrophobic, or amphipathic peptides. The term "cationic peptide" refers to a peptide that has a positive average net charge when in water at a physiological pH, e.g., a pH of 7.0-7.4. In some embodiments a CPP comprises or consists of a cationic peptide at least 6 amino acids long, e.g., 6-12, 12-20, or 20-30 amino acids long. In some embodiments at least 30%, 40%, 50%, 60%, 70%, 80%, 90%, or 100% of the amino acids in a cationic peptide are basic amino acids. In some embodiments a basic amino acid comprises a side chain that has a $pK_a$ of at least 8.0, at least 9.0, or at least 10.0 in water. In general, a basic amino acid may be a standard amino acid or a non-standard amino acid. In some embodiments a basic amino acid comprises a side chain comprising a primary or secondary amine or a guanidinium group. In some embodiments at least 30%, 40%, 50%, 60%, 70%, 80%, 90%, or 100% of the amino acids in a cationic peptide are independently selected from arginine, ornithine, lysine, and basic analogs of any of these. In some embodiments at least 30%, 40%, 50%, 60%, 70%, 80%, 90%, or 100% of the amino acids in a cationic peptide are independently selected from arginine, lysine, and basic analogs of either of these. In some embodiments at least 30%, 40%, 50%, 60%, 70%, 80%, 90%, or 100% of the amino acids in a cationic peptide are arginine or lysine. In some embodiments at least 30%, 40%, 50%, 60%, 70%, 80%, 90%, or 100% of the amino acids in a cationic peptide are arginine. A basic analog of a basic amino acid may comprise substituent(s) at any one or more positions, so long as the resulting compound retains a net positive charge. In some embodiments a substituent is a lower alkyl or lower alkanoyl group.

In some embodiments a CPP comprises a hydrophobic peptide at least 6 amino acids long, e.g., 6-12, 12-20, or 20-30 amino acids long. In general, a hydrophobic peptide is composed predominantly of hydrophobic and neutral amino acids. In some embodiments a hydrophobic peptide comprises at least 50%, 60%, 70%, 80%, 90%, or more hydrophobic and neutral amino acids. A neutral amino acid may be selected from alanine, isoleucine, leucine, valine, phenylalanine, tryptophan, tyrosine, cysteine, methionine, threonine, glycine, serine, glutamine, and neutral analogs thereof. Unless otherwise indicated or evident from the context or use, "neutral" refers to neutral (uncharged) within a physiological pH range, e.g., between 7.0 and 7.4. A neutral analog of an amino acid may comprise a neutral substituent as compared with the amino acid of which it is an analog. A hydrophobic amino acid may be selected from alanine, isoleucine, leucine, valine, phenylalanine, tryptophan, tyrosine, cysteine, methionine, and hydrophobic analogs of any of the foregoing nine amino acids, wherein the hydrophobicity of a hydrophobic analog falls within the range of hydrophobicities of the foregoing nine amino acids or exceeds the upper limit of the range when measured using the same or substantially the same method and conditions as used to determine the range. In some embodiments a hydrophobic analog is an amino acid that has increased hydrophobic character as compared with the amino acid of which it is an analog. Increased hydrophobic character may, for example, result from presence of one or more additional hydrophobic groups or atoms in a side chain. In general, a hydrophobic group may be unsubstituted or substituted, provided that the substituent(s), if present, are sufficiently hydrophobic so as to not reduce the overall hydrophobicity of the amino acid below the lower limit of the aforementioned range. In some embodiments a hydrophobic group comprises or consists of an alkyl group, alkoxy group, or monocyclic or bicyclic aromatic ring. In some embodiments an alkyl group is a lower alkyl, e.g., methyl or ethyl. In some embodiments an alkoxy group is a lower alkoxy, e.g., methoxy or ethoxy. In some embodiments increased hydrophobic character results from presence of one or more additional —$CH_2$— groups in an alkyl chain. In some embodiments a hydrophobic group or substituent comprises a halogen. In some embodiments a hydrophobic substituent is present at one or more atoms that form part of the peptide backbone. In some embodiments a hydrophobic peptide comprises at least a portion of a signal sequence. A number of examples of hydrophobic peptides are provided herein. Peptide or amino acid hydrophobicity may be measured using a variety of methods. In some embodiments reverse phase HPLC may be used. For example, RP-HPLC may be performed using a C8 column with 10 mM aqueous $NaH_2PO_4$, adjusted to pH 7 with NaOH and containing 50 mM NaCl as eluent A and using 50% acetonitrile containing 50 mM NaCl as eluent B. When comparing hydrophobicities of two or more peptides or amino acids, the hydrophobicities may be measured using the same method and same or approximately the same conditions (e.g., pH, salt concentration, buffer) may be used, or different methods that are expected to give approximately the same results may be used. In some embodiments a hydrophobic peptide comprises at least a portion of a signal sequence (discussed further below).

The term "amphipathic peptide" refers to a peptide that possesses at least one hydrophilic region and at least one hydrophobic region. In some embodiments the hydrophilic and hydrophobic regions are present in distinct portions of the peptide sequence (primary structure). In some embodiments a CPP comprises an amphipathic peptide at least 6 amino acids long e.g., 6-9, 9-12, 12-20, or 20-30 amino acids long. In some embodiments the sequence of an amphipathic peptide comprises at least one sequence at least 4 amino acids long composed predominantly of hydrophilic amino acids and at least one sequence at least one sequence at least 4 amino acids long composed predominantly of hydrophobic amino acids. In some embodiments the amphiphilic character of an amphipathic peptide results at least in part from its secondary structure. For example, in some embodiments an amphipathic peptide comprises a helix, e.g., an alpha helix, having predominantly hydrophilic amino acid residues aligned along one side of the helix and predominantly hydrophobic amino acid residues aligned along the opposite side. The term "predominantly" is used to mean at least 75%, 80%, 85%, 90%, 95%, or 100%. Presence of a helix, e.g., an alpha helix, may be determined experimentally (e.g., spectrophotometrically, e.g., by circular dichroism spectroscopy in the far-ultraviolet (far-UV) spectral region (170-250 nm) or infrared spectroscopy), or may alternately or additionally be predicted using various computer programs or algorithms, such as the Chou-Fasman algorithm (Chou, P. Y., et al. (1974) *Biochemistry*, 13: 222-45) or a modified version thereof (see, e.g., Chen H, Gu F, Huang Z (2006). "Improved Chou-Fasman method for protein secondary structure prediction". BMC Bioinformatics 7 (Suppl 4): S14), or other suitable algorithms or programs known in the art.

In some embodiments a CPP is both cationic and amphipathic.

In some embodiments a CPP comprises or is derived from at least a portion of a signal sequence. Signal sequences, also referred to as signal peptides, are typically between 5 to about 30 amino acids long and are found in most polypeptides that are destined for the secretory pathway. Such proteins include proteins that are secreted from the cell or reside within certain organelles (the endoplasmic reticulum, golgi, or endosomes) or are inserted into various cellular membranes (e.g., the plasma membrane). Examples of secreted proteins include, e.g., various growth factors, cytokines, clotting factors, and other proteins found in the blood or extracellular space. Examples of membrane proteins include, e.g., receptors, channels, transporters, and various proteins that interact with such proteins. In secreted proteins and a number of transmembrane proteins, a signal sequence is typically located at the N-terminus and is cleaved from the nascent polypeptide once it has been translocated into the membrane of the ER (in eukaryotes) or plasma membrane (in prokaryotes) by signal peptidase. A polypeptide that comprise a signal sequence that (at least under typical conditions) is subsequently removed and is therefore absent in the mature, functional form of the polypeptide may be referred to as a "precursor polypeptide". Typical signal peptides contain a hydrophobic domain, which may be composed predominantly of hydrophobic amino acids and may form an alpha-helix. In some embodiments a CPP comprises or is derived from at least a portion of such a hydrophobic domain of a signal sequence. Many signal peptides begin with a short positively charged stretch of amino acids. A stretch of amino acids that is recognized and cleaved by signal peptidase is typically located at the end of the signal peptide. Signal sequences of certain membrane and transmembrane proteins are not cleaved off but rather serve to anchor the protein to the membrane and therefore are sometimes referred to as signal anchor sequences. They may be located, e.g., in the first transmembrane domain. Signal sequences of numerous secreted and membrane-bound polypeptides have been determined experimentally and/or predicted based on the sequence. Signal peptides may be annotated in database records (e.g., GenBank records) for the protein. In some embodiments a CPP is derived from the hydrophobic domain of the human fibroblast growth factor 4 (FGF4) signal sequence.

A CPP may be linear or cyclic. A cyclic CPP may be cyclized via a bond between the N- and C-termini, a bond between a terminus and a side chain, a bond between two side chains, or a bond between the backbone and a side chain. In some embodiments a CPP may be cyclized via a linker that forms a bond to each terminus, to a terminus and a side chain, to two side chains, or to the backbone and a side chain. In some embodiments the linker comprises or consists of a peptide.

Table 2 lists a variety of CPPs that may be used in various embodiments. The numbers in parentheses following a protein name herein indicate the first and last amino acids in a fragment of the protein. For example, Tat (49-56) refers to a peptide whose sequence consists of amino acids 49-56 of Tat. In some embodiments a CPP that is derived from or related to a CPP listed in Table 2 may be used. Table 2 also provides in some instances, whether a peptide is composed of L or D amino acids, the name of a peptide or protein in which a CPP is found or from which a CPP is derived. Lower case letters represents D-amino acids.

TABLE 2

Various CPPs

| SEQ ID NO: | Sequence | | Protein fragment |
|---|---|---|---|
| 77 | GRKKRRQRRRPPQ | L | Tat (48-60) HIV-1 |
| 78 | GISYGRKKRRQRRRPPQ | L | Tat (43-60) HIV-1 |
| 79 | FITKALGISYGRKKRRQRRRPPQ | L | Tat (37-60) HIV-1 |
| 80 | GRKKRRQRRR | L | Tat (48-57) HIV-1 |
| 81 | RKKRRQRRR | L | Tat (49-57) HIV-1 |
| 82 | RKKRRQRR | L | Tat (49-56) HIV-1 |
| 83 | rkkrrqrrr | D | D-Tat (49-57) HIV-1 |
| 84 | RRRQRRKKR | L | Retro - Tat (57-49) HIV-1 |
| 85 | rrrqrrkkr | D | D-Tat (57-49) HIV-1 |

TABLE 2-continued

Various CPPs

| SEQ ID NO: | Sequence | Protein fragment |
|---|---|---|
| 86 | RKKRRARRR | L Ala54 substitution mutant of Tat (49-57) HIV-1 |
| 87 | GRKKRRQRRRC | L Pro deletion mutant of Tat (48-60) HIV-1 |
| 88 | TRQARRNRRRRWRERQR | L Rev (34-50) HIV-1 |
| 89 | GWTLNSAGYLLGPHAVGNHRSFSDKNGLTS | L Galanin |
| 90 | INLKALAALAKKIL | L MP Wasp venom peptide Mastoparan |
| 91 | RQIKIWFQNRRMKWKK | L Antennapedia homeodomain of drosophila |
| 92 | RQIKIWFQNRRMKWKK | L pAntpHD (43-58) Antennapedia |
| 93 | KKWKMRRNQFWIKIQR | L pAntpHD (58-43) Antennapedia |
| 94 | rqikiwfqnrrmkwkk D | D form of pAntpHD (43-58) Antennapedia |
| 95 | RQIKIWFPNRRMKWKK | L pAntpHD (Pro50) Antennapedia |
| 96 | RQPKIWFPNRRKPWKK | L pAntpHD (3Pro) Antennapedia |
| 97 | RQIKIWFQNRRMKWKK | L pAntp (43-58) Antennapedia |
| 98 | RQIKIWFQNRRMKWK | L pAntp (43-57) Antennapedia |
| 99 | RQIKIWFQNRRMKW | L pAntp (43-56) Antennapedia |
| 100 | IKIWFQNRRMKWKK | L pAntp (45-58) Antennapedia |
| 101 | RQIKIWFPNRRMKWKK | L Penetratin (pAntp) (43-58) Antennapedia |
| 102 | RAAARQARAG | L PTD4 |
| 103 | YARAAARQARAG | L PTD4 |
| 104 | KMDCRWRWKCCKK | L Crot (27-39) Retal snake venom (Crotamine) |
| 105 | RKKRRRESRKKRRRES | L DPV3 Human Superoxide dismutase |
| 106 | GRPRESGKKRKRKRLKP | L DPV6 Human platelet-derived growth factor |
| 107 | GKRKKKGKLGKKRDP | L DPV7 Human Epidermal-like growth factor |
| 108 | SRRARRSPRESGKKRKRKR | L DPV10/6 |
| 109 | VPMLK | L Bip1 Bax-binding domain of human Ku70 |
| 110 | KLPVM | L Bip9 Bax-binding domain of human Ku70 |
| 111 | TKRRITPKDVIDVRSVTTEINT | L Inv3 Mycobacterium cell entry protein (Mce1A) |
| 112 | AEKVDPVKLNLTLSAAAEALTGLGDK | L Inv5 Mycobacterium cell entry protein (Mce1A) |
| 113 | TKRRITPKDVIDVRSVTTKINT | L Inv3.5 Mycobacterium cell entry protein (Mce1A) |
| 114 | KLIKGRTPIKFGKADCDRPPKHSQNGMGK | L Res1 L3 loop of restrictocin |
| 115 | KRIPNKKPGKKTTTKPTKKPTIKTTKKDLKPQTTKPK | L RSV-A1 Human respiratory |
| 116 | DRRRGSRPSGAERRRRAAAA | L RSG 1.2 Arg-rich peptide |
| 117 | GTKMIFVGIKKKEERADLIAYLKKA | L Cyt C 71-101 Human Cytochrome C |

TABLE 2-continued

Various CPPs

| SEQ ID NO: | Sequence | | Protein fragment |
|---|---|---|---|
| 118 | RRRRNRTRRNRRRVRGC | L | FHV coat (35-49) RNA Binding Peptides |
| 119 | MIIYRDLISKK | L | TCTP-CPP 1 Human translationally controlled tumor protein |
| 120 | MIIYRDKKSH | L | TCTP-CPP 2 Human translationally controlled tumor protein |
| 121 | MIIFRDLISH | L | TCTP-CPP 3 Human translationally controlled tumor protein |
| 122 | MIIYRDLISH | L | TCTP Human translationally controlled tumor protein |
| 123 | RRRRRRRR | L | R8 |
| 124 | RRRRRRRRR | L | R9 |
| 125 | rrrrrr | D | D-R6 |
| 126 | rrrrrrr | D | D-R7 |
| 127 | rrrrrrrr | D | D-R8 |
| 128 | rrrrrrrrr | D | D-R9 |
| 129 | GWTLNSAGYLLGKINLKALAALAKKIL | L | Transportan (TP) |
| 130 | ALWKTLLKKVLKAPKKKRKV | L | S4(13)-PV Dermaseptin S4 peptide + SV40 NLS |
| 131 | EEEAAGRKRKKRT | L | Glu-Oct-6 Transcription factor Oct-6 based chimeric peptide |
| 132 | KETWWETWWTEWSQPKKKRKV | L | Pep-1 |
| 133 | GLRRLRQRRRLRRERVRA | L | human neurturin |
| 134 | AAVALLPAVLLALLAP | L | |
| 135 | KWKLFKKIGAVLKVL | L | |
| 136 | KKLFKKILKYL | L | |

In some embodiments a CPP is derived from or related to the Tat protein of human immunodeficiency virus (HIV), e.g., Tat protein of HIV-1. For example, in some embodiments a CPP comprises or consists of a fragment of Tat comprising Tat (49-56). For example in some embodiments a CPP comprises or consists of Tat (49-56), Tat (49-57), Tat (48-56), Tat (48-57), Tat (47-56), Tat (47-57), or a retro-inverso version of any of these.

In some embodiments a CPP is related to or derived from the Rev protein of human immunodeficiency virus, e.g., Rev protein of HIV-1.

In some embodiments a CPP is derived from or related to a transcription factor. In some embodiments the transcription factor is a homeodomain protein. In some embodiments a CPP comprises or is derived from or related to at least a portion of a homeodomain, e.g., at least a portion of the third helix of a homeodomain. In some embodiments the homeodomain protein is Antennapedia protein, e.g., of Drosophila, e.g., Drosophila melanogaster. In some embodiments the homeodomain protein is the Isl-1 protein. In some embodiments the homeodomain protein is knotted-1, e.g., of maize.

In some embodiments a CPP is derived from or related to crotamine (Crot). Crotamine is a 42-residue polypeptide derived from the venom of the South American rattlesnake Crotalus durissus terrificus. For example, in some embodiments a CPP comprises or consists of a fragment of crotamine. In some embodiments a CPP comprises or consists of Crot (30-39), also known as CyLoP1, or is derived from or related to CyLoP1.

In some embodiments a CPP comprises or is derived from or related to an antimicrobial peptide (AMP). Many AMPs possess two functionally important properties, namely a net positive charge (cationic) and the ability to assume an amphipathic structure. Numerous AMPs have been isolated (see, e.g., the list available on the world wide web, at the hypertext protocol transfer address of "bbcm.univ.trieste.it/~tossi/pag1") and many additional AMPs have been designed and synthesized based on naturally occurring AMPs. For example, cecropins, first isolated from the hemolymph of the giant silk moth Hyalophora cecropia, are a family of peptides composed of 31-39 amino acids with antibacterial activity against both Gram-negative and Gram-positive bacteria. Melittin, another AMD, is the principal active component of apitoxin (bee venom). Additional examples of AMPs include, e.g., magainin and buforin 2. In some embodiments a CPP comprises BP100 or is derived from or related to Pep3 or BP100. Pep3 (CA(1-7)M(2-9) (KWKLFKKIGAVLKVL-NH2) (SEQ ID NO: 137) and BP100 (KKLFKKILKYL-NH2) (SEQ ID NO: 138) are cecropin A-melittin hybrid peptides.

In some embodiments a CPP is derived from or related to a sequence found in a human protein. In some embodiments the human protein is translationally-controlled tumor protein 1, neurturin, FGF4, calcitonin, period 1 circadian protein, superoxide dismutase, or secretory leukoprotease inhibitor. It will be appreciated that in some embodiments the sequence may also be found in one or more non-human species, e.g., one or more non-human mammalian species.

In some aspects, the present invention provides a polypeptide comprising a compstatin analog sequence and a sequence listed in Table 2. In some aspects, the present invention provides a polypeptide comprising a compstatin analog sequence and a sequence derived from a sequence listed in Table 2. In some embodiments the polypeptide may comprise any of SEQ ID NOs: 3, 4, 5, or 6, and any of the sequences listed in Table 2 or any sequence derived therefrom. In some embodiments the polypeptide may comprise any of SEQ ID NOs: 9-36 and any of the sequences listed in Table 2 or any sequence derived therefrom. In some embodiments the compstatin analog sequence is located N-terminal to the sequence from or derived from Table 2. In some embodiments the compstatin analog sequence is located C-terminal to the sequence in or derived from a sequence in Table 2. In some embodiments one or more amino acids is positioned between the compstatin analog sequence is located C-terminal to the sequence in or derived from a sequence in Table 2. In some embodiments AEEAc is positioned between the compstatin analog sequence is located C-terminal to the sequence in or derived from a sequence in Table 2. Any such polypeptide may comprise a blocking moiety at the N-terminus, C-terminus, or both.

In some embodiments L comprises one or more amino acids. For example, L may be a single amino acid or a peptide comprising, e.g., between 2 and 5, 5 and 10, or 10 and 20 amino acids. In some embodiments a CPCA is between 18 and 25 amino acids, between 25 and 35 amino acids, or between 25 and 50 amino acids in length. In certain embodiments a CPCA is 18, 19, 20, 21, 22, 23, 24, 25, 26, 27, 28, 29, or 30 amino acids long. In certain embodiments wherein A is a peptide (e.g., a CPP), L is absent or comprises an amino acid or peptide, a CPCA may be produced using solid phase peptide synthesis procedures known in the art. In some embodiments, for example, L comprises or consists of AEEAc.

In some embodiments a CPP is joined directly to the N- or C-terminal amino acid of a compstatin analog by a peptide bond. The structure of the resulting compound may be represented as CPP-CA or CA-CPP, where "CA" represents a compstatin analog. In some embodiments a CPP is joined to a compstatin analog via a linker. In some embodiments the linker comprises one or more amino acids. In some embodiments the linker is a peptide. The linker may be joined to the N- or C-terminus of the compstatin analog or to a side chain in various embodiments. In some embodiments the linker is an amino acid or peptide, the N-terminus of the linker is joined to the C-terminus of either the CPP or the CA, and the C-terminus of the linker is joined to N-terminus of the CA or CPP, respectively. The structure of the resulting CPCA may be represented as CPP-(Xaa)n-CA or CA-(Xaa)n-CPP, where (Xaa)n is an amino acid or amino acid sequence and wherein each Xaa may be any amino acid. In some embodiments the number of amino acids (n) in the linker is between 1 and 5, between 1 and 10, between 5 and 10, between 10 and 15, 15 and 20, or 20 and 25. Typically n is relatively small, e.g., between 1 and 15, though longer sequences, e.g., between 25 and 50, 50 and 100, or 100 and 1,000 may be used in certain embodiments. In some embodiments (Xaa)n is composed of standard amino acids. In some embodiments (Xaa)n comprises at least one non-standard amino acid. In some embodiments (Xaa)n comprises at least one standard amino acid and at least one non-standard amino acid. In some embodiments (Xaa)n is composed of non-standard amino acids. In some embodiments n is 1 and Xaa is glycine. In some embodiments n is 1 and Xaa is AEEAc (amino-3, 6-dioxaoctanoic acid, also known as 2-[-2-(-amino)-ethoxy]-ethoxy)-acetic acid). The CPCA may in such cases be represented as CPP-AEEAc-CA or CA-AEEAc-CPP. In some embodiments n is greater than 1, e.g., between 1 and 5, and (Xaa)n comprises at least one AEEAc. In some embodiments (Xaa)n comprises at least one neutral or hydrophobic amino acid. In some embodiments (Xaa)n comprises at least one neutral or hydrophobic amino acid and AEEAc. For example, in some embodiments (Xaa)n comprises or consists of L-AEEAc, LC-AEEAc, CL-AEEAc, I-AEEAc, IC-AEEAc, CI-AEEAc, or LIC-AEEAc. In some embodiments each Xaa is independently glycine, serine, or AEEAc. In some embodiments each Xaa is independently neutral or hydrophobic amino acid or AEEAc. In some embodiments in which a CPP is joined directly to the N- or C-terminal amino acid of a compstatin analog by a peptide bond or in which a CPP is joined to a compstatin analog by peptide linker, the CPCA is produced using standard solid phase peptide synthesis techniques.

In some embodiments a CPP-CA or CA-CPP sequence lacks predicted MHC Class I epitopes and/or lacks predicted or experimentally confirmed MHC Class II epitopes. In some embodiments a CPP-(Xaa)n and/or (Xaa)n-CPP sequence lacks predicted or experimentally confirmed MHC Class I epitopes and/or lacks predicted MHC Class II epitopes. In some embodiments a CPP-(Xaa)n-CA and/or CA-(Xaa)n-CPP sequence lacks predicted MHC Class I epitopes and/or lacks predicted or experimentally confirmed MHC Class II epitopes. In some embodiments a CPP-(Xaa) n-CA and/or CA-(Xaa)n-CPP sequence lacks predicted MHC Class II epitopes as predicted by TEPITOPE or TEPITOPEpan, available on the world wide web, at the hypertext protocol transfer address of "biokdd.fudan.edu.cn/Service/TEPITOPEpan/" ((Zhang, et al., TEPITOPEpan: Extending TEPITOPE for Peptide Binding Prediction Covering over 700 HLA-DR Molecules, PLoS ONE 7(2): e30483. doi:10.1371/journal.pone.0030483).

In some embodiments a CPM-CA, when injected into a mammal, e.g., a rabbit, non-human primate, or human according to a standard protocol suitable for generating antibodies to a typical protein, does not result in production of antisera that are capable of detecting the CPM-CA by Western blot above the level of control antisera from an unimmunized animal or an animal immunized with a suitable control peptide, e.g., a peptide of unrelated sequence or a scrambled sequence of the same amino acids that does not share any subsequences greater than 3 amino acids long. Examples of standard immunization protocols are found, e.g., in Ausubel, Current Protocols in Immunology, supra and/pr Harlow, supra.

In some embodiments a cell penetrating moiety may comprise or consist of a poly-N-substituted amino acid, e.g., a poly-N-alkylated amino acid. In some embodiments a poly-N-substituted amino acid comprises poly-N-substituted glycine, e.g., poly-N-alkylated amino acid sometimes termed an □-peptoid. As known in the art, such compounds are composed of residues in which the side chain is attached to the nitrogen atom of the peptide backbone, rather than to the α-carbon as it is in the standard amino acids. Poly-N-substituted amino acids include, e.g., N-alkylated β-alanine (sometimes termed □-peptoids); α,β-alternating peptoids; α,β-mixed peptoids, extended peptoids, or oligomers comprising other variant backbone amino-acid monomer units. Side chains present in a poly-N-substituted amino acid may, for example, be among those found in standard and/or non-standard □-amino acids. In some embodiments a cell penetrating moiety comprises two or more peptide architectures, e.g., containing a backbone comprising or consisting both of alpha- and beta-amino acids (alpha/beta-peptides) or comprising or consisting both of alpha-amino acids and N-alkylated amino acids. In some embodiments a cell penetrating moiety comprises alpha-amino acids and N-alkylated β-alanine residues. Different types of amino acids may be present in any proportion or arrangement. For example, a peptide may comprise two or more segments having different peptide architectures or may comprise alternating types of residues. For example, in some embodiments a cell penetrating moiety comprises alternating N-alkylated β-alanine and α-amino acid residues. Further information regarding peptoids, peptoid variants, and/or hybrid molecules is found e.g., in Simon, R J, et al. "Peptoids: a modular approach to drug discovery" Proceedings of the National Academy of Sciences USA, (1992), 89(20), 9367-9371; U.S. Pat. No. 5,811,387; Yoo, B. and Kirshenbaum, K., Peptoid architectures: elaboration, actuation, and application. Curr. Opin. Chem. Biol. (2008), 12, 714-721; Culf, A S and Ouellette, R J, Solid-Phase Synthesis of N-Substituted Glycine Oligomers (α-Peptoids) and Derivatives, Molecules (2010), 15, 5282-5335; Olsen C A, Peptoid-Peptide hybrid backbone architectures. Chembiochem. (2010), 11(2):152-60. The references cited in these references are incorporated herein by reference.

In general, linking portion L can comprise any one or more aliphatic and/or aromatic moieties consistent with the formation of a stable compound joining the linked moieties. The term "stable", as used herein, preferably refers to compounds which possess stability sufficient to allow manufacture and which maintain the integrity of the compound for a sufficient period of time, e.g., to be useful for one or more purposes described herein. In some embodiments, L comprises a saturated or unsaturated, substituted or unsubstituted, branched or unbranched, aliphatic chain having a length of between 1 and 50, between 1 and 40, between 1 and 30, between 1 and 20, between 1 and 10, between 1 and 6, or 5 or less carbon atoms, where length refers to the number of C atoms in the main (longest) chain. In some embodiments, the aliphatic chain comprises one or more heteroatoms (O, N, S), which may be independently selected. In some embodiments, at least 50% of the atoms in the main chain of L are carbon atoms. In some embodiments, L comprises a saturated alkyl moiety $(CH_2)_n$, wherein n is between 1 and 30.

In some embodiments, L comprises one or more heteroatoms and has a length of between 1 and 50, between 1 and 40, between 1 and 30, between 1 and 20, or between 1 and 10 total carbon atoms in a chain, or less. In some embodiments, L comprises an oligo(ethylene glycol) moiety $(-(O-CH_2-CH_2-)_n)$ wherein n is between 1 and 50, between 1 and 40, between 1 and 30, between 1 and 20, or between 1 and 10. In some embodiments, L comprises an unsaturated moiety such as —CH=CH— or —CH$_2$—CH=CH—; a moiety comprising a non-aromatic cyclic ring system (e.g., a cyclohexyl moiety), an aromatic moiety (e.g., an aromatic cyclic ring system such as a phenyl moiety); an ether moiety (—C—O—C—); an amide moiety (—C(=O)—N—); an ester moiety (—CO—O—); a carbonyl moiety (—C(=O)—); an imine moiety (—C=N—); a thioether moiety (—C—S—C—); an amino acid residue; and/or any moiety that can be formed by the reaction of two compatible reactive functional groups. In certain embodiments, one or more moieties of a linking portion is/are substituted by independent replacement of one or more of the hydrogen (or other) atoms thereon with one or more moieties including, but not limited to aliphatic; aromatic, aryl; alkyl, aralkyl, alkanoyl, aroyl, alkoxy; thio; F; Cl; Br, I; —NO2; —CN; —CF3; —CH2CF3; —CHC12; —CH2OH; —CH2CH2OH; —CH2NH2; —CH2SO2CH3; —or -GRG1 wherein G is —O—, —S—, —NRG2-, —C(=O)—, —S(=O)—, —SO2-, —C(=O)O—, —C(=O)NRG2-, —OC(=O)—, —NRG2C(=O)—, —OC(=O)O—, —OC(=O)NRG2-, -NRG2C(=O)O—, —NRG2C(=O)NRG2-, —C(=S)—, —C(=S)S—, —SC(=S)—, —SC(=S)S—, —C(=NRG2)-, —C(=NRG2)O—, —C(=NRG2)NRG3-, —OC(=NRG2)-, —NRG2C(=NRG3)-, —NRG2SO2-, -NRG2SO2NRG3-, or —SO2NRG2-, wherein each occurrence of RG1, RG2 and RG3 independently includes, but is not limited to, hydrogen, halogen, or an optionally substituted aliphatic, aromatic, or aryl moiety. It will be appreciated that cyclic ring systems when present as substituents may optionally be attached via a linear moiety. Combinations of substituents and variables envisioned by this invention are preferably those that result in the formation of stable compounds useful in any one or more of the methods described herein, e.g., useful for the treatment of one or more disorders and/or for contacting a cell, tissue, or organ, as described herein, and/or useful as intermediates in the manufacture of one or more such compounds.

In some embodiments multiple linking portions can be attached to one another to form a larger linking portion L, and at least some of such linking portions can have one or more compstatin analog moietie(s) attached thereto. In molecules comprising multiple compstatin analog moieties, the compstatin analogs can be the same or different and, if different, can be independently selected. The same applies to the linking portions and cell-penetrating groups. In various embodiments the invention encompasses the synthesis and use of multivalent compstatin analogs comprising one or more cell-penetrating group(s) and use of concatamers of compstatin analogs comprising one or more cell-penetrating group(s). In some embodiments, a linkage is a stable non-covalent linkage such as a biotin/(strept)avidin linkage or other noncovalent linkage of approximately equivalent strength. In some embodiments a linkage comprises a moiety that is susceptible to intracellular cleavage in at least some cells or under at least some intracellular conditions. In some embodiments a cleavage-susceptible linkage comprises a cleavage site for a protease that is active intracellularly under at least some conditions. Without wishing to be bound by any theory, intracellular cleavage may in some embodiments enhance the ability of a compstatin analog to bind to C3 or C3b intracellularly.

In some embodiments a cell-penetrating compstatin analog comprises a compstatin analog in which any of SEQ ID NOs: 3-36, 72, 73, 74, 75, or 76 is extended by one or more amino acids at the N-terminus, C-terminus, or both, wherein in some embodiments at least one of the amino acids has a side chain that comprises a reactive functional group such as a primary or secondary amine, a sulfhydryl group, a carboxyl group (which may be present as a carboxylate group), a guanidino group, a phenol group, an indole ring, a thioether, or an imidazole ring. In some embodiments, the amino acid(s) is/are L-amino acids. In some embodiments, any one or more of the amino acid(s) is a D-amino acid. If multiple amino acids are added, the amino acids can be independently selected. In some embodiments, the reactive functional group (e.g., a primary or secondary amine) is used as a target for addition of a moiety comprising a cell penetrating moiety. Amino acids having a side chain that comprises a primary or secondary amine include lysine (Lys) and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. In some embodiments at least one amino acid is cysteine, aspartic acid, glutamic acid, arginine, tyrosine, tryptophan, methionine, or histidine. Cysteine has a side chain comprising a sulfhydryl group. Aspartic acid and glutamic acid have a side chain comprising a carboxyl group (ionizable to a carboxylate group). Arginine has a side chain comprising a guanidino group. Tyrosine has a side chain comprising a phenol group (ionizable to a phenolate group). Tryptophan has a side chain comprising an indole ring include include, e.g., tryptophan. Methionine has a side chain comprising a thioether group include, e.g., methionine. Histidine has a side chain comprising an imidazole ring. A wide variety of non-standard amino acids having side chains that comprise one or more such reactive functional group(s) are available, including naturally occurring amino acids and amino acids not found in nature. See, e.g., Hughes, B. (ed.), *Amino Acids, Peptides and Proteins in Organic Chemistry*, Volumes 1-4, Wiley-VCH (2009-2011); Blaskovich, M., Handbook on Syntheses of Amino Acids General Routes to Amino Acids, Oxford University Press, 2010. The invention encompasses embodiments in which one or more non-standard amino acid(s) is/are used to provide a target for addition of a moiety of interest, such as a moiety comprising a cell-penetrating group or a clearance-reducing moiety (discussed further below). Any one or more of the amino acid(s) may be protected as appropriate during synthesis of the compound. For example, one or more amino acid(s) may be protected during reaction(s) involving the target amino acid side chain. In some embodiments, wherein a sulfhydryl-containing amino acid is used as a target for addition of a moiety of interest, such as a moiety comprising a cell-penetrating group or clearance reducing moiety, the sulfhydryl is protected while the compound is being cyclized by formation of an intramolecular disulfide bond between other amino acids such as cysteines.

In the discussion in this paragraph, an amino acid having a side chain containing an amine group is used as an example. The invention encompasses analogous embodiments in which an amino acid having a side chain containing a different reactive functional group is used. In some embodiments, an amino acid having a side chain comprising a primary or secondary amine is attached directly to the N-terminus or C-terminus of any of SEQ ID NOs: 3-36, 37, 72, 73, 74, 75, or 76 or via a peptide bond. In some embodiments, an amino acid having a side chain comprising a primary or secondary amine is attached to the N- or C-terminus of any of SEQ ID NOs: 3-36, 37, 72, 73, 74, 75 or 76 or via a linking portion, which may contain any one or more of the linking moieties described above. In some embodiments, at least two amino acids are appended to either or both termini. The two or more appended amino acids may be joined to each other by peptide bonds or at least some of the appended amino acids may be joined to each other by a linking portion, which may contain any one or more of the linking moieties described herein. Thus in some embodiments, a cell-penetrating compstatin analog comprises a compstatin analog moiety M of formula B1-R1-$M_1$-R2-B2, wherein $M_1$ represents any of SEQ ID NOs: 3-36, 37, 72, 73, 74, 75, or 76, either R1 or R2 may be absent, at least one of R1 and R2 comprises an amino acid having a side chain that contains a primary or secondary amine, and B1 and B2 are optionally present blocking moieties. R1 and/or R2 may be joined to $M_1$ by a peptide bond or a non-peptide bond. R1 and/or R2 may comprise a linking portion $L^{P3}$. For example, R1 can have formula $M_2$-$L^{P3}$ and/or R2 can have formula $L^{P3}$-$M_2$ wherein $L^{P3}$ is a linking portion, and $M_2$ comprises at least one amino acid having a side chain comprising a primary or secondary amine. For example, $M_2$ can be Lys or an amino acid chain comprising Lys. In some embodiments, $L^{P3}$ comprises of consists of one or more amino acids. For example, $L^{P3}$ can be between 1 and about 20 amino acids in length, e.g., between 4 and 20 amino acids in length. In some embodiments, $L^{P3}$ comprises or consist of multiple Gly, Ser, and/or Ala residues. In some embodiments, $L^{P3}$ does not comprise an amino acid that comprises a reactive SH group, such as Cys. In some embodiments, $L^{P3}$ comprises an oligo(ethylene glycol) moiety and/or a saturated alkyl chain. In some embodiments, $L^{P3}$ is attached to the N-terminal amino acid of $M_1$ via an amide bond. In some embodiments, $L^{P3}$ is attached to the C-terminal amino acid of $M_1$ via an amide bond. The compound may be further extended at either or both termini by addition of further linking portion(s) and/or amino acid(s). The amino acids can the same or different and, if different, can be independently selected. In some embodiments, two or more amino acids having side chains comprising reactive functional groups are used, wherein the reactive functional groups can be the same or different. The two or more reactive functional groups can be used as targets for addition of two or more moieties. In some embodiments, two or more cell-internalizing moieties are added. In some embodiments, a cell penetrating moiety and a clearance reducing moiety are added. In some embodiments, a linker and/or cell penetrating moiety is attached to an amino acid side chain after incorporation of the amino acid into a peptide chain. In some embodiments, a linker and/or cell penetrating moiety is already attached to the amino acid side chain prior to use of the amino acid in the synthesis of a cell-reactive compstatin analog. For example, a Lys derivative having a linker attached to its side chain can be used. The linker may comprise a cell-penetrating functional group or may subsequently be modified to comprise a cell-penetrating functional group.

Certain reactive compstatin analogs, which may be used to produce cell-penetrating compstatin analogs, are described in further detail below. In some embodiments such reactive compstain analogs may be reacted with a CPM comprising a compatible reactive functional group to produce a cell-penetrating compstatin analog. In some embodiments such reactive compstain analogs may be reacted with a linker comprising a compatible reactive functional group, wherein the linker is or may be attached to a CPM, to produce a cell-penetrating compstatin analog. In the following discussion, a peptide having the amino acid sequence

```
                                                    (SEQ ID NO: 37)
Ile-Cys*-Val-(1Me)Trp-Gln-Asp-Trp-Gly-Ala-His-Arg-

Cys*-Thr
```

(corresponding to the compstatin analog of SEQ ID NO: 28, wherein asterisks in SEQ ID NO: 37 represent cysteines joined by a disulfide bond in the active compound, and (1Me)Trp represents 1-methyl-tryptophan)), is used as an exemplary compstatin analog moiety; maleimide (abbreviated Mal) is used as an example of a reactive functional group; $(CH2)_n$ and $(O-CH2-CH2)_n$ are used as examples of linking portions; lysine is used as an example of an amino acid comprising a reactive functional group (in some compounds), and acetylation and amidation of the N- and C-termini, respectively, are used as optionally present exemplary blocking moieties in some compounds and are represented in italics, i.e., as Ac and $NH_2$ respectively. It will be appreciated that the compounds can be prepared using a variety of synthetic approaches and using a variety of precursors. The discussion of various synthetic approaches and precursors below is not intended to limit the invention. In general, any of the features of any of the compounds described below or herein can be freely combined with feature(s) of other compounds described below or elsewhere herein, and the invention encompasses such embodiments.

In some embodiments, a reactive moiety is provided by a reactive compound comprising a maleimide group (as a reactive functional group) and an alkanoic acid (RCOOH), where R is an alkyl group. For example, 6-malemeidocaproic acid (Mal-$(CH_2)_5$—COOH), depicted below, can be used.

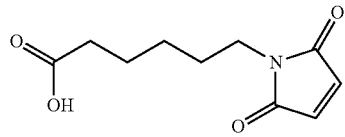

Compound I

In some embodiments, a reactive moiety is provided by a derivative of an alkanoic acid in which the carboxylic acid moiety has been activated, e.g., the OH moiety has been converted to a better leaving group. For example, the carboxyl group of compound I may be reacted with EDC, followed by reaction with NHS (which can optionally be provided as water-soluble sulfo-NHS), resulting in an N-hydroxysuccinimide ester derivative of 6-malemeidocaproic acid, i.e., 6-maleimidohexanoic acid N-hydroxysuccinimide (NHS) ester (depicted below).

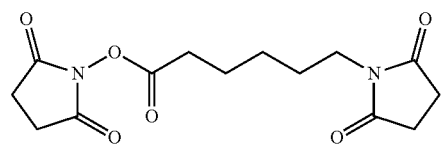

Compound II

The compound of SEQ ID NO: 37 can be modified at the N- and/or C-terminus to generate a reactive compstatin analog. For example, compound II can be used to generate the following reactive compstatin analog by reaction with the N-terminal amino group of Ile.

```
                                                    (SEQ ID NO: 38)
Maleimide-(CH2)5-C(=O)-Ile-Cys*-Val-(1Me)Trp-Gln- Asp-Trp-Gly-Ala-His-Arg-Cys*-Thr-NH2.
```

It will be appreciated that in SEQ ID NO: 38 the —C(═O) moiety is attached to the immediately C-terminal amino acid (Ile), via a C—N bond, wherein the N is part of the amino acid and is not shown.

In other embodiments, a maleimide group is linked to Thr at the C-terminus, resulting in the following reactive compstatin analog:

```
                                                    (SEQ ID NO: 39)
Ac-Ile-Cys*-Val-(1Me)Trp-Gln-Asp-Trp-Gly-Ala-His-

Arg-Cys*-Thr-(C=O)-(CH2)5-maleimide.
```

In some embodiments, a reactive compstatin analog can be synthesized using bifunctional linker (e.g., a heterobifunctional linker). An exemplary heterobifunctional linker comprising $(CH_2-CH_2-O)_n$ and $(CH_2)_m$ (where m=2) moieties is shown below:

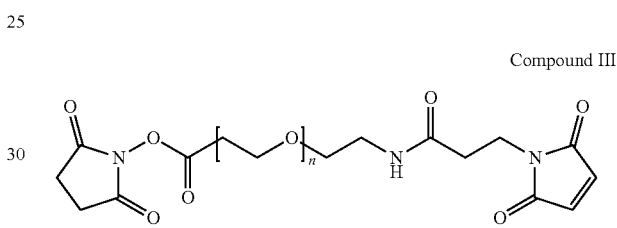

Compound III

Compound III comprises a maleimide group as a reactive functional group and an NHS ester moiety that reacts readily with an amino group (e.g., an N-terminal amino group or an amino group of an amino acid side chain).

An embodiment of compound III in which n=2 can be used to generate the following reactive compstatin analog using the compstatin analog of SEQ ID NO: 37:

```
                                                    (SEQ ID NO: 40)
Maleimide- (CH2)2-C(=O)-NH-CH2CH2OCH2CH2OCH2CH2C(=O)-Ile- Cys*-Val-(1Me)Trp-Gln-Asp-Trp-Gly-Ala-His-Arg- Cys*-Thr-NH2
```

It will be appreciated that in the compound of SEQ ID NO: 40 a —C(═O) moiety is attached to the N-terminal amino acid (Ile residue via a C—N bond, wherein the N is part of the amino acid and is not shown. In some embodiments a linker has the formula of Compound III wherein n≥1. Exemplary values for n in a $(CH_2-CH_2-O)_n$ moiety are provided herein.

In some embodiments, the alkyl chain that links the maleimide moiety to the rest of the molecule contains more or fewer methylene units, the oligo(ethylene glycol) moiety contains more or fewer ethylene glycol units, and/or there are more or fewer methylene units flanking either or both sides of the oligo(ethylene glycol) moiety, as compared with the compound of SEQ ID NO: 39 or SEQ ID NO: 40. Exemplary reactive compstatin analogs illustrative of a few such variations are presented below (SEQ ID NOs: 41-46):

```
                                                (SEQ ID NO: 41)
Maleimide-(CH₂)₂-C(=O)-NH-CH₂CH₂OCH₂C(=O)-Ile- Cys*-Val-(1Me)Trp-Gln-Asp-Trp-Gly-Ala-His-Arg- Cys*-Thr-NH₂
                                                (SEQ ID NO: 42)
Maleimide-(CH₂)₃-C(=O)-NH-CH₂CH₂OCH₂CH₂OCH₂C(=O)-

Ile-Cys*-Val-(1Me)Trp-Gln-Asp-Trp-Gly-Ala-His-Arg-

Cys*-Thr-NH₂
                                                (SEQ ID NO:43)
Maleimide- (CH₂)₅-C(=O)-NH-CH₂CH₂OCH₂CH₂OCH₂C(=O)-Ile-Cys*-

Val-(1Me)Trp-Gln-Asp-Trp-Gly-Ala-His-Arg-Cys*-Thr-

NH₂
                                                (SEQ ID NO: 44)
Maleimide- (CH₂)₄-C(=O)-NH-CH₂CH₂OCH₂CH₂OCH₂CH₂C(=O)-Ile- Cys*-Val-(1Me)Trp-Gln-Asp-Trp-Gly-Ala-His-Arg- Cys*-Thr-NH₂
                                                (SEQ ID NO: 45)
Maleimide- (CH₂)₂-C(=O)-NH-CH₂CH₂OCH₂CH₂OCH₂CH₂C(=O)-Ile- Cys*-Val-(1Me)Trp-Gln-Asp-Trp-Gly-Ala-His-Arg- Cys*-Thr-NH₂
                                                (SEQ ID NO: 46)
Maleimide-(CH₂)₅-C(=O)-NH-CH₂CH₂OCH₂CH₂OCH₂C(=O)-

Ile-Cys*-Val-(1Me)Trp-Gln-Asp-Trp-Gly-Ala-His-Arg-

Cys*-Thr-NH₂
```

In some embodiments, SEQ ID NO: 37 is extended to comprise a Lys residue at the N- or C-terminus of the peptide, e.g., as exemplified below for a C-terminal linkage:

```
                                                (SEQ ID NO: 47)
Ac-Ile-Cys*-Val-(1Me)Trp-Gln-Asp-Trp-Gly-Ala-His-

Arg-Cys*-Thr-Lys-NH₂.
```

In some embodiments, a Lys residue is attached to the N- or C-terminus of SEQ ID NO: 37 via a peptide linker, e.g., as exemplified below for a C-terminal linkage:

```
                                                (SEQ ID NO: 48)
Ac-Ile-Cys*-Val-(1Me)Trp-Gln-Asp-Trp-Gly-Ala-His-

Arg-Cys*-Thr-(Gly)₅-Lys-NH₂.
```

In some embodiments, a linker comprising a primary or secondary amine is added to the N- or C-terminus of a compstatin analog. In some embodiments, the linker comprises an alkyl chain and/or an oligo(ethylene glycol) moiety. For example, NH₂(CH₂CH₂O)nCH₂C(=O)OH (e.g., 8-amino-3,6-dioxaoctanoic acid (AEEAc) or 11-amino-3,6,9-trioxaundecanoic acid) or an NHS ester thereof (e.g., an NHS ester of 8-amino-3,6-dioxaoctanoic acid or 11-amino-3,6,9-trioxaundecanoic acid), can be used. In some embodiments, the resulting compound is as follows (wherein the portion contributed by the linker is shown in bold):

```
                                                (SEQ ID NO: 49)
NH₂(CH₂)₅C(=O)-Ile-Cys-Val-(1Me)Trp-Gln-Asp-Trp-

Gly-Ala-His-Arg-Cys-Thr-NH₂
                                                (SEQ ID NO: 50)
NH₂(CH₂CH₂O)₂CH₂C(=O)-Ile-Cys-Val-(1Me)Trp-Gln-

Asp-Trp-Gly-Ala-His-Arg-Cys-Thr-NH₂
```

In some embodiments, a Lys residue is attached to the N- or C-terminus of SEQ ID NO: 37 via a linker comprising a non-peptide portion. For example, the linker can comprise an alkyl chain, oligo(ethylene glycol) chain, and/or cyclic ring system. In some embodiments, 8-AEEAc or an NHS ester thereof is used, resulting (in the case of attachment of Lys at the C-terminus) in the following compound (wherein the portion contributed by 8-AEEAc is shown in bold):

```
                                                (SEQ ID NO: 51)
Ac-Ile-Cys*-Val-(1Me)Trp-Gln-Asp-Trp-Gly-Ala-His-

Arg-Cys*-Thr-NH-CH₂CH₂OCH₂CH₂OCH₂-C=O)-Lys-NH₂
```

It will be appreciated that in SEQ ID NOs: 49 and 50, a —C(=O) moiety is attached to the adjacent Ile residue via a C—N bond, wherein the N is part of the amino acid and is not shown. Similarly, in SEQ ID NO: 51, a —C(=O) moiety is attached to the adjacent Lys residue via a C—N bond, wherein the N is part of the amino acid and is not shown. It will also be appreciated that that in SEQ ID NO: 51 the NH moiety is attached to the immediately N-terminal amino acid (Thr), via a C—N bond, wherein the C is the carbonyl carbon of the amino acid and is not shown.

The compounds of SEQ ID NOs: 47-51 can readily be modified at the primary amine group to produce a reactive compstatin analog. For example, the compounds of SEQ ID NOs: 47-51 (or other compounds comprising a primary or secondary amine and a compstatin analog moiety) can be reacted with 6-maleimidocaproic acid N-succinimidyl ester to produce the following reactive compstatin analogs:

```
                                                (SEQ ID NO: 52)
Ac-Ile-Cys*-Val-(1Me)Trp-Gln-Asp-Trp-Gly-Ala-His-

Arg-Cys*-Thr-Lys-(C(=O)-(CH₂)₅-Mal)-NH₂.
                                                (SEQ ID NO: 53)
Ac-Ile-Cys*-Val-(1Me)Trp-Gln-Asp-Trp-Gly-Ala-His-

Arg-Cys*-Thr-(Gly)₅-Lys--(C(=O)-(CH₂)₅-Mal)-NH₂.
                                                (SEQ ID NO: 54)
Mal-(CH₂)₅-(C(=O)-NH(CH2)₅C(=O)-Ile-Cys-Val- (1Me)Trp-Gln-Asp-Trp-Gly-Ala-His-Arg-Cys-Thr-NH₂
                                                (SEQ ID NO: 55)
Mal-(CH₂)₅-(C(=O)NH(CH₂CH₂O)₂CH₂C(=O)-Ile-Cys-

Val-(1Me)Trp-Gln-Asp-Trp-Gly-Ala-His-Arg-Cys-Thr-

NH₂
                                                (SEQ ID NO: 56)
Ac-Ile-Cys*-Val-(1Me)Trp-Gln-Asp-Trp-Gly-Ala-His-

Arg-Cys*-Thr-NH-CH₂CH₂OCH₂CH₂OCH₂-C(=O)-Lys- (C(=O)-(CH₂)₅-Mal)-NH₂
```

In another embodiment, a reactive compstatin analog is represented as: Ac-Ile- (SEQ ID NO: 57)
Ac-Ile-Cys*-Val-(1Me)Trp-Gln-Asp-Trp-Gly-Ala-His-Arg-Cys*-Thr-Lys-C(=O)-CH$_2$(OCH$_2$CH2)$_2$NH(C(=O)-(CH$_2$)$_5$-Mal)-NH$_2$.

In some embodiments variants of SEQ ID NOs: 38-57 may be used in which -Ile-Cys*-Val-(1Me)Trp-Gln-Asp-Trp-Gly-Ala-His-Arg-Cys*-Thr- is replaced by an amino acid sequence comprising the amino acid sequence of any other compstatin analog, e.g., of any of SEQ ID NOs 3-27 or 29-36, 37, 72, 73, 74, 75, or 76 with the proviso that blocking moiet(ies) present at the N- and/or C-termini of a compstatin analog may be absent, replaced by a linker (which may comprise a blocking moiety), or attached to a different N- or C-terminal amino acid present in the corresponding variant(s).

Other bifunctional cross-linkers comprising a maleimide as a reactive moiety and an NHS ester as an amine-reactive moiety of use in various embodiments include, e.g., succinimidyl 4-(p-maleimidophenyl)butyrate (SMPB); succinimidyl 4-(N-maleimidomethyl)-cyclohexane-1-carboxylate (SMCC); N-γ-maleimidobutyryl-oxysuccinimide ester (GMBS). Addition of a sulfonate to the NHS ring results in water-soluble analogs such as sulfo-succinimidyl(4-iodoacetyl)-aminobenzoate (sulfo-SIAB), sulfo-succinimidyl 4-(N-maleimidomethyl)-cyclohexane-1-carboxylate (sulfo-SMCC), sulfo-succinimidyl 4-(p-maleimidophenyl)butyrate (sulfo-SMPB), sulfo-N-γ-maleimidobutyryl-oxysuccinimide ester (sulfo-GMBS) etc., which can avoid the need for an organic solvent. In some embodiments, a long chain version of any of the foregoing, comprising a spacer arm between the NHS ester moiety and the remainder of the molecule, is used. The spacer can comprise, e.g., an alkyl chain. An example is succinimidyl-4-[N-Maleimidomethyl]cyclohexane-1-carboxy-[6-amidocaproate].

In some embodiments, a bifunctional linker comprising an NHS ester (as an amine-reactive moiety) and an iodoacetyl group (reactive with sulfhydryl groups) is used. Such linkers include, e.g., N-succinimidyl(4-iodoacetyl)-aminobenzoate (SIAB); succinimidyl 6-[(iodoacetyl)-amino] hexanoate (SIAX); succinimidyl 6-[6-(((iodoacetyl)amino)-hexanoyl) amino]hexanoate (SIAXX); succinimidyl 4-((iodoacetyl)amino)methyl)-cyclohexane-1-carboxylate (SIAC); succinimidyl 6-((((4-(iodoacetyl)amino)methyl-cyclohexane-1-carbonyl)amino)hexanoate (SIACX);

In some embodiments, a bifunctional linker comprising an NHS ester (as an amine-reactive moiety) and a pyridy disulfide group (as a cell-reactive moiety reactive with sulfhydryl groups) is used. Examples include N-succinimidyl 3-(2-pyridyldithio)propionate (SPDP); succinimidyloxycarbonyl-α-methyl-α-(2-pyridyldithio)toluene (SMPT) and versions comprising a sulfonate on the NHS ring and/or a spacer comprising an alkyl chain between the NHS ester moiety and the rest of the molecule (e.g., succinimidyl 6-(3-[2-pyridyldithio]-propionamido)hexanoate) (LC-SPDP). Variations of such linkers that include additional or different moieties could be used. For example, a longer or shorter alkyl chain could be used in a spacer, or an oligo (ethylene glycol) moiety instead of an alkyl chain.

Any of the reactive compstatin analog moieties may be reacted with a compound comprising a CPM and a compatible reactive functional group. For example, a CPP or other CPM may be modified to incorporate a reactive functional group capable of reacting with the reactive functional group of a reactive compstatin analog or of a linker to form a compound of formula formula A-L-M.

In general, a cell-penetrating compstatin analog can be synthesized using a variety of approaches. Compounds that comprise a reactive functional group and a linker can often be purchased as preformed building blocks. For example, 6-malemeidocaproic acid and 6-maleimidocaproic acid N-hydroxysuccinimide ester can be purchased from various suppliers. Alternately, such compounds can be synthesized using methods known in the art. See, e.g., Keller O, Rudinger J. Helv Chim Acta. 58(2):531-41, 1975 and Hashida S, et al., J Appl Biochem., 6(1-2):56-63, 1984. See also, Hermanson, G. supra, and references therein, for discussion of methods and reagents of use for synthesizing conjugates.

In some embodiments, an amino acid having a linker attached to a side chain is used in the synthesis of a linear peptide. The linear peptide can be synthesized using standard methods for peptide synthesis known in the art, e.g., standard solid-phase peptide synthesis. The linear peptide is then cyclized (e.g., by oxidation of the Cys residues to form an intramolecular disulfide). The cyclic compound may then be reacted with a linker attached to a CPM. In other embodiments, a moiety comprising a CPM is reacted with a linear compstatin analog prior to cyclization thereof. In general, reactive functional groups can be appropriately protected to avoid undesired reaction with each other during synthesis of a cell-reactive compstatin analog. A reactive functional group, any of the amino acid side chains, and/or either or both termini of a peptide may be protected during the reaction and subsequently deprotected. For example, SH groups of Cys residues and/or SH-reactive moieties such as maleimides can be protected until after cyclization to avoid reaction between them. The reaction conditions are selected based at least in part on the requirements of the particular reactive functional group(s) to achieve reasonable yield in a reasonable time period. Temperature, pH, and the concentration of the reagents can be adjusted to achieve the desired extent or rate of reaction. See, e.g., Hermanson, supra. The desired product can be purified, e.g., to remove unreacted compound(s), linker(s), products other than the desired cell-penetrating compstatin analog that may have been generated in the reaction, other substances present in the reaction mixture, etc. Compositions and methods for making the cell-penetrating compstatin analogs, and intermediates in the synthesis, are aspects of the invention.

In some aspects of the invention, a compound comprises a cell-penetrating compstatin analog and a moiety such as a polyethylene glycol (PEG) chain or other polymer(s) that, e.g., stabilizes the compound, increases its lifetime in the body, increases its solubility, decreases its immunogenicity, and/or increases its resistance to degradation. Without limiting the invention in any way, such a moiety may be referred to herein as a "clearance reducing moiety" (CRM).

In certain embodiments a CPCA is stable in physiological conditions for at least 24 hours or more. In certain embodiments a CPCA is stable in mammalian, e.g., primate, e.g., human or non-human primate (e.g., monkey) blood, plasma, or serum for at least 24 hours. In various embodiments at least 50%, 60%, 70%, 80%, 90%, 95%, 96%, 97%, 98%, 99%, or more, of the CPCA molecules remains intact upon incubation in physiological conditions for 24 hours, 48 hours, 72 hours, 96 hours, 120 hours, 144 hours, 168 hours, or more. In various embodiments at least 50%, 60%, 70%, 80%, 90%, 95%, 96%, 97%, 98%, 99%, or more, of the CPCA molecules remains intact upon incubation in blood, plasma, or serum at 37 degrees C. for 48 hours, 72 hours, 96 hours, 120 hours, 144 hours, 168 hours, or more. Incubation may be performed using a CPCA at a concentration of between 1 microgram/ml to about 100 mg/ml in various embodiments. Samples may be analyzed at various time points. Size or intactness may be assessed using, e.g., chromatography (e.g., HPLC), mass spectrometry, Western blot, or any other suitable method.

In some embodiments, a CPCA has a molar activity of at least about 10%, 20%, 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a CPM. In some embodiments wherein a compound comprises multiple compstatin analog moieties, the molar activity of the long-acting compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties. In some embodiments, a polyethylene glycol (PEG) comprises a $(CH_2CH_2O)_n$ moiety having a molecular weight of at least 500 daltons, e.g., an average molecular weight of between about 500; 1,000; 1,500; 2,000; 5,000; 10,000; 20,000; 30,000; 40,000; 50,000; 60,000; 70,000; 80,000; 90,000; and 100,000 daltons. In some embodiments the average molecular weight of a PEG is at least 20,000 daltons, up to about 100,000; 120,000; 140,000; 160,000; 180,000; or 200,000 daltons. "Average molecular weight" refers to the number average molecular weight. In some embodiments, the polydispersity D of a $(CH_2CH_2O)n$ moiety is between 1.0005 and 1.50, e.g., between 1.005 and 1.10, 1.15, 1.20, 1.25, 1.30, 1.40, or 1.50, or any value between 1.0005 and 1.50.

In some embodiments, a $(CH_2CH_2O)n$ moiety is monodisperse and the polydispersity of a $(CH_2CH_2O)n$ moiety is 1.0. Such monodisperse $(CH_2CH_2O)n$ moieties are known in the art and are commercially available from Quanta BioDesign (Powell, Ohio), and include, by way of nonlimiting example, monodisperse moieties where n is 2, 4, 6, 8, 12, 16, 20, or 24.

In some embodiments, a compound comprises multiple $(CH_2CH_2O)_n$ moieties wherein the total molecular weight of said $(CH_2CH_2O)_n$ moieties is between about 1,000; 5,000; 10,000; 20,000; 30,000; 40,000; 50,000; 60,000; 70,000; 80,000; 90,000; and 100,000 daltons. In some embodiments the average total molecular weight of the compound or $(CH_2CH_2O)_n$ moieties is at least 20,000 daltons, up to about 100,000; 120,000; 140,000; 160,000; 180,000; or 200,000 daltons. In some embodiments, the compound comprises multiple $(CH_2CH_2O)_n$ moieties having defined lengths, e.g., n=4, 6, 8, 10, 12, 14, 16, 18, 20, 22, 24, 26, 28, or 30 or more. In some embodiments, the compound comprises a sufficient number of $(CH_2CH_2O)_n$ moieties having defined lengths to result in a total molecular weight of said $(CH_2CH_2O)_n$ moieties of between about 1,000; 5,000; 10,000; 20,000; 30,000; 40,000; 50,000; 60,000; 70,000; 80,000; 90,000; and 100,000 daltons. In some embodiments the average total molecular weight of the compound or $(CH_2CH_2O)_n$ moieties is at least 20,000 daltons, up to about 100,000; 120,000; 140,000; 160,000; 180,000; or 200,000 daltons. In some embodiments n is between about 30 and about 3000. In some embodiments a CPCA is attached at each end of a linear PEG. A bifunctional PEG having a reactive functional group at each end of the chain may be used. In some embodiments the reactive functional groups are identical while in some embodiments different reactive functional groups are present at each end. In some embodiments, multiple $(CH_2CH_2O)_n$ moieties are provided as a branched structure. The branches may be attached to a linear polymer backbone (e.g., as a comb-shaped structure) or may emanate from one or more central core groups, e.g., as a star structure. In some embodiments, a branched molecule has 3 to 10 $(CH_2CH_2O)_n$ chains. In some embodiments, a branched molecule has 4 to 8 $(CH_2CH_2O)_n$ chains. In some embodiments, a branched molecule has 10, 9, 8, 7, 6, 5, 4, or 3 $(CH_2CH_2O)_n$ chains. In some embodiments, a star-shaped molecule has 10-100, 10-50, 10-30, or 10-20 $(CH_2CH_2O)_n$ chains emanating from a central core group. In some embodiments a compound thus may comprise, e.g., 3-10 CPCA moieties, e.g., 4-8 CPCA moities, each attached to a $(CH_2CH_2O)_n$ chain via a functional group at the end of the chain. In some embodiments a compound may comprise, e.g., 10-100 CPCA moieties, each attached to a $(CH_2CH_2O)_n$ chain via a functional group at the end of the chain. In some embodiments, branches (sometimes referred to as "arms") of a branched or star-shaped PEG contain about the same number of $(CH_2CH_2O)$ moieties. In some embodiments, at least some of the branch lengths may differ. It will be understood that in some embodiments one or more $(CH_2CH_2O)_n$ chains does not have a CPCA attached thereto. In some embodiments at least about 30%, 40%, 50%, 60%, 70%, 80%, 90%, 95%, or 100% of the chains has a CPCA attached thereto. In some embodiments any such compound may comprise both CPCA and compstatin analog moieties without a CPM. At least some of the CPCA are attached to a PEG via a linker sufficiently labile to allow release of the CPCA, e.g., under physiological conditions in vitro, or in vivo.

In genera and compounds depicted herein, a polyethylene glycol moiety is drawn with the oxygen atom on the right side of the repeating unit or the left side of the repeating unit. In cases where only one orientation is drawn, the present invention encompasses both orientations (i.e., $(CH_2CH_2O)_n$ and $(OCH_2CH_2)_n$) of polyethylene glycol moieties for a given compound or genus, or in cases where a compound or genus contains multiple polyethylene glycol moieties, all combinations of orientations are encompasses by the present disclosure.

Formulas of some exemplary monofunctional PEGs comprising a reactive functional group are illustrated below. For illustrative purposes, formulas in which the reactive functional group(s) comprise an NHS ester are depicted, but other reactive functional groups could be used, e.g., as described above. In some embodiments, the $(CH_2CH_2O)_n$ are depicted as terminating at the left end with a methoxy group (OCH$_3$) but it will be understood that the chains depicted below and elsewhere herein may terminate with a different OR moiety (e.g., an aliphatic group, an alkyl group, a lower alkyl group, or any other suitable PEG end group) or an OH group. It will also be appreciated that moieties other than those depicted may connect the $(CH_2CH_2O)_n$ moieties with the NHS group in various embodiments.

In some embodiments, a monofunctional PEG is of formula A:

Formula A

wherein "Reactive functional group" and n are as defined above and described in classes and subclasses herein;

$R^1$ is hydrogen, aliphatic, or any suitable end group; and
T is a covalent bond or a $C_{1-12}$ straight or branched, hydrocarbon chain wherein one or more carbon units of T are optionally and independently replaced by —O—, —S—, —N($R^x$)—, —C(O)—, —C(O)O—, —OC(O)—, —N($R^x$)C(O)—, —C(O)N($R^x$)—, —S(O)—, —S(O)$_2$—, —N($R^x$)SO$_2$—, or —SO$_2$N($R^x$)—; and
each $R^x$ is independently hydrogen or $C_{1-6}$ aliphatic.

Exemplary monofunctional PEGs of formula A include:

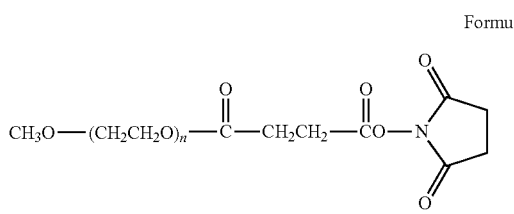

Formula I

In Formula I, the moiety comprising the reactive functional group has the general structure —CO—(CH$_2$)$_m$—COO—NHS, where m=2. In some embodiments, a monofunctional PEGs has the structure of Formula I, where m is between 1 and 10, e.g., between 1 and 5. For example, in some embodiments m is 3, as shown below:

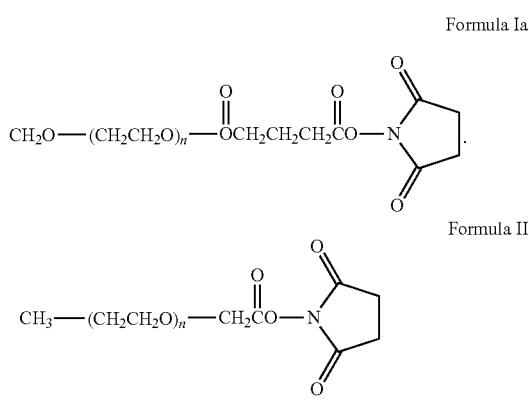

Formula Ia

Formula II

In Formula II, the moiety comprising the reactive functional group has the general structure —(CH$_2$)$_m$—COO—NHS, where m=1. In some embodiments a monofunctional PEG has the structure of Formula II, where m is between 1 and 10 (e.g., wherein m is 5 as shown in Formula III below), or wherein m is 0 (as shown below in Formula IIIa).

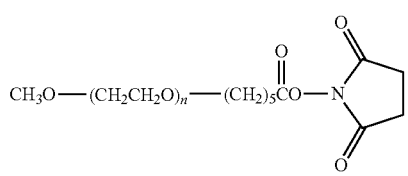

Formula III

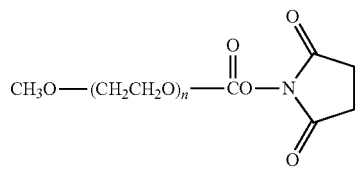

Formula IIIa

In some embodiments a bifunctional linear PEG comprises a moiety comprising a reactive functional group at each of its ends. The reactive functional groups may be the same (homobifunctional) or different (heterobifunctional). In some embodiments the structure of a bifunctional PEG may be symmetric, wherein the same moiety is used to connect the reactive functional group to oxygen atoms at each end of the —(CH$_2$CH$_2$O)$_n$ chain. In some embodiments different moieties are used to connect the two reactive functional groups to the PEG portion of the molecule. The structures of exemplary bifunctional PEGs are depicted below. For illustrative purposes, formulas in which the reactive functional group(s) comprise an NHS ester are depicted, but other reactive functional groups could be used.

In some embodiments, a bifunctional linear PEG is of formula B:

Formula B wherein each T and "Reactive functional group" is independently as defined above and described in classes and subclasses herein, and n is as defined above and described in classes and subclasses herein.

Exemplary bifunctional PEGs of formula B include:

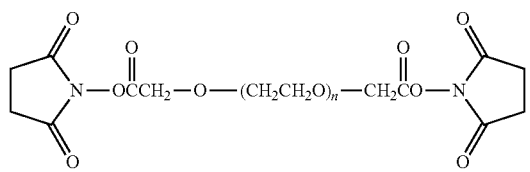

Formula IV

In Formula IV, the moiety comprising the reactive functional group has the general structure —(CH$_2$)$_m$—COO—NHS, where m=1. In some embodiments, a bifunctional PEG has the structure of Formula IV, where m is between 1 and 10, e.g., between 1 and 5. In certain embodiments m is 0, e.g., embodiments the moiety comprising the reactive functional group has the general structure —COO—NHS. For example, in some embodiments a bifunctional PEG has the structure of Formula IVa, as shown below:

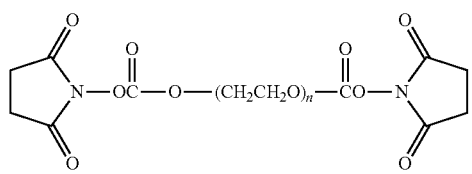

Formula IVa

Formula V

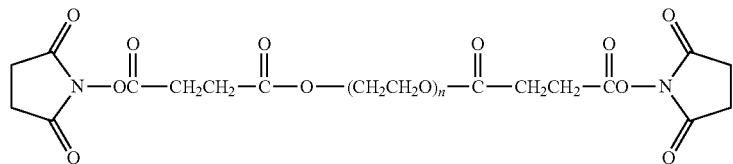

In Formula V, the moiety comprising the reactive functional group has the general structure —CO—$(CH_2)_m$—COO—NHS, where m=2. In some embodiments, a bifunctional PEGs has the structure of Formula V, where m is between 1 and 10, e.g., between 1 and 5. In certain embodiments, for example, m is 2, as shown below:

Formula Va

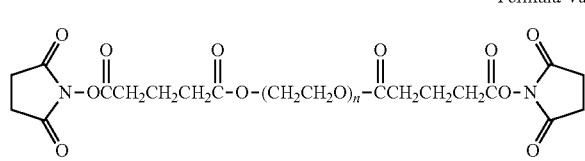

In some embodiments, the present invention provides a compstatin analog conjugated to a polymer. In some embodiments the compstatin analog is a cell-penetrating compstatin analog. In certain embodiments, the present invention provides compstatin analog conjugates of PEG-containing compounds and genera depicted herein, wherein in some embodiments the compstatin analog is a CPCA. In some embodiments, a functional group (for example, an amine, hydroxyl, or thiol group) on a compstatin analog is reacted with a PEG-containing compound having a "reactive functional group" as described herein, to generate such conjugates. By way of example, Formulae III and IV, respectively, can form compstatin analog conjugates having the structure:

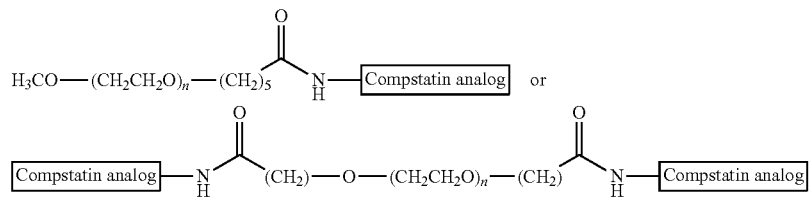

wherein,

represents the attachment point of an amine group on a compstatin analog, which may be a cell-penetrating compstatin analog. It should be understood that anywhere in formulas and genera herein, "COMPSTATIN ANALOG" may represent a cell-penetrating compstatin analog in some embodiments. In certain embodiments, an amine group is a lysine side chain group. It will be appreciated that corresponding conjugates can be formed with any of the PEG-containing compounds and genera depicted herein, depending on the choice of reactive functional group and/or compstatin functional group. For example, Formulae IVa and Va, respectively, can form compstatin analog conjugates having the following structures

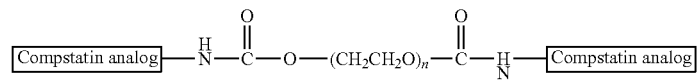

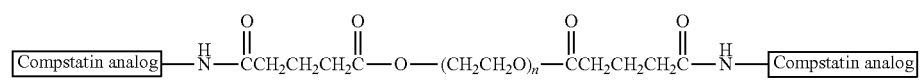

The term "bifunctional" or "bifunctionalized" is sometimes used herein to refer to a compound comprising two compstatin analog moieties linked to a CRM. Such compounds may be designated with the letter "BF". In some embodiments a bifunctionalized compound is symmetrical. In some embodiments the linkages between the CRM and each of the compstatin analog moieties of a bifunctionalized compound are the same.

In some embodiments, a branched, comb, or star-shaped PEG comprises a moiety comprising a reactive functional group at the end of each of multiple —(CH$_2$CH$_2$O)$_n$ chains. The reactive functional groups may be the same or there may be at least two different groups. In some embodiments, a branched, comb, or star-shaped PEG is of the following formulae:

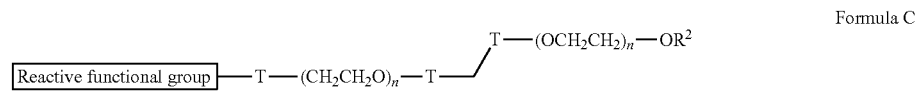

Formula C

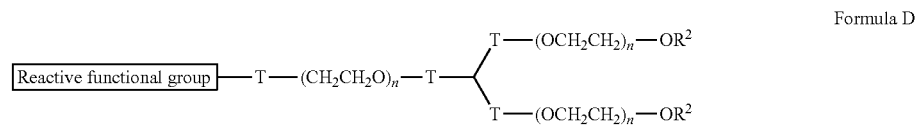

Formula D

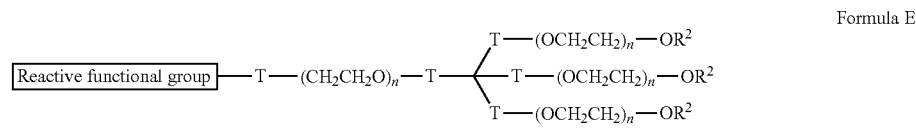

Formula E

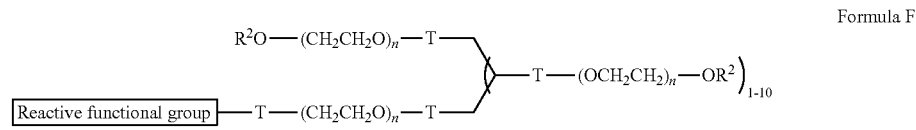

Formula F

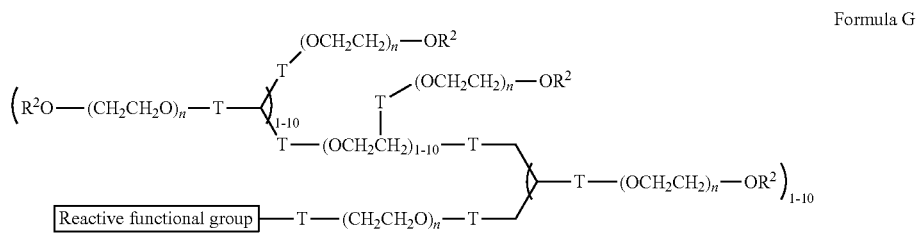

Formula G

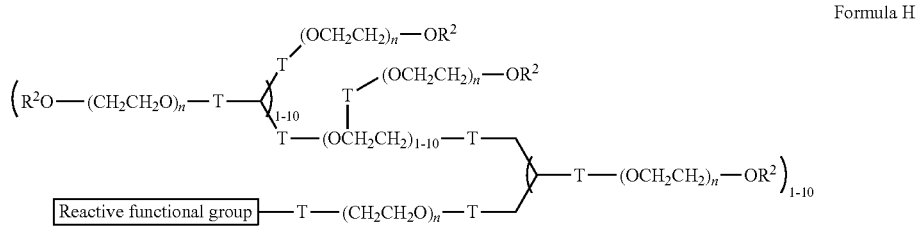

Formula H wherein each $R^2$ is independently a "Reactive functional group" or $R^1$, and each T, n, and "Reactive functional group" is independently as defined above and described in classes and subclasses herein. The structure of exemplary branched PEGs (having 8 arms, or branches) comprising NHS moieties as reactive functional groups is depicted below:

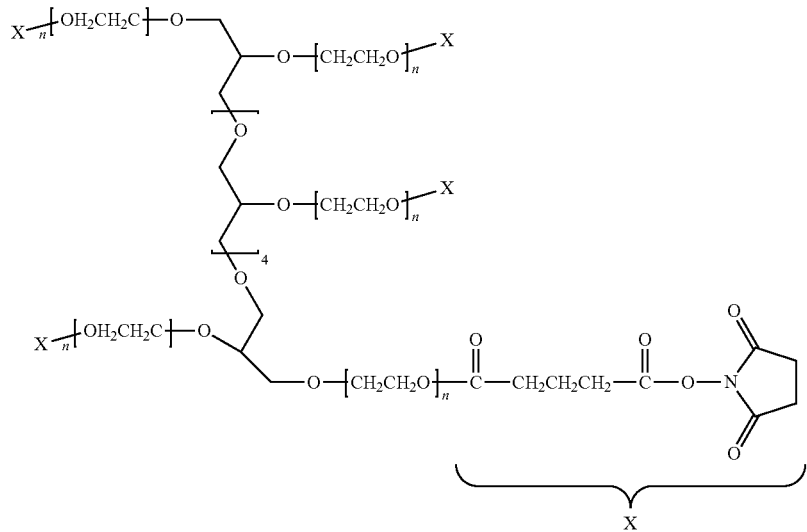
Formula VI
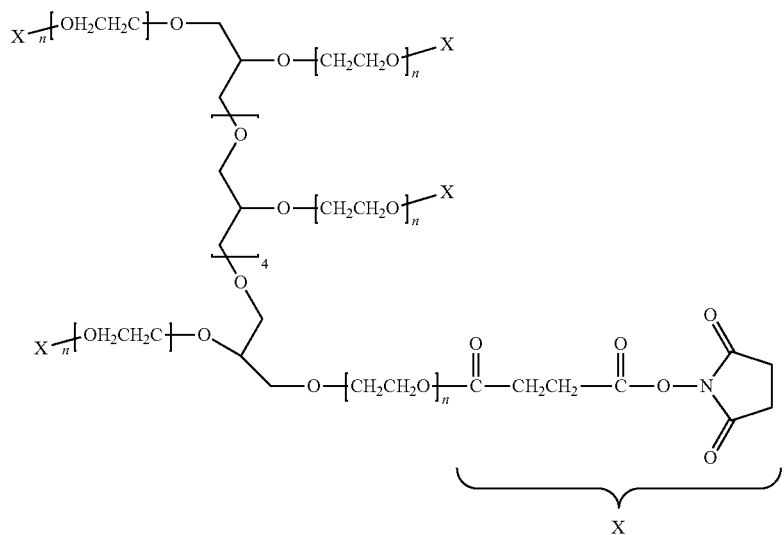
Formula VII
The structure of exemplary branched PEGs (having 4 arms, or branches) comprising NHS moieties as reactive functional groups is depicted below:
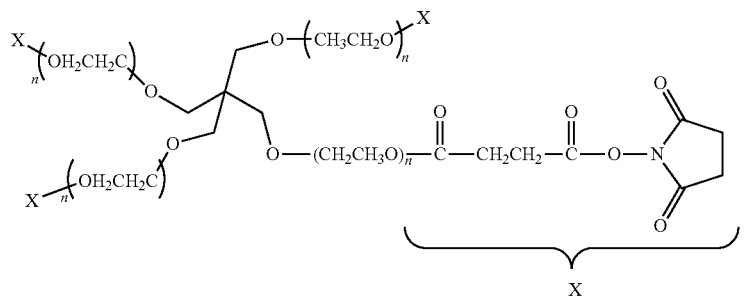
Formula VIII Formula IX

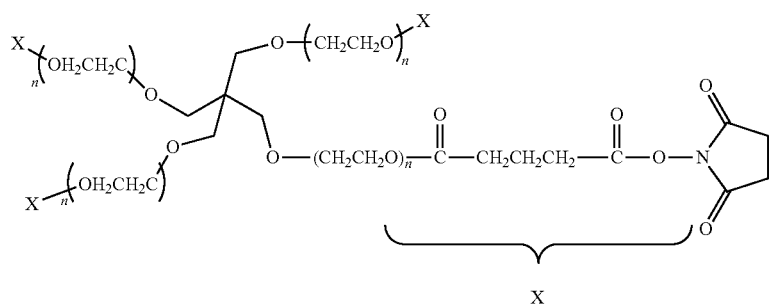

The number of branches emanating from the backbone may be varied. For example, the number 4 in the above formulae VI and VII may be changed to any other integer between 0 and 10 in various embodiments. In certain embodiments, one or more branches does not contain a reactive function group and the branch terminates with a —CH₂CH₂OH or —CH₂CH₂OR group, as described above.

In some embodiments a branched PEG has the structure of Formula VII, VIII, or IX (or variants thereof having different numbers of branches) with the proviso that x is

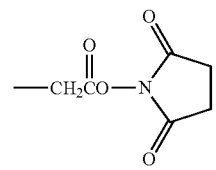

In some embodiments a branched PEG has the structure of Formula VII, VIII, or IX (or variants thereof having different numbers of branches) with the proviso that x is Of course the methylene ($CH_2$) group in the above x moiety may instead comprise a longer alkyl chain $(CH_2)_m$, where m is up to 2, 3, 4, 5, 6, 8, 10, 20, or 30, or may comprise one or more other moieties described herein.

In some embodiments, exemplary branched PEGs having NHS or maleimde reactive groups are depicted below:

Formula X

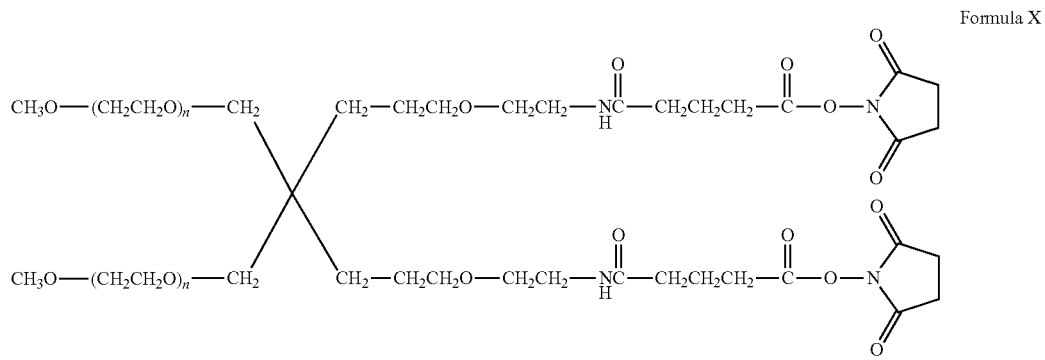

Formula XI

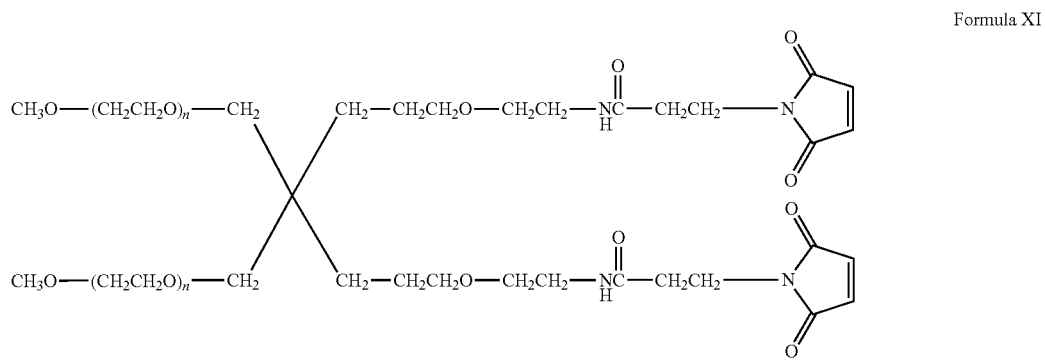

In some embodiments, a variant of Formula X or XI are used, wherein 3 or each of the 4 branches comprise a reactive functional group.

Still other examples of PEGs may be represented as follows:

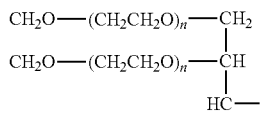

Formula XII

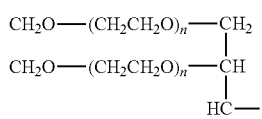
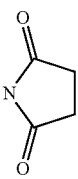

Formula XIII

As noted above, it will be appreciated that, as described herein, in various embodiments any of a variety of moieties may be incorporated between the peptide component and $(CH_2CH_2O)_n$—R moiety of a cell-penetrating or long-acting compstatin analog, such as an linear alkyl, ester, amide, aromatic ring (e.g., a substituted or unsubstituted phenyl), a substituted or unsubstituted cycloalkyl structure, or combinations thereof. In some embodiments such moiet(ies) may render the compound more susceptible to hydrolysis, which may release the peptide portion of the compound from the CRM. In some embodiments, such release may enhance the in vivo tissue penetration and/or activity of the compound. In some embodiments such release releases a CPCA, which may then be able to be internalized by cells. In some embodiments hydrolysis is general (e.g., acid-base) hydrolysis. In some embodiments hydrolysis is enzyme-catalyzed, e.g., esterase-catalyzed. Of course both types of hydrolysis may occur. Examples of PEGs comprising one or more such moieties and an NHS ester as a reactive functional group are as follows:

Formula XIV

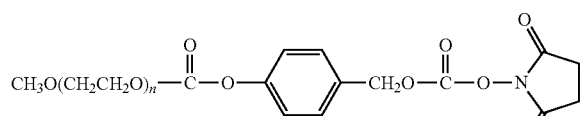

Formula XV

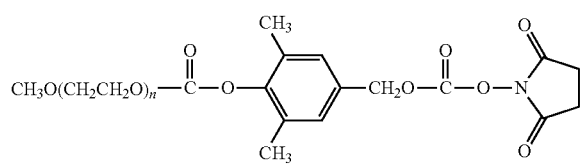

Formula XVI

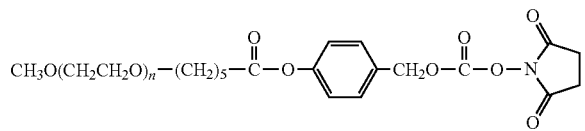

In some embodiments a branched (multi-arm) PEG or star-shaped PEG comprises a pentaerythritol core, hexaglycerin core, or tripentaerythritol core. It will be understood that the branches may not all emanate from a single point in certain embodiments.

Monofunctional, bifunctional, branched, and other PEGs comprising one or more reactive functional groups may, in some embodiments, be obtained from, e.g., NOF America Corp. White Plains, N.Y. or BOC Sciences 45-16 Ramsey Road Shirley, N.Y. 11967, USA, among others, or may be prepared using methods known in the art.

In some embodiments, the present invention provides a compstatin analog conjugated with a polymer, wherein the polymer is other than PEG. In some embodiments, a polymer is a polyoxazoline (POZ). Exemplary mono- and polyfunctionalized polyoxazoline derivatives for direct conjugation, or for conjugation via a linker, are depicted below:

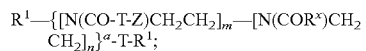

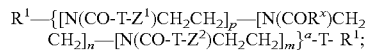

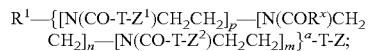

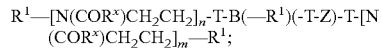

wherein:
each of Z, $Z^1$ and $Z^2$ is independently a reactive functional group as defined above and described in classes and subclasses herein;
each of T, $R^x$, and $R^1$ is independently as defined above and described in classes and subclasses herein;
each of m, n, and p is independently an integer 0-1000, with the limitation that the sum of m, n, and p for each formula is not 0;
a is "ran," which indicates a random copolymer, or "block," which indicates a block copolymer;
B is a branching moiety that is linked with or without a linker to the other parts of the polymer.

Other examples of functionalized polyoxazoline derivatives for conjugation are extensively described in the art, including but not limited to those described in PCT Patent Application Publication Nos. WO/2010/006282, WO/2009/

089542, WO/2009/043027 and WO/2008/106186, the entirety of each of which is hereby incorporated by reference.

Exemplary compstatin analog conjugates with polyoxazoline polymers are depicted below:

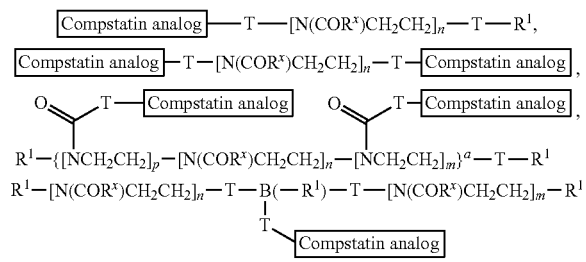

wherein each variable is independently as defined above and described in classes and subclasses herein.

In some embodiments, the present invention provides a compstatin analog conjugated with a polymer, wherein the compstatin analog is connected to the polymer via one or more linkers. In some embodiments, a polymer is selected from PEG-containing compounds and genera described above and in classes and subclasses herein. In some embodiments, the present invention provides compstatin analog conjugates of PEG-containing compounds and genera depicted herein, wherein the compstatin analog is connected to the PEG-containing moieties via one or more linkers. Mono- and poly-functional PEGs that comprise one or more reactive functional groups for conjugation are defined above and described in classes and subclasses herein, including but not limited to those of formula A, I, Ia, II, III, IIIa, B, IV, IVa, V, Va, C, D, E, F, G, H, VI, VII, VIII, IX, X, XI, XII, XIII, XIV, XV, or XVI.

Suitable linkers for connecting a compstatin analog and a polymer moiety such as PEG or polyoxazoline are extensively described above and in classes and subclasses herein. In some embodiments, a linker has multiple functional groups, wherein one functional group is connected to a compstatin analog and another is connected to a polymer moiety. In some embodiments, a linker is a bifunctional compound. In some embodiments, a linker has the structure of $NH_2(CH_2CH_2O)nCH_2C(=O)OH$, wherein n is 1 to 1000. In some embodiments, a linker is 8-amino-3,6-dioxaoctanoic acid (AEEAc). In some embodiments, a linker is activated for conjugation with a polymer moiety or a functional group of a compstatin analog. For example, in some embodiments, the carboxyl group of AEEAc is activated before conjugation with the amine group of the side chain of a lysine group.

In some embodiments, a suitable functional group (for example, an amine, hydroxyl, thiol, or carboxylic acid group) on a compstatin analog is used for conjugation with a polymer moiety, either directly or via a linker. In some embodiments, a compstatin analog is conjugated through an amine group to a PEG moiety via a linker. In some embodiments, an amine group is the α-amino group of an amino acid residue. In some embodiments, an amine group is the amine group of the lysine side chain. In some embodiments, a compstatin analog is conjugated to a PEG moiety through the amino group of a lysine side chain (s-amino group) via a linker having the structure of $NH_2(CH_2CH_2O)nCH_2C(=O)OH$, wherein n is 1 to 1000. In some embodiments, a compstatin analog is conjugated to the PEG moiety through the amino group of a lysine side chain via an AEEAc linker. In some embodiments, the $NH_2(CH_2CH_2O)nCH_2C(=O)OH$ linker introduces a $-NH(CH_2CH_2O)nCH_2C(=O)-$ moiety on a compstatin lysine side chain after conjugation. In some embodiments, the AEEAc linker introduces a $-NH(CH_2CH_2O)_2CH_2C(=O)-$ moiety on a compstatin lysine side chain after conjugation.

In some embodiments, a compstatin analog is conjugated to a polymer moiety via a linker, wherein the linker comprises an AEEAc moiety and an amino acid residue. In some embodiments, a compstatin analog is conjugated to a polymer moiety via a linker, wherein the linker comprises an AEEAc moiety and a lysine residue. In some embodiments, a polymer is PEG. In some embodiments, the C-terminus of a compstatin analog is connected to the amino group of AEEAc, and the C-terminus of AEEAc is connected to a lysine residue. In some embodiments, the C-terminus of a compstatin analog is connected to the amino group of AEEAc, and the C-terminus of AEEAc is connected to the α-amino group of a lysine residue. In some embodiments, the C-terminus of a compstatin analog is connected to the amino group of AEEAc, the C-terminus of AEEAc is connected to the α-amino group of the lysine residue, and a polymer moiety, such as a PEG moiety, is conjugated through the ε-amino group of said lysine residue. In some embodiments, the C-terminus of the lysine residue is modified. In some embodiments, the C-terminus of the lysine residue is modified by amidation. In some embodiments, the N-terminus of a compstatin analog is modified. In some embodiments, the N-terminus of a compstatin analog is acetylated.

Exemplary conjugates comprising an AEEAc linker and a polymer are depicted below, wherein

represents the attachment point of an amine group on a compstatin analog,

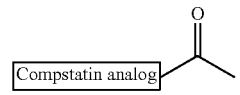

represents a compstatin analog attaching through its C-terminus, and wherein each of the other variables is independently as defined above and described in classes and subclasses herewith. In some embodiments, an amine group is the amino group of a lysine side chain.

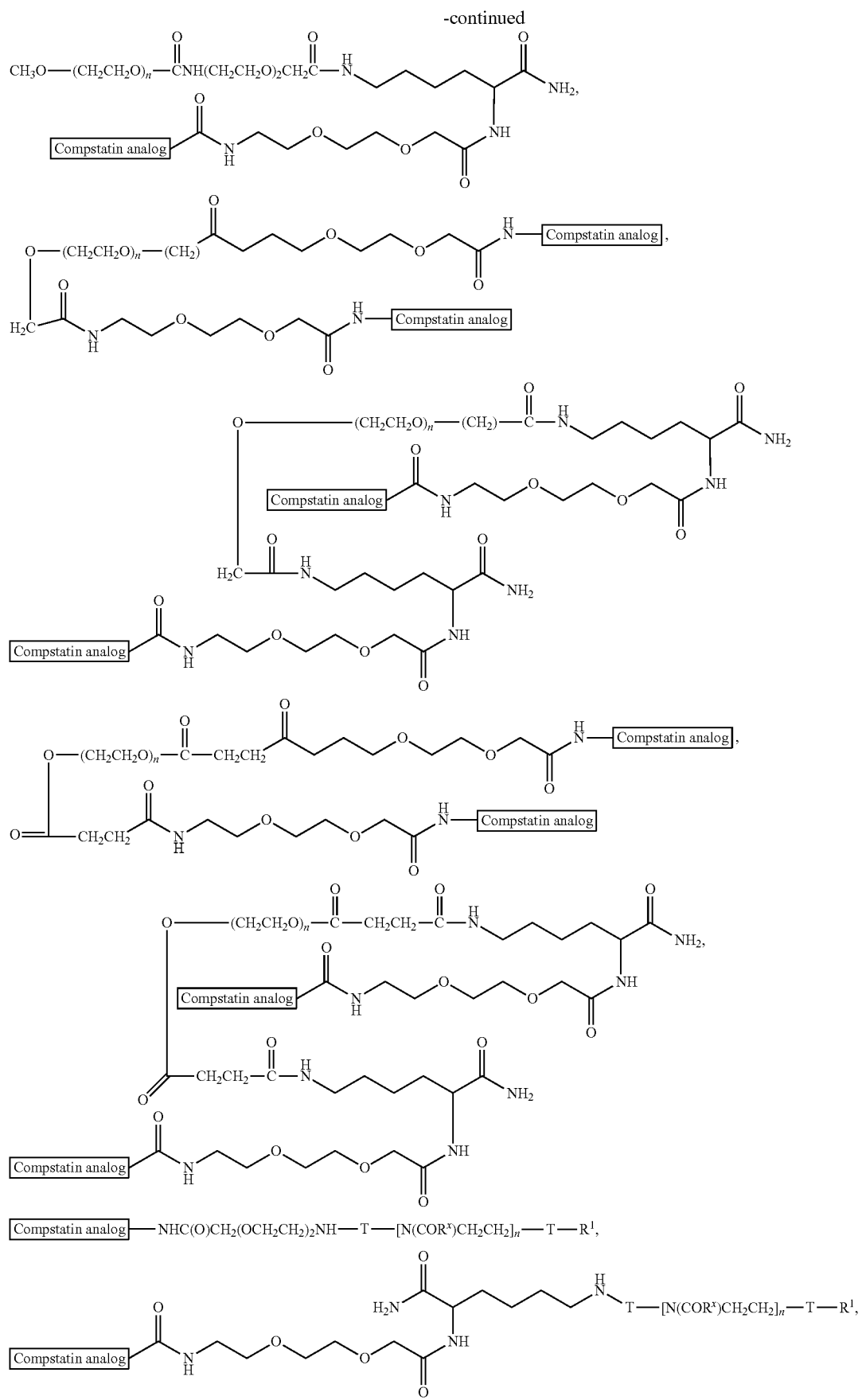

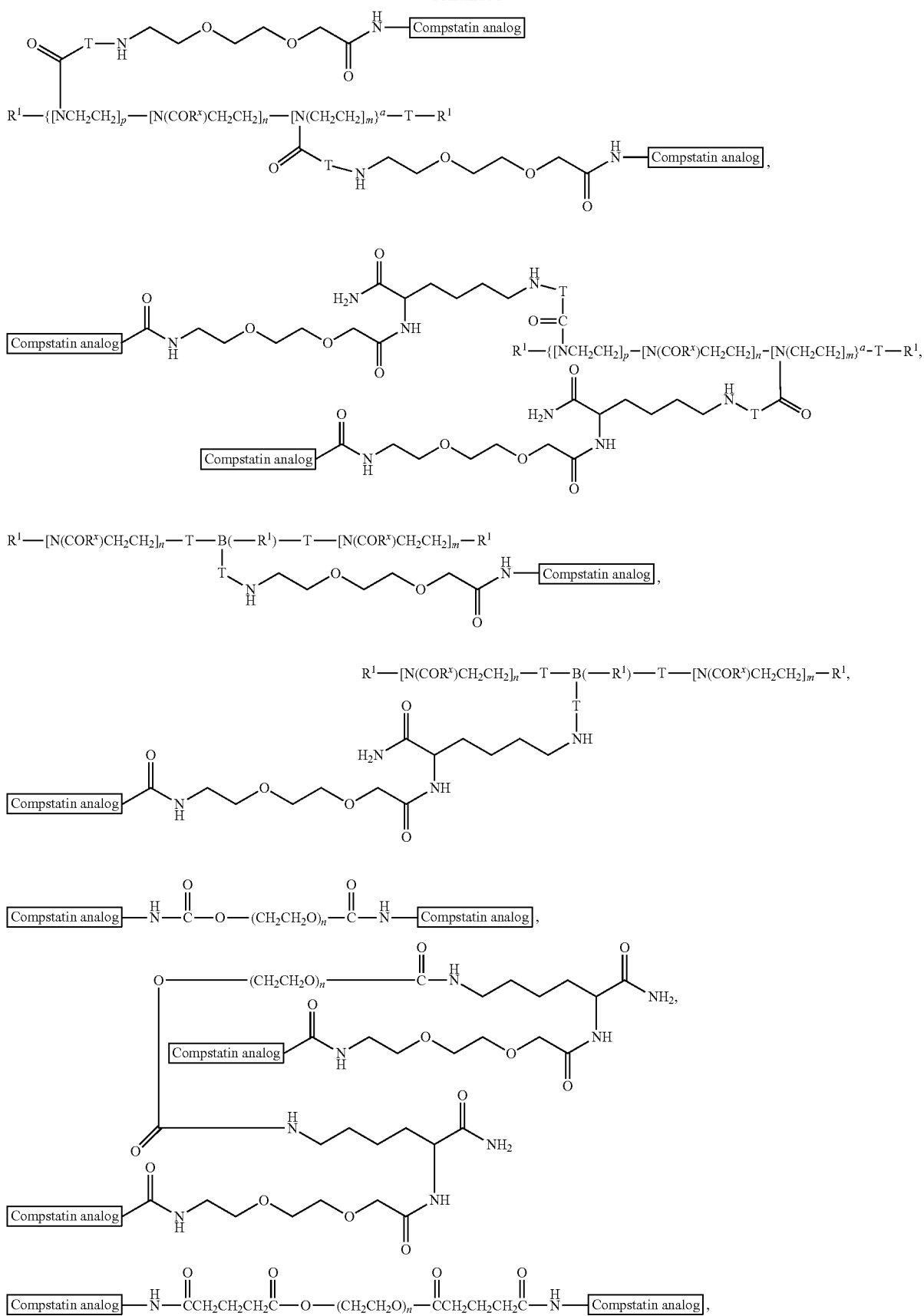

-continued

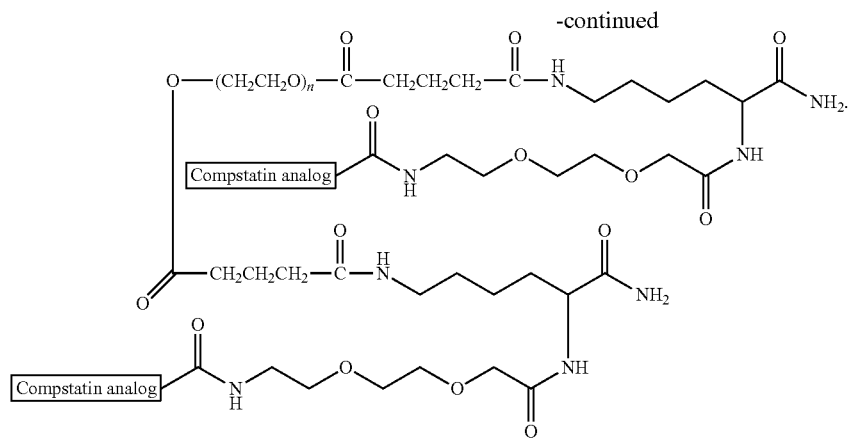

In certain embodiments a compstatin analog may be represented as M-AEEAc-Lys-B$_2$. wherein B$_2$ is a blocking moiety, e.g., NH$_2$, M represents any of SEQ ID NOs: 3-36, 37, 72, 73, 74, 75, or 76, with the proviso that the C-terminal amino acid of any of SEQ ID NOs: 3-36, 37, 72, 73, 74, 75, or 76 is linked via a peptide bond to AEEAc-Lys-B$_2$. The NHS moiety of a monofunctional or multifunctional (e.g., bifunctional) PEG reacts with the free amine of the lysine side chain to generate a monofunctionalized (one compstatin analog moiety) or multifunctionalized (multiple compstatin analog moieties) long-acting compstatin analog. In various embodiments any amino acid comprising a side chain that comprises a reactive functional group may be used instead of Lys (or in addition to Lys). A monofunctional or multifunctional PEG comprising a suitable reactive functional group may be reacted with such side chain in a manner analogous to the reaction of NHS-ester activated PEGs with Lys.

With regard to any of the above formulae and structures, it is to be understood that embodiments in which the compstatin analog component comprises any compstatin analog described herein, e.g., any compstatin analog of SEQ ID NOs; 3-36, 37, 72, 73, 74, 75, or 76, are expressly disclosed. For example, and without limitation, a compstatin analog may comprise the amino acid sequence of SEQ ID NO: 28.

In some aspects, the present invention relates to use of click chemistry in connection with compstatin analogs. "Click chemistry" is well known in the art and is useful in some aspects of the present invention. Click chemistry embodies, in certain embodiments, versatile cycloaddition reactions between azides and alkynes that enable a number of useful applications. Methods of carrying out click chemistry are known in the art, and are described by Kolb, H. C.; Sharpless, K. B., Drug Disc. Today, 2003, 1128-1137; Moses, J. E.; Moorhouse, A. D.; Chem. Soc. Rev., 2007, 1249-1262; the entire contents of each are hereby incorporated by reference. Click chemistry is a popular method of bioconjugation due to its high reactivity and selectivity, even in biological media. See Kolb, H. C.; Finn, M. G.; Sharpless, K. B. Angew. Chem. Int. Ed. 2001, 40, 2004-2021; and Wang, Q.; Chan, T. R.; Hilgraf, R.; Fokin, V. V.; Sharpless, K. B.; Finn, M. G. J. Am. Chem. Soc. 2003, 125, 3192-3193. In addition, currently available recombinant techniques and synthetic methods permit the introduction of azides and alkyne-bearing non-canonical amino acids into peptides, proteins, cells, viruses, bacteria, and other biological entities that consist of or display proteins. See Link, A. J.; Vink, M. K. S.; Tirrell, D. A. J. Am. Chem. Soc. 2004, 126, 10598-10602; Deiters, A.; Cropp, T. A.; Mukherji, M.; Chin, J. W.; Anderson, C.; Schultz, P. G. J. Am. Chem. Soc. 2003, 125, 11782-11783.

As used herein, the term "click chemistry group" is sometimes used to refer to a reactive functional group capable of participating in a click chemistry reaction with an appropriate second reactive functional group, which second reactive functional group is also a click chemistry group. The first and second click chemistry groups, or entities (e.g., molecules) comprising such groups, may be referred to as complementary. First and second entities, e.g., molecules, that comprise complementary click chemistry groups may be referred to as click chemistry partners. An entity or molecule comprising a click chemistry group may be referred to as "click-functionalized". A bond formed by reaction of complementary click chemistry partners may be referred to as a "click chemistry bond".

In some embodiments, the present invention provides click-functionalized compstatin analogs for, e.g., conjugation to a complementary moiety on a partner molecule or biomolecule. In some embodiments, a complementary partner molecule or biomolecule is a polymer, peptide, protein, or a molecule that functions as a clearance-reducing moiety. In some embodiments, the "click-functionalized" moiety is an alkyne or an alkyne derivative which is capable of undergoing [3+2] cycloaddition reactions with complementary azide-bearing molecules and biomolecules. In another embodiment, the "click-functionalized" functionality is an azide or an azide derivative which is capable of undergoing [3+2]cycloaddition reactions with complementary alkyne-bearing molecules and biomolecules (i.e. click chemistry).

In some embodiments, a click-functionalized compstatin analog bears an azide group on any side chain group of the compstatin analog. In some embodiments, a click-functionalized compstatin analog bears an azide group on a lysine side chain group.

In some embodiments, a click-functionalized compstatin analog bears an alkyne group on any side chain group of the compstatin compstatin analog. In some embodiments, a click-functionalized compstatin analog bears an alkyne group on a lysine side chain group.

In some embodiments, the present invention provides compstatin conjugates comprising a compstatin analog, a molecule that functions as a clearance-reducing moiety, and a triazole linker. In some embodiments, a triazole linker is the result of click conjugation chemistry between a compstatin conjugate and a molecule that functions as a clearance-reducing moiety. In some embodiments the CRM may be any CRM disclosed herein. For example, the CRM may be a PEG, a polypeptide, or a POZ.

In some embodiments, the present invention provides compstatin conjugates comprising a compstatin analog, a PEG moiety, and a triazole linker. In some embodiments, a triazole linker is the result of click conjugation chemistry between a compstatin conjugate and a PEG moiety.

In some embodiments, the present invention provides compstatin conjugates comprising a compstatin analog, a polyoxazoline moiety, and a triazole linker. In some embodiments, a triazole linker is the result of click conjugation chemistry between a compstatin conjugate and a polyoxazoline moiety.

In some embodiments, click chemistry between a compstatin analog and another moiety is transition metal catalyzed. Copper-containing molecules which catalyze the "click" reaction include, but are not limited to, copper wire, copper bromide (CuBr), copper chloride (CuCl), copper sulfate (CuSO$_4$), copper sulfate pentahydrate (CuSO$_4$.5H$_2$O), copper acetate (Cu$_2$(AcO$_4$), copper iodide (CuI), [Cu(MeCN)$_4$](OTf), [Cu(MeCN)$_4$](PF$_6$), colloidal copper sources, and immobilized copper sources. In some embodiments other metals, such as ruthenium. Reducing agents as well as organic and inorganic metal-binding ligands can be used in conjunction with metal catalysts and include, but are not limited to, sodium ascorbate, tris(triazolyl)amine ligands, tris(carboxyethyl)phosphine (TCEP), sulfonated bathophenanthroline ligands, and benzimidazole-based ligands.

In some embodiments, compstatin analogs are conjugated to other moieties, e.g., CPMs, CRMs, using metal free click chemistry (also known as copper free click chemistry) to give a metal free composition or conjugates. In contrast to standard click chemistry, also known as copper assisted click chemistry (CuACC), metal free click chemistry occurs between either a strained, cyclic alkyne or an alkyne precursor such as an oxanorbornadiene, and an azide group. As the name implies, no metal catalyst is necessary for the reaction to occur. Examples of such chemistries include reactions involving cyclooctyne derivatives (Codelli, et. al. *J. Am. Chem. Soc.,* 2008, 130, 11486-11493; Jewett, et. al. *J. Am. Chem. Soc.,* 2010, 132, 3688-3690; Ning, et. al. *Angew. Chem. Int. Ed.,* 2008, 47, 2253-2255), difluorooxanorbornene derivatives (van Berkel, et. al. *ChemBioChem,* 2007, 8, 1504-1508), or nitrile oxide derivatives (Lutz, et. al. *Macromolecules,* 2009, 42, 5411-5413). In certain embodiments a metal-free click chemistry reaction is a metal-free [3+2] cycloaddition reaction, Diels-Alder reaction, or thiol-alkene radical addition reaction. Exemplary click chemistry reactions and click chemistry groups are described in, e.g., Joerg Lahann, Click Chemistry for Biotechnology and Materials Science, 2009, John Wiley & Sons Ltd, ISBN 978-0-470-69970-6; Becer, Hoogenboom, and Schubert, Click Chemistry beyond Metal-Catalyzed Cycloaddition, Angewandte Chemie International Edition (2009) 48: 4900-4908. In certain embodiments a click chemistry group comprises a diarylcyclooctyne.

Certain examples of metal free click chemistry are shown in the scheme below.

R—N$_3$ +

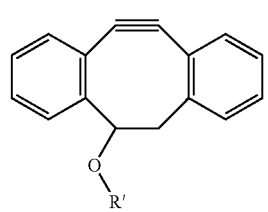

$\xrightarrow{\text{Room Temperature Water}}$

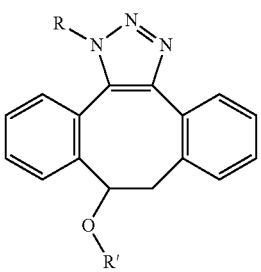

R—N$_3$ +

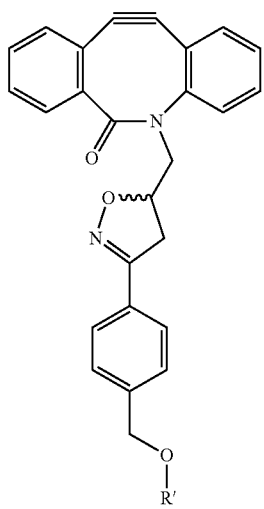

$\xrightarrow{\text{Room Temperature Water}}$

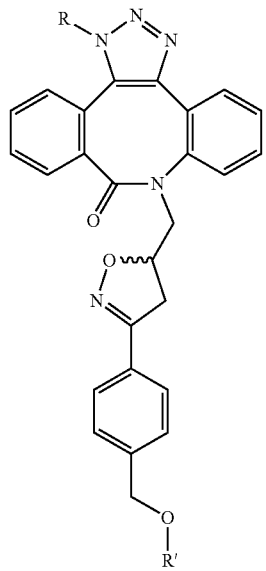

R—N$_3$ +

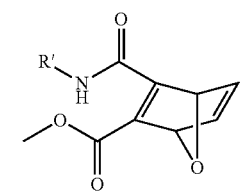

$\xrightarrow{\text{Room Temperature Water}}$

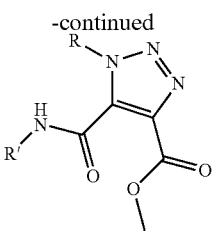

Certain metal-free click moieties are known in the literature. Examples include 4-dibenzocyclooctynol (DIBO)

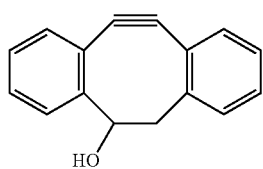 [SMILES: OC1Cc2ccccc2C#Cc2ccccc21]

(from Ning et. al; *Angew Chem Int Ed*, 2008, 47, 2253); difluorinated cyclooctynes (DIFO or DFO)

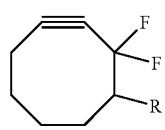

(from Codelli, et. al.; *J. Am. Chem. Soc.* 2008, 130, 11486-11493); biarylazacyclooctynone (BARAC)

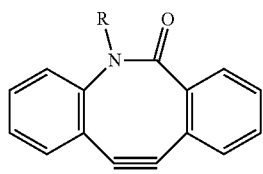

(from Jewett et. al.; *J. Am. Chem. Soc.* 2010, 132, 3688); or bicyclononyne (BCN)

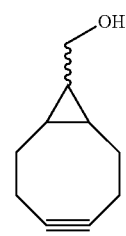 [SMILES: OCC1C2CCC#CCCC12]

(From Dommerholt, et. al.; *Angew Chem Int Ed*, 2010, 49, 9422-9425) or dibenzylcyclooctyne (DBCO)

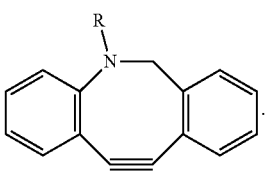

A reaction scheme involving reaction of DBCO and an azide is shown below:

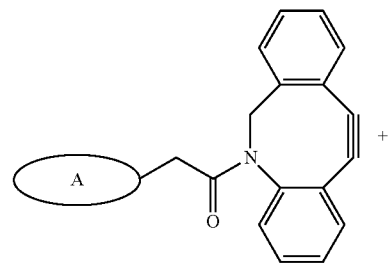

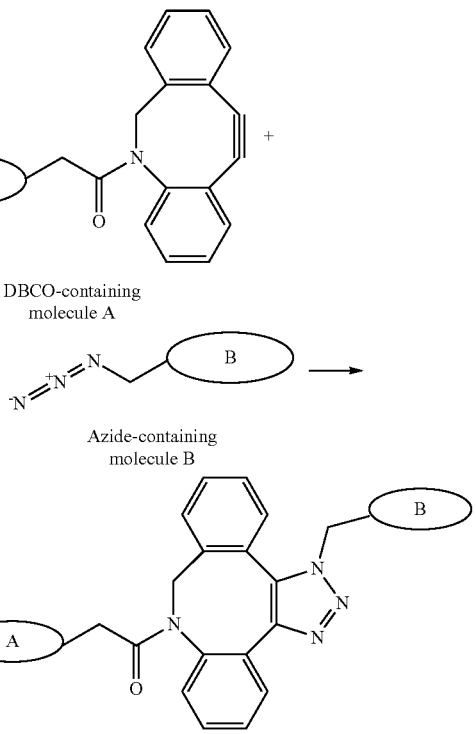

In the above scheme, in various embodiments, A may comprise or consist of a compstatin analog moiety and B may comprise or consist of a CPM or CRM, e.g., a polymer, such as a PEG or POZ a polypeptide, or B may comprise or consist of a compstatin analog moiety and A may comprise or consist of a CPM or CRM, e.g., a polymer, such as a PEG or POZ or a polypeptide.

In some embodiments, the "metal free click-functionalized" moiety is an acetylene or an acetylene derivative which is capable of undergoing [3+2] cycloaddition reactions with complementary azide-bearing molecules and biomolecules without the use of a metal catalyst.

In some embodiments, the R and R' groups of the metal-free click chemistry reagents are a compstatin analog or any molecule described herein to which a compstatin analog may be conjugated. In some embodiments, such compstatin analogs bear a click-functionalized moiety on a lysine side chain. In some embodiments, such compstatin analogs are connected to a click-functionalized moiety via a linker. In some embodiments, such compstatin analogs are connected to a click-functionalized moiety via AEEAc.

In some embodiments, a click chemistry reagent comprises DBCO. Exemplary reagents and exemplary uses thereof are set forth below:

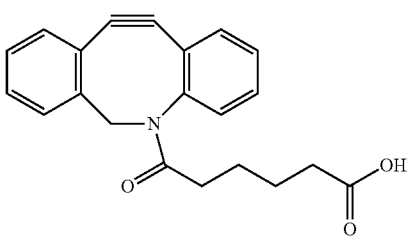 [SMILES: O=C(O)CCCCC(=O)N1Cc2ccccc2C#Cc2ccccc21]

DBCO-Acid. In some embodiments a DBCO-Acid may be used to react with an amine-containing moiety.

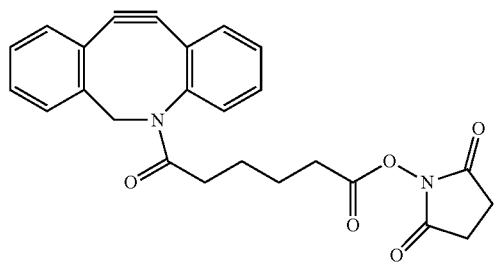 [SMILES: O=C(CCCCC(=O)N1Cc2ccccc2C#Cc2ccccc21)ON1C(=O)CCC1=O]

DBCO-NHS ester (above) or DBCO-sulfo-NHS ester (below) may be used to incorporate a DBCO functionality into an amine-containing molecule, such as a compstatin analog or a polypeptide comprising a lysine residue.

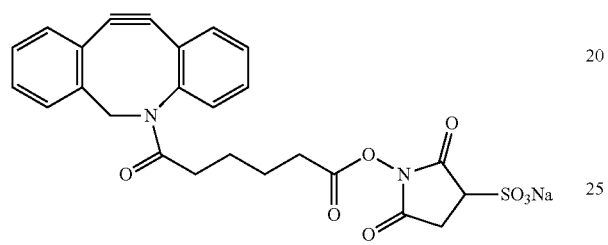

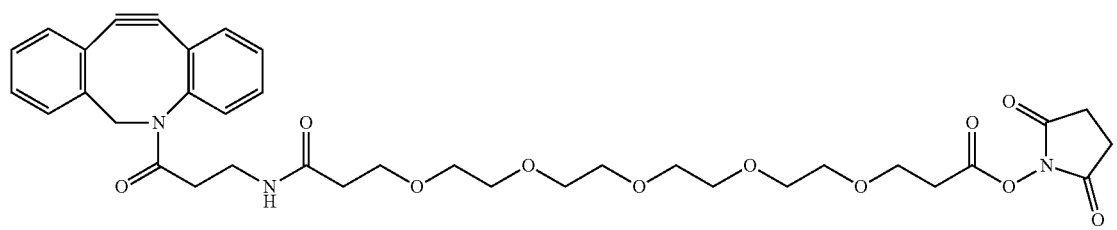 [SMILES: O=C(CCOCCOCCOCCOCCOCCC(=O)ON1C(=O)CCC1=O)NCCC(=O)N1Cc2ccccc2C#Cc2ccccc21]

DBCO-PEG4-NHS ester. In some embodiments such reagent is useful for introducing a DBCO moiety by reaction with an available amine functionality. In some aspects, the presence of a PEG chain as a hydrophilic spacer may be useful to, e.g., increase solubility or provide flexibility.

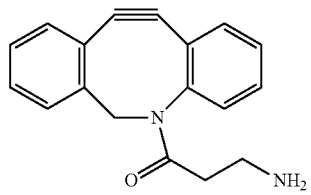 [SMILES: NCCC(=O)N1Cc2ccccc2C#Cc2ccccc21]

DBCO-Amine. In some embodiments a click chemistry reagent comprises a carbonyl/carboxyl reactive dibenzylcyclooctyne, which may react with acids, active esters and/or aldehydes.

In certain embodiments a click chemistry reaction involves a cyclooctyne depicted below:

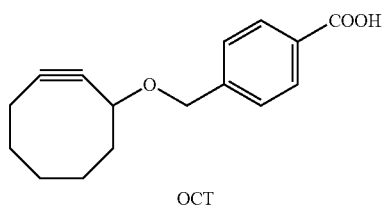

OCT

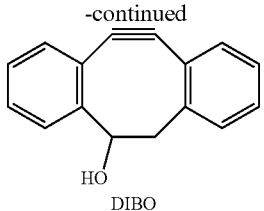

DIBO

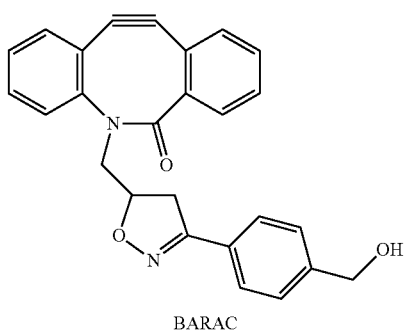

BARAC

-continued

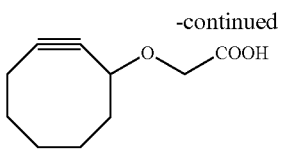

ALO

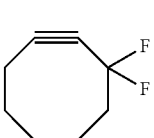

DIFO

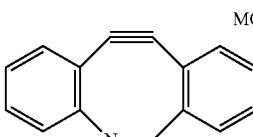

MOFO

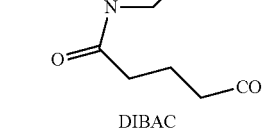

DIBAC

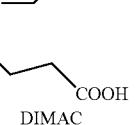

DIMAC

In certain embodiments click chemistry reactions comprise reactions between nitrones and cyclooctynes (see, e.g., Ning, Xinghai; Temming, Rinske P.; Dommerholt, Jan; Guo, Jun; Ania, Daniel B.; Debets, Marjoke F.; Wolfert, Margreet A.; Boons, Geert-Jan et al. (2010). "Protein Modification by Strain-Promoted Alkyne-Nitrone Cycloaddition". Angewandte Chemie International Edition 49 (17): 3065), oxime/hydrazone formation from aldehydes and ketones, tetrazine ligations (see, e.g., Blackman, Melissa L.; Royzen, Maksim; Fox, Joseph M. (2008). "The Tetrazine Ligation: Fast Bioconjugation based on Inverse-electron-demand Diels-Alder Reactivity". Journal of the American Chemical Society 130 (41): 13518-9), tetrazole ligations, the isonitrile-based click reaction (see, e.g., Stackmann, Henning; Neves, André A.; Stairs, Shaun; Brindle, Kevin M.; Leeper, Finian J. (2011). "Exploring isonitrile-based click chemistry for ligation with biomolecules". Organic & Biomolecular Chemistry 9 (21): 7303), and the quadricyclane ligation (see, e.g., Sletten, Ellen M.; Bertozzi, Carolyn R. (2011). "A Bioorthogonal Quadricyclane Ligation". Journal of the American Chemical Society 133 (44): 17570-3). In certain embodiments a click chemistry reaction is a Staudinger ligation (phosphine-azide).

Any compstatin analog may be modified to incorporate a click chemistry group in various embodiments. For example, a compstatin analog comprising the sequence of any of SEQ ID NOs: 3-36, 37, 72, 73, 74, 75, or 76 may be so modified. In some embodiments any such sequence further comprises a lysine residue or an AEEAc-Lys moiety, e.g., at the C-terminus. In some embodiments a click chemistry group is incorporated after peptide synthesis. For example, a Lys side chain may be reacted with azido acetic acid in order to introduce an azide moiety as a click chemistry group. In some embodiments a click chemistry group is incorporated after cyclization and, in some embodiments, after addition of a blocking moiety at the N- and/or C-terminus. In some embodiments a click chemistry group is incorporated during peptide synthesis. For example, an amino acid comprising a side chain that comprises a click chemistry group may be used in the synthesis of a compstatin analog. A variety of such amino acids are commercially available from a number of sources, e.g., AAPPTec (Louisville, Ky.), Jena Bioscience GmBH (Jena, Germany). In some aspects, methods of making a click chemistry functionalized compstatin analog are provided herein.

In some embodiments compositions comprising a compstatin analog and a click chemistry reagent are used to install a click chemistry group, e.g., any click chemistry group known in the art, to a compstatin analgo. In some aspects, the composition may be incubated under suitable conditions (which may include providing a suitable catalyst, light (e.g., UV)) to functionalize the compstatin analog with a click chemistry functionality. In some embodiments methods of making a cell-penetrating compstatin analog are provided. In some embodiments the methods comprise mixing a compstatin analog comprising a first click chemistry group with a CPM comprising a complementary click chemistry group under conditions suitable for a click chemistry reaction to occur. Additional steps may comprise purifying the resulting conjugate. In some embodiments purifying comprises removing at least some unreacted components, e.g., with an appropriate scavenger.

In some embodiments a cell-penetrating compstatin analog may be used together with a long-acting compstatin analog. For example, a method of treatment may comprise administering a cell-penetrating compstatin analog and a long-acting compstatin analog. Exemplary long-acting compstatin analogs are set forth below and herein.

(SEQ ID NO: 58)
$(CH_2CH_2O)_nC(=O)$-Ile-Cys-Val-(1Me)Trp-Gln-Asp-Trp-Gly-Ala-His-Arg-Cys-Thr-$NH_2$)

(SEQ ID NO: 59)
Ac-Ile-Cys*-Val-(1Me)Trp-Gln-Asp-Trp-Gly-Ala-His-Arg-Cys*-Thr-NH—$CH_2CH_2OCH_2CH_2OCH_2$—C(=O)-Lys-C(=O)—$(CH_2CH_2O)n$-$NH_2$ (SEQ ID NO: 60)
Ac-Ile-Cys*-Val-(1Me)Trp-Gln-Asp-Trp-Gly-Ala-His-Arg-Cys*-Thr-Lys-C(=O)—$(CH_2CH_2O)n$-$NH_2$.

(SEQ ID NO: 61)
Ac-Ile-Cys*-Val-(1Me)Trp-Gln-Asp-Trp-Gly-Ala-His-Arg-Cys*-Thr-(Gly)$_5$-Lys-C(=O)—$(CH_2CH_2O)n$-$NH_2$ (SEQ ID NO: 62)
Ac-$(CH_2CH_2O)$nC(=O)Lys-(Gly)5-Ile-Cys*-Val-(1Me)Trp-Gln-Asp-Trp-Gly-Ala-His-Arg-Cys*-Thr-$NH_2$)

(SEQ ID NO: 63)
Ac-$(CH_2CH_2O)$nC(=O)Lys-Ile-Cys*-Val-(1Me)Trp-Gln-Asp-Trp-Gly-Ala-His-Arg-Cys*-Thr-$NH_2$)

In SEQ ID NO: 58, the $(CH_2CH_2O)n$ is coupled via an amide bond to the N-terminal amino acid. In SEQ ID NOs: 59-63, the $(CH_2CH_2O)n$ moiety is coupled via an amide bond to a Lys side chain; thus it will be understood that the $NH_2$ at the C-terminus in SEQ ID NOs: 59, 60, and 61, represents amidation of the C-terminus of the peptide, and it will be understood that in SEQ ID NOs: 62 and 63, the Ac at the N-terminus represents acetylation of the N-terminus of the peptide, as described above. It will also be appreciated by those of ordinary skill in the art that a free end of a $(CH_2CH_2O)_n$ moiety typically terminates with an (O̲R) where the underlined O represents the O atom in the terminal $(CH_2CH_2O)$ group. (O̲R) is often a moiety such as a hydroxyl (O̲H) or methoxy (—O̲CH$_3$) group though other groups (e.g., other alkoxy groups) could be used. Thus SEQ ID NO: 59, for example, may be represented as (SEQ ID NO: 64)
Ac-Ile-Cys*-Val-(1Me)Trp-Gln-Asp-Trp-Gly-Ala-His-Arg-Cys*-Thr-NH-$CH_2CH_2OCH_2CH_2OCH_2$—C(=O)-Lys-(C(=O)—$(CH_2CH_2O)_n$—R)—NH2 wherein R is, e.g., either H or CH$_3$ in the case of linear PEG. In the case of a bifunctional, branched or star-shaped PEG, R represents the remainder of the molecule. Further, it will be understood that the moiety comprising the reactive functional group may vary, as described herein (e.g., according to any of the formulas described herein). For example, long-acting compstatin analogs comprising the same peptide sequence as SEQ ID NO: 64, in which the moiety comprising the reactive functional group comprises an ester and/or alkyl chain may be represented as follows (SEQ ID NO: 65)
Ac-Ile-Cys*-Val-(1Me)Trp-Gln-Asp-Trp-Gly-Ala-His-Arg-Cys*-Thr-NH—$CH_2CH_2OCH_2CH_2OCH_2$—C(=O)-Lys-(C(=O)—$(CH_2)_m$—$(CH_2CH_2O)_n$—R)—NH2;

-continued (SEQ ID NO: 66)
Ac-Ile-Cys*-Val-(1Me)Trp-Gln-Asp-Trp-Gly-Ala-His-

Arg-Cys*-Thr-NH—CH$_2$CH$_2$OCH$_2$CH$_2$OCH$_2$—C(=O)-

Lys-(C(=O)-(CH$_2$)$_m$-C(=O)-(CH$_2$CH$_2$O)$_n$-R)-*NH2*

(SEQ ID NO: 67)
Ac-Ile-Cys*-Val-(1Me)Trp-Gln-Asp-Trp-Gly-Ala-His-

Arg-Cys*-Thr-NH—CH$_2$CH$_2$OCH$_2$CH$_2$OCH$_2$—C(=O)-

Lys-(C(=O)-(CH$_2$)$_m$-C(=O)-(CH$_2$)j (CH$_2$CH$_2$O)$_n$-R)-*NH2*

In SEQ ID NOs: 65-67 m may range from 1 up to about 2, 3, 4, 5, 6, 7, 8, 10, 15, 20, or 30 in various embodiments. In SEQ ID NOs: 67 j may range from 1 up to about 2, 3, 4, 5, 6, 7, 8, 10, 15, 20, or 30 in various embodiments.

It will also be appreciated that, as described herein, in various embodiments other moieties may be incorporated between the Lys-(C(=O)— and (CH$_2$CH$_2$O)$_n$—R, such as an amide, aromatic ring (e.g., a substituted or unsubstituted phenyl), or a substituted or unsubstituted cycloalkyl structure.

In some embodiments variants of SEQ ID NOs: 58-67 are used in which -Ile-Cys*-Val-(1Me)Trp-Gln-Asp-Trp-Gly-Ala-His-Arg-Cys*-Thr- is replaced by an amino acid sequence comprising the amino acid sequence of any other compstatin analog, e.g., of any of SEQ ID NOs 3-27 or 29-36, 37, 72, 73, 74, 75, and 76 with the proviso that blocking moiet(ies) present at the N- and/or C-termini of a compstatin analog may be absent, replaced by a linker (which may comprise a blocking moiety), or attached to a different N- or C-terminal amino acid present in the corresponding variant(s).

Any compstatin analog, e.g., any compound comprising any of SEQ ID NOs: 3-37, 72, 73, 74, 75, or 76 may, in various embodiments, can be attached via or near its N-terminal or C-terminal end (e.g., via a side chain of an amino acid at or near its N-terminal or C-terminal amino acid) directly or indirectly to any moiety comprising a CPM, e.g., a CPP, e.g., a CPP comprising or derived from a sequence listed in Table 2.

Any compstatin analog, e.g., any compound comprising any of SEQ ID NOs: 3-37, 72, 73, 74, 75, or 76 may, in various embodiments, can be attached via or near its N-terminal or C-terminal end (e.g., via a side chain of an amino acid at or near its N-terminal or C-terminal amino acid) directly or indirectly to any moiety comprising a reactive functional group, e.g., any compound of Formulae I-XVI or Formulae A-H.

In some embodiments, producing a cell-penetrating compstatin analog comprises reacting a compstatin analog comprising a reactive functional group with the N-terminal amine and/or C-terminal carboxyl group of a polypeptide comprising a CPP. In some embodiments, producing a long-acting compstatin analog comprises reacting a compstatin analog comprising an amine-reactive functional group with amino acids having a side chain comprising a primary amine (e.g., lysine) and/or with the N-terminal amine of a polypeptide comprising a CPP. In some embodiments, producing a cell-penetrating compstatin analog comprises reacting a compstatin analog comprising a carboxyl-reactive functional group with the C-terminal carboxyl group of a polypeptide comprising a CPP. In some embodiments, producing a cell-penetrating compstatin analog comprises reacting a compstatin analog comprising a sulfhydryl-reactive functional group with one or more sulfhydryl groups of the polypeptide.

In some embodiments, at least one reactive functional group is introduced into a polypeptide comprising a CPP. For example, in some embodiments at least one side chain of the polypeptide is modified to convert a first reactive functional group to a different reactive functional group prior to reaction with the compstatin analog. In some embodiments a thiol is introduced. Several methods are available for introducing thiols into biomolecules, including the reduction of intrinsic disulfides, as well as the conversion of amine, aldehyde or carboxylic acid groups to thiol groups. Disulfide crosslinks of cysteines in proteins can be reduced to cysteine residues by dithiothreitol (DTT), tris-(2-carboxyethyl)phosphine (TCEP), or or tris-(2-cyanoethyl)phosphine. Amines can be indirectly thiolated by reaction with succinimidyl 3-(2-pyridyldithio)propionate (SPDP) followed by reduction of the 3-(2-pyridyldithio)propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Amines can be directly thiolated by reaction with 2-iminothiolane, which preserve the overall charge of the molecule and introduces a free thiol. Tryptophan residues in thiol-free proteins can be oxidized to mercaptotryptophan residues, which can then be modified by iodoacetamides or maleimides. A polypeptide comprising a CPP and comprising one or more thiols may be reacted with a compstatin analog comprising a maleimide group, such as Ac-Ile-Cys*-Val-Trp(1-Me)-Gln-Asp-Trp-Gly-Ala-His-Arg-Cys*-Thr-AEEAc-Lys-(C(=O)—(CH$_2$)$_5$-Mal)-NH$_2$ (SEQ ID NO: 139) to generate a cell-penetrating compstatin analog.

VII. Various Aspects

In some aspects, the invention provides a composition comprising a CPCA and at least one isolated cell. In some embodiments the cell comprises a nucleic acid that encodes a primate C3. In some embodiments the cell is a primate cell, and the nucleic acid is endogenous to the cell (i.e., it is naturally part of the genome of the cell and was not introduced into the cell or an ancestor of the cell by man). In some embodiments the nucleic acid is not endogenous to the cell but instead was introduced into the cell or an ancestor of the cell by man. In some embodiments the nucleic acid that encodes a primate C3 is in a vector. In some embodiments the nucleic acid that encodes a primate C3 is integrated into the genome. In some embodiments the nucleic acid that encodes a primate C3 is operably linked to a heterologous promoter. In some embodiments the heterologous promoter is a regulatable promoter, e.g., an inducible or repressible promoter. The cell may be of any cell type in various embodiments. In some embodiments the cell is of a type that naturally expresses a primate C3 under at least some conditions. In some embodiments the cell expresses a human C3 under at least some conditions. In some embodiments the cell is a human cell. In some embodiments the cell is maintained under conditions in which it expresses C3. In some embodiments the composition comprises two or more different types of cells, wherein a first cell type expresses C3 and a second cell type expresses a C3a receptor (either naturally or as a result of introduction of a heterologous nucleic acid encoding a C3a receptor). In some embodiments a cell in any of the compositions is an epithelial cell, e.g., an epithelial cell originating from any of the epithelial tissues mentioned above. In some embodiments a cell is a respiratory epithelial cell, retinal pigment epithelial (RPE) cell, endothelial cell, hepatocyte, immune system cell, e.g., lymphocyte (B cell, T cell (e.g., CD4+ T cell, CD8+ T cell, Th17 cell, Treg cell, NK T cell), NK cell), granulocyte (e.g., neutrophil, eosinophil, basophil) mast cell, monocyte, or macrophage. In some embodiments a cell is a nervous system cell, e.g., a neural cell or glial cell. In some embodiments a cell is a fully differentiated cell. In some embodiments a cell is a precursor cell, e.g., a precursor of any of the afore-mentioned cell types. In the compositions comprising two or more cell types, the first and second cell types may be any of these cell types in various embodiments. All combinations are encompassed. In some embodiments the composition comprises culture medium suitable for culturing the cells. In some embodiments the culture medium comprises an agent that stimulates C3 expression or intracellular C3 cleavage. In some embodiments the culture medium comprises an agent that activates or inhibits one or more biological activities of one or more cell types in the composition. In some embodiments the agent comprises a cytokine, growth factor, or agent that modulates expression or activity of a cytokine or cytokine receptor. In some embodiments the culture medium comprises one, two, three or more cytokines and/or growth factors. In some embodiments the culture medium comprises one, two, three or more agents (e.g., small molecules, antibodies, polypeptides, or nucleic acids) that modulate (e.g., increase or decrease) expression or activity of a cytokine or cytokine receptor. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IFN-alpha, IFN-beta, IFN-gamma, TNF-alpha, MIP-1, MIP-2, MIP-3, MCP-1, MCP-2, MCP-3. In some embodiments a cytokine is a Th17-associated cytokine (e.g., IL-17, IL-23, or IL-26, or other cytokine produced by Th17 cells or that activates Th17 cells). In some embodiments a cytokine is a member of the extended IL-10 family (e.g., IL-10, IL-19, IL-20, IL-22, IL-24, IL-26, IL-28, or IL-29). Where a cytokine is referred to herein by number, all family members having the same number are encompassed. For example, IL-17 refers to any or all IL-17 family members (e.g., IL-17A, IL-17B, IL-17C, IL-17D, IL17E, IL-17F).

In some embodiments a CPCA may be used to analyze one or more effects of intracellular C3 activation. In some embodiments a CPCA may be used to analyze the effects of inhibiting intracellular C3 activation. In some embodiments analysis is performed using isolated cells in culture, e.g., using a composition comprising isolated cells and a CPCA (e.g., any of the compositions described above). A composition comprising isolated cells and a CPCA is prepared. One or more biological activities or phenotypes of the cells is detected or measured. The nature or amount of the biological activity or phenotype is compared with a control. A suitable control may be cells of the same type maintained under the same conditions in the absence of the CPCA. In some embodiments a biological activity comprises secretion of one or more biologically active agents, e.g., a protein or signaling molecule. In some embodiments a biological activity comprises cytokine secretion, protease secretion, cell proliferation, or cell-mediated cytotoxicity.

In some embodiments a CPCA may be used to analyze one or more effects of intracellular C3 activation using a non-human mammal that, either naturally or as a result of genetic engineering, expresses primate C3, e.g., human C3. In some embodiments the non-human animal is a mammal, e.g., a primate. In some embodiments the non-human animal is a transgenic rodent, e.g., a transgenic mouse or rat, wherein at least some cells of the transgenic rodent comprise a transgene that encodes a primate C3, e.g., human C3. In some embodiments the rodent is also transgenic for any one or more additional primate complement components. In some embodiments the non-human animal is a mammal that has received a graft of primate cells, e.g., human cells, that express C3. In some embodiments the cells comprise hematopoietic cells, hepatic cells, or both. In some embodiments the endogenous hematopoietic system and/or liver of the animal is ablated or removed. In some embodiments the mammal has a humanized hematopoietic system or at least a humanized immune system. Methods for generating such mammals, e.g., mice, are known. For example, the hu-HSC model is created by transplantation of human hematopoietic stem cells (HSC), whereas the BLT mouse model is prepared by transplantation of human fetal liver, thymus and HSC. In some embodiments the non-human animal is an animal model for a disease, e.g., a disease that affects humans. In some embodiments the disease is a complement-mediated disease.

In some embodiments a CPCA is administered one or more times to a subject. In some embodiments the subject has a complement-mediated disease or is at increased risk of developing a complement-mediated disease. In some embodiments the effect of the CPCA on development, severity, or progression of the disease or on the development, severity, or progression of one or more manifestations of the disease is assessed. The complement-mediated disease may be any of the complement-mediated diseases described herein. For example, in some embodiments the complement-mediated disease is a respiratory disease, e.g., asthma or COPD. In some embodiments the complement-mediated disease is a Th17-associated disease. In some embodiments a CPCA is administered to treat a complement-mediated disease.

In some embodiments human cells or non-human primate cells contacted with a CPCA at a concentration and for a time that is sufficient to reduce intracellular C3 cleavage and/or reduce release of one or more C3 cleavage product(s) by such cells by at least 10%, 20%, 30%, 40%, 50%, 60%, 70%, 80%, 90%, or 100% exhibit no more than a 20% cytotoxicity (reduction in viability) as compared to the viability of suitable control cells, e.g., no detectable cytotoxicity, less than a 1% reduction in viability, between 1% and 2.5%, 2.5% and 5%, 5% and 10%, 10% and a 20% reduction in viability as compared to the viability of suitable control cells. In some embodiments mammalian cells (which may be human cells, non-human primate cells, or non-primate mammalian cells) contacted with a CPCA at a concentration and for a time that is sufficient to reduce intracellular C3 cleavage and/or reduce release of one or more C3 cleavage product(s) by human cells of at least one cell type by at least 10%, 20%, 30%, 40%, 50%, 60%, 70%, 80%, 90%, or 100% exhibit no more than a 20% reduction in viability (rounded to the nearest tenth of a percent) as compared to the viability of suitable control cells, e.g., no detectable cytotoxicity, less than a 1% reduction in viability, between 1% and 2.5%, 2.5% and 5%, 5% and 10%, 10% and a 20% reduction in viability as compared to the viability of suitable control cells. Cells are typically maintained under normal cell culture conditions for the particular cells (e.g., 37 degrees C., standard culture medium (except for the presence of the CPCA in the test cell medium) for the cells, etc. In some embodiments suitable control cells are cells that are not contacted with the CPCA. Control cells are typically closely matched with the cells that are contacted with the CPCA ("test cells") and are maintained under similar conditions (but without the CPCA. For example, test cells and control cells may be derived from the same cell line, same subject (or genetically identical subject or subject from the same inbred non-human animal strain). In some embodiments test and control cells are from the same cell culture. In some embodiments control cells may be contacted with the vehicle in which the CPCA is provided when contacted with test cells in order to control for possible of the vehicle. In some embodiments control cells may be contacted with a compstatin analog of the same sequence as the CA moiety in the CPCA. In some embodiments control cells are cultured and their viability tested as part of the same experiment in which viability of test cells is measured. In some embodiments a historical control value, e.g., a value that was previously determined for the same cell type cultured under the same or essentially the same conditions in the absence of the CPCA and the viability of which was measured using the same viability assay may be used. In some embodiments a difference in viability between two or more groups, e.g., test cells and control cells, test cells contacted with different CPCAs, test cells contacted with the same CPCA at different concentrations and/or for different time periods, is considered to exist if such difference is statistically significant with a p value of 0.05. In some embodiments a difference is considered to exist if is statistically significant with a p value of 0.025. In some embodiments a difference is considered to exist if is statistically significant with a p value of 0.01. In some embodiments viability is considered to be reduced by a given percentage based on an indicator of viability, such as a result of a viability assay, where the assay measures a substance, property, or event that correlates with cell viability. In some embodiments a raw value may be converted into a percent viability or percent change in viability using a suitable conversion factor or standard curve.

In some embodiments a CPCA is contacted with cells at a concentration up to about 1 μm, up to about 5 μM, up to about 10 μM, up to about 20 μM, up to about 50 μM, or up to about 100 μM for a time period of up to 1 hour (e.g., 15-60 minutes), 4 hours, 8 hours, 12 hours, 16 hours, 24 hours or a time period up to 1, 2, 4, 8, 12, 16, 24, 48, 60, 72, 96, 120, or 144 hours or a time period up to 7, 10, 14, 21, or 28 days. Cytotoxicity may be assessed using any of a variety of methods known in the art. Examples of such methods include a cell counting assay, a replication labeling assay, a cell membrane integrity assay (which may measure release of intracellular contents such as various enzymes or may detect entry across the cell membrane of a substance that would normally not cross the membrane of a viable cell), a cellular ATP-based viability assay, a mitochondrial reductase activity assay, a caspase activity assay, an annexin V staining assay, a DNA content assay, a DNA degradation assay, and a nuclear fragmentation assay. Exemplary assays include BrdU, EdU, or H3-Thymidine incorporation assays; DNA content assays using a nucleic acid dye such as Hoechst dye, DAPI, actinomycin D, 7-aminoactinomycin D or propidium iodide; cellular metabolism assays such as AlamarBlue, MTT, XTT, WST-8, and CellTitre Glo; dye exclusion assay (e.g., trypan blue exclusion assay), LDH release assay, cytoplasmic histone-associated DNA fragments (e.g., mono- and/or oligonucleosomes); PARP cleavage assay; TUNEL staining. Appropriate method(s) may be selected by one of ordinary skill in the art. For example, certain of the assays measure events associated with cell proliferation such as DNA synthesis and may reflect effects of an agent on both viability and proliferation. If non-proliferating cells are used an assay that does not rely on measuring an indicator of cell proliferation may be selected. It will also be appreciated that certain assays are specifically appropriate for measuring apoptotic cell death. In some embodiments one or more assays collectively capable of detecting cell death regardless of mechanism by which cell death occurs (e.g., whether due to necrosis or apoptosis) is used. In some embodiments a cell metabolism assay is used.

In some embodiments cells are contacted with a CPCA in vitro at a concentration and for a time period sufficient to reduce intracellular C3 cleavage and/or reduce release of one or more C3 cleavage product(s) by such cells by at least 10%, 20%, 30%, 40%, 50%, 60%, 70%, 80%, 90%, or 100% measured over a particular time interval or in response to a stimulus, as compared with the amount of intracellular C3 cleavage or amount of release of such C3 cleavage product(s) that would occur over such time period or in response to such stimulus if the cells were not contacted with the CPCA. In some embodiments the time interval may be, e.g., between 5 minutes and 48 hours, e.g., between 5 and 60 minutes, 1-2 hours, 2-4 hours, 4-8 hours, 8-16 hours, 16 to 24 hours, 24 to 48 hours. In some embodiments the time period may be at least 48 hours, e.g., 2-5 days, 5-10 days, etc. If culture medium is replaced during the time period, additional CPCA may be added to the new medium. In various embodiments the time interval over which intracellular C3 cleavage and/or release of one or more C3 cleavage product(s) is measured may overlap with, be within, be the same as, or follow the time period during which cells are exposed to the CPCA in the medium.

Activity of a CPCA may be assessed using any of a variety of methods in various embodiments. In some embodiments cells that produce primate (e.g., human) C3 are contacted with a CPCA in vitro. In some embodiments the cells are washed, lysed, and the cell lysate is analyzed to determine the amount (e.g., concentration) of intact C3, the amount one or more C3 cleavage products (e.g., C3a, C3b, iC3b, C3d, etc.), and/or the ratio of the amount of intact C3 to that of one or more C3 cleavage products. A reduction in the level of C3 cleavage product(s) as compared with the level of such product(s) in control cells not contacted with the CPCA indicates that the CPCA was internalized, bound to intracellular C3, and inhibited its activation. Care may be taken during the washing step to remove CPCA that may have become physically associated with the cell surface during the contacting step. In some embodiments the cells are washed and lysed, and intact C3 is isolated, e.g., by an affinity-based method such as immunoprecipitation using a suitable antibody (or other binding agent). The isolated C3 is assessed to determine the amount of bound CPCA and/or to determine the amount or fraction of C3 that does not have a CPCA molecule bound to it. The CPCA may be detected using any of a variety of methods. For example, the CPCA may be detected using an affinity-based detection method (e.g., immunoblot, ELISA assay), by mass spectrometry, by liquid chromatography, or combinations thereof. C3 that does not have a CPCA molecule bound to it may be detected using any appropriate method.

In some embodiments a functional assay is used. In some embodiments a functional assay comprises contacting cells that produce primate (e.g., human) C3 with a CPCA in vitro and detecting the ability of C3 from such cells to subsequently participate in complement activation. In some embodiments, cell lysate or C3 isolated from the lysate is combined with complement components necessary for C3 activation and, in some embodiments, complement components needed for downstream events such as MAC formation. The complement components may be provided as C3-depleted serum. Complement activation capacity of the resulting composition may be assessed using a suitable assay, e.g., a functional assay such as a hemolysis assay, as a measure of the amount of active C3. Complement activation via any of the complement activation pathways may be measured. In some embodiments the amount of one or more products of complement activation, e.g., C3 cleavage products, C5 cleavage products (e.g., C5a), or MAC that is generated is measured. Such measurement may be performed using any suitable method, e.g., affinity-based, bioassay, etc. A reduction in complement activation capacity of C3 from cells contacted with a CPCA as compared with the level of complement activation capacity of C3 from control cells not contacted with the CPCA indicates that the CPCA was internalized, bound to intracellular C3, and inhibited its activation.

In some embodiments cells that produce primate C3 are contacted in vitro with a CPCA. The cells are maintained in culture for a suitable time period, e.g., between 15 minutes and 48 hours. In some embodiments the cells are exposed to a stimulus that would typically, in the absence of a CPCA, cause them to release C3 cleavage products. The amount of one or more C3 cleavage products (e.g., C3a or C3b) secreted by the cells into the medium is measured. A reduction in the amount C3 cleavage products secreted from cells that are or have been contacted with a CPCA as compared with the amount of C3 cleavage products secreted by control cells maintained under the same or substantially the same conditions but not contacted with the CPCA indicates that the CPCA was internalized, bound to intracellular C3, and inhibited its activation.

A variety of methods of assessing complement components, complement activation, and/or products of complement activation, and various reagents (e.g., antibodies) that may be used in such methods, are described in US Patent Application Publication 20120135430. Kits for measuring total complement activity or for measuring one of more C3 or C3 cleavage products are commercially available, e.g., from Quidel, DRG International (e.g., Complement Activation Assay CAE (EIA-1530). In some embodiments C3a is measured using an ELISA assay or using surface plasmon resonance. In some embodiments C3a is measured using a bioassay that measures one or more biological activities of C3a, such as activation of a C3a receptor expressed by living cells. Activation of a C3aR may, for example, cause calcium influx into the cytoplasm, increased cytokine expression, degranulation, or chemotaxis of cells that express C3aR. Such effects may be detected in a variety of ways known in the art such as use of calcium-sensitive dyes, reporter assays, etc.

VIII. Uses

Cell-penetrating compstatin analogs have a wide variety of uses. Without limiting the invention in any way, certain uses of cell-penetrating compstatin analogs, and related aspects of the invention, are described herein. In some embodiments, a cell-penetrating compstatin analog is administered to a subject suffering from or at risk of complement-mediated damage to an organ, tissue, or cells. In some embodiments, a cell-penetrating compstatin analog is contacted with an organ, tissue, or cells ex vivo and become internalized by at least some cells. The organ, tissue, or cells are introduced into a subject and are protected at least in part from dysfunction or damage that may otherwise be caused by intracellular complement activation and/or by secretion of one or more complement activation products.

Certain uses of interest include: protecting various body structures, cells, tissues, organs from complement mediated dysfunction or damage in any of a variety of different complement-mediated disorders, reducing ischemia/reperfusion (I/R) injury (e.g., in individuals suffering from trauma, vascular obstruction, myocardial infarction, or other situations in which I/R injury may occur). The beneficial effects of inhibiting complement activation or formation or deposition of complement activation products (e.g., C3a, C3b) inside or at the surface of cells or other body structures are not limited to those resulting directly from protection of the cells or structures themselves against direct complement-mediated damage (e.g., preventing cell lysis). For example, inhibiting complement activation using a cell-penetrating compstatin analog may reduce the generation of anaphylotoxins and resulting influx/activation of cells such as neutrophils, mast cells, and/or other pro-inflammatory events and/or reduce potentially damaging release of intracellular contents. In thereby potentially having beneficial effects locally, on remote cells, tissues, organ systems, or throughout the body. In some embodiments a cell-penetrating compstatin analog may be contacted with a cell or administered to a subject having abnormally high cathepsin expression or activity, e.g., abnormally high cathepsin L expression or activity.

Complement-Mediated Disorders

In some embodiments, a cell-penetrating compstatin analog is introduced into the eye for treatment of an eye disorder such as age-related macular degeneration (AMD), diabetic retinopathy, glaucoma, or uveitis. For example, a cell-penetrating compstatin analog may be introduced into the vitreous cavity (e.g., by intravitreal injection), for treatment of a subject at suffering from or at risk of AMD. In some embodiments a cell-penetrating compstatin analog is introduced into the anterior chamber, e.g., to treat anterior uveitis.

In some embodiments a cell-penetrating compstatin analog is used to treat a subject suffering from or at risk of an autoimmune disease, e.g., an autoimmune disease mediated at least in part by antibodies, T cells, or other immune system cells or substances directed against one or more self antigens.

In some embodiments a cell-penetrating compstatin analog may be introduced into the synovial cavity, e.g., in a subject suffering from arthritis (e.g., rheumatoid arthritis).

In some embodiments, a cell-penetrating compstatin analog is used to treat a subject suffering from or at risk of an intracerebral hemorrhage.

In some embodiments a cell-penetrating compstatin analog is used to treat a subject suffering from or at risk of myasthenia gravis.

In some embodiments a cell-penetrating compstatin analog is used to treat a subject suffering from or at risk of neuromyelitis optica (NMO), In some embodiments a cell-penetrating compstatin analog is used to treat a subject suffering from or at risk of membranoproliferative glomerulitis (MPGN), e.g., MPGN type I, MPGN type II, or MPGH type III.

In some embodiments a cell-penetrating compstatin analog is used to treat a subject suffering from or at risk of a neurodegenerative disease. In some embodiments a cell-penetrating compstatin analog is used to treat a subject suffering from neuropathic pain or at risk of developing neuropathic pain. In some embodiments a cell-penetrating compstatin analog is used to treat a subject suffering from or at risk of rhinosinusitis or nasal polyposis. In some embodiments a cell-penetrating compstatin analog is used to treat a subject suffering from or at risk of cancer. In some embodiments a cell-penetrating compstatin analog is used to treat a subject suffering from or at risk of sepsis. In some embodiments a cell-penetrating compstatin analog is used to treat a subject suffering from or at risk of adult respiratory distress syndrome.

In some embodiments a cell-penetrating compstatin analog is used to treat a subject suffering from or at risk of anaphylaxis or infusion reaction. For example, in some embodiments a subject may be pretreated prior to, during, or after receiving a drug or a vehicle that may cause anaphylaxis or infusion reaction. In some embodiments a subject at risk of or suffering from anaphylaxis from a food (e.g., peanut, shellfish, or other food allergens), insect sting (e.g., bee, wasp), is treated with a cell-penetrating compstatin analog.

A cell-penetrating compstatin analog may be administered locally or systemically, in various embodiments of the invention.

In some embodiments, a cell-penetrating compstatin analog is used to treat a respiratory disease, e.g., asthma or chronic obstructive pulmonary disease (COPD). The cell-penetrating compstatin analog may, for example, be administered to the respiratory tract by inhalation, e.g., as a dry powder or via nebulization, or may be administered by injection, e.g., intravenously, intramuscularly, or subcutenously, in various embodiments. In some embodiments, a cell-penetrating compstatin analog is used to treat severe asthma, e.g., asthma that is not sufficiently controlled by bronchodilators and/or inhaled corticosteroids.

In some aspects, methods of treating a complement-mediated disorder, e.g., a chronic complement-mediated disorder, are provided, the methods comprising administering a cell-penetrating compstatin to a subject in need of treatment for the disorder. The long-acting compstatin analog may be any long-acting compstatin analog described herein, in various embodiments. In some aspects, methods of treating a Th17-associated disorder are provided, the methods comprising administering a cell-penetrating complement inhibitor to a subject in need of treatment for the disorder.

In some aspects, a "chronic disorder" is a disorder that persists for at least 3 months and/or is accepted in the art as being a chronic disorder. In many embodiments, a chronic disorder persists for at least 6 months, e.g., at least 1 year, or more, e.g., indefinitely. One of ordinary skill in the art will appreciate that at least some manifestations of various chronic disorders may be intermittent and/or may wax and wane in severity over time. A chronic disorder may be progressive, e.g., having a tendency to become more severe or affect larger areas over time. A number of chronic complement-mediated disorders are discussed herein. A chronic complement-mediated disorder may be any chronic disorder in which complement activation (e.g., excessive or inappropriate complement activation) is involved, e.g., as a contributing and/or at least partially causative factor. For convenience, disorders are sometimes grouped by reference to an organ or system that is often particularly affected in subjects suffering from the disorder. It will be appreciated that a number of disorders can affect multiple organs or systems, and such classification(s) are in no way limiting. Furthermore, a number of manifestations (e.g., symptoms) may occur in subjects suffering from any of a number of different disorders. Non-limiting information regarding disorders of interest herein may be found, e.g., in standard textbooks of internal medicine such as Cecil Textbook of Medicine (e.g., 23rd edition), Harrison's Principles of Internal Medicine (e.g., 17th edition), and/or standard textbooks focusing on particular areas of medicine, particular body systems or organs, and/or particular disorders.

In some embodiments, a chronic complement-mediated disorder is a Th2-associated disorder. As used herein, a Th2-associated disorder is a disorder characterized by an excessive number and/or excessive or inappropriate activity of CD4+ helper T cells of the Th2 subtype ("Th2 cells") in the body or a portion thereof, e.g., in at least one tissue, organ, or structure. For example, there may be a predominance of Th2 cells relative to CD4+ helper T cells of the Th1 subtype ("Th1 cells") e.g., in at least one tissue, organ, or structure affected by a disorder. As known in the art, Th2 cells typically secrete characteristic cytokines such as interleukin-4 (IL-4), interleukin-5 (IL-5), and interleukin-13 (IL-13), while Th1 cells typically secrete interferon-γ (IFN-γ) and tumor necrosis factor β (TNF β). In some embodiments, a Th2-associated disorder is characterized by excessive production and/or amount of IL-4, IL-5, and/or IL-13, e.g., relative to IFN-γ and/or TNF β e.g., in at least some at least one tissue, organ, or structure In some embodiments, a chronic complement-mediated disorder is a Th17-associated disorder. In some aspects, as described in further detail in PCT/US2012/043845, filed Jun. 22, 2012, entitled "Methods of Treating Chronic Disorders with Complement Inhibitors", complement activation and Th17 cells participate in a cycle that involves dendritic cells and antibodies and that contributes to maintenance of a pathologic immunologic microenvironment underlying a range of disorders. Without wishing to be bound by any theory, the pathologic immunologic microenvironment, once established, is self-sustaining and contributes to cell and tissue injury. In some aspects, cell-penetrating compstatin analogs are of use to treat Th17-associated disorders.

As used herein, a Th17-associated disorder is a disorder characterized by an excessive number and/or excessive or inappropriate activity of CD4+ helper T cells of the Th17 subtype ("Th17 cells") in the body or a portion thereof, e.g., in at least one tissue, organ, or structure. For example, there may be a predominance of Th17 cells relative to Th1 and/or Th2 cells, e.g., in at least one tissue, organ, or structure affected by a disorder. In some embodiments a predominance of Th17 cells is a relative predominance, e.g., the ratio of Th17 cells to Th1 cells and/or the ratio of Th17 cells to Th2 cells, is increased relative to normal values. In some embodiments the ratio of Th17 cells to T regulatory cells ($CD4^+CD25^+$ regulatory T cells, also termed "Treg cells"), is increased relative to normal values. Formation of Th17 cells and/or activation of Th 17 cells is promoted by various cytokines, e.g., interleukin 6 (IL-6), interleukin 21 (IL-21), interleukin 23 (IL-23), and/or interleukin 1β (IL-1β). Formation of Th17 cells encompasses differentiation of precursor T cells, e.g., naïve CD4+ T cells, towards a Th17 phenotype and their maturation into functional Th17 cells. In some embodiments, formation of Th17 cells encompasses any aspect of development, proliferation (expansion), survival, and/or maturation of Th17 cells. In some embodiments, a Th17-associated disorder is characterized by excessive production and/or amount of IL-6, IL-21, IL-23, and/or IL-1β. Th17 cells typically secrete characteristic cytokines such as interleukin-17A (IL-17A), interleukin-17F (IL-17F), interleukin-21 (IL-21), and interleukin-22 (IL-22). In some embodiments, a Th17-associated disorder is characterized by excessive production and/or amount of a Th17 effector cytokine, e.g., IL-17A, IL-17F, IL-21, and/or IL-22. In some embodiments excessive production or amount of a cytokine is detectable in the blood. In some embodiments excessive production or amount of a cytokine is detectable locally, e.g., in at least one tissue, organ or structure. In some embodiments a Th17-associated disorder is associated with a decreased number of Tregs and/or decreased amount of a Treg-associated cytokine. In some embodiments a Th17 disorder is any chronic inflammatory disease, which term encompasses a range of ailments characterized by self-perpetuating immune insults to a variety of tissues and that seem to be dissociated from the initial insult that caused the ailment (which may be unknown). In some embodiments a Th17-associated disorder is any autoimmune disease. Many if not most "chronic inflammatory diseases" may in fact be auto-immune diseases. Examples of Th17-associated disorders include inflammatory skin diseases such as psoriasis and atopic dermatitis; systemic scleroderma and sclerosis; inflammatory bowel disease (IBD) (such as Crohn's disease and ulcerative colitis); Behcet's Disease; dermatomyositis; polymyositis; multiple sclerosis (MS); dermatitis; meningitis; encephalitis; uveitis; osteoarthritis; lupus nephritis; rheumatoid arthritis (RA), Sjorgen's syndrome, multiple sclerosis, vasculitis; central nervous system (CNS) inflammatory disorders, chronic hepatitis; chronic pancreatitis, glomerulonephritis; sarcoidosis; thyroiditis, pathologic immune responses to tissue/organ transplantation (e.g., transplant rejection); COPD, asthma, bronchiolitis, hypersensitivity pneumonitis, idiopathic pulmonary fibrosis (IPF), periodontitis, and gingivitis. In some embodiments a Th17 disease is a classically known auto-immmune disease such as Type I diabetes or psoriasis. In some embodiments a Th17-associated disorder is age-related macular degeneration.

In some embodiments, a chronic complement-mediated disorder is an IgE-associated disorder. As used herein, an "IgE-associated disorder" is a disorder characterized by excessive and/or inappropriate production and/or amount of IgE, excessive or inappropriate activity of IgE producing cells (e.g., IgE producing B cells or plasma cells), and/or excessive and/or inappropriate activity of IgE responsive cells such as eosinophils or mast cells. In some embodiments, an IgE-associated disorder is characterized by elevated levels of total IgE and/or in some embodiments, allergen-specific IgE, in the plasma of a subject and/or locally.

In some embodiments, a chronic complement-mediated disorder is characterized by the presence of autoantibodies and/or immune complexes in the body, which may activate complement via, e.g., the classical pathway. Autoantibodies may, for example, bind to self antigens, e.g., on cells or tissues in the body. In some embodiments, autoantibodies bind to antigens in blood vessels, skin, nerves, muscle, connective tissue, heart, kidney, thyroid, etc. In some embodiments, a chronic complement-mediated disorder is not characterized by autoantibodies and/or immune complexes.

In some embodiments, a chronic complement-mediated disorder is a respiratory disorder. In some embodiments, a chronic respiratory disorder is asthma or chronic obstructive pulmonary disease (COPD). In some embodiments, a chronic respiratory disorder is pulmonary fibrosis (e.g., idiopathic pulmonary fibrosis), radiation-induced lung injury, allergic bronchopulmonary aspergillosis, hypersensitivity pneumonitis (also known as allergic alveolitis), eosinophilic pneumonia, interstitial pneumonia, sarcoid, Wegener's granulomatosis, or bronchiolitis obliterans. In some embodiments, the invention provides a method of treating a subject in need of treatment for a chronic respiratory disorder, e.g., asthma, COPD, pulmonary fibrosis, radiation-induced lung injury, allergic bronchopulmonary aspergillosis, hypersensitivity pneumonitis (also known as allergic alveolitis), eosinophilic pneumonia, interstitial pneumonia, sarcoid, Wegener's granulomatosis, or bronchiolitis obliterans, the method comprising administering a cell-penetrating compstatin analog to a subject in need of treatment for the disorder.

In some embodiments, a chronic complement-mediated disorder is allergic rhinitis, rhinosinusitis, or nasal polyposis. In some embodiments, the invention provides a method of treating a subject in need of treatment for allergic rhinitis, rhinosinusitis, or nasal polyposis, the method comprising administering a cell-penetrating compstatin analog to a subject in need of treatment for the disorder.

In some embodiments, a chronic complement-mediated disorder is a disorder that affects the musculoskeletal system. Examples of such disorders include inflammatory joint conditions (e.g., arthritis such as rheumatoid arthritis or psoriatic arthritis, juvenile chronic arthritis, spondyloarthropathies Reiter's syndrome, gout). In some embodiments, a musculoskeletal system disorder results in symptoms such as pain, stiffness and/or limitation of motion of the affected body part(s). Inflammatory myopathies include dermatomyositis, polymyositis, and various others are disorders of chronic muscle inflammation of unknown etiology that result in muscle weakness. In some embodiments a chronic complement-mediated disorder is myasthenia gravis. In some embodiments, the invention provides a method of treating any of the foregoing disorders affecting the musculoskeletal system, the method comprising administering a cell-penetrating compstatin analog to a subject in need of treatment for the disorder.

In some embodiments, a chronic complement-mediated disorder is a disorder that affects the integumentary system. Examples of such disorders include, e.g., atopic dermatitis, psoriasis, pemphigus, systemic lupus erythematosus, dermatomyositis, scleroderma, sclerodermatomyositis, Sjögren syndrome, and chronic urticaria. In some aspects, the invention provides a method of treating any of the foregoing disorders affecting the integumentary system, the method comprising administering a cell-penetrating compstatin analog to a subject in need of treatment for the disorder.

In some embodiments, a chronic complement-mediated disorder affects the nervous system, e.g., the central nervous system (CNS) and/or peripheral nervous system (PNS). Examples of such disorders include, e.g., multiple sclerosis, other chronic demyelinating diseases, amyotrophic lateral sclerosis, chronic pain, stroke, allergic neuritis, Huntington's disease, Alzheimer's disease, and Parkinson's disease. In some embodiments, the invention provides a method of treating any of the foregoing disorders affecting the nervous system, the method comprising administering a cell-penetrating compstatin analog to a subject in need of treatment for the disorder.

In some embodiments, a chronic complement-mediated disorder affects the circulatory system. For example, in some embodiments the disorder is a vasculitis or other disorder associated with vessel inflammation, e.g., blood vessel and/or lymph vessel inflammation. In some embodiments, a vasculitis is polyarteritis *nodosa*, Wegener's granulomatosis, giant cell arteritis, Churg-Strauss syndrome, microscopic polyangiitis, Henoch-Schonlein purpura, Takayasu's arteritis, Kawasaki disease, or Behcet's disease. In some embodiments, a subject, e.g., a subject in need of treatment for vasculitis, is positive for antineutrophil cytoplasmic antibody (ANCA).

In some embodiments, a chronic complement-mediated disorder affects the gastrointestinal system. For example, the disorder may be inflammatory bowel disease, e.g., Crohn's disease or ulcerative colitis. In some embodiments, the invention provides a method of treating a chronic complement-mediated disorder that affects the gastrointestinal system, the method comprising administering a cell-penetrating compstatin analog to a subject in need of treatment for the disorder.

In some embodiments, a chronic complement-mediated disorder is a thyroiditis (e.g., Hashimoto's thryoiditis, Graves' disease, post-partum thryoiditis), myocarditis, hepatitis (e.g., hepatitis C), pancreatitis, glomerulonephritis (e.g., membranoproliferative glomerulonephritis or membranous glomerulonephritis), or panniculitis.

In some embodiments, the invention provides methods of treating a subject suffering from chronic pain, the methods comprising administering a cell-penetrating compstatin analog t to a subject in need thereof. In some embodiments, a subject suffers from neuropathic pain. Neuropathic pain has been defined as pain initiated or caused by a primary lesion or dysfunction in the nervous system, in particular, pain arising as a direct consequence of a lesion or disease affecting the somatosensory system. For example, neuropathic pain may arise from lesions that involve the somatosensory pathways with damage to small fibres in peripheral nerves and/or to the spino-thalamocortical system in the CNS. In some embodiments, neuropathic pain arises from autoimmune disease (e.g., multiple sclerosis), metabolic disease (e.g., diabetes), infection (e.g., viral disease such as shingles or HIV), vascular disease (e.g., stroke), trauma (e.g., injury, surgery), or cancer. For example, neuropathic pain can be pain that persists after healing of an injury or after cessation of a stimulus of peripheral nerve endings or pain that arises due to damage to nerves. Exemplary conditions of or associated with neuropathic pain include painful diabetic neuropathy, post-herpetic neuralgia (e.g., pain persisting or recurring at the site of acute herpes zoster 3 or more months after the acute episode), trigeminal neuralgia, cancer related neuropathic pain, chemotherapy-associated neuropathic pain, HIV-related neuropathic pain (e.g., from HIV neuropathy), central/post-stroke neuropathic pain, neuropathy associated with back pain, e.g., low back pain (e.g., from radiculopathy such as spinal root compression, e.g., lumbar root compression, which compression may arise due to disc herniation), spinal stenosis, peripheral nerve injury pain, phantom limb pain, polyneuropathy, spinal cord injury related pain, myelopathy, and multiple sclerosis. In certain embodiments of the invention a cell-penetrating compstatin analog is administered to treat neuropathic pain in a subject with one or more of the afore-mentioned conditions.

In some embodiments, a chronic complement-mediated disorder is a chronic eye disorder. In some embodiments, the chronic eye disorder is characterized by macular degeneration, choroidal neovascularization (CNV), retinal neovascularization (RNV), ocular inflammation, or any combination of the foregoing. Macular degeneration, CNV, RNV, and/or ocular inflammation may be a defining and/or diagnostic feature of the disorder. Exemplary disorders that are characterized by one or more of these features include, but are not limited to, macular degeneration related conditions, diabetic retinopathy, retinopathy of prematurity, proliferative vitreoretinopathy, uveitis, keratitis, conjunctivitis, and scleritis. Macular degeneration related conditions include, e.g., age-related macular degeneration (AMD). In some embodiments, a subject is in need of treatment for wet AMD. In some embodiments, a subject is in need of treatment for dry AMD. In some embodiments, a subject is in need of treatment for geographic atrophy (GA). In some embodiments, a subject is in need of treatment for ocular inflammation. Ocular inflammation can affect a large number of eye structures such as the conjunctiva (conjunctivitis), cornea (keratitis), episclera, sclera (scleritis), uveal tract, retina, vasculature, and/or optic nerve. Evidence of ocular inflammation can include the presence of inflammation-associated cells such as white blood cells (e.g., neutrophils, macrophages) in the eye, the presence of endogenous inflammatory mediator(s), one or more symptoms such as eye pain, redness, light sensitivity, blurred vision and floaters, etc. Uveitis is a general term that refers to inflammation in the uvea of the eye, e.g., in any of the structures of the uvea, including the iris, ciliary body or choroid. Specific types of uveitis include iritis, iridocyclitis, cyclitis, pars planitis and choroiditis. In some embodiments, a subject is in need of treatment for geographic atrophy (GA). In some embodiments, the chronic eye disorder is an eye disorder characterized by optic nerve damage (e.g., optic nerve degeneration), such as glaucoma.

As noted above, in some embodiments the chronic respiratory disease is asthma. Information regarding risk factors, epidemiology, pathogenesis, diagnosis, current management of asthma, etc., may be found, e.g., in "Expert Panel Report 3: Guidelines for the Diagnosis and Management of Asthma". National Heart Lung and Blood Institute. 2007. http://www.nhlbi.nih.gov/guidelines/asthma/asthgdln.pdf. ("NHLBI Guidelines"; www.nhlbi.nih.gov/guidelines/asthma/asthgdin.htm), Global Initiative for Asthma, Global Strategy for Asthma Management and Prevention 2010 "GINA Report") and/or standard textbooks of internal medicine such as Cecil Textbook of Medicine (20th edition), Harrison's Principles of Internal Medicine (17th edition), and/or standard textbooks focusing on pulmonary medicine. Asthma is a chronic inflammatory disorder of the airways in which many cells and cellular elements play a role, such as, mast cells, eosinophils, T lymphocytes, macrophages, neutrophils, and epithelial cells Asthmatic individuals experience recurrent episodes associated with symptoms such as wheezing, breathlessness (also termed dyspnea or shortness of breath), chest tightness, and coughing. These episodes are usually associated with widespread but variable airflow obstruction that is often reversible, either spontaneously or with treatment. The inflammation also causes an associated increase in the existing bronchial hyperresponsiveness to a variety of stimuli. Airway hyperresponsiveness (an exaggerated bronchoconstrictor response to stimuli) is a typical feature of asthma. In general, airflow limitation results from bronchoconstriction and airway edema. Reversibility of airflow limitation may be incomplete in some patients with asthma. For example, airway remodeling can lead to fixed airway narrowing. Structural changes can include thickening of the sub-basement membrane, subepithelial fibrosis, airway smooth muscle hypertrophy and hyperplasia, blood vessel proliferation and dilation, and mucous gland hyperplasia, and hypersecretion.

Individuals with asthma may experience exacerbations, which are identified as events characterized by a change from the individual's previous status. Severe asthma exacerbations can be defined as events that require urgent action on the part of the individual and his/her physician to prevent a serious outcome, such as hospitalization or death from asthma. For example, a severe asthma exacerbation may require use of systemic corticosteroids (e.g., oral corticosteroids) in a subject whose asthma is usually well controlled without OCS or may require an increase in a stable maintenance dose. Moderate asthma exacerbations can be defined as events that are troublesome to the subject, and that prompt a need for a change in treatment, but that are not severe. These events are clinically identified by being outside the subject's usual range of day-to-day asthma variation.

Current medications for asthma are typically categorized into two general classes: long-term control medications ("controller medications") such as inhaled corticosteroids (ICS), oral corticosteroids (OCS), long-acting bronchodilators (LABAs), leukotriene modifiers (e.g., leukotriene receptor antagonists or leukotriene synthesis inhibitors, anti- IgE antibodies (omalizumab (Xolair®)), cromolyn and nedocromil, which are used to achieve and maintain control of persistent asthma and quick-relief medications such as short-acting bronchodilators (SABAs), which are used to treat acute symptoms and exacerbations. For purposes of the present invention, these treatments may be referred to as "conventional therapy". Treatment of exacerbations may also include increasing the dose and/or intensity of controller medication therapy. For example, a course of OCS can be used to regain asthma control. Current guidelines mandate daily administration of controller medication or, in many cases, administration of multiple doses of controller medication each day for subjects with persistent asthma (with the exception of Xolair, which is administered every 2 or 4 weeks).

A subject is generally considered to have persistent asthma if the subject suffers from symptoms on average more than twice a week and/or typically uses a quick relief medication (e.g., SABA) more than twice a week for symptom control. "Asthma severity" can be classified based on the intensity of treatment required to control the subject's asthma once relevant comorbidities have been treated and inhaler technique and adherence have been optimized (see, e.g., GINA Report; Taylor, DR, Eur Respir J 2008; 32:545-554). The description of treatment intensity can be based on the medications and doses recommended in the stepwise treatment algorithm found in guidelines such as NHLBI Guidelines 2007, GINA Report, and their predecessors and/or in standard medical textbooks. For example, asthma can be classified as intermittent, mild, moderate, or severe as indicated in Table X, where "treatment" refers to treatment sufficient to achieve subject's best level of asthma control. (It will be understood that the categories of mild, moderate, and severe asthma in general imply persistent rather than intermittent asthma). One of ordinary skill in the art will appreciate that Table X is exemplary, and that not all of these medications will be available in all healthcare systems, which may affect the assessment of asthma severity in some environments. It will also be appreciated that other emerging or new approaches may affect the classification of mild/moderate asthma. However, the same principle, of mild asthma being defined by the ability to achieve good control using very low-intensity treatment and severe asthma being defined by the requirement for high-intensity treatment, can still be applied. Asthma severity can also or alternately be classified based on intrinsic intensity of the disease in the absence of treatment (see, e.g., NHBLI Guidelines 2007). Assessment can be made on the basis of current spirometry and the patient's recall of symptoms over the previous 2-4 weeks. Parameters of current impairment and future risk may be assessed and included in a determination of the level of asthma severity. In some embodiments, asthma severity is defined as shown in FIG. 3.4(a), 3.4(b), 3.4(c) of the NHBLI Guidelines, for individuals 0-4, 5-11, or ≥12 years of age, respectively.

TABLE X

Treatment-based Asthma Classification

| Asthma Classification | Treatment |
|---|---|
| Intermittent | SABA as needed (typically no more than twice a week) |
| Mild | Low-dose ICS or other low-intensity treatment (e.g., LTRA, cromolyn, nedocromil, theophylline) |
| Moderate | Low to moderate dose ICS and LABA or other extra treatment |
| Severe | High-intensity treatment (high-dose ICS and LABA ± oral corticosteroids and/or other extra treatment) |

"Asthma control" refers to the extent to which the manifestations of asthma have been reduced or removed by treatment (whether pharmacological or non-pharmacological). Asthma control can be assessed based on factors such as symptom frequency, nighttime symptoms, objective measures of lung function such as spirometry parameters (e.g., % $FEV_1$ of predicted, $FEV_1$ variability, requirement for use of SABA for symptom control. Parameters of current impairment and future risk may be assessed and included in a determination of the level of asthma control. In some embodiments, asthma control is defined as shown in FIG. 4.3(a), 4.3(b), or 4.3(c) of NHBLI Guidelines, for individuals 0-4, 5-11, or ≥12 years of age, respectively.

In general, one of ordinary skill in the art can select an appropriate means of determining asthma severity level and/or degree of control, and any classification scheme considered reasonable by those of ordinary skill in the art can be used.

In some embodiments of the invention, a subject suffering from persistent asthma is treated with a cell-penetrating compstatin analog. In some embodiments, the subject suffers from mild or moderate asthma. In some embodiments, the subject suffers from severe asthma. In some embodiments, a subject has asthma that is not well controlled using conventional therapy. In some embodiments, a subject has asthma that, when treated using conventional therapy, requires use of ICS in order to be well controlled. In some embodiments, a subject has asthma that fails to be well controlled despite use of ICS. In some embodiments, a subject has asthma that, if treated using conventional therapy, would require use of OCS in order to be well controlled. In some embodiments, a subject has asthma that fails to be well controlled despite use of high intensity conventional therapy that includes OCS.

In some embodiments, the subject suffers from allergic asthma, which is the case for most asthmatic individuals. In some embodiments, an asthmatic subject is considered to have allergic asthma if a non-allergic trigger for the asthma (e.g., cold, exercise) is not known and/or is not identified in a standard diagnostic evaluation. In some embodiments, an asthmatic subject is considered to have allergic asthma if the subject (i) reproducibly develops asthma symptoms (or worsening of asthma symptoms) following exposure to an allergen or allergen(s) to which the subject is sensitive; (ii) exhibits IgE specific for an allergen or allergen(s) to which the subject is sensitive; (iii) exhibits a positive skin-prick test to an allergen or allergen(s) to which the subject is sensitive; and/or (iv) exhibits other symptom(s) of characteristic(s) consistent with atopy such as allergic rhinitis, eczema, or elevated total serum IgE. It will be appreciated that a specific allergic trigger may not be identified but may be suspected or inferred if the subject experiences worsening symptoms in particular environments, for example.

Allergen challenge by inhalation is a technique that is widely used in evaluating allergic airway disease. Inhalation of allergen leads to cross-linking of allergen-specific IgE bound to IgE receptors on, e.g., mast cells and basophils. Activation of secretory pathways ensues, resulting in release of mediators of bronchoconstriction and vascular permeability. Individuals with allergic asthma may develop various manifestations following allergen challenge, e.g., early asthmatic response (EAR), late asthmatic response (LAR), airway hyperreactivity (AHR), and airway eosinophilia, each of which can be detected and quantified as known in the art. For example, airway eosiphophilia may be detected as an increase in eosinophils in sputum and/or BAL fluid. The EAR, sometimes referred to as the immediate asthmatic response (IAR), is a response to allergen challenge by inhalation that becomes detectable shortly after the inhalation, typically within 10 minutes (min) of the inhalation, e.g., as a decrease in $FEV_1$. The EAR typically reaches a maximum within 30 min and resolves within 2-3 hours (h) post-challenge. For example, a subject may be considered to exhibit a "positive" EAR if his/her $FEV_1$ decreases by at least 15%, e.g., at least 20%, within this time window relative to baseline $FEV_1$ (where "baseline" in this context refers to conditions before the challenge, e.g., conditions equivalent to the subject's usual condition when not experiencing an asthma exacerbation and not exposed to allergic stimuli to which the subject is sensitive). The late asthmatic response (LAR) typically starts between 3 h and 8 h post-challenge and is characterized by cellular inflammation of the airway, increased bronchiovascular permeability, and mucus secretion. It is typically detected as a decrease in $FEV_1$, which may be greater in magnitude than that associated with the EAR and potentially more clinically important. For example, a subject may be considered to exhibit a "positive" LAR if his/her $FEV_1$ decreases by at least 15%, e.g., at least 20%, relative to baseline $FEV_1$ within the relevant time period as compared with baseline $FEV_1$. A delayed airway response (DAR) may occur beginning between about 26 and 32 h, reaching a maximum between about 32 and 48 h and resolving within about 56 h after the challenge (Pelikan, Z. Ann Allergy Asthma Immunol. 2010, 104(5):394-404).

In some embodiments, the chronic respiratory disorder is chronic obstructive pulmonary disease (COPD). COPD encompasses a spectrum of conditions characterized by airflow limitation that is not fully reversible even with therapy and is usually progressive. Symptoms of COPD include dyspnea (breathlessness), decreased exercise tolerance, cough, sputum production, wheezing, and chest tightness. Persons with COPD can experience episodes of acute (e.g., developing over course of less than a week and often over the course of 24 hours or less) worsening of symptoms (termed COPD exacerbations) that can vary in frequency and duration and are associated with significant morbidity. They may be triggered by events such as respiratory infection, exposure to noxious particles, or may have an unknown etiology. Smoking is the most commonly encountered risk factor for COPD, and other inhalational exposures can also contribute to development and progression of the disease. The role of genetic factors in COPD is an area of active research. A small percentage of COPD patients have a hereditary deficiency of alpha-1 antitrypsin, a major circulating inhibitor of serine proteases, and this deficiency can lead to a rapidly progressive form of the disease.

Characteristic pathophysiologic features of COPD include narrowing of and structural changes in the small airways and destruction of lung parenchyma (in particular around alveoli), most commonly due to chronic inflammation. The chronic airflow limitation observed in COPD typically involves a mixture of these factors, and their relative importance in contributing to airflow limitation and symptoms varies from person to person. The term "emphysema" refers to enlargement of the air spaces (alveoli) distal to the terminal bronchioles, with destruction of their walls. It should be noted that the term "emphysema" is often used clinically to refer to the medical condition associated with such pathological changes. Some individuals with COPD have chronic bronchitis, which is defined in clinical terms as a cough with sputum production on most days for 3 months of a year, for 2 consecutive years. Further information regarding risk factors, epidemiology, pathogenesis, diagnosis, and current management of COPD may be found, e.g., in "Global Strategy for the Diagnosis, Management, and Prevention of Chronic Obstructive Pulmonary Disease" (updated 2009) available on the Global Initiative on Chronic Obstructive Pulmonary Disease, Inc. (GOLD) website on the world wide web, at the hypertext protocol transfer address of "goldcopd.org", also referred to herein as the "GOLD Report", the American Thoracic Society/European Respiratory Society Guidelines (2004) available on the ATS website on the world wide web, at the hypertext protocol transfer address of "thoracic.org/clinical/copd-guidelines/resources/copddoc.pdf", referred to herein as "ATC/ERS COPD Guidelines" and standard textbooks of internal medicine such as Cecil Textbook of Medicine ($20^{th}$ edition), Harrison's Principles of Internal Medicine ($17^{th}$ edition), and/or standard textbooks focusing on pulmonary medicine.

In some embodiments methods disclosed herein inhibit (interfere with, disrupt) the DC-Th17-B-Ab-C-DC cycle described in PCT/US2012/043845. For example, administration of a complement inhibitor may break the cycle by which complement stimulates DC cells to promote the Th17 phenotype. As a result, the number and/or activity of Th17 cells diminishes, which in turn reduces the amount of Th17-mediated stimulation of B cells and polyclonal antibody production. In some embodiments, these effects result in "resetting" the immunological microenvironment to a more normal, less pathological state. In some embodiments, inhibiting the DC-Th17-B-Ab-C-DC cycle has a disease-modifying effect. Without wishing to be bound by any theory, rather than merely treating symptoms of a disorder, inhibiting the DC-Th17-B-Ab-C-DC cycle may interfere with fundamental pathologic mechanisms that may contribute to ongoing tissue damage even when symptoms are well controlled and/or that may contribute to exacerbations of the disease. In some embodiments, inhibiting the DC-Th17-B-Ab-C-DC cycle causes a chronic disorder to go into remission. In some embodiments, remission refers to a state of absence or substantial absence of disease activity in a subject with a chronic disorder, with the possibility of return of disease. In some embodiments remission may be sustained for a prolonged period of time (e.g., at least 6 months, e.g., 6-12 months, 12-24 months, or more) in the absence of continued therapy or with a reduced dose or increased dosing interval. In some aspects, inhibition of complement may change the immunological micro-environment of a tissue that is rich in Th17 cells and modify it into a micro-environment that is rich in regulatory T cells (Tregs). Doing so could allow the immune system to "reset" itself and go into a state of remission. In some embodiments, for example, remission may be sustained until occurrence of a triggering event. A triggering event may be, for example, an infection (which may result in production of polyclonal antibodies that react both with an infectious agent and a self protein), exposure to particular environmental conditions (e.g., high levels of air pollutants such as ozone or particulate matter or components of smoke such as cigarette smoke, allergens), etc. Genetic factors may play a role. For example, individuals having particular alleles of genes encoding complement components may have a higher baseline level of complement activity, a more reactive complement system and/or a lower baseline level of endogenous complement regulatory protein activity. In some embodiments an individual has a genotype associated with increased risk of AMD. For example, the subject may have a polymorphism in a gene encoding a complement protein or complement regulatory protein, e.g., CFH, C3, factor B, wherein the polymorphism is associated with an increased risk of AMD.

In some embodiments an immunologic microenvironment may become progressively more polarized towards a pathological state over time, e.g., in a subject who has not yet developed symptoms of a chronic disorder or in a subject who has developed the disorder and has been treated as described herein. Such a transition may occur stochastically (e.g., due at least in part to apparently random fluctuations in antibody levels and/or affinity) and/or as a result of accumulated "sub-threshold" trigger events that are not of sufficient intensity to trigger a symptomatic outbreak of a disorder.

In some embodiments it is contemplated that a relatively short course of a long-acting compstatin analog, e.g., between 1 week and 6 weeks, e.g., about 2-4 week, may provide a long-lasting benefit. In some embodiments a remission is achieved for a prolonged period of time, e.g., 1-3 months, 3-6 months, 6-12 months, 12-24 months, or more. In some embodiments a subject may be monitored and/or treated prophylactically before recurrence of symptoms. For example, a subject may be treated prior to or upon exposure to a triggering event. In some embodiments a subject may be monitored, e.g., for an increase in a biomarker, e.g., a biomarker comprising an indicator of Th17 cells or Th17 cell activity, or complement activation, and may be treated upon increase in the level of such biomarker. See, e.g., PCT/US2012/043845 for further discussion.

Transplantation

Transplantation is a therapeutic approach of increasing importance, providing a means to replace organs and tissues that have been damaged through trauma, disease, or other conditions. Kidneys, liver, lungs, pancreas, and heart are among the organs that can be successfully transplanted. Tissues that are frequently transplanted include bones, cartilage, tendons, cornea, skin, heart valves, and blood vessels. Pancreatic islet or islet cell transplantation is a promising approach for treatment of diabetes, e.g., type I diabetes. For purposes of the invention, an organ, tissue, or cell (or population of cells) that is be transplanted, is being transplanted, or has been transplanted may be referred to as a "graft". For purposes hereof, a blood transfusion is considered a "graft".

Transplantation subjects the graft to a variety of damaging events and stimuli that can contribute to graft dysfunction and, potentially, failure. For example, ischemia-reperfusion (I/R) injury is a common and significant cause of morbidity and mortality in the case of many grafts (particularly solid organs) and can be a major determinant of likelihood of graft survival. Transplant rejection is one of the major risks associated with transplants between genetically different individuals and can lead to graft failure and a need to remove the graft from the recipient.

In some embodiments of the invention, a cell-penetrating compstatin analog is used to protect a graft from complement-mediated damage. A cell-penetrating compstatin analog enters cells of the graft and inhibits complement activation. A graft can be contacted with a compstatin analog prior to, during, and/or after being transplanted, in various embodiments of the invention. For example, prior to transplantation a graft removed from a donor can be contacted with a liquid comprising a compstatin analog. For example, the graft can be bathed in and/or perfused with the solution. In another embodiment, a compstatin analog is administered to a donor prior to removal of the graft. In some embodiments, compstatin analog is administered to a recipient during and/or after the introduction of the graft. In some embodiments, a compstatin analog is delivered locally to the transplanted graft. In some embodiments a compstatin analog is administered systemically, e.g., intravenously.

The invention provides a composition comprising: (a) an isolated graft; and (b) a cell-penetrating compstatin analog. In some embodiments the composition further comprises a liquid solution suitable for contacting (e.g., suitable for rinsing, washing, bathing, perfusing, maintaining, or storing) a graft (e.g., an organ) such as an isolated graft that has been removed from a donor and is awaiting transplantation to a recipient. In some embodiments the invention provides a composition comprising: (a) a liquid solution suitable for contacting a graft (e.g., an organ); and (b) a cell-penetrating compstatin analog. The liquid solution can be any liquid solution that is physiologically acceptable to the graft (e.g., appropriate osmotic composition, non-cytotoxic) and medically acceptable in view of the subsequent introduction of the graft into the recipient (e.g., preferably sterile or at least reasonably free from microorganisms or other contaminants) and compatible with the compstatin analog (i.e., will not destroy the reactivity of the compstatin analog). In some embodiments, a solution is any solution own in the art for any such purposes. In some embodiments, a liquid solution is Marshall's or Hyperosmolar Citrate (Soltran®, Baxter Healthcare), University of Wisconsin (UW) solution (ViaSpan™, Bristol Myers Squibb), Histidine Tryptophan Ketoglutarate (HTK) solution (Custodial®, Kohler Medical Limited), EuroCollins (Fresenius), and Celsior® (Sangstat Medical), Polysol, IGL-1, or AQIX® RS-1. Of course other solutions, e.g., containing equivalent or similar ingredients in the same or different concentrations could be used within the scope of physiologically acceptable compositions. In some embodiments a solution does not contain ingredient(s) with which the compstatin analog would be expected to significantly react, and any solution may be modified or designed to lack such ingredients. In some embodiments, the ompstatin analog is present in the graft-compatible solution at a concentration of, e.g., between 0.01 mg/ml and 100 mg/ml or may be added to the solution to achieve such concentration.

In some embodiments, the invention provides a kit comprising: (a) a cell-penetrating compstatin analog; and (b) a graft-compatible solution or solid (e.g., powder) components thereof. The cell-penetrating compstatin analog may be provided in solid form (e.g., powder) or at least in part dissolved in a solution. In some embodiments the compstatin analog and/or graft-compatible solution are provided in predetermined amounts, so that when combined, a solution of appropriate concentration for contacting a graft with the compstatin analog is produced. In many embodiments the compstatin analog and graft-compatible solution or solid (e.g., powder) components thereof are in separate containers within the kit. In some embodiments the cell-penetrating compstatin analog and components of a graft-compatible solution are both provided in solid (e.g., powder) form, either in separate containers or mixed. In some embodiments the kit comprises instructions for use, e.g., instructions for adding a cell-penetrating compstatin analog to a graft-compatible solution and/or instructions for contacting a graft with a cell-penetrating compstatin analog. Optionally the kit contains a label approved by a government agency responsible for regulating products used in transplantation, cell therapy, and/or blood transfusion.

The invention further provides a method of introducing a cell-penetrating compstatin analog into cells of an isolated graft comprising contacting the isolated graft with cell-penetrating compstatin analog. The invention further provides an isolated graft having a cell-penetrating compstatin analog in at least some cells of the graft. Typically the isolated graft comprises multiple molecules of compstatin analog. In some embodiments, a graft is or comprises a solid organ such as a kidney, liver, lung, pancreas, or heart. In some embodiments, a graft is or comprises bone, cartilage, fascia, tendon, ligament, cornea, sclera, pericardium, skin, heart valve, blood vessel, amniotic membrane, or dura mater. In some embodiments, a graft comprises multiple organs such as a heart-lung or pancreas-kidney graft. In some embodiments, a graft comprises less than a complete organ or tissue. For example, a graft may contain a portion of an organ or tissue, e.g., a liver lobe, section of blood vessel, skin flap, or heart valve. In some embodiments, a graft comprises a preparation comprising isolated cells or tissue fragments that have been isolated from their tissue of origin but retain at least some tissue architecture, e.g., pancreatic islets. In some embodiments, a preparation comprises isolated cells that are not attached to each other via connective tissue, e.g., hematopoietic stem cells or progenitor cells derived from peripheral and/or cord blood, or whole blood or any cell-containing blood product such as red blood cells (RBCs) or platelets. In some embodiments a graft is obtained from a deceased donor (e.g., a "donation after brain death" (DBD) donor or "donation after cardiac death" donor). In some embodiments, depending on the particular type of graft, a graft is obtained from a living donor. For example, kidneys, liver sections, blood cells, are among the types of grafts that can often be obtained from a living donor without undue risk to the donor and consistent with sound medical practice.

In some embodiments, a graft is a xenograft (i.e., the donor and recipient are of different species). In some embodiments a graft is an autograft (i.e., a graft from one part of the body to another part of the body in the same individual). In some embodiments, a graft is an isograft (i.e., the donor and recipient are genetically identical). In most embodiments, the graft is an allograft (i.e., the donor and recipient are genetically non-identical members of the same species). In the case of an allograft, the donor and recipient may or may not be genetically related (e.g., family members). Typically, the donor and recipient have compatible blood groups (at least ABO compatibility and optionally Rh, Kell and/or other blood cell antigen compatibility). The recipient's blood may have been screened for alloantibodies to the graft and/or the recipient and donor since the presence of such antibodies can lead to hyperacute rejection (i.e., rejection beginning almost immediately, e.g., within several minutes after the graft comes into contact with the recipient's blood). A complement-dependent cytoxicity (CDC) assay can be used to screen a subject's serum for anti-HLA antibodies. The serum is incubated with a panel of lymphcytes of known HLA phenotype. If the serum contains antibodies against HLA molecules on the target cells, cell death due to complement-mediated lysis occurs. Using a selected panel of target cells allows one to assign specificity to the detected antibody. Other techniques useful for determining the presence or absence anti-HLA antibodies and, optionally, determining their HLA specificity, include ELISA assays, flow cytometry assays, microbead array technology (e.g., Luminex technology). The methodology for performing these assays is well known, and a variety of kits for performing them are commercially available.

In some embodiments a cell-penetrating compstatin analog inhibits complement-mediated rejection. For example, in some embodiments may inhibit acute or chronic rejection. Without wishing to be bound by any theory, inhibiting complement activation at the graft may reduce complement fragment deposition on a cell surface and/or may inhibit leukocyte (e.g., neutrophil) infiltration, a contributor to graft failure.

In some embodiments, a cell-penetrating compstatin analog may inhibit complement-mediated I/R injury to a graft. As discussed further below, I/R injury can occur upon reperfusion of tissue whose blood supply has been temporarily disrupted, as occurs in transplanted organs. Reducing I/R injury would reduce the likelihood of acute graft dysfunction or reduce its severity, and reduce the likelihood of acute graft failure.

In some embodiments, a cell-penetrating compstatin analog inhibits chronic rejection and/or chronic graft failure. As used herein, "chronic rejection or graft failure" refers to rejection or failure occurring at least 6 months post-transplant, e.g., between 6 months and 1, 2, 3, 4, 5 years, or more post-transplant, often after months to years of good graft function. It is caused by a chronic inflammatory and immune response against the graft. For purposes hereof, chronic rejection can include chronic allograft vasculopathy, a term used to refer to fibrosis of the internal blood vessels of the transplanted tissue.

In some embodiments, a cell-penetrating compstatin analog is administered to a graft recipient to inhibit graft rejection and/or graft failure.

Ischemia/Reperfusion Injury

Ischemia-reperfusion (I/R) injury is an important cause of tissue damage following trauma and in other conditions associated with temporary disruption of blood flow such as myocardial infarction, stroke, severe infection, vascular disease, aneurysm repair, cardiopulmonary bypass, and transplantation.

In the setting of trauma, systemic hypoxemia, hypotension, and local interruption of the blood supply resulting from contusions, compartment syndrome, and vascular injuries cause ischemia that damages metabolically active tissues. Restoration of the blood supply triggers an intense systemic inflammatory reaction that is often more harmful than the ischemia itself. Once the ischemic region is reperfused, factors that are produced and released locally enter the circulatory system and reach remote locations, sometimes causing significant damage to organs not affected by the original ischemic insult, such as the lungs and intestine, leading to single and multiple organ dysfunction. Complement activation occurs soon after reperfusion and is a key mediator of post-ischemic damage, both directly and through its chemoattractive and stimulatory effects on neutrophils. All three major complement pathways are activated and, acting cooperatively or independently, are involved in I/R related adverse events affecting numerous organ systems. In some embodiments of the invention, a cell-penetrating compstatin analog is administered to a subject who has recently (e.g., within the preceding 2, 4, 8, 12, 24, or 48 hours) experienced trauma, e.g., trauma that puts the subject at risk of I/R injury, e.g., due to systemic hypoxemia, hypotension, and/or local interruption of the blood supply. In some embodiments the cell-penetrating compstatin analog may be administered intravascularly, optionally into a blood vessel that supplies an injured body part or directly to the body part. In some embodiments, the subject suffers from spinal cord injury, traumatic brain injury, burn, and/or hemorrhagic shock.

In some embodiments, a cell-penetrating compstatin analog is administered to a subject prior to, during, or after a surgical procedure, e.g., a surgical procedure that is expected to temporarily disrupt blood flow to a tissue, organ, or portion of the body. Examples of such procedures include cardiopulmonary bypass, angioplasty, heart valve repair/replacement, aneurysm repair, or other vascular surgeries. The cell-penetrating compstatin analog may be administered prior to, after, and/or during an overlapping time period with the surgical procedure.

In some embodiments, a cell-penetrating compstatin analog is administered to a subject who has suffered an MI, thromboembolic stroke, deep vein thrombosis, or pulmonary embolism. The cell-penetrating compstatin analog may be administered in combination with a thrombolytic agent such as tissue plasminogen activator (tPA) (e.g., alteplase (Activase), reteplase (Retavase), tenecteplase (TNKase)), anistreplase (Eminase), streptokinase (Kabikinase, Streptase), or urokinase (Abbokinase). The cell-penetrating compstatin analog may be administered prior to, after, and/or during an overlapping time period with the thrombolytic agent.

In some embodiments, a cell-penetrating compstatin analog is administered to a subject to treat I/R injury.

IX. Compositions and Administration

The invention provides a variety of compositions comprising a cell-penetrating compstatin compstatin analog. In various embodiments, a composition can have any feature or combination of features discussed herein so long as they are not mutually exclusive. The invention provides embodiments of such compositions, and methods of use thereof, in which the compstatin analog is any compstatin analog.

In some embodiments, a composition comprises a purified cell-penetrating compstatin analog. Purification can be achieved using a variety of approaches that can be selected by one of ordinary skill in the art based to achieve a desired degree of purity with respect to various components present in the composition prior to purification. For example, filtration, high performance liquid chromatography, affinity chromatography, and/or other approaches and combinations thereof can be used. In some embodiments, the composition comprises at least 80%, 85%, 90%, 95%, 98%, 99%, or more cell-penetrating compstatin analog as a percentage of the total compstatin analog by weight. In some embodiments, the composition comprises at least 80%, 85%, 90%, 95%, 98%, 99%, or cell-penetrating compstatin analog as a percentage of the total compstatin analog on a molar basis. In some embodiments, a composition consists or consists essentially of a cell-penetrating compstatin analog. In some embodiments weight is dry weight.

In some aspects, the invention provides a pharmaceutical grade composition comprising a cell-penetrating compstatin analog. The pharmaceutical grade composition can have any of the above-mentioned characteristics in terms of purity in various embodiments. The pharmaceutical grade composition is sufficiently free of endotoxin, heavy metals, and unidentified and/or uncharacterized substances so as to be acceptable, without further purification, as a pharmaceutical composition suitable for administration to a human subject or for the manufacture of a pharmaceutical composition to be administered to a human subject. In some embodiments, the pharmaceutical grade composition is sterile.

Suitable preparations, e.g., substantially pure preparations of a cell-penetrating compstatin analog or other active agent, may be combined with pharmaceutically acceptable carriers or vehicles, etc., to produce an appropriate pharmaceutical composition. The term "pharmaceutically acceptable carrier or vehicle" refers to a non-toxic carrier or vehicle that does not destroy the pharmacological activity of the compound with which it is formulated. One of skill in the art will understand that a carrier or vehicle is "non-toxic" if it is compatible with administration to a subject in an amount appropriate to deliver the compound without causing undue toxicity. Pharmaceutically acceptable carriers or vehicles that may be used in the compositions of this invention include, but are not limited to, water, physiological saline, Ringer's solution, sodium acetate or potassium acetate solution, 5% dextrose, and the like. The composition may include other components as appropriate for the formulation desired, e.g., as discussed herein. Supplementary active compounds, e.g., compounds independently useful for treating a subject suffering from a complement-mediated disorder, can also be incorporated into the compositions. The invention provides such pharmaceutical compositions comprising a cell-penetrating compstatin analog and, optionally, a second active agent useful for treating a subject suffering from a complement-mediated disorder.

In some embodiments, the invention provides a pharmaceutically acceptable composition suitable for administration to humans, packaged together with a label approved by a government agency responsible for regulating pharmaceutical agents, e.g., the U.S. Food & Drug Administration. In some embodiments, the invention provides a pharmaceutical kit or pack comprising: (a) a pharmaceutically acceptable cell-penetrating compstatin analog in solid form; (b) a pharmaceutically acceptable carrier or vehicle. Optionally the kit or pack contains instructions for dissolving the cell-penetrating compstatin analog in the carrier. In some embodiments a pharmaceutical kit or pack is provided. The pack or kit comprises sufficient amount of pharmaceutical composition for at least 1 dose, e.g., between 1 and 200 doses or any intervening number or subrange. In some embodiments a pharmaceutical pack or kit comprises one or more needles and, optionally, one or more syringes. In some embodiments at least one prefilled syringe is provided. In some embodiments one or more unit dosage forms or premeasured aliquots are provided. In some embodiments instructions for administration, which in some embodiments comprise instructions for self-administration, e.g., via subcutaneous injection, are provided.

A pharmaceutical composition can be administered to a subject by any suitable route of administration including, but not limited to, intravenous, intramuscular, subcutaneously, by inhalation, by nasal delivery, intrathecally, intracranially, intraarterially, orally, rectally, transdermally, intradermally, subdermally, etc. In some embodiments, a composition comprising a cell-penetrating compstatin analog is administered intravenously. In some embodiments, a composition comprising a cell-penetrating compstatin analog is administered intra-arterially. The composition can be administered locally, either into the vascular system supplying an organ or tissue, or extra-vascularly in the vicinity of an organ or tissue. It will be understood that "administration" encompasses directly administering a compound or composition to a subject, instructing a third party to administer a compound or composition to a subject, prescribing or suggesting a compound or composition to a subject (e.g., for self-administration), self-administration, and, as appropriate, other means of making a compound or composition available to a subject.

Pharmaceutical compositions suitable for injectable use (e.g., intravenous administration) or by pump or catheter typically include sterile aqueous solutions (where water soluble) or dispersions and sterile powders for the extemporaneous preparation of sterile injectable solutions or dispersion. Sterile solutions can be prepared by incorporating the compound in the required amount in an appropriate solvent, optionally with one or a combination of ingredients such as buffers such as acetates, citrates, lactates or phosphates; agents for the adjustment of tonicity such as sodium chloride or dextrose; antibacterial agents such as benzyl alcohol or methyl parabens; antioxidants such as ascorbic acid, glutathione, or sodium bisulfite; chelating agents such as ethylenediaminetetraacetic acid; and other suitable ingredients etc., as desired, followed by filter-based sterilization. One of skill in the art will be aware of numerous physiologically acceptable compounds that may be included in a pharmaceutical composition. Other useful compounds include, for example, carbohydrates, such as glucose, sucrose, lactose; dextrans; amino acids such as glycine; polyols such as mannitol. These compounds may, for example, serve as bulking agents and/or stabilizers, e.g., in a powder and/or when part of the manufacture or storage process involves lyophilization. Surfactant(s) such as Tween-80, Pluronic-F108/F68, deoxycholic acid, phosphatidylcholine, etc., may be included in a composition, e.g., to increase solubility or to provide microemulsion to deliver hydrophobic drugs. pH can be adjusted with acids or bases, such as hydrochloric acid or sodium hydroxide, if desired. The parenteral preparation can be enclosed in ampoules, disposable syringes or infusion bags or multiple dose vials made of glass or plastic. Preferably solutions for injection are sterile and acceptably free of endotoxin.

Generally, dispersions are prepared by incorporating the active compound into a sterile vehicle which contains a basic dispersion medium and appropriate other ingredients from those enumerated above. In the case of sterile powders for the preparation of sterile injectable solutions, methods of preparation can include vacuum drying and freeze-drying which yields a powder of the active ingredient plus any additional desired ingredient, e.g., from a previously sterile-filtered solution thereof.

Oral administration may be used in certain embodiments. Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. A liquid composition can also be administered orally. Formulations for oral delivery may incorporate agents to improve stability within the gastrointestinal tract and/or to enhance absorption.

For administration by inhalation, a compstatin analog may be delivered in the form of an aerosol spray from a pressured container or dispenser which contains a suitable propellant, e.g., a gas such as carbon dioxide. A metered dose inhaler or nebulizer may be used. The aerosol may comprise liquid particles or dry aerosol (e.g., dry powders, large porous particles, etc.).

For topical application, a compstatin analog may be formulated in a suitable ointment containing the active component suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated as a suitable lotion or cream containing a compstatin analog suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

Systemic administration can also be by transmucosal or transdermal means. For transmucosal or transdermal administration, penetrants appropriate to the barrier to be permeated may be used in the formulation. Such penetrants are generally known in the art, and include, for example, for transmucosal administration, detergents, bile salts, and fusidic acid derivatives. Transmucosal administration can be accomplished, e.g., through the use of nasal sprays or suppositories. For transdermal administration, the active compounds are typically formulated into ointments, salves, gels, or creams as generally known in the art.

The compounds can also be prepared in the form of suppositories (e.g., with conventional suppository bases such as cocoa butter and other glycerides) or retention enemas for rectal delivery.

In certain embodiments of the invention, a cell-penetrating compstatin analog or other active compound is prepared with carriers that will protect the compound against rapid elimination from the body, such as a controlled release formulation, including implants and microencapsulated delivery systems. For example, a cell-penetrating compstatin analog may be incorporated into or encapsulated in a microparticle or nanoparticle formulation. Biodegradable, biocompatible polymers can be used, such as ethylene vinyl acetate, polyanhydrides, polyglycolic acid, collagen, polyorthoesters, polyethers, polylactic acid, PLGA, etc. Liposomes or other lipid-based particles can be used as pharmaceutically acceptable carriers. These can be prepared according to methods known to those skilled in the art, for example, as described in U.S. Pat. No. 4,522,811 and/or other references listed herein. Depot formulations containing a cell-penetrating compstatin analog may be used. The cell-penetrating compstatin analog is released from the depot over time, e.g., so as to provide a therapeutic concentration for longer than if the compound was administered intravenously. In some aspects, a CRM confers depot properties on a cell-penetrating compstatin analog. One of ordinary skill in the art will appreciate that the materials and methods selected for preparation of a controlled release formulation, implant, etc., should be such as to retain activity of the compound. In some aspects, described herein are particles, e.g., liposomes, nanoparticles, microparticles, comprising a cell-penetrating compstatin analog. A nanoparticle may have a diameter or longest dimension up to about 100 nm, e.g., between about 10 nm and about 100 nm.

A microparticle may have a diameter or longest dimension up to between about 100 nm about 100 microns.

It will be appreciated that a compstatin analog, e.g., a cell-penetrating compstatin analog, and/or additional active agent(s) can be provided as a pharmaceutically acceptable salt. Pharmaceutically acceptable salts include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Also, pharmaceutically-acceptable salts can be prepared as alkaline metal or alkaline earth salts, such as sodium, potassium or calcium salts, if appropriate depending on the identity of the active agent.

It will be understood that the pharmaceutically acceptable carriers, compounds, and preparation methods mentioned herein are exemplary and non-limiting. See, e.g., Remington: The Science and Practice of Pharmacy. 21st Edition. Philadelphia, Pa. Lippincott Williams & Wilkins, 2005, for additional discussion of pharmaceutically acceptable compounds and methods of preparing pharmaceutical compositions of various types.

A pharmaceutical composition can be administered in an amount effective to achieve a desired beneficial effect. In some embodiments, an effective amount is sufficient to provide one or more of the following benefits: (i) reduction in at least one symptom or sign of a complement-mediated disorder; (ii) increased quality of life; (iii) reduced hospitalization; (iv) reduced mortality. One of ordinary skill in the art will appreciate that the particular beneficial effect will depend at least in part on various factors, such as the particular disorder being treated. One of ordinary skill in the art will be aware of the symptoms and signs that may occur in subjects with complement-mediated disorders. Examples of symptoms and signs of various complement disorders are provided herein. For example, in some embodiments, e.g., wherein a subject suffers from PNH or aHUS, a beneficial effect is a reduction in complement-mediated red blood cell lysis. In some aspects, a beneficial effect is statistically significant and/or therapeutically meaningful within the judgement of one or ordinary skill in the art.

In certain embodiments of the invention a pharmaceutical composition comprising a cell-penetrating compstatin analog is administered parenterally. In some embodiments, the composition is administered intravenously. In some embodiments, the composition is administered by intravenous injection. In some embodiments the composition is administered as an IV bolus or an IV infusion. In some embodiments the composition is administered as an IV drip. In some embodiments the composition is administered as an IV bolus followed by an IV infusion or IV drip. In some embodiments an IV infusion is administered over about 1, 2, 3, 4, 5, 15, 20, 30, 60, or 120 minutes. In some embodiments an IV drip is administered over more than about 60 minutes, e.g., over about 1, 2, 3, or more hours. In some embodiments, a total amount of between about 0.1 mg/kg/day and about 2,000 mg/kg/day of compstatin analog is administered, e.g., between about 1 mg/kg/day and about 1,000 mg/kg/day, e.g., between about 5 mg/kg/day and about 500 mg/kg/day. In some embodiments, a total amount of between about 10 mg/kg/day and about 100 mg/kg/day of compstatin analog is administered, e.g., between about 10 mg/kg/day and about 50 mg/kg/day e.g., between about 10 mg/kg/day and about 20 mg/kg/day. It will be appreciated that a variety of different dosing regimens could be used to administer a desired total daily amount. For example, a desired amount of compstatin analog could be administered in a single administration or in multiple administrations, e.g., during a 24 hour period. For example, a subject could receive two or more doses within a 24 hour period, which doses could be administered over the same length of time or over different lengths of time. In some embodiments, a cell-penetrating compstatin analog is administered at time intervals greater than 24 hours. For example, doses could be administered on average every other day, every 3-4 days, weekly, every other week, etc., in various embodiments. In some embodiments, covalently attached, long-acting, or targeted compstatin analogs protect cells, tissues, organs, for a period of weeks or months without need for retreatment. For example, subjects may be maintained with retreatment at intervals of between 1-2 weeks, 2-4 weeks, 4-6 weeks, 6-8 weeks, or even longer. In some embodiments subcutaneous administration is used to administer at least some doses. For example, administration of approximately 0.1-5 mg/kg/day, e.g., about 0.5-2 mg/kg/day is contemplated in some embodiments, e.g., in a volume of about 0.25 ml-2 mL, e.g., a volume of about 1 ml. In some embodiments the concentration is about 50 mg/ml to about 300 mg/ml, e.g., about 50 mg/ml-about 100 mg/ml or about 100 mg/ml-about 200 mg/ml. In some embodiments administration is daily. In some embodiments administration is 1 or 2 times per day. In some embodiments a cell-penetrating compstatin analog is administered using a therapeutically effective amount to a subject, wherein such administration results in blood concentrations of the compound that achieve a level above at least 4 µM, at least 5 µM, at least 6 µM, at least 7 µM, at least 8 µM, at least 9 µM, at least 10 µM, at least 11 µM, at least 12 µM, or at least 13 µM, at least 14 µM, at least 15 µM, at least 16 µM, at least 18 µM, or at least about 20 µM, or at least about 25 µM or within any range between 4 µM and about 15 µM or about 20 µM or about 25 µM. In some embodiments such level is maintained for at least about 24 hours, or at least about 48 hours, or at least about 72 hours, or at least about 96 hours, or at least about 120 hours, or at least about 144 hours, which may be achieved one or more IV injections, infusion, subcutaneous injections, for example. Sustained levels may be achieved for longer, e.g., up to about 10 days, 12 days, 14 days, or more.

It will be understood that there may be an initial treatment phase during which treatment is more frequent and/or in which higher doses are administered. After that, lower doses and/or less frequent dosing may be used. In some embodiments treatment is started using IV administration and then switched to subcutaneous, intramuscular, or intradermal for maintenance therapy. Depending on the disease, treatment may continue at intervals for, e.g., months, years, or indefinitely. Appropriate doses and dosing regimen depend at least in part upon the potency and half-life of the compstatin analog (or other active agent), and may optionally be tailored to the particular recipient, for example, through administration of increasing doses until a preselected desired response is achieved, such as a desired degree of complement inhibition and/or cell protection. If desired, the specific dose level for any particular subject may be selected based at least in part upon a variety of factors including the activity of the specific compound employed, the particular condition being treated, the age, body weight, general health, route of administration, the rate of excretion, any drug combination, and/or the degree of complement protein expression or activity measured in one or more samples obtained from the subject.

The invention encompasses administration of a cell-penetrating compstatin analog in combination with additional therapy. Such additional therapy may include administration of any agent(s) used in the art or potentially useful for treating a subject suffering from the disease. In any embodiment or aspect a cell-penetrating compstatin analog may be administered in combination with a compstatin analog lacking a cell penetrating moiety, a long-acting, targeted, or cell-reactive compstatin analog, or a combination thereof. Long-acting, targeted, or cell-reactive compstatin analogs are described in PCT/US US12/37648; U.S. Ser. No.: 61/727,094; and/or U.S. Ser. No.: 61/727,093.

When two or more therapies (e.g., compounds or compositions) are used or administered "in combination" with each other, they may be given at the same time, within overlapping time periods, or sequentially (e.g., separated by up to 2-4 weeks in time), in various embodiments of the invention. They may be administered via the same route or different routes. In some embodiments, the compounds or compositions are administered within 48 hours of each other. In some embodiments, a cell-penetrating compstatin analog analog can be given prior to or after administration of the additional compound(s), e.g., sufficiently close in time that the compstatin analog and additional compound(s) are present at useful levels within the body at least once. In some embodiments, the compounds or compositions are administered sufficiently close together in time such that no more than 90% of the earlier administered composition has been metabolized to inactive metabolites or eliminated, e.g., excreted, from the body, at the time the second compound or composition is administered.

In some embodiments, a composition that includes both a cell-penetrating compstatin analog and additional compound(s) is administered.

Example 1: Development of Cell Penetrating Compstatin Analogs

Three compounds, each of which incorporated the amino acid sequence listed as SEQ ID NO: 28 and a different cell penetrating peptide, were synthesized and designated as CPCA28-1, CPCA28-2, and CPCA28-3. Briefly, amino acids (including AEEAc) were obtained as Fmoc-protected amino acids, in which the α-amino group of each amino acid was protected with Fmoc. Side chain functional groups were also blocked with various appropriate protective groups. Synthesis was accomplished following the solid phase methodology described by Merrifield (J. Amer. Chem. Soc. 85, 2149 (1963)). Chain assembly was performed on solid phase, at the conclusion of which the N-terminus was acetylated (in the case of CPCA28-2 and CPCA28-3); the peptide was then cleaved from the solid phase and simultaneously deprotected via acidolysis using TFA and amidated. The linear peptide was then oxidized and purified. Compounds were provided as acetate salts. Sequences are presented below:

CPCA28-1:
(SEQ ID NO: 68)
H-D-Arg-D-Arg-D-Arg-D-Gln-D-Arg-D-Arg-D-Lys-D-Lys-

D-Arg-AEEAc-Ile-Cys-Val-Trp(Me)-Gln-Asp-Trp-Gly-

Ala-His-Arg-Cys-Thr-$NH_2$ (Trp(Me) = 1-methyl-1-tryptophan;
"D" represents D amino acids)

CPCA28-2:
(SEQ ID NO: 69)
Ac-YARAAARQARAG-AEEAc-IC*V-(1-methyl-1-tryptophan)

QDWGAHRC*T-$NH_2$

CPCA28-3:
(SEQ ID NO: 70)
Ac-AAVALLPAVLLALLAP-AEEAc-IC*V(1-methyl-1- tryptophan)QDWGAHRC*T-$NH_2$

To confirm that the compounds retains ability to inhibit C3 activation, inhibitory activity of the synthesized compounds is assessed by measuring the effect of the compounds on complement activation via the classical pathway using a standard complement inhibition assay. The protocol measures C3b deposition in an ELISA format. C3b deposition monitored using this method is generated through complement activated by the classical pathway. Briefly, 96-well plates are coated with BSA. Human plasma, chicken ovalbumin (OVA), polyclonal anti-OVA antibodies and compound being tested (referred to as "drug") are added and incubated, followed by addition of Anti-human C3 HRP-conjugated antibody. After an additional incubation, substrate is added and signal detected. Details of the protocol are as follows:

Protocol for Classical Complement Inhibition Assay
Materials:
  Ninety-six well plate (polystyrene plate, Thermo Scientific, 9205)
  Chicken OVA (Sigma A5503-5G)
  Rabbit anti-chicken OVA (Abcam ab1221)
  Blocking buffer (Startingblock buffer, Thermo Scientific 37538)
  Veronal Buffer (5× concentration, Lonza 12-624E)
  Human plasma (collected with Lepirudin at 50 ug/ml final concentration)
  Goat anti-human C3 HRP-conjugated Ab (MP Biomedicals, 55237)
  Tween-20 Wash Buffer (0.05% Tween 20-PBS buffer)
  TMB (Peroxidase substrate, BD 555214)—1:1 mixture of BD 51-2607KC and 51-2606KC.
  1M $H_2SO_4$
Protocol:
  1. Add 100 ul/well of 1% chicken OVA (in PBS)
  2. Incubate overnight @ 4'C or room temperature for 1-2 hr.
  3. Remove by shaking and tapping the plate.
  4. Block by adding 200 ul of blocking buffer
  5. Incubate for 1 h at room temp 6. Remove by shaking and tapping the plate
7. Add 100 ul of 1:1000 dilution of Polyclonal anti-chicken OVA in blocking buffer
8. Incubate for 1 h at room temp
9. Wash twice with wash buffer
10. Add 50 ul VB$^{++}$ to wells #2 to 12
11. Add 100 ul of starting drug dilution (2× in VB$^{++}$) to well 1.
12. Serially dilute (1:2) the drug from wells 1 to 10 as follow
    a. Take 50 ul of solution from the originating well
    b. Add this to the next well
    c. Mix by pipetting several times
    d. Repeat up to well #10
Note: from well #10 remove 50 ul and discard.
13. Add 50 ul of 2× plasma (1:37.5 dilution of original plasma) dilution to wells 1 to 11
14. Incubate for 1 h
15. Wash with wash buffer
16. Add 100 ul of 1/1000 dilution of anti-C3-HRP Ab in blocking buffer
17. Incubate for 1 h
18. Wash with wash buffer
19. Add 100 ul of TMB to all wells
20. Incubate for 5-10 min in dark
21. Add 50 ul 1M $H_2SO_4$
22. Read the plate at 450 nm VB$^{++}$
Formula:

| | |
|---|---|
| Barbital | 5 mM |
| NaCl | 72.5 mM |
| MgCl$_2$ | 0.5 mM |
| CaCl$_2$ | 0.15 mM |
| PH | 7.4 |

Stock Solutions:

| Veronal Buffer (5×) | | | |
|---|---|---|---|
| | Prod # | MW | For 500 ml |
| 9 mM Sodium Barbitone | Sigma B0500 | 206.17 | 927 mg |
| 15.5 mM diethylbarbituric acid | Sigma B0375 | 184.19 | 1.42 grams |

| Mg—Cl2 (200×) | | | |
|---|---|---|---|
| | Prod # | MW | For 50 ml |
| 100 mM MgCl$_2$—6H$_2$O | Sigma M0250 | 203.30 | 1.00 gram |

| CaCl$_2$ (500×) | | | |
|---|---|---|---|
| | Prod # | MW | For 50 ml |
| 75 mM CaCl$_2$ | Sigma C7902 | 147.01 | 551.28 mg |

To Prepare 50 ml of Working Buffer:
Weight 210 mg NaCl
Add 10 ml of 5×VB
Add 100 ul of CaCl$_2$ (500×)
Add 250 ul MgCl (200×)
Adjust volume to 50 ml with H$_2$O
Adjust pH to 7.4

Data is analyzed using GraphPad Prism5 software. Data sets from each experiment were normalized to percent activation compared to the 100% activation control corresponding to the well to which no compound is added. Drug concentration values (X values) are transformed to their logarithms, and percent activation (Pa) (Y values) was transformed to percent inhibition (Pi) using the following formula Pi=100−Pa (Yi=100−Ya). The percent inhibition is plotted against the drug concentration and the resulting data set was fit to a sigmoidal-dose response function [Y=Bottom+(Top−Bottom)/(1+10 ((Log EC-X)))]. IC$_{50}$ values were obtained from the fit parameters.

Example 2: Activity of Cell-Penetrating Compstatin Analogs in In Vitro Assay

CPCA28-1, CPCA28-2, and CPCA28-3 are individually contacted in vitro with C3 in the presence of cathepsin L. The ability of each compound to inhibit cathepsin L-mediated cleavage of C3 is assessed, e.g., by ELISA for C3a. Various concentrations of compound are tested.

Example 3: Activity of Cell-Penetrating Compstatin Analogs in Cell-Based Assay

CPCA28-1, CPCA28-2, and CPCA28-3 are individually contacted in vitro with CD4+ Tcells. The T cells are activated (e.g., by contacting them with antibody to CD3 or with antibody to CD3 and antibody to CD28). Ability of each compound to inhibit release of C3a and/or to inhibit deposition of C3b on cell surfaces is assessed, e.g., using appropriate antibodies, e.g., with ELISA or flow cytometry. Various concentrations of compound are tested.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. For example, and without limitation, it is understood that where claims or description indicate that a residue at a particular position may be selected from a particular group of amino acids or amino acid analogs, the invention includes individual embodiments in which the residue at that position is any of the listed amino acids or amino acid analogs. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of administering the composition according to any of the methods disclosed herein, and methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. Methods of treating a subject can include a step of providing a subject in need of such treatment (e.g., a subject who has had, or is at increased risk of having, a disease), a step of diagnosing a subject as having a disease and/or a step of selecting a subject for treatment with a cell-penetrating compstatin analog. Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc. Discussion of various diseases, disorders, and conditions under various headings herein is for convenience and is not intended to limit the invention.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention may be explicitly excluded from the claims even if such exclusion is not set forth explicitly herein. For example, any compstatin analog, functional group, linking portion, clearance-reducing moiety, disease, or indication can be explicitly excluded.

We claim:

1. A compound comprising:
   (i) a compstatin analog moiety comprising a peptide comprising an amino acid sequence of one of SEQ ID NOs: 3-6 and 9-36; and
   (ii) a cell penetrating moiety (CPM) comprising a cell penetrating peptide comprising an amino acid sequence of one of SEQ ID NOs: 77-136,
   wherein the compstatin analog moiety is covalently linked to the CPM.

2. The compound of claim 1, wherein the compstatin analog moiety is linked to the CPM via a linker.

3. The compound of claim 1, wherein the compstatin analog moiety comprises a cyclic peptide having a core sequence of (SEQ ID NO: 3)
X'aa-Gln-Asp-Xaa-Gly, where X'aa and Xaa are selected from Trp and analogs of Trp.

4. The compound of claim 1, wherein the compstatin analog moiety comprises a cyclic peptide having a core sequence of (SEQ ID NO: 4)
X'aa-Gln-Asp-Xaa-Gly-X"aa, where X'aa and Xaa are selected from Trp and analogs of Trp, and X"aa is selected from His, Ala, single methyl unbranched amino acids, Phe, Trp, and analogs of Trp.

5. The compound of claim 1, wherein the compstatin analog is a compound that comprises a cyclic peptide having a sequence of (SEQ ID NO: 5)
X'aa1-X'aa2-X'aa3-X'aa4-Gln-Asp-Xaa-Gly-X"aa1-

X"aa2-X"aa3-X"aa4-X"aa5, where X'aa4 and Xaa are selected from Trp and analogs of Trp, wherein X'aa1, X'aa2, X'aa3, X"aa1, X"aa2, X"aa3, X"aa4, and X"aa5, are independently selected from among amino acids and amino acid analogs, wherein the peptide is cyclized via a bond between X'aa2 and X"aa4.

6. The compound of claim 1, wherein the compstatin analog is a compound that comprises a cyclic peptide having a sequence:

(SEQ ID NO: 6)
Xaa1-Cys-Val-Xaa2-Gln-Asp-Xaa2*-Gly-Xaa3-His-Arg-

Cys-Xaa4;

wherein:
   Xaa1 is Ile, Val, Leu, $B^1$-Ile, $B^1$-Val, $B^1$-Leu or a dipeptide comprising Gly-Ile or $B^1$-Gly-Ile, and $B^1$ represents a first blocking moiety, wherein $B^1$ comprises an acetyl group;
   Xaa2 and Xaa2* are independently selected from Trp and analogs of Trp;
   Xaa3 is His, Ala or an analog of Ala, Phe, Trp, or an analog of Trp;

Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B^2$, wherein $B^2$ comprises an —$NH_2$ group; and the two Cys residues are joined by a disulfide bond.

7. The compound of claim 6, wherein

Xaa1 is Ile, Val, Leu, Ac-Ile, Ac-Val, Ac-Leu or a dipeptide comprising Gly-Ile or Ac-Gly-Ile;

Xaa2 and Xaa2* are independently selected from Trp and analogs of Trp;

Xaa3 is His, Ala or an analog of Ala, Phe, Trp, or an analog of Trp;

Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by —$NH_2$.

8. The compound of claim 6, wherein Xaa2 is an analog of Trp comprising a substituted or unsubstituted bicyclic aromatic ring component or two or more substituted or unsubstituted monocyclic aromatic ring components.

9. The compound of claim 6, wherein Xaa2 is an analog of Trp comprising a lower alkoxy or lower alkyl substituent at the 1 or 5 position of tryptophan or a halogen substituent at the 5 or 6 position of tryptophan.

10. The compound of claim 9, wherein Xaa2 is an analog of Trp comprising a lower alkoxy or lower alkyl substituent at the 1 or 5 position of tryptophan or a halogen substituent at the 5 or 6 position of tryptophan and Xaa2* is Trp.

11. The compound of claim 1, wherein the compstatin analog comprises a cyclic peptide having a sequence selected from the group consisting of SEQ ID NOs: 14, 21, 28, 29, 32, 33, 34, or 36.

12. A composition comprising (a) an isolated cell; and (b) a compound comprising:
(i) a compstatin analog moiety comprising a peptide comprising an amino acid sequence of one of SEQ ID NOs: 3-6 and 9-36; and
(ii) a cell penetrating moiety (CPM) comprising a cell penetrating peptide comprising an amino acid sequence of one of SEQ ID NOs: 77-136,
wherein the compstatin analog moiety is covalently linked to the CPM.

13. The composition of claim 12, wherein the isolated cell is a liver cell, endothelial cell, epithelial cell, or immune system cell.

* * * * *

UNITED STATES PATENT AND TRADEMARK OFFICE
CERTIFICATE OF CORRECTION

PATENT NO. : 10,308,687 B2
APPLICATION NO. : 14/775663
DATED : June 4, 2019
INVENTOR(S) : Cedric Francois et al.

Page 1 of 1

It is certified that error appears in the above-identified patent and that said Letters Patent is hereby corrected as shown below:

In the Claims

Column 195, Lines 64-65 (Claim 4, Lines 9-10) delete "where X'aa and Xaa are selected from Trp and analogs of Trp and analogs of Trp", and insert --where X'aa and Xaa are each independently selected from Trp and analogs of Trp-- therefore.

Signed and Sealed this
Third Day of September, 2019

Andrei Iancu
*Director of the United States Patent and Trademark Office*